US007803765B2

(12) United States Patent
Watt et al.

(10) Patent No.: US 7,803,765 B2
(45) Date of Patent: Sep. 28, 2010

(54) METHODS OF CONSTRUCTING BIODIVERSE GENE FRAGMENT LIBRARIES AND BIOLOGICAL MODULATORS ISOLATED THEREFROM

(75) Inventors: Paul Michael Watt, Mt. Claremont (AU); Wayne Robert Thomas, Nedlands (AU); Richard Hopkins, North Perth (AU)

(73) Assignee: Phylogica Limited (AU)

( * ) Notice: Subject to any disclaimer, the term of this patent is extended or adjusted under 35 U.S.C. 154(b) by 152 days.

(21) Appl. No.: 10/546,333

(22) PCT Filed: Feb. 20, 2004

(86) PCT No.: PCT/AU2004/000214

§ 371 (c)(1),
(2), (4) Date: Apr. 10, 2006

(87) PCT Pub. No.: WO2004/074479

PCT Pub. Date: Sep. 2, 2004

(65) Prior Publication Data

US 2007/0031832 A1 Feb. 8, 2007

(51) Int. Cl.
*A61K 38/00* (2006.01)
*C07K 5/00* (2006.01)
*C40B 40/02* (2006.01)

(52) U.S. Cl. ......................... 514/12; 514/773; 530/324; 530/325; 530/350; 530/391.1; 530/391.7; 506/14

(58) Field of Classification Search ................... 514/12, 514/773; 530/324, 325, 350, 391.1, 391.7; 506/14

See application file for complete search history.

(56) References Cited

U.S. PATENT DOCUMENTS

| | | | |
|---|---|---|---|
| 5,516,637 | A | 5/1996 | Huang et al. |
| 5,763,239 | A | 6/1998 | Short et al. |
| 5,783,431 | A | 7/1998 | Peterson et al. |
| 5,821,047 | A | 10/1998 | Garrard et al. |
| 5,834,247 | A | 11/1998 | Comb et al. |
| 6,083,715 | A | 7/2000 | Georgiou et al. |
| 6,174,673 | B1 | 1/2001 | Short et al. |
| 6,190,908 | B1 | 2/2001 | Kang |
| 6,225,530 | B1 | 5/2001 | Weigel et al. |
| 6,238,884 | B1 | 5/2001 | Short et al. |
| 6,297,004 | B1 | 10/2001 | Russell et al. |
| 6,316,223 | B1 | 11/2001 | Payan et al. |
| 6,319,690 | B1 | 11/2001 | Little et al. |
| 6,361,969 | B1 | 3/2002 | Galeotti |
| 6,436,694 | B1 | 8/2002 | Tally et al. |
| 6,475,726 | B1 | 11/2002 | Tally et al. |
| 6,521,425 | B2 | 2/2003 | Perler et al. |
| 6,560,542 | B1 | 5/2003 | Mandell et al. |
| 6,579,675 | B2 | 6/2003 | Kamb |
| 6,583,275 | B1 | 6/2003 | Doucette-Stamm et al. |
| 6,720,139 | B1 | 4/2004 | Zyskind et al. |
| 6,720,413 | B1 | 4/2004 | Schweinfest et al. |
| 6,846,625 | B1 | 1/2005 | Tally et al. |
| 7,117,096 | B2 | 10/2006 | Luo et al. |
| 7,270,969 | B2 | 9/2007 | Watt et al. |
| 2002/0150906 | A1 | 10/2002 | Debe |
| 2002/0155564 | A1 | 10/2002 | Medrano et al. |
| 2002/0164735 | A1 | 11/2002 | Olson et al. |
| 2003/0215846 | A1 | 11/2003 | Watt et al. |

FOREIGN PATENT DOCUMENTS

| | | | |
|---|---|---|---|
| AU | 18603/95 | A1 | 6/1995 |
| AU | 48085/97 | A1 | 4/1997 |
| AU | 22587/99 | A1 | 7/1999 |
| AU | 756617 | B2 | 2/2000 |
| AU | 771534 | B2 | 11/2000 |
| EP | 1 277 835 | A1 | 1/2003 |
| WO | WO-95/17412 | A1 | 6/1995 |
| WO | WO-98/15172 | A2 | 4/1998 |
| WO | WO-98/16835 | A2 | 4/1998 |
| WO | WO-99/35282 | A1 | 7/1999 |
| WO | WO-00/68373 | A1 | 11/2000 |
| WO | WO-00/76308 | A1 | 12/2000 |
| WO | WO-01/11086 | A2 | 2/2001 |
| WO | WO-01/11086 | A3 | 2/2001 |
| WO | WO-01/11086 | C1 | 2/2001 |
| WO | WO-01/25461 | A1 | 4/2001 |
| WO | WO-01/75178 | A2 | 10/2001 |
| WO | WO-01/75178 | A3 | 10/2001 |
| WO | WO-02/29101 | A2 | 4/2002 |
| WO | WO-02/29101 | A3 | 4/2002 |
| WO | WO-02/060946 | A2 | 8/2002 |
| WO | WO-02/060946 | A3 | 8/2002 |

(Continued)

OTHER PUBLICATIONS

Amann et al. (1985). "ATG Vectors for Regulated High-Level Expression of Cloned Genes in *Escherichia coli*," *Gene* 40:183-190.

Arenkov, P. et al. (2000). "Protein Microchips: Use for Immunoassay and Enzymatic Reactions," *Analytical Biochemistry* 278:123-131.

Balaban et al. (Apr. 17, 1998). "Autoinducer of Virulence as a Target for Vaccine and Therapy Against *Staphylococcus aureus*," *Science* 280:438-440.

Baud et al. (1999). "Measures of Residue Density in Protein Structures," *Proc. Natl. Acad. Sci. USA* 96:12494-12499.

Behrens, A. et al. (Mar. 1999). "Amino-Terminal Phosphorylation of c-Jun Regulates Stress-Induced Apoptosis and Cellular Proliferation," *Nature Genetics* 21:326-329.

Berzofsky, J.A. (1985). "Intrinsic and Extrinsic Factors in Protein Antigenic Structure," *Science* 229:932-940.

Blum et al. (2000). "Isolation of Peptide Aptamers That Inhibit Intracellular Processes," *Proc. Natl. Acad. Sci. USA* 97:2241-2246.

(Continued)

*Primary Examiner*—T. D. Wessendorf
(74) *Attorney, Agent, or Firm*—Morrison & Foerster LLP

(57) ABSTRACT

The present invention provides novel methods for producing nucleic acid fragment libraries that express highly diverse peptides or protein domains and, in particular, methods for producing nucleic acid fragment libraries wherein the nucleic acid.

18 Claims, 22 Drawing Sheets

FOREIGN PATENT DOCUMENTS

| | | | |
|---|---|---|---|
| WO | WO-02/068373 | A2 | 9/2002 |
| WO | WO-02/068373 | A3 | 9/2002 |
| WO | WO-02/086111 | A2 | 10/2002 |
| WO | WO-02/086111 | A3 | 10/2002 |
| WO | WO-02/088314 | A2 | 11/2002 |
| WO | WO-02/088314 | A3 | 11/2002 |
| WO | WO-03/004528 | A1 | 1/2003 |
| WO | WO-03/010540 | A1 | 2/2003 |
| WO | WO-03/012055 | A2 | 2/2003 |
| WO | WO-03/012055 | A3 | 2/2003 |
| WO | WO-03/040168 | A2 | 5/2003 |
| WO | WO-03/040168 | A3 | 5/2003 |
| WO | WO-03/046147 | A2 | 6/2003 |
| WO | WO-03/046147 | A3 | 6/2003 |
| WO | WO-03/076621 | A2 | 9/2003 |
| WO | WO-03/076621 | A3 | 9/2003 |
| WO | WO-2004/074479 | A1 | 9/2004 |
| WO | WO-2006/017913 | A1 | 2/2006 |

OTHER PUBLICATIONS

Bonaldo et al. (1997). "Normalization and Subtraction: Two Approaches to Facilitate Gene Discovery," *Genome Res.* 6:791-806.

Bremnes et al. (1998). "Selection of Phage Displayed Peptides From a Random 10-mer Library Recognizing a Peptide Target," *Immunotechnology* 4:21-28.

Britten et al. (1968). "Repeated Sequences in DNA," *Science* 161:529-540.

Burioni et al. (1998). "A New Subtraction Technique for Molecular Cloning of Rare Antiviral Antibody Specificities From Phage Display Libraries," *Res. Virol.* 149:327-330.

Campbell et al. (1997). "Solution Secondary Structure of a Bacterially Expressed Peptide from the Receptor Binding Domain of *Pseudomonas aeruginosa* pili Strain pak: A Heteronuclear Multidimensional NMR Study," *Biochem.* 36:12791-12801.

Caponigro, G. et al. (Jun. 1998). "Transdominant Genetic Analysis of a Growth Control Pathway," *Proc. Natl. Acad. Sci. USA* 95:7508-7513.

Chapman et al. (1984). "Recognition of two *Dermatophagoides pteronyssinus*-specific Epitopes on Antigen $p_1$ by using Monoclonal Antibodies: Binding to Each Epitope can be Inhibited by Serum from Dust Mite-Allergic Patients," *J. Imunol.* 133:2488-2495.

Chong et al. (1997). In: *The Yeast Two-Hybrid System* Bartel et al. eds. New York, NY pp. 289-297.

Colas et al. (Apr. 11, 1996). "Genetic Selection of Peptide Aptamers That Recognize and Inhibit Cyclin-Dependent Kinase 2," *Nature* 380:548-550.

Colbere-Garapin et al. (1981). "A New Dominant Hybrid Selective Marker for Higher Eukaryotic Cells," *J. Mol. Biol.* 150:1-14.

Davies, J.M. et al. (Jun. 2000). "Use of Phage Display Technology to Investigate Allergen-Antibody Interactions," *J. Allergy Clin. Immunol.* 105(6):1085-1092.

De Soultrait et al. (2002). "A Novel Short Peptide is a Specific Inhibitor of the Human Immunodeficiency Virus Type 1 Integrase," *J. Mol. Biol.* 318:45-58.

Dent et al. (1999). "The Genetics of Ivermectin Resistance in *Caenorhabditis elegans," Proc. Natl. Acad. Sci. USA* 97:2674-267.

Derossi et al. (1994). "The Third Helix of the Antennapedia Homeodomain Translocates Through Biological Membranes," *J. Biol. Chem.* 269(14):10444-10450.

Devereaux et al. (1984). "A Comprehensive Set of Sequence Analysis Programs for the VAX," *Nucl. Acids Res.* 12:387-395.

DeVito et al. (2002). "An Array of Target-Specific Screening Strains for Antibacterial Discovery," *Nature Biotechnology* 20:478-483.

Estus, S. et al. (Dec. 1994). "Altered Gene Expression in Neurons During Programmed Cell Death: Identification of c-*Jun* as Necessary for Neuronal Apoptosis," *The Journal of Cell Biology* 127(6):1717-1727.

Faber et al. (1999). "Polyglutamine-Mediated Dysfunction and Apoptotic Death of a *Caenorhabditis elegans* Sensory Neuron," *Proc. Natl. Acad. Sci. USA* 96:179-184.

Fabret et al. (2000). "Efficient Gene Targeted Random Mutagenesis in Genetically Stable *Escherichia coli* strains," *Nucl. Acids Res.* 28:e95.

Fahraeus et al. (1996). "Inhibition of prb Phosphorylation and Cell-Cycle Progression by a 20-Residue Peptide Derived From $p16^{CDKN2ANK4An}$," *Curr. Biol.* 6(1):84-91.

Fang, Y. et al. (2002). "G-Protein-Coupled Receptor Microarrays," *ChemBioChem* 3:987-991.

Fehrsen et al. (1999). "Cross-Reactive Epitope Mimics in a Fragmented-Genome Phage Display Library Derived from the Rickettsia, *Cowdria ruminantium," Immunotechnology* 4:175184.

Filipe, S. R. (2001). "The Role of *murMN* Operon in Penicillin Resistance and Antibiotic Tolerance of *Streptococcus pneumoniae," Microbial Drug Resistance* 7(4):303-316.

Fitzgerald (2000). "In vitro Display Technologies—New Tools for Drug Discovery," *Drug Discovery Today* 5:253-258.

Franzoni et al. (1997). "Structure of the C-Terminal Fragment 300-320 of the Rat Angiotensin II $AT_{1a}$ Receptor and Its Relevance with Respect to G-Protein Coupling," *J. Biol Chem.* 272:9734-9741.

Furmonaviciene, R. et al. (1999). "The Use of Phage-Peptide Libraries to Define the Epitope Specificity of a Mouse Monoclonal Anti-Der p 1 Antibody Representative of a Major Component of the Human Immunoglobulin E Anti-Der p 1 Response," *Clin. Exp. Allergy* 29:1563-1571.

Garcia, M. et al. (Mar. 15, 2002). "The Mitochondrial Toxin 3-Nitropropionic Acid Induces Striatal Neurodegeneration via a c-Jun N-Terminal Kinase/c-Jun Module," *The Journal of Neuroscience* 22(6):2174-2184.

Gargala, G. et al. (1999). "Enzyme Immunoassay Detection of *Cryptosporidium parvum* Inhibition by Sinefungin in Sporozoite Infected HCT-8 Enterocytic Cells," *International Journal of Parasitology* 29:703-709.

Gegg et al. (1997). "Probing Minimal Independent Folding Units in Dihydrofolate Reductase by Molecular Dissection," *Protein Sci.* 6:1885-1892.

Getzoff et al. (1987). "Mechanisms of Antibody Binding to a Protein," *Science* 235:1191-1192.

Greene et al. (1992). "IgE Binding Structures of the Major House Dust Mite Allergen *DER P* 1," *Mol. Immunology* 29:257-262.

Hegde, S. S. et al. (Mar. 9, 2001). "FemABX Family Members Are Novel Nonribosomal Peptidyltransferases and Important Pathogen-Specific Drug Targets," *The Journal of Biological Chemistry* 276(10):6998-7003.

Hengeveld et al. (2002). "Functional and Structural Characterization of a Synthetic Peptide Representing the N-Terminal Domain of Prokaryotic Pyruvate Dehydrogenase," *Biochem.* 41:7490-7500.

Heymann et al. (1989). "Antigenic and Structural Analysis of Group II Allergens (*Der* f II and *Der* p II) From House Dust Mites (*Dermatophagoides* spp.)" *J. Allergy Clin. Immunol.* 83:1055-1067.

Hofmann et al. (1996). "Rapid Retroviral Delivery of Tetracycline-Inducible Genes in a Single Autoregulatory Cassette," *Proc. Natl. Acad. Sci. USA* 93:5185-5189.

Hoogenboom et al. (1991). "Multi-Subunit Proteins on the Surface of Filamentous Phage: Methodologies for Displaying Antibody (Fab) Heavy and Light Chains," *Nucleic Acids Res.* 19:4133-4137.

Horng et al. (2002). "Characterization of Large Peptide Fragments Derived from the N-Terminal Domain of the Ribosomal Protein L9: Definition of the Minimum Folding Motif and Characterization of Local Electrostatic Interactions," *Biochem.* 41:13360-13369.

Hosen, N. et al. (2004). "Identification of a Gene Element Essential for Leukemia-Specific Expression of Transgenes," *Leukemia* 18:415-419.

Houshmand et al. (1999). "Use of Bacteriophage T7 Displayed Peptides for Determination of Monoclonal Antibody Specificity and Biosensor Analysis of the Binding Reaction," *Anal. Biochem.* 268:363-370.

Humphrey et al. (1997). "Chemical Synthesis of Natural Product Peptides; Coupling Methods for the Incorporation of Noncoded Amino Acids into Peptides," *Chem. Rev.* 97:2243-2266.

Irbäck et al. (1996). "Evidence for Nonrandom Hydrophobicity Structures in Protein Chains," *Proc. Natl. Acad. Sci. USA* 93:9533-9538.

Kabouridis, P. S. (Nov. 2003). "Biological Applications of Protein Transduction Technology," *Trends in Biotechnology* 21(11):498-503.

Kinzler et al. (1989). "Whole Genome PCR: Application to the Identification of Sequences Bound by Gene Regulatory Proteins," *Nucleic Acids Res.* 17:3645-3653.

Kolonin et al. (Nov. 1998). "Targeting Cyclin-Dependent Kinases in *Drosophila* with Peptide Aptamers," *Proc. Natl. Acad. Sci. USA* 95(24):14266-14271.

Koncz et al. (1987). "Expression and Assembly of Functional Bacterial Luciferase in Plants," *Proc. Natl. Acad. Sci. USA* 84:131-135.

Kopczynski et al. (1998). "A High Throughput Screen to Identify Secreted and Transmembrane Proteins Involved in *Drosophila* embryogenesis," *Proc. Natl. Acad. Sci. USA* 95:9973-9978.

Lambros, C. et al. (Jun. 1979). "Synchronization of Plasmodium Falciparum Erythrocytic Stages in Culture," *J. Parasitol.* 65(3):418-420.

Lee et al. (1994). "Structure-Antigenicity Relationship of Peptides from the Pre-s2 Region of the Hepatitis B Virus Surface Antigen," *Biochem. Mol. Biology and Mol. Biology Int.* 34:159-168.

Lee, Y. et al. (2003). "ProteoChip: A Highly Sensitive Protein Microarray Prepared by a Novel Method of Protein Immobilization for Application of Protein—Protein Interaction Studies," *Proteomics* 3:2289-2300.

Leitner, A. et al. (1998). "A Mimotope Defined by Phage Display Inhibits IgE Binding to the Plant Panallergen Profiling," *Eur. J. Immunol.* 28:2921-2927.

Lesley et al. (1991). "Use of in vitro Protein Syntheses from Polymerase Chain Reaction-Generated Templates to Study Interaction of *Escherichia coli* Transcription Factors with Core RNA Polymerase and for Epitope Mapping of Monoclonal Antibodies," *J. Biol. Chem.* 266:2632-2638.

Lind et al. (1988). "The Binding of Mouse Hybridoma and Human IgE Antibodies to the Major Fecal Allergen, *Der p* 1, of *Dermatophagoides pteronyssinus," J. Immunol.* 40:4256-4262.

Maidhof, H. et al. (Jun. 1991). "*femA*, Which Encodes a Factor Essential for Expression of Methicillin Resistance, Affects Glycine Content of Peptidoglycan in Methicillin-Resistant and Methicillin-Susceptible *Staphylococcus aureus* Strains," *Journal of Bacteriology* 173(11):3507-3513.

Marcello et al. (Sep. 1994). "Specific Inhibition of Herpes Virus Replication by Receptor-Mediated Entry of an Antiviral Peptide Linked to *Escherichia coli* Enterotoxin B Subunit," *Proc. Natl. Acad. Sci. USA* .91:8994-8998.

Marsh et al. (2000). "Expanded Polyglutamine Peptides Alone are Intrinsically Cytotoxic and Cause Neurodegeneration in *Drosophila," Hum. Mol. Genet.* 9:13-25.

Mazmanian, S. K. et al. (Jul. 30, 1999). "*Staphylococcus aureus* Sortase, an Enzyme that Anchors Surface Proteins to the Cell Wall," *Science* 285:760-763.

Mazmanian, S. K. et al. (May 9, 2000). "*Staphylococcus aureus* Sortase Mutants Defective in the Display of Surface Proteins and in the Pathogenesis of Animal Infections," *Proc. Natl. Acad. Sci. USA* 97(10):5510-5515.

McCafferty et al. (1990). "Phage Antibodies: Filamentous Phage Displaying Antibody Variable Domains," *Nature* 348:552-554.

McConnell et al. (1994). "Constrained Peptide Libraries as a Tool for Finding Mimotopes," *Gene* 151:115-118.

McElveen, J. E. (1998). "Primary Sequence and Molecular Model of the Variable Region of a Mouse Monoclonal Anti-Der p 1 Antibody Showing a Similar Epitope Specificity as Human IgE," *Clinical and Experimental Allergy* 28:1427-1434.

Mennuni et al. (1997). "Identification of a Novel Type 1 Diabetes-Specific Epitope by Screening Phage Libraries with Sera from Pre-Diabetic Patients," *J. Mol. Biol.* 268:599-606.

Morris et al. (2000). "Translocating Peptides and Proteins and Their Use for Gene Delivery," *Curr. Opinion Biotech.* 11:461-466.

Morris et al. (2001). "A Peptide Carrier for the Delivery of Biologically Active Proteins into Mammalian Cells," *Nature Biotech.* 19:1173-1176.

Mulligan et al. (1981). "Selection for Animal Cells that Express the *Escherichia coli* Gene Coding for Xanthine-Guanine Phosphoribosyltransferase," *Proc. Natl. Acad. Sci. USA* 78:2072-2076.

Nedelkov, D. et al. (2001). "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes," *Biosensors & Bioelectronics* 16:1071-1078.

Needleman et al. (1970). "A General Method Applicable to the Search for Similarities in the Amino Acid Sequence of Two Proteins," *J. Mol. Biol.* 48:443-453.

Neidigh et al. (2002). "Designing a 20-Residue Protein," *Nature Structural Biology* 9:425-430.

Nelson, R. W. et al. (2000). "Biosensor Chip Mass Spectrometry: A Chip-Based Proteomics Approach," *Electrophoresis* 21:1155-1163.

Nemoto, N. et al. (1999). "Fluorescence Labeling of the C-Terminus of Proteins with a Puromycin Analogue in Cell-Free Translation Systems," *FEBS Letters* 462:43-46.

Ness et al. (2002). "Synthetic Shuffling Expands Functional Protein Diversity by Allowing Amino Acids to Recombine Independently," *Nature Biotechnology* 20:1251-1255.

Norman et al. (1999). "Genetic Selection of Peptide Inhibitors of Biological Pathways," *Science* 285:591-595.

O'Hare et al. (1981). "Transformation of Mouse Fibroblasts to Methotrexate Resistance by a Recombinant Plasmid Expressing a Prokaryotic Dihydrofolate Reductase," *Proc. Natl. Acad. Sci. USA* 78:1527-1531.

Palzkill et al. (1998). "Mapping Protein-Ligand Interactions Using Whole Genome Phage Display Libraries," *Gene* 221:79-83.

Pande et al. (1994). "Nonrandomness in Protein Sequences: Evidence for a Physically Driven Stage of Evolution?" *Proc. Natl. Acad. Sci. USA* 91:12972-12975.

Pavlickova, P. et al. (2003). "Microarray of Recombinant Antibodies Using a Streptavidin Sensor Surface Self-Assembled onto a Gold Layer," *BioTechniques* 34(1):124-130.

Phelan et al. (May 1998). "Intercellular Delivery of Functional p53 by the Herpes Virus Protein VP22," *Nature Biotechnol.* 16:440-443.

Pincus et al. (1998). "Peptides that Mimic the Group B Streptococcal Type III Capsular Polysaccharide Antigen," *J. Immunol.* 160:293-298.

Pini et al. (Aug. 21, 1998). "Design and Use of a Phage Display Library," *J. Biol. Chem.* 273:21769-21776.

Read et al. (2001). "Finding Drug Targets in Mircobial Genomes," *Drug Disc. Today* 6:887-892.

Richter et al. (2000). "Refolding, Purification, and Characterization of Human Recombinant pde4a Constructs Expressed in *Escherichia coli," Protein Expression Purification* 19:375-383.

Robben et al. (2002). "Selection and Identification of Dense Granule Antigen GRA3 by *Toxoplasma gondii* Whole Genome Phage Display," *J. Biol. Chem.* 277:17544-17547.

Roberts et al. (1997). "RNA-Peptide Fusions for the in vitro Selection of Peptides and Proteins," *Proc. Natl. Acad. Sci. USA* 94:12297-12302.

Rocco et al. (1998). "Wide-Spectrum Antibiotic Activity of Synthetic, Amphipathic Peptides," *Biochem. & Biophys. Res. Comm.* 249:202-206.

Rogers et al. (1997). "Behavioral and Functional Analysis of Mouse Phenotype: SHIRPA, a Proposed Protocol for Comprehensive Phenotype Assessment," *Mamm. Genome* 8:711-713.

Rohrer, S. et al. (Aug. 1999). "The Essential *Staphylococcus aureus* Gene *fmhB* is Involved in the First Step of Peptidoglycan Pentaglycine Interpeptide Formation," *Proc. Natl. Acad. Sci. USA* 96:9351-9356.

Rosenthal, P. J. et al. (Jul. 1996). "Antimalarial Effects of Vinyl Sulfone Cysteine Proteinase Inhibitors," *Antimicrobial Agents and Chemotherapy* 40(7): 1600-1603.

Sali et al. (1993). "Comparative Protein Modelling by Satisfaction of Spatial Restraints," *J. Mol. Biol.* 234:779-815.

Sambook et al. (1989). Chapters 12 and 13 In *Molecular Cloning: A Laboratory Manual* Second Edition. Cold Spring Harbor Laboratory Press, USA.

Santerre et al. (1984). "Expression of Prokaryotic Genes for Hygromycin B and G418 Resistance as Dominant-Selection Markers in Mouse L Cells," *Gene* 30:147-156.

Satyal et al. (2000). "Polyglutamine Aggregates Alter Protein Folding Homeostatis in *Caenorhabditis elegans," Proc. Natl. Acad. Sci. USA* 97:5750-5755.

Shafikhani et al. (1997). "Generation of Large Libraries of Random Mutants in *Bacillus subtilis* by PCR-based Plasmid Multimerization," *BioTechniques* 23:304-306.

Shimatake et al. (1981). "Purified λ Regulatory Protein cll Positively Activates Promoters for Lysogenic Development," *Nature* 292:128-132.

Sieber et. al. (2001). "Libraries of Hybrid Proteins from Distantly Related Sequences," *Nature Biotechnology* 19:456-450.

Soares, M.B. (1997). "Identification and Cloning of Differentially Expressed Genes," *Curr. Opinion Biotechnol.* 8:542-546.

Stengelin et al. (1988). "Isolation of cDNAs for Two Distinct Human Fc Receptors by Ligand Affinity Cloning," *EMBO Journal* 7:1053-1059.

Stranden, A. M. et al. (Jan. 1997). "Cell Wall Monoglycine Cross-Bridges and Methicillin Hypersusceptibility in a *femAB* Null Mutant of Methicillin-Resistant *Staphylococcus aureus," Journal of Bacteriology* 179(1):9-16.

Studier et al. (1986). "Use of Bacteriophage T7 RNA Polymerase to Direct Selective High-Level Expression of Cloned Genes," *J. Mol. Biol.* 189:113-130.

Sugita et al. (2002). "Combined Use of Oligonucleotide and Tissue Microarrays Identifies Cancer/Testis Antigens as Biomarkers in Lung Carcinoma," *Cancer Res.* 62:3971-3979.

Theiss, H.D. et al. (2003). "Enhancement of Gene Transfer With Recombinant Adeno-Associated Virus (rAAV) Vectors into Primary B-Cell Chronic Lymphocytic Leukemia Cells by CpG-oligodeoxynucleotides," *Experimental Hematology* 31:1223-1229.

Thomas et al. (1990). "Expression in *Escherichia coli* of a High-Molecular-Weight Protective Surface Antigen Found in Nontypeable and Type B *Haemophilus influenzae," Infect. Immunol.* 58:1909-1915.

Thumm, G. et al. (1997). "Studies on Prolysostaphin Processing and Characterization of the Lysostaphin Immunity Factor (Lif) of *Staphylococcus simulans* Biovar *Staphylolyticus," Molecular Microbiology* 23(6):1251-1265.

Tokmakov et al. (1997). "Inhibition of MAPK Pathway by a Synthetic Peptide Corresponding to the Activation Segment of MAPK," *Biochem. Biophys. Res. Comm.* 252:214-219.

Tokmakov et al. (1998). "Phosphorylation-Sensitive Secondary Structure in a Synthetic Peptide Corresponding to the Activation Loop of MAP Kinase," *Biochem. Biophys. Res. Commun.* 236:243-247.

Tripet et al. (1997). "Demonstration of Coiled-Coli Interactions Within the Kinesin Neck Region Using Synthetic Peptides," *J. Biol. Chem.* 272:8946-8956.

Van Regenmortel, M.H.V. (1989). "Structural and Functional Approaches to the Study of Protein Antigenicity," *Immunology Today* 10:266-272.

Vidal et al. (1999). "Yeast Forward and Reverse 'n'-hybrid Systems," *Nucl. Acids Res.* 27:919-929.

Vranken et al. (2002). "Solution Structures of a 30-Residue Amino-Terminal Domain of the Carp Granulin-1 Protein and its Amino-Terminally Truncated 3-30 Subframent: Implications for the Conformational Stability of the Stack of Two β-Hairpins," *Proteins* 47:14-24.

Wigler et al. (1980). "Transformation of Mammalian Cells with an Amplifiable Dominant-Acting Gene," *Proc. Natl. Acad. Sci. USA* 77:3567-3570.

Wong et al. (1996). "Use of Tagged Random Hexamer Amplificiation (TRHA) to Clone and Sequence Minute Quantities of DNA-Application to a 180 kb Plasmid Isolated From *Sphingomonas* F199," *Nucleic Acids Res.* 24:3778-3783.

Xu et al. (Nov. 1997). "Cells That Register Logical Relationships Among Proteins," *Proc. Natl. Acad. Sci. USA* 94:12473-12478.

Xu et al. (2001). "Dominant Effector Genetics in Mammalian Cells," *Nature Genetics* 27:23-29.

Yang (1999). "Cloning, Expression, and Characterization of a DNA Binding Domain of gpNu1, a Phage λ DNA Packaging Protein," *Biochem.* 38:465-477.

Yang et al. (1998). "A 20-Kilodalton N-Terminal Fragment of the D15 Protein Contains a Protective Epitope(s) Against *Haemophilus influenzae* Type A and Type B," *Infect. and Immun.* 66:3349-3354.

Yang et al. (2000). "An Integrated Approach to the Analysis and Modeling of Protein Sequences and Structrures. III. A Comparative Study of Sequence Conservation in Protein Structural Families using Multiple Structural Alignments," *J. Mol. Biol.* 301:691-711.

Yao, S.Q. et al. (1997). "Inhibiting Dimerization and DNA Binding of c-Jun," In *Peptides: Frontiers of Peptide Science, Proceedings of the 15th American Peptide Symposium*, Nashville, TN Jun. 14-19, 1997, Tam, J.P. et al. eds. Kluwer Academic Publishers, Dordrecht, Netherlands, pp. 751-752.

Yasueda et al. (1996). "Species-Specific Measurement of the Second Group of *Dermatophagoides* Mite Allergens, Der p 2 and Der f 2, Using a Monoclonal Antibody-Based ELISA," *Clin. Exp. Allergy* 26:171-177.

Young, K.H. (1998). "Yeast Two-Hybrid: So Many Interactions, (in) so Little Time," *Biol. Reproduction* 58:302-311.

Zhang et al. (1992). "Whole Genome Amplification From a Single Cell: Implications for Genetic Analysis," *Proc. Natl. Acad. Sci. USA* 89:5847-5851.

Zhou, X-F. et al. (Feb. 1999). "Ligand-Activated Retinoic Acid Receptor Inhibits AP-1 Transactivation by Disrupting c-Jun/c-Fos Dimerization," *Mol. Endocrin.* 13(2):267-285.

Supplementary Partial European Search Report for EP Application No. 04712970 mailed Apr. 26, 2006, two pages.

Yao, S. et al. (1998). "Uncoiling c-Jun Coiled Coils: Inhibitory Effects of Truncated Fos Peptides on Jun Dimerization and DNA Binding In Vitro," *Biopoly* 47:277-283.

Alekshun, M.N. (Dec. 2001). "Beyond Comparison—Antibiotics From Genome Data?" *Nature Biotechnology* 19:1124-1125.

Amstutz, P. et al. (2001). "In vitro Display Technologies: Novel Developments and Applications," *Current Opinion in Biotechnology* 12:400-405.

Angrist, M. (1998). "Less is More: Compact Genomes Pay Dividends," *Genome Research* 8:683-685.

Cordwell, S.J. (1999). "Microbial Genomes and 'Missing' Enyzmes: Redefining Biochemical Pathways," *Arch. Microbiol.* 172:269-279.

Erdos, G. et al. (2006). "Construction and Characterization of a Highly Redundant *Pseudonomas aeruginosa* Genomic Library Prepared From 12 Clinical Isolates: Application to Studies of Gene Distribution Among Populations," *Intl. Journal of Pediatric Otorhinolaryngology* 70:1891-1900.

Halstead, J.R. et al. (1999). "A Family 26 Mannanase Produced by *Clostridium thermocellum* as a Component of the Cellulosome Contains a Domain Which is Conserved in Mannanases from Anaerobic Fungi," *Microbiology* 145:3101-3108.

Michiels, F. et al. (Nov. 2002). "Arrayed Adenoviral Expression Libraries for Functional Screening," *Nature Biotechnology* 20:1154-1157.

Nelson, K.E. et al. (Oct. 2000). "Status of Genome Projects for Nonpathogenic Bacteria and Archaea," *Nature Biotechnology* 18:1049-1054.

Nelson, R.W. et al. (1999). "BIA/MS of Epitope-Tagged Peptides Directly from *E. coli* Lysate: Multiplex Detection and Protein Identification at Low-Femtomole to Subfemtomole Levels," *Anal. Chem.* 71:2858-2865.

Oefner, P.J. et al. (1996). "Efficient Random Subcloning of DNA Sheared in a Recirculating Point-Sink Flow System," *Nucleic Acids Research* 24(20):3879-3886.

Postier, B.L. et al. (2003). "The Construction and Use of Bacterial DNA Microarrays Based on an Optimized Two-Stage PCR Strategy," *BMC Genomics* 4:23, 11 pages.

Supplementary Partial European Search Report for EP Application No. 04712970.5 mailed Aug. 3, 2006, seven pages.

Wittrup, K.D. (2001). "Protein Engineering by Cell-Surface Display," *Current Opinion in Biotechnology* 12:395-399.

Zhou, J-M. et al. (2002). "A Novel Strategy by the Action of Ricin That Connects Phenotype and Genotype Without Loss of the Diversity of Libraries," *J. Am. Chem. Soc.* 124(4):538-543.

André, S. et al. (Jan. 17, 2005). "Identification of Peptide Ligands for Malignancy- and Growth-Regulating Galectins Using Random Phage-Display and Designed Combinatorial Peptide Libraries," *Bioorganic & Medicinal Chemistry* 13(2):563-573.

Basbous, J. et al. (Oct. 31, 2003). "The HBZ Factor of Human T-cell Leukemia Virus Type I Dimerizes with Transcription Factors JunB and c-Jun and Modulates Their Transcriptional Activity," *The Journal of Biological Chemistry* 278(44):43620-43627.

Brodin, N.T. et al. (May 15, 1990). "Rat Monoclonal Antibodies Produced Against Rat Colorectal Adenocarcinomas Define Tumor- and Colon-Associated, Auto-Immunogenic Antigens," *Int. J. Cancer* 45(5):902-910.

Chevray, P.M. et al. (Jul. 1992). "Protein Interaction Cloning in Yeast: Identification of Mammalian Proteins that React with the Leucine Zipper of Jun," *Proc. Natl. Acad. Sci. USA* 89:5789-5793.

Choi, Y. et al. (Mar. 2003). "Identification of Bioactive Molecules by Adipogenesis Profiling of Organic Compounds," *FASEB Meeting on Experimental Biology: Translating the Genome*, San Diego, CA, Apr. 11-15, 2003, 17(4-5):A605, Abstract No. 377.23.

Futch, W.S., Jr. et al. (Dec. 1985). "Dissection of Macrophage Tumoricidal and Protozoacidal Activities Using T-Cell Hybridomas and Recombinant Lymphokines," *Infection and Immunity* 50(3):709-715.

GenBank Accession No. AAH36335, last updated May 20, 2005, located at <http://www.ncbi.nlm.nih.gov/entrez/viewer.fcgi?db=protein&id=23273658>, last visited Apr. 1, 2008, three pages.

GenBank Accession No. AAN49594, last updated Feb. 1, 2006, located at <http://www.ncbi.nlm.nih.gov/entrez/viewer.fcgi?db=protein&id=24196153>, last visited Apr. 1, 2008, two pages.

GenBank Accession No. AAS70149, last updated Jan. 4, 2006, located at <http://www.ncbi.nlm.nih.gov/entrez/viewer.fcgi?db=protein&id=45600665>, last visited Apr. 1, 2008, two pages.

GenBank Accession No. AAV59791, last updated Jan. 21, 2005, located at <http://www.ncbi.nlm.nih.gov/entrez/viewer.fcgi?db=protein&id=55736149>, last visited Apr. 1, 2008, three pages.

GenBank Accession No. CAD25932, last updated Apr. 16, 2005, located at <http://www.ncbi.nlm.nih.gov/entrez/viewer.fcgi?db=protein&id=19069547>, last visited Apr. 1, 2008, two pages.

GenBank Accession No. CAH10659, last updated Sep. 22, 2004, located at <http://www.ncbi.nlm.nih.gov/entrez/viewer.fcgi?db=protein&id=50949409>, last visited Apr. 1, 2008, two pages.

Granger-Schnarr, M. et al. (May 1992). "Transformation and Transactivation Suppressor Activity of the c-Jun Leucine Zipper Fused to a Bacterial Repressor," *Proc. Natl. Acad. Sci. USA* 89:4236-4239.

Haley, K.J. et al. (Aug. 1998). "Tumor Necrosis Factor Induces Neuroendocrine Differentiation in Small Cell Lung Cancer Cell Lines," *American Journal of Physiology* 275(2 pt 1):L311-L321.

International Preliminary Report on Patentability mailed on Feb. 20, 2007, for PCT Application No. PCT/AU2005/001255, filed Aug. 22, 2005, ten pages.

International Search Report mailed Aug. 16, 2005, for PCT Application No. PCT/AU2005/000801, filed Jun. 3, 2005, eight pages.

International Search Report mailed Nov. 17, 2005, for PCT Application No. PCT/AU2005/001255, filed Aug. 22, 2005, six pages.

Koo, J.H. et al. (Mar. 8, 2001). "Purification and Characterization of Bex, an OMP Parter," *Annual Meeting of the Federation of American Societies for Experimental Biology on Experimental Biology*, Orlando, FL, Mar. 31-Apr. 4, 2001, 15(5):A894, Abstract No. 695.14.

Layne, M.D. et al. (Jun. 19, 1998). "Aortic Carboxypeptidase-Like Protein, a Novel Protein with Discoidin and Carboxypeptidase-Like Domains, Is Up-Regulated During Vascular Smooth Muscle Cell Differentiation," *The Journal of Biological Chemistry* 273(25):15654-15660.

Miller, V.L. et al. (Sep. 2001). "Identification of Regions of Ail Required for the Invasion and Serum Resistance Phenotypes," *Molecular Microbiology* 41(5):1053-1062.

Tortosa, P. et al. (Mar. 2000). "Characterization of *ylbF*, a New Gene Involved in Competence Development and Sporulation in *Bacillus subtilis*," *Molecular Microbiology* 35(5):1110-1119.

Urbanek, M. et al. (Jan. 2003). "Variation in Resistin Gene Promoter Not Associated With Polycystic Ovary Syndrome," *Diabetes* 52:214-217.

Valentini, S.R. et al. (Feb. 1994). "Glucocorticoid-Regulated Gene in Transformed to Normal Phenotypic Reversion," *Brazilian J. Med. Biol. Res.* 27(2):541-546.

Yang, P. et al. (Dec. 17, 1999). "Direct Activation of the Fission Yeast PAK Shk1 by the Novel SH3 Domain Protein, Skb5," *The Journal of Biological Chemistry* 274(51):36052-36057.

Bains, N.P.S. et al. (1997). "Zipping Up Transcription Factors: Rational Design of Anti-Jun and Anti-Fos Peptides," Letters in Peptide Science 4:67-77.

Bianco, A. et al. (2006, e-pub. Mar. 10, 2006). "Solid-phase Synthesis of CD-40L Mimetics," *Org. Biomol. Chem.* 4:1461-1463.

Canchaya, C. et al. (Jun. 2003). "Prophage Genomics," *Microbiology and Molecular Biology Reviews* 67(2):238-276.

Canchaya, C. et al. (Sep. 2003). "Erratum—Prophage Genomics," erratum, *Microbiology and Molecular Biology Reviews* 67(3):473.

Chen, L-W. et al. (2006). "Thermal Injury-induced Peroxynitrite Production and Pulmonary Inducible Nitric Oxide Synthase Expression Depend on JNK/AP-1 Signaling," *Crit. Care Med.* 34(1):142-150.

Deambrosis, I. et al. (2009, e-pub. Nov. 9, 2008). "Inhibition of CD40-CD154 Costimulatory Pathway by a Cyclic Peptide Targeting CD 154," *J Mol Med* 87:181-197.

Fromant, M. et al. (1995). "Direct Random Mutagenesis of Gene-Sized DNA Fragments Using Polymerase Chain Reaction," *Analytical Biochemistry* 224:347-353.

GenBank Accession No. XP97325, last updated Jul. 21, 2008, located at <http:www.ncbi.nlm.nih.gov/protein/91084013> last visited on Jan. 19, 2010, two pages.

GenBank Accession No. YP284595, last updated Apr. 24, 2009, located at <http://www.ncbi.nlm.nih.gov/protein/71907008, last visited on Jan. 19, 2010, three pages.

GenBank Accession No. ZP01044355, last updated on Jan. 25, 2006, located at <http://www.ncbi.nlm.nih.gov/protein/85713338, last visited on Jan. 19, 2010, three pages.

Inouye, C. et al. (Oct. 1997). "Mutational Analysis of *STE5* in the Yeast *Saccharomyces cerevisiae*: Application of a Differential Interaction Trap Assay for Examining Protein-Protein Interactions," Genetics 147:479-492.

Kitagawa, M. et al. (2005). "Identification of Three Novel Peptides That Inhibit CD40-CD154 Interaction," *Mod Rheumatol* 15:423-426.

Lessel, U. et al. (1997). "Creation and Characterization of a New, Non-redundant Fragment Data Bank," *Protein Engineering* 10(6):659-664.

Raivich, G. et al. (2006). "Role of the AP-1 Transcription Factor c-Jun in Developing, Adult and Injured Brain," *Progress in Neurobiology* 78:347-363.

Serebriiskii, I.G. et al. (2004). "Anaysis of Protein-Protein Interactions Utilizing Dual Bait Yeast Two-Hybrid System," Chapter 19 in *Methods of Molecular Biology*, Fu, H. ed., Humana Press, Inc. Totwas: New Jersey, 261:263-296.

Serebriiskii, I.G. et al. (2002). "Detection of Peptides, Proteins, and Drugs that Selectively Interact with Protein Targets," *Genome Res.* 12:1785-1791.

Serebriiskii, I. et al. (Jun. 11, 1999). "A Two-hybrid Dual Bait System to Discriminate Specificity of Protein Interactions," *The Journal of Biological Chemistry* 274(24):17080-17087.

Serebriiskii, I. et al. (Feb. 2000). "Approaches to Detecting False Positives in Yeast Two-Hybrid Systems," *BioTechniques* 28(2):328-336.

Tiozzo, E. et al. (1998). "Wide-Spectrum Antibiotic Activity of Synthetic, Amphipathic Peptides," *Biochem. & Biophys. Res. Comm.* 249(1):202-206.

Wang, G. (2005). "Pisces: Recent Improvements to a PDB Sequence Culling Server," *Nucleic Acids Research* 33:W94-W98.

Wang, L-H. et al. (2004). "Predicting Protein Secondary Structure by a Support Vector Machine Based on a New Coding Scheme," *Genome Informatics* 15(2):181-190.

Watt, P.M. (Feb. 2006, e-pub. Feb. 7, 2006). "Screening for Peptide Drugs From the Natural Repertoire of Biodiverse Protein Folds," Nature Biotechnology 24(2):177-183.

pYES-TRP/BLK 3.4 (DEATH TRP)

pJFK (HIS5/Kan)

pDD

HW HWU⁻ 0.06% Galactose HWL⁻ 0.06% Galactose anti-2C7pan26 serum reacting with Der p 1 - competition assay

| | 0 | 1000 | 2000 | 3000 | 4000 | 5000 |
|---|---|---|---|---|---|---|

TRF: 0, 20000, 40000, 60000, 80000, 100000, 120000, 140000

Der p 1
BSA

SEQUENCE LISTING

```
<160> NUMBER OF SEQ ID NOS: 198

<210> SEQ ID NO 1
<211> LENGTH: 6
<212> TYPE: DNA
<213> ORGANISM: Artificial
<220> FEATURE:
<223> OTHER INFORMATION: Kozak consensus sequence
<220> FEATURE:
<221> NAME/KEY: misc_feature
<222> LOCATION: (2)..(3)
<223> OTHER INFORMATION: N at position 2 and 3 is any nucleotide

<400> SEQUENCE: 1

rnnatg                                                                  6


<210> SEQ ID NO 2
<211> LENGTH: 8
<212> TYPE: DNA
<213> ORGANISM: Artificial
<220> FEATURE:
<223> OTHER INFORMATION: Kozak consensus sequence

<400> SEQUENCE: 2

ccrccatg                                                                8


<210> SEQ ID NO 3
<211> LENGTH: 11
<212> TYPE: DNA
<213> ORGANISM: Artificial
<220> FEATURE:
<223> OTHER INFORMATION: Kozak consensus sequence

<400> SEQUENCE: 3

gccagccatg g                                                           11


<210> SEQ ID NO 4
<211> LENGTH: 8
<212> TYPE: DNA
<213> ORGANISM: Artificial
<220> FEATURE:
<223> OTHER INFORMATION: Kozak consensus sequence

<400> SEQUENCE: 4

ctaccatg                                                                8


<210> SEQ ID NO 5
```

-continued

<211> LENGTH: 10
<212> TYPE: DNA
<213> ORGANISM: Artificial
<220> FEATURE:
<223> OTHER INFORMATION: Shine Dalgarno sequence

<400> SEQUENCE: 5
gaagaagata 10

<210> SEQ ID NO 6
<211> LENGTH: 7
<212> TYPE: DNA
<213> ORGANISM: Artificial
<220> FEATURE:
<223> OTHER INFORMATION: translational slippage sequence

<400> SEQUENCE: 6 aaaaaac 7

<210> SEQ ID NO 7
<211> LENGTH: 7
<212> TYPE: DNA
<213> ORGANISM: Artificial
<220> FEATURE:
<223> OTHER INFORMATION: translational slippage sequence

<400> SEQUENCE: 7 aaattta 7

<210> SEQ ID NO 8
<211> LENGTH: 7
<212> TYPE: DNA
<213> ORGANISM: Artificial
<220> FEATURE:
<223> OTHER INFORMATION: translational slippage sequence

<400> SEQUENCE: 8 aaatttt 7

<210> SEQ ID NO 9
<211> LENGTH: 7
<212> TYPE: DNA
<213> ORGANISM: Artificial
<220> FEATURE:
<223> OTHER INFORMATION: translational slippage sequence

<400> SEQUENCE: 9 gggaaac 7

<210> SEQ ID NO 10
<211> LENGTH: 7
<212> TYPE: DNA
<213> ORGANISM: Artificial
<220> FEATURE:
<223> OTHER INFORMATION: translational slippage sequence

<400> SEQUENCE: 10 gggcccc 7

<210> SEQ ID NO 11
<211> LENGTH: 7
<212> TYPE: DNA
<213> ORGANISM: Artificial
<220> FEATURE:
<223> OTHER INFORMATION: translational slippage sequence

<400> SEQUENCE: 11

-continued gggttta 7

<210> SEQ ID NO 12
<211> LENGTH: 7
<212> TYPE: DNA
<213> ORGANISM: Artificial
<220> FEATURE:
<223> OTHER INFORMATION: translational slippage sequence

<400> SEQUENCE: 12 gggtttt 7

<210> SEQ ID NO 13
<211> LENGTH: 7
<212> TYPE: DNA
<213> ORGANISM: Artificial
<220> FEATURE:
<223> OTHER INFORMATION: translational slippage sequence

<400> SEQUENCE: 13 tttaaac 7

<210> SEQ ID NO 14
<211> LENGTH: 7
<212> TYPE: DNA
<213> ORGANISM: Artificial
<220> FEATURE:
<223> OTHER INFORMATION: translational slippage sequence

<400> SEQUENCE: 14 tttaaat 7

<210> SEQ ID NO 15
<211> LENGTH: 6
<212> TYPE: DNA
<213> ORGANISM: Artificial
<220> FEATURE:
<223> OTHER INFORMATION: translational slippage sequence

<400> SEQUENCE: 15 ttttta 6

<210> SEQ ID NO 16
<211> LENGTH: 7
<212> TYPE: DNA
<213> ORGANISM: Artificial
<220> FEATURE:
<223> OTHER INFORMATION: translational slippage sequence

<400> SEQUENCE: 16 ggattta 7

<210> SEQ ID NO 17
<211> LENGTH: 7
<212> TYPE: DNA
<213> ORGANISM: Artificial
<220> FEATURE:
<223> OTHER INFORMATION: translational slippage sequence

<400> SEQUENCE: 17 cttaggc 7

<210> SEQ ID NO 18
<211> LENGTH: 7
<212> TYPE: DNA

-continued

<213> ORGANISM: Artificial
<220> FEATURE:
<223> OTHER INFORMATION: translational slippage sequence

<400> SEQUENCE: 18 gcgagtt 7

<210> SEQ ID NO 19
<211> LENGTH: 7
<212> TYPE: DNA
<213> ORGANISM: Artificial
<220> FEATURE:
<223> OTHER INFORMATION: translational slippage sequence

<400> SEQUENCE: 19 tcctgat 7

<210> SEQ ID NO 20
<211> LENGTH: 7
<212> TYPE: DNA
<213> ORGANISM: Artificial
<220> FEATURE:
<223> OTHER INFORMATION: translational slippage sequence

<400> SEQUENCE: 20 aaaaaag 7

<210> SEQ ID NO 21
<211> LENGTH: 7
<212> TYPE: DNA
<213> ORGANISM: Artificial
<220> FEATURE:
<223> OTHER INFORMATION: translational slippage sequence

<400> SEQUENCE: 21 aaaaaaa 7

<210> SEQ ID NO 22
<211> LENGTH: 7
<212> TYPE: DNA
<213> ORGANISM: Artificial
<220> FEATURE:
<223> OTHER INFORMATION: translational slippage sequence

<400> SEQUENCE: 22 aaaaaac 7

<210> SEQ ID NO 23
<211> LENGTH: 7
<212> TYPE: DNA
<213> ORGANISM: Artificial
<220> FEATURE:
<223> OTHER INFORMATION: translational slippage sequence

<400> SEQUENCE: 23 gggaaag 7

<210> SEQ ID NO 24
<211> LENGTH: 7
<212> TYPE: DNA
<213> ORGANISM: Artificial
<220> FEATURE:
<223> OTHER INFORMATION: translational slippage sequence

<400> SEQUENCE: 24 aaaaggg 7

<210> SEQ ID NO 25
<211> LENGTH: 7
<212> TYPE: DNA
<213> ORGANISM: Artificial
<220> FEATURE:
<223> OTHER INFORMATION: translational slippage sequence

<400> SEQUENCE: 25 gggaaaa 7

<210> SEQ ID NO 26
<211> LENGTH: 7
<212> TYPE: DNA
<213> ORGANISM: Artificial
<220> FEATURE:
<223> OTHER INFORMATION: translational slippage sequence

<400> SEQUENCE: 26 tttaaag 7

<210> SEQ ID NO 27
<211> LENGTH: 7
<212> TYPE: DNA
<213> ORGANISM: Artificial
<220> FEATURE:
<223> OTHER INFORMATION: translational slippage sequence

<400> SEQUENCE: 27 aaagggg 7

<210> SEQ ID NO 28
<211> LENGTH: 3
<212> TYPE: DNA
<213> ORGANISM: Artificial
<220> FEATURE:
<223> OTHER INFORMATION: translational slippage sequence

<400> SEQUENCE: 28 ctt 3

<210> SEQ ID NO 29
<211> LENGTH: 17
<212> TYPE: PRT
<213> ORGANISM: Artificial
<220> FEATURE:
<223> OTHER INFORMATION: Drosophila penetratin targetting sequence

<400> SEQUENCE: 29

```
Cys Arg Gln Ile Lys Ile Trp Phe Gln Asn Arg Arg Met Lys Trp Lys
1               5                   10                  15

Lys
```

<210> SEQ ID NO 30
<211> LENGTH: 21
<212> TYPE: PRT
<213> ORGANISM: Artificial
<220> FEATURE:
<223> OTHER INFORMATION: synthetic Pep1 peptide

<400> SEQUENCE: 30

```
Lys Glu Thr Trp Trp Glu Thr Trp Trp Thr Glu Trp Ser Gln Lys Lys
1               5                   10                  15

Lys Lys Arg Lys Val
            20
```

-continued

<210> SEQ ID NO 31
<211> LENGTH: 5
<212> TYPE: DNA
<213> ORGANISM: Artificial
<220> FEATURE:
<223> OTHER INFORMATION: initiator sequence recognized by P2A protein

<400> SEQUENCE: 31 tcgga 5

<210> SEQ ID NO 32
<211> LENGTH: 5
<212> TYPE: PRT
<213> ORGANISM: Artificial
<220> FEATURE:
<223> OTHER INFORMATION: membrane anchor sequence

<400> SEQUENCE: 32

Pro Asp Gly Phe Arg
1 5

<210> SEQ ID NO 33
<211> LENGTH: 46
<212> TYPE: DNA
<213> ORGANISM: Artificial
<220> FEATURE:
<223> OTHER INFORMATION: synthetic oligonucleotide primer
<220> FEATURE:
<221> NAME/KEY: misc_feature
<222> LOCATION: (41)..(46)
<223> OTHER INFORMATION: N at any one of positions 41 through 46 is any nucleotide residue

<400> SEQUENCE: 33
gactacaagg acgacgacga caaggcttat caatcaatca nnnnnn 46

<210> SEQ ID NO 34
<211> LENGTH: 49
<212> TYPE: DNA
<213> ORGANISM: Artificial
<220> FEATURE:
<223> OTHER INFORMATION: synthetic oligonucleotide primer
<220> FEATURE:
<221> NAME/KEY: misc_feature
<223> OTHER INFORMATION: N at any one of positions 41 through 49 is any nucleotide residue
<220> FEATURE:
<221> NAME/KEY: misc_feature
<222> LOCATION: (41)..(49)
<223> OTHER INFORMATION: N at any one of positions 41 through 49 is any nucleotide residue

<400> SEQUENCE: 34
gactacaagg acgacgacga caaggcttat caatcaatca nnnnnnnnn 49

<210> SEQ ID NO 35
<211> LENGTH: 40
<212> TYPE: DNA
<213> ORGANISM: Artificial
<220> FEATURE:
<223> OTHER INFORMATION: synthetic oligonucleotide primer

<400> SEQUENCE: 35
gagagaattc aggtcagact acaaggacga cgacgacaag 40

<210> SEQ ID NO 36
<211> LENGTH: 5562

-continued

<212> TYPE: DNA
<213> ORGANISM: Artificial
<220> FEATURE:
<223> OTHER INFORMATION: pDEATH-TRYP vector

<400> SEQUENCE: 36
ctagcgattt tggtcatgag atcagatcaa cttcttttct tttttttct tttctctctc 60 ccccgttgtt gtctcaccat atccgcaatg acaaaaaaat gatggaagac actaaaggaa 120
aaaattaacg acaaagacag caccaacaga tgtcgttgtt ccagagctga tgaggggtat 180
ctcgaagcac acgaaacttt ttccttcctt cattcacgca cactactctc taatgagcaa 240
cggtatacgg ccttccttcc agttacttga atttgaaata aaaaaaagtt tgctgtcttg 300
ctatcaagta taaatagacc tgcaattatt aatcttttgt ttcctcgtca ttgttctcgt 360
tccctttctt ccttgtttct ttttctgcac aatatttcaa gctataccaa gcatacaatc 420
aactccaagc ttccccggat cggactacta gcagctgtaa tacgactcac tatagggaat 480
attaagctca ccatgggtaa gcctatccct aaccctctcc tcggtctcga ttctacacaa 540
gctatgggtg ctcctccaaa aaagaagaga aaggtagctg aattcgagct cagatctcag 600
ctgggcccgg taccaattga tgcatcgata ccggtactag tcggaccgca tatgcccggg 660
cgtaccgcgg ccgctcgagg catgcatcta gagggccgca tcatgtaatt agttatgtca 720
cgcttacatt cacgccctcc ccccacatcc gctctaaccg aaaaggaagg agttagacaa 780
cctgaagtct aggtccctat ttattttttt atagttatgt tagtattaag aacgttattt 840
atatttcaaa tttttctttt ttttctgtac agacgcgtgt acgcatgtaa cattatactg 900
aaaaccttgc ttgagaaggt tttgggacgc tcgaaggctt taatttgcgg ccctgcatta 960
atgaatcggc caacgcgcgg ggagaggcgg tttgcgtatt gggcgctctt ccgcttcctc 1020
gctcactgac tcgctgcgct cggtcgttcg gctgcggcga gcggtatcag ctcactcaaa 1080
ggcggtaata cggttatcca cagaatcagg ggataacgca ggaaagaaca tgtgagcaaa 1140
aggccagcaa aagcccagga accgtaaaaa ggccgcgttg ctggcgtttt tccataggct 1200
ccgcccccct gacgagcatc acaaaaatcg acgctcaagt cagaggtggc gaaacccgac 1260
aggactataa agataccagg cgtttccccc tggaagctcc ctcgtgcgct ctcctgttcc 1320
gaccctgccg cttaccggat acctgtccgc ctttctccct tcgggaagcg tggcgctttc 1380
tcatagctca cgctgtaggt atctcagttc ggtgtaggtc gttcgctcca agctgggctg 1440
tgtgcacgaa ccccccgttc agcccgaccg ctgcgcctta tccggtaact atcgtcttga 1500
gtccaacccg gtaagacacg acttatcgcc actggcagca gccactggta acaggattag 1560
cagagcgagg tatgtaggcg gtgctacaga gttcttgaag tggtggccta actacggcta 1620
cactagaagg acagtatttg gtatctgcgc tctgctgaag ccagttacct tcggaaaaag 1680
agttggtagc tcttgatccg gcaaacaaac caccgctggt agcggtggtt tttttgtttg 1740
caagcagcag attacgcgca gaaaaaaagg atctcaagaa gatcctttga tcttttctac 1800
ggggtctgac gctcagtgga acgaaaactc acgttaaggg attttggtca tgagattatc 1860
aaaaaggatc ttcacctaga tccttttaaa ttaaaaatga agttttaaat caatctaaag 1920
tatatatgag taaacttggt ctgacagtta ccaatgctta atcagtgagg cacctatctc 1980
agcgatctgt ctatttcgtt catccatagt tgcctgactc cccgtcgtgt agataactac 2040
gatacgggag cgcttaccat ctggccccag tgctgcaatg ataccgcgag acccacgctc 2100
accggctcca gatttatcag caataaacca gccagccgga agggccgagc gcagaagtgg 2160

-continued

```
tcctgcaact ttatccgcct ccatccagtc tattaattgt tgccgggaag ctagagtaag   2220
tagttcgcca gttaatagtt tgcgcaacgt tgttgccatt gctacaggca tcgtggtgtc   2280
acgctcgtcg tttggtatgg cttcattcag ctccggttcc caacgatcaa ggcgagttac   2340
atgatccccc atgttgtgca aaaaagcggt tagctccttc ggtcctccga tcgttgtcag   2400
aagtaagttg gccgcagtgt tatcactcat ggttatggca gcactgcata attctcttac   2460
tgtcatgcca tccgtaagat gcttttctgt gactggtgag tactcaacca agtcattctg   2520
agaatagtgt atgcggcgac cgagttgctc ttgcccggcg tcaacacggg ataataccgc   2580
gccacatagc agaactttaa aagtgctcat cattggaaaa cgttcttcgg ggcgaaaact   2640
ctcaaggatc ttaccgctgt tgagatccag ttcgatgtaa cccactcgtg cacccaactg   2700
atcttcagca tcttttactt tcaccagcgt ttctgggtga gcaaaaacag gaaggcaaaa   2760
tgccgcaaaa aagggaataa gggcgacacg gaaatgttga atactcatac tcttcctttt   2820
tcaatattat tgaagcattt atcagggtta ttgtctcatg agcggataca tatttgaatg   2880
tatttagaaa aataaacaaa taggggttcc gcgcacattt ccccgaaaag tgccacctga   2940
cgtctaagaa accattatta tcatgacatt aacctataaa aataggcgta tcacgaggcc   3000
ctttcgtctt caagaaattc ggtcgaaaaa agaaaaggag agggccaaga gggagggcat   3060
tggtgactat tgagcacgtg agtatacgtg attaagcaca caaaggcagc ttggagtatg   3120
tctgttatta atttcacagg tagttctggt ccattggtga aagtttgcgg cttgcagagc   3180
acagaggccg cagaatgtgc tctagattcc gatgctgact tgctgggtat tatatgtgtg   3240
cccaatagaa agagaacaat tgacccggtt attgcaagga aaatttcaag tcttgtaaaa   3300
gcatataaaa atagttcagg cactccgaaa tacttggttg gcgtgtttcg taatcaacct   3360
aaggaggatg ttttggctct ggtcaatgat tacggcattg atatcgtcca actgcacgga   3420
gatgagtcgt ggcaagaata ccaagagttc ctcggtttgc cagttattaa aagactcgta   3480
tttccaaaag actgcaacat actactcagt gcagcttcac agaaacctca ttcgtttatt   3540
cccttgtttg attcagaagc aggtgggaca ggtgaacttt tggattggaa ctcgatttct   3600
gactgggttg gaaggcaaga gagccccgag agcttacatt ttatgttagc tggtggactg   3660
acgccagaaa atgttggtga tgcgcttaga ttaaatggcg ttattggtgt tgatgtaagc   3720
ggaggtgtgg agacaaatgg tgtaaaagac tctaacaaaa tagcaaattt cgtcaaaaat   3780
gctaagaaat aggttattac tgagtagtat ttatttaagt attgtttgtg cacttgcctg   3840
cagcttctca atgatattcg aatacgcttt gaggagatac agcctaatat ccgacaaact   3900
gttttacaga tttacgatcg tacttgttac ccatcattga attttgaaca tccgaacctg   3960
ggagttttcc ctgaaacaga tagtatattt gaacctgtat aataatatat agtctagcgc   4020
tttacggaag acaatgtatg tatttcggtt cctggagaaa ctattgcatc tattgcatag   4080
gtaatcttgc acgtcgcatc cccggttcat tttctgcgtt tccatcttgc acttcaatag   4140
catatctttg ttaacgaagc atctgtgctt cattttgtag aacaaaaatg caacgcgaga   4200
gcgctaattt ttcaaacaaa gaatctgagc tgcattttta cagaacagaa atgcaacgcg   4260
aaagcgctat tttaccaacg aagaatctgt gcttcatttt tgtaaaacaa aaatgcaacg   4320
cgagagcgct aatttttcaa acaaagaatc tgagctgcat ttttacagaa cagaaatgca   4380
acgcgagagc gctattttac caacaaagaa tctatacttc ttttttgttc tacaaaaatg   4440
catcccgaga gcgctatttt tctaacaaag catcttagat tacttttttt ctcctttgtg   4500
cgctctataa tgcagtctct tgataacttt ttgcactgta ggtccgttaa ggttagaaga   4560
```

-continued aggctacttt ggtgtctatt ttctcttcca taaaaaaagc ctgactccac ttcccgcgtt 4620
tactgattac tagcgaagct gcgggtgcat tttttcaaga taaaggcatc cccgattata 4680
ttctataccg atgtggattg cgcatacttt gtgaacagaa agtgatagcg ttgatgattc 4740
ttcattggtc agaaaattat gaacggtttc ttctattttg tctctatata ctacgtatag 4800
gaaatgttta cattttcgta ttgttttcga ttcactctat gaatagttct tactacaatt 4860
tttttgtcta aagagtaata ctagagataa acataaaaaa tgtagaggtc gagtttagat 4920
gcaagttcaa ggagcgaaag gtggatgggt aggttatata gggatatagc acagagatat 4980
atagcaaaga gatacttttg agcaatgttt gtggaagcgg tattcgcaat gggaagctcc 5040
accccggttg ataatcagaa aagccccaaa aacaggaaga ttgtataagc aaatatttaa 5100
attgtaaacg ttaatatttt gttaaaattc gcgttaaatt tttgttaaat cagctcattt 5160
tttaacgaat agcccgaaat cggcaaaatc ccttataaat caaaagaata gaccgagata 5220
gggttgagtg ttgttccagt ttccaacaag agtccactat taaagaacgt ggactccaac 5280
gtcaaagggc gaaaaagggt ctatcagggc gatggcccac tacgtgaacc atcaccctaa 5340
tcaagttttt tggggtcgag gtgccgtaaa gcagtaaatc ggaagggtaa acggatgccc 5400
ccatttagag cttgacgggg aaagccggcg aacgtggcga gaaaggaagg gaagaaagcg 5460
aaaggagcgg gggctagggc ggtgggaagt gtaggggtca cgctgggcgt aaccaccaca 5520
cccgccgcgc ttaatggggc gctacagggc gcgtggggat ga 5562

<210> SEQ ID NO 37
<211> LENGTH: 40
<212> TYPE: DNA
<213> ORGANISM: Artificial
<220> FEATURE:
<223> OTHER INFORMATION: synthetic oligonucleotide primer

<400> SEQUENCE: 37
agaggaattc aggtcagact acaaggacga cgacgacaag 40

<210> SEQ ID NO 38
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 38
cagaagctta aggacgacga cgacaag 27

<210> SEQ ID NO 39
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 39
caggaattca aggacgacga cgacaag 27

<210> SEQ ID NO 40
<211> LENGTH: 28
<212> TYPE: DNA
<213> ORGANISM: Artificial
<220> FEATURE:
<223> OTHER INFORMATION: synthetic oligonucleotide primer -continued

<400> SEQUENCE: 40
caggaattcc aaggacgacg acgacaag 28

<210> SEQ ID NO 41
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 41
caggaattca caaggacgac gacgacaag 29

<210> SEQ ID NO 42
<211> LENGTH: 16
<212> TYPE: DNA
<213> ORGANISM: Artificial
<220> FEATURE:
<223> OTHER INFORMATION: synthetic adaptor oligonucleotide

<400> SEQUENCE: 42
aattcgaacc ccttcg 16

<210> SEQ ID NO 43
<211> LENGTH: 12
<212> TYPE: DNA
<213> ORGANISM: Artificial
<220> FEATURE:
<223> OTHER INFORMATION: synthetic adaptor oligonucleotide

<400> SEQUENCE: 43
cgaaggggtt cg 12

<210> SEQ ID NO 44
<211> LENGTH: 17
<212> TYPE: DNA
<213> ORGANISM: Artificial
<220> FEATURE:
<223> OTHER INFORMATION: synthetic adaptor oligonucleotide

<400> SEQUENCE: 44
aattcgaacc ccttcgc 17

<210> SEQ ID NO 45
<211> LENGTH: 13
<212> TYPE: DNA
<213> ORGANISM: Artificial
<220> FEATURE:
<223> OTHER INFORMATION: synthetic adaptor oligonucleotide

<400> SEQUENCE: 45
gcgaaggggt tcg 13

<210> SEQ ID NO 46
<211> LENGTH: 18
<212> TYPE: DNA
<213> ORGANISM: Artificial
<220> FEATURE:
<223> OTHER INFORMATION: synthetic adaptor oligonucleotide

<400> SEQUENCE: 46
aattcgaacc ccttcgcg 18

<210> SEQ ID NO 47
<211> LENGTH: 13

-continued

<212> TYPE: DNA
<213> ORGANISM: Artificial
<220> FEATURE:
<223> OTHER INFORMATION: synthetic adaptor oligonucleotide

<400> SEQUENCE: 47
gcgaaggggt tcg 13

<210> SEQ ID NO 48
<211> LENGTH: 16
<212> TYPE: DNA
<213> ORGANISM: Artificial
<220> FEATURE:
<223> OTHER INFORMATION: synthetic adaptor oligonucleotide

<400> SEQUENCE: 48
agctcgaagg ggttcg 16

<210> SEQ ID NO 49
<211> LENGTH: 12
<212> TYPE: DNA
<213> ORGANISM: Artificial
<220> FEATURE:
<223> OTHER INFORMATION: synthetic adaptor oligonucleotide

<400> SEQUENCE: 49
cgaacccctt cg 12

<210> SEQ ID NO 50
<211> LENGTH: 8
<212> TYPE: PRT
<213> ORGANISM: Artificial
<220> FEATURE:
<223> OTHER INFORMATION: FLAG epitope

<400> SEQUENCE: 50

Asp Tyr Lys Asp Asp Asp Asp Lys
1               5

<210> SEQ ID NO 51
<211> LENGTH: 31
<212> TYPE: DNA
<213> ORGANISM: Artificial
<220> FEATURE:
<223> OTHER INFORMATION: synthetic FLAG-encoding oligonucleotide

<400> SEQUENCE: 51
aattccgact acaaggacga cgatgacaag a 31

<210> SEQ ID NO 52
<211> LENGTH: 31
<212> TYPE: DNA
<213> ORGANISM: Artificial
<220> FEATURE:
<223> OTHER INFORMATION: synthetic FLAG-encoding oligonucleotide

<400> SEQUENCE: 52
agcttcttgt catcgtcgtc cttgtagtcg g 31

<210> SEQ ID NO 53
<211> LENGTH: 89
<212> TYPE: DNA
<213> ORGANISM: Artificial
<220> FEATURE:
<223> OTHER INFORMATION: synthetic tagged random oligonucleotide
<220> FEATURE:
<221> NAME/KEY: misc_feature -continued

```
<222> LOCATION: (81)..(89)
<220> FEATURE:
<221> NAME/KEY: misc_feature
<222> LOCATION: (81)..(89)
<223> OTHER INFORMATION: N at any one of positions 81 through 89 is any
      nucleotide residue

<400> SEQUENCE: 53

tttcccgaat tgtgagcgga taacaataga aataattttg tttaacttta agaaggagat     60

atatccatgg actacaaaga nnnnnnnnn                                       89


<210> SEQ ID NO 54
<211> LENGTH: 61
<212> TYPE: DNA
<213> ORGANISM: Artificial
<220> FEATURE:
<223> OTHER INFORMATION: synthetic oligonucleotide

<400> SEQUENCE: 54

ggggccaagc agtaataata cgagtcacta tagggagacc acaacggttt cccgaattgt     60

g                                                                     61


<210> SEQ ID NO 55
<211> LENGTH: 23
<212> TYPE: DNA
<213> ORGANISM: Artificial
<220> FEATURE:
<223> OTHER INFORMATION: synthetic adaptor oligonucleotide

<400> SEQUENCE: 55

tttaagcagc tcgatagcag cac                                             23


<210> SEQ ID NO 56
<211> LENGTH: 23
<212> TYPE: DNA
<213> ORGANISM: Artificial
<220> FEATURE:
<223> OTHER INFORMATION: synthetic adaptor oligonucleotide

<400> SEQUENCE: 56

gtgctgctat cgagctgctt aaa                                             23


<210> SEQ ID NO 57
<211> LENGTH: 51
<212> TYPE: DNA
<213> ORGANISM: Artificial
<220> FEATURE:
<223> OTHER INFORMATION: synthetic lipoprotein terminator
      oligonucleotide

<400> SEQUENCE: 57

agacccgttt agaggcccca aggggttatg gaattcacct ttaagcagct c              51


<210> SEQ ID NO 58
<211> LENGTH: 26
<212> TYPE: DNA
<213> ORGANISM: Artificial
<220> FEATURE:
<223> OTHER INFORMATION: synthetic M13 gene III oligonucleotide

<400> SEQUENCE: 58

cgtgaaaaaa ttattattcg caattc                                          26


<210> SEQ ID NO 59
<211> LENGTH: 30
```

-continued

<212> TYPE: DNA
<213> ORGANISM: Artificial
<220> FEATURE:
<223> OTHER INFORMATION: synthetic M13 gene III oligonucleotide

<400> SEQUENCE: 59
ttaagactcc ttattacgca gtatgttagc 30

<210> SEQ ID NO 60
<211> LENGTH: 7551
<212> TYPE: DNA
<213> ORGANISM: Artificial
<220> FEATURE:
<223> OTHER INFORMATION: pJFK vector

<400> SEQUENCE: 60
ccccattatc ttagcctaaa aaaaccttct ctttggaact ttcagtaata cgcttaactg 60
ctcattgcta tattgaagta cggattagaa gccgccgagc gggtgacagc cctccgaagg 120
aagactctcc tccgtgcgtc ctcgtcttca ccggtcgcgt tcctgaaacg cagatgtgcc 180
tcgcgccgca ctgctccgaa caataaagat tctacaatac tagcttttat ggttatgaag 240
aggaaaaatt ggcagtaacc tggccccaca aaccttcaaa tgaacgaatc aaattaacaa 300
ccataggatg ataatgcgat tagtttttta gccttatttc tggggtaatt aatcagcgaa 360
gcgatgattt ttgatctatt aacagatata taaatgcaaa aactgcataa ccactttaac 420
taatactttc aacattttcg gtttgtatta cttcttattc aaatgtaata aaagtatcaa 480
caaaaaattg ttaatatacc tctatacttt aacgtcaagg aggaattaag cttatgggtg 540
ctcctccaaa aaagaagaga aaggtagctg gtatcaataa agatatcgag gagtgcaatg 600
ccatcattga gcagtttatc gactacctgc gcaccggaca ggagatgccg atggaaatgg 660
cggatcaggc gattaacgtg gtgccgggca tgacgccgaa aaccattctt cacgccgggc 720
cgccgatcca gcctgactgg ctgaaatcga atggttttca tgaaattgaa gcggatgtta 780
acgataccag cctcttgctg agtggagatg cctcctaccc ttatgatgtg ccagattatg 840
cctctcccga attcggccga ctcgagaagc tttggacttc ttcgccagag gtttggtcaa 900
gtctccaatc aaggttgtcg gcttgtctac cttgccagaa atttacgaaa agatggaaaa 960
gggtcaaatc gttggtagat acgttgttga cacttctaaa taagcgaatt tcttatgatt 1020
tatgattttt attattaaat aagttataaa aaaaataagt gtatacaaat tttaaagtga 1080
ctcttaggtt ttaaaacgaa aattcttgtt cttgagtaac tctttcctgt aggtcaggtt 1140
gctttctcag gtatagcatg aggtcgctct tattgaccac acctctaccg gcatgccgag 1200
caaatgcctg caaatcgctc cccatttcac ccaattgtag atatgctaac tccagcaatg 1260
agttgatgaa tctcggtgtg tattttatgt cctcagagga caacacctgt tgtaatcgtt 1320
cttccacacg gatcctctag agtcgactag cggccgcttc gacctgcagc aattctgaac 1380
cagtcctaaa acgagtaaat aggaccggca attcttcaag caataaacag gaataccaat 1440
tattaaaaga taacttagtc agatcgtaca ataaagcttt gaagaaaaat gcgccttatt 1500
caatctttgc tataaaaaat ggcccaaaat ctcacattgg aagacatttg atgacctcat 1560
ttctttcaat gaagggccta acggagttga ctaatgttgt gggaaattgg agcgataagc 1620
gtgcttctgc cgtggccagg acaacgtata ctcatcagat aacagcaata cctgatcact 1680
acttcgcact agtttctcgg tactatgcat atgatccaat atcaaaggaa atgatagcat 1740
tgaaggatga gactaatcca attgaggagt ggcagcatat agaacagcta aagggtagtg 1800

-continued

```
ctgaaggaag catacgatac cccgcatgga atgggataat atcacaggag gtactagact   1860
acctttcatc ctacataaat agacgcatat aagtacgcat ttaagcataa acacgcacta   1920
tgccgttctt ctcatgtata tatatataca ggcaacacgc agatataggt gcgacgtgaa   1980
cagtgagctg tatgtgcgca gctcgcgttg cattttcgga agcgctcgtt ttcggaaacg   2040
ctttgaagtt cctattccga agttcctatt ctctagaaag tataggaact tcagagcgct   2100
tttgaaaacc aaaagcgctc tgaagacgca ctttcaaaaa accaaaaacg caccggactg   2160
taacgagcta ctaaaatatt gcgaataccg cttccacaaa cattgctcaa aagtatctct   2220
ttgctatata tctctgtgct atatccctat ataacctacc catccacctt tcgctccttg   2280
aacttgcatc taaactcgac ctctacattt tttatgttta tctctagtat tactctttag   2340
acaaaaaaat tgtagtaaga actattcata gagtgaatcg aaaacaatac gaaaatgtaa   2400
acatttccta tacgtagtat atagagacaa aatagaagaa accgttcata attttctgac   2460
caatgaagaa tcatcaacgc tatcactttc tgttcacaaa gtatgcgcaa tccacatcgg   2520
tatagaatat aatcggggat gcctttatct tgaaaaaatg cacccgcagc ttcgctagta   2580
atcagtaaac gcgggaagtg gagtcaggct ttttttatgg aagagaaaat agacaccaaa   2640
gtagccttct tctaacctta acggacctac agtgcaaaaa gttatcaaga gactgcatta   2700
tagagcgcac aaaggagaaa aaaagtaatc taagatgctt tgttagaaaa atagcgctct   2760
cgggatgcat ttttgtagaa caaaaaagaa gtatagattc tttgttggta aaatagcgct   2820
ctcgcgttgc atttctgttc tgtaaaaatg cagctcagat tctttgtttg aaaaattagc   2880
gctctcgcgt tgcatttttg ttttacaaaa atgaagcaca gattcttcgt tggtaaaata   2940
gcgctttcgc gttgcatttc tgttctgtaa aaatgcagct cagattcttt gtttgaaaaa   3000
ttagcgctct cgcgttgcat ttttgttcta caaaatgaag cacagatgct tcgttaacaa   3060
agatatgcta ttgaagtgca agatggaaac gcagaaaatg aaccggggat gcgacgtgca   3120
agattaccta tgcaatagat gcaatagttt ctccaggaac cgaaatacat acattgtctt   3180
ccgtaaagcg ctagactata tattattata caggttcaaa tatactatct gtttcaggga   3240
aaactcccag gttcggatgt tcaaaattca atgatgggta acaagtacga tcgtaaatct   3300
gtaaaacagt ttgtcggata ttaggctgta tctcctcaaa gcgtattcga tctgtctttc   3360
gccgaaacct gtttgatgac tacttcatca attttttttt tttctgccgc attccaaagg   3420
tcataacttt gcaaaaataa agggtaaatg gttaaaaatt gttatcataa ataaggtgac   3480
cggttatatt gagacctttc ctggacagta actaatacag aagccattgg taatgcaata   3540
atttatttga tcatgtgact acgatccggg tgagactatt caaaaaagga gtcaagcatt   3600
gaaataatta atgactaatc cgaagttaat tgttaggagt caattgtttt ttccaatgaa   3660
tggaatctga gatgactaaa ctaccaattt tcaatagttc atggtatagt gacgtagtta   3720
gtgctttttt ttcttggatc tgttgactca cttcaattga tgtttcttac cctgacatga   3780
catacttgat attttatctc tcacgttata taacttgaaa aggatgcaca cagttctgtt   3840
caatataccc tccaatatgt aaaaacagtt tttccattga ttactcttaa tttgtttcct   3900
gctaaaccag cagtacgtgt gtgccgtata tattaaaatt acactatggt ttttgatttg   3960
aaaagaattg ttagaccaaa aatttataac ttggaacctt atcgctgtgc aagagatgat   4020
ttcaccgagg gtatattgct agacgccaat gaaaatgccc atggacctac tccagttgaa   4080
ttgagcaaga ccaatttaca tcgttacccg gatcctcacc aattggagtt caagaccgca   4140
atgacgaaat acaggaacaa aacaagcagt tatgccaatg acccagaggt aaaaccttta   4200
```

-continued

```
actgctgaca atctgtgcct aggtgtggga tctgatgaga gtattgatgc tattattaga   4260
gcatgctgtg ttcccgggaa agaaaagatt ctggttcttc caccaacata ttctatgtac   4320
tctgtttgtg caaacattaa tgatatagaa gtcgtccaat gtcctttaac tgtttccgac   4380
ggttcttttc aaatggatac cgaagctgta ttaaccattt tgaaaaacga ctcgctaatt   4440
aagttgatgt tcgttacttc accaggtaat ccaaccggag ccaaaattaa gaccagttta   4500
atcgaaaagg tcttacagaa ttgggacaat gggttagtcg ttgttgatga agcttacgta   4560
gatttttgtg gtggctctac agctccacta gtcaccaagt atcctaactt ggttactttg   4620
caaactctat ccaagtcatt cggtttagcc gggattaggt tgggtatgac atatgcaaca   4680
gcagagttgg ccagaatttt aaatgcaatg aaggcgcctt ataatatttc ctccctagcc   4740
tctgaatatg cactaaaagc tgttcaagac agtaatctaa agaagatgga agccacttcg   4800
aaaataatca atgaagagaa aatgcgcctc ttaaaggaat taactgcttt ggattacgtt   4860
gatgaccaat atgttggtgg attagatgct aattttcttt taatacggat caacgggggt   4920
gacaatgtct tggcaaagaa gttatattac caattggcta ctcaatctgg ggttgtcgtc   4980
agatttagag gtaacgaatt aggctgttcc ggatgtttga gaattaccgt tggaacccat   5040
gaggagaaca cacatttgat aaagtacttc aaggagacgt tatataagct ggccaatgaa   5100
taaatagacg tcaacaaaat tcagaagaac tcgtcaagaa ggcgatagaa ggcgatgcgc   5160
tgcgaatcgg gagcggcgat accgtaaagc acgaggaagc ggtcagccca ttcgccgcca   5220
agctcttcag caatatcacg ggtagccaac gctatgtcct gatagcggtc cgccacaccc   5280
agccggccac agtcgatgaa tccagaaaag cggccatttt ccaccatgat attcggcaag   5340
caggcatcgc catgggtcac gacgagatcc tcgccgtcgg gcatgctcgc cttgagcctg   5400
gcgaacagtt cggctggcgc gagcccctga tgctcttcgt ccagatcatc ctgatcgaca   5460
agaccggctt ccatccgagt acgtgctcgc tcgatgcgat gtttcgcttg gtggtcgaat   5520
gggcaggtag ccggatcaag cgtatgcagc cgccgcattg catcagccat gatggatact   5580
ttctcggcag gagcaaggtg agatgacagg agatcctgcc ccggcacttc gcccaatagc   5640
agccagtccc ttcccgcttc agtgacaacg tcgagcacag ctgcgcaagg aacgcccgtc   5700
gtggccagcc acgatagccg cgctgcctcg tcttgcagtt cattcagggc accggacagg   5760
tcggtcttga caaaaagaac cgggcgcccc tgcgctgaca gccggaacac ggcggcatca   5820
gagcagccga ttgtctgttg tgcccagtca tagccgaata gcctctccac ccaagcggcc   5880
ggagaacctg cgtgcaatcc atcttgttca atcatgcgaa acgatcctca tcctgtctct   5940
tgatcagatc ttgatcccct gcgccatcag atccttggcg gcgagaaagc catccagttt   6000
actttgcagg gcttcccaac cttaccagag ggcgccccag ctggcaattc cggttcgctt   6060
gctgtccata aaaccgccca gtctagctat cgccatgtaa gcccactgca agctacctgc   6120
tttctctttg cgcttgcgtt ttcccttgtc cagatagccc agtagctgac attcatccgg   6180
ggtcagcacc gtttctgcgg actggctttc tacgtgaaaa ggatctaggt gaagatcctt   6240
tttgataatc tcatgaccaa aatcccttaa cgtgagtttt cgtgactccc cgtcaggcaa   6300
ctatggatga acgaaataga cagatcgctg agataggtgc ctcactgatt aagcattggt   6360
aactgtcaga ccaagtttac tcatatatac tttagattga tttaaaactt catttttaat   6420
ttaaaaggat ctaggtgaag atcctttttg ataatctcat gaccaaaatc ccttaacgtg   6480
agttttcgtt ccactgagcg tcagaccccg tagaaaagat caaaggatct tcttgagatc   6540
```

-continued

```
cttttttttct gcgcgtaatc tgctgcttgc aaacaaaaaa accaccgcta ccagcggtgg   6600

tttgtttgcc ggatcaagag ctaccaactc tttttccgaa ggtaactggc ttcagcagag   6660

cgcagatacc aaatactgtc cttctagtgt agccgtagtt aggccaccac ttcaagaact   6720

ctgtagcacc gcctacatac ctcgctctgc taatcctgtt accagtggct gctgccagtg   6780

gcgataagtc gtgtcttacc gggttggact caagacgata gttaccggat aaggcgcagc   6840

ggtcgggctg aacggggggt tcgtgcacac agcccagctt ggagcgaacg acctacaccg   6900

aactgagata cctacagcgt gagctatgag aaagcgccac gcttcccgaa gggagaaagg   6960

cggacaggta tccggtaagc ggcagggtcg gaacaggaga gcgcacgagg gagcttccag   7020

ggggaaacgc ctggtatctt tatagtcctg tcgggtttcg ccacctctga cttgagcgtc   7080

gatttttgtg atgctcgtca ggggggcgga gcctatggaa aaacgccagc aacgcggcct   7140

ttttacggtt cctggccttt tgctggcctt ttgctcacat gttctttcct gcgttatccc   7200

ctgattctgt ggataaccgt attaccgcct ttgagtgagc tgataccgct cgccgcagcc   7260

gaacgaccga gcgcagcgag tcagtgagcg aggaagcgga agagcgccca atacgcaaac   7320

cgcctctccc cgcgcgttgg ccgattcatt aatgcagctg gcacgacagg tttcccgact   7380

ggaaagcggg cagtgagcgc aacgcaatta atgtgagtta gctcactcat taggcacccc   7440

aggctttaca ctttatgctt ccggctcgta tgttgtgtgg aattgtgagc ggataacaat   7500

ttcacacagg aaacagctat gacatgatta cgaattaatt cgagctcggt a            7551
```

<210> SEQ ID NO 61
<211> LENGTH: 7308
<212> TYPE: DNA
<213> ORGANISM: Artificial
<220> FEATURE:
<223> OTHER INFORMATION: pDD vector

<400> SEQUENCE: 61

```
cttgaatttt caaaaattct tacttttttt ttggatggac gcaaagaagt ttaataatca     60

tattacatgg cattaccacc atatacatat ccatatacat atccatatct aatcttactt    120

atatgttgtg gaaatgtaaa gagccccatt atcttagcct aaaaaaacct tctctttgga    180

actttcagta atacgcttaa ctgctcattg ctatattgaa gtacggatta gaagccgccg    240

agcgggtgac agccctccga aggaagactc tcctccgtgc gtcctcgtct tcaccggtcg    300

cgttcctgaa acgcagatgt gcctcgcgcc gcactgctcc gaacaataaa gattctacaa    360

tactagcttt tatggttatg aagaggaaaa attggcagta acctggcccc acaaaccttc    420

aaatgaacga atcaaattaa caaccatagg atgataatgc gattagtttt ttagccttat    480

ttctggggta attaatcagc gaagcgatga tttttgatct attaacagat atataaatgc    540

aaaaactgca taaccacttt aactaatact ttcaacattt tcggtttgta ttacttctta    600

ttcaaatgta ataaaagtat caacaaaaaa ttgttaatat acctctatac tttaacgtca    660

aggagaaaaa accccggatc aagggtgcga tatgaaagcg ttaacggcca ggcaacaaga    720

ggtgtttgat ctcatccgtg atcacatcag ccagacaggt atgccgccga cgcgtgcgga    780

aatcgcgcag cgtttggggt tccgttcccc aaacgcggct gaagaacatc tgaaggcgct    840

ggcacgcaaa ggcgttattg aaattgtttc cggcgcatca cgcgggattc gtctgttgca    900

ggaagaggaa gaagggttgc cgctggtagg tcgtgtggct gccggtgaac cacttctggc    960

gcaacagcat attgaaggtc attatcaggt cgatccttcc ttattcaagc cgaatgctga   1020

tttcctgctg cgcgtcagcg ggatgtcgat gaaagatatc ggcattatgg atggtgactt   1080
```

-continued

```
gctggcagtg cataaaactc aggatgtacg taacggtcag gtcgttgtcg cacgtattga   1140
tgacgaagtt accgttaagc gcctgaaaaa acagggcaat aaagtcgaac tgttgccaga   1200
aaatagcgag tttaaaccaa ttgtcgtaga tcttcgtcag cagagcttca ccattgaagg   1260
gctggcggtt ggggttattc gcaacggcga ctggctggaa ttcccgggga tccgtcgacc   1320
atggcggccg ctcgagtcga cctgcagcca agctaattcc gggcgaattt cttatgattt   1380
atgattttta ttattaaata agttataaaa aaaataagtg tatacaaatt ttaaagtgac   1440
tcttaggttt taaaacgaaa attcttgttc ttgagtaact ctttcctgta ggtcaggttg   1500
ctttctcagg tatagcatga ggtcgctctt attgaccaca cctctaccgg catgccgagc   1560
aaatgcctgc aaatcgctcc ccatttcacc caattgtaga tatgctaact ccagcaatga   1620
gttgatgaat ctcggtgtgt attttatgtc ctcagaggac aacacctgtt gtaatccgtc   1680
cgagctccaa ttcgccctat agtgagtcgt attacaattc actggccgtc gttttacaac   1740
gtcgtgactg ggaaaaccct ggcgttaccc aacttaatcg ccttgcagca catccccctt   1800
tcgccagctg gcgtaatagc gaagaggccc gcaccgatcg cccttcccaa cagttgcgca   1860
gcctgaatgg cgaatggcgc gacgcgccct gtagcggcgc attaagcgcg gcgggtgtgg   1920
tggttacgcg cagcgtgacc gctacacttg ccagcgccct agcgcccgct cctttcgctt   1980
tcttcccttc ctttctcgcc acgttcgccg gctttccccg tcaagctcta aatcgggggc   2040
tccctttagg gttccgattt agtgctttac ggcacctcga ccccaaaaaa cttgattagg   2100
gtgatggttc acgtagtggg ccatcgccct gatagacggt ttttcgccct ttgacgttgg   2160
agtccacgtt ctttaatagt ggactcttgt tccaaactgg aacaacactc aaccctatct   2220
cggtctattc ttttgattta taagggattt tgccgatttc ggcctattgg ttaaaaaatg   2280
agctgattta acaaaaattt aacgcgaatt ttaacaaaat attaacgttt acaatttcct   2340
gatgcggtat tttctcctta cgcatctgtg cggtatttca caccgcatat gatccgtcga   2400
gttcaagaga aaaaaaaaga aaaagcaaaa agaaaaaagg aaagcgcgcc tcgttcagaa   2460
tgacacgtat agaatgatgc attaccttgt catcttcagt atcatactgt tcgtatacat   2520
acttactgac attcataggt atacatatat acacatgtat atatatcgta tgctgcagct   2580
ttaaataatc ggtgtcacta cataagaaca cctttggtgg agggaacatc gttggtacca   2640
ttgggcgagg tggcttctct tatggcaacc gcaagagcct tgaacgcact ctcactacgg   2700
tgatgatcat tcttgcctcg cagacaatca acgtggaggg taattctgct agcctctgca   2760
aagctttcaa gaaaatgcgg gatcatctcg caagagagat ctcctacttt ctccctttgc   2820
aaaccaagtt cgacaactgc gtacggcctg ttcgaaagat ctaccaccgc tctggaaagt   2880
gcctcatcca aaggcgcaaa tcctgatcca aacctttttta ctccacgcgc cagtagggcc   2940
tctttaaaag cttgaccgag agcaatcccg cagtcttcag tggtgtgatg gtcgtctatg   3000
tgtaagtcac caatgcactc aacgattagc gaccagccgg aatgcttggc cagagcatgt   3060
atcatatggt ccagaaaccc tatacctgtg tggacgttaa tcacttgcga ttgtgtggcc   3120
tgttctgcta ctgcttctgc ctctttttct gggaagatcg agtgctctat cgctagggga   3180
ccaccccttta aagagatcgc aatctgaatc ttggtttcat ttgtaatacg ctttactagg   3240
gctttctgct ctgtcatctt tgccttcgtt tatcttgcct gctcattttt tagtatattc   3300
ttcgaagaaa tcacattact ttatataatg tataattcat tatgtgataa tgccaatcgc   3360
taagaaaaaa aaagagtcat ccgctaggtg gaaaaaaaaa aatgaaaatc attaccgagg   3420
```

-continued

```
cataaaaaaa tatagagtgt actagaggag gccaagagta atagaaaaag aaaattgcgg   3480
gaaaggactg tgttatgact tccctgacta atgccgtgtt caaacgatac ctggcagtga   3540
ctcctagcgc tcaccaagct cttaaaacgg aattatggtg cactctcagt acaatctgct   3600
ctgatgccgc atagttaagc cagccccgac acccgccaac acccgctgac gcgccctgac   3660
gggcttgtct gctcccggca tccgcttaca gacaagctgt gaccgtctcc gggagctgca   3720
tgtgtcagag gttttcaccg tcatcaccga aacgcgcgag acgaaagggc ctcgtgatac   3780
gcctattttt ataggttaat gtcatgataa taatggtttc ttaggacgga tcgcttgcct   3840
gtaacttaca cgcgcctcgt atcttttaat gatggaataa tttgggaatt tactctgtgt   3900
ttatttattt ttatgttttg tatttggatt ttagaaagta aataaagaag gtagaagagt   3960
tacggaatga agaaaaaaaa ataaacaaag gtttaaaaaa tttcaacaaa aagcgtactt   4020
tacatatata tttattagac aagaaaagca gattaaatag atatacattc gattaacgat   4080
aagtaaaatg taaaatcaca ggattttcgt gtgtggtctt ctacacagac aagatgaaac   4140
aattcggcat taatacctga gagcaggaag agcaagataa aaggtagtat ttgttggcga   4200
tccccctaga gtcttttaca tcttcggaaa acaaaaacta ttttttcttt aatttctttt   4260
tttactttct atttttaatt tatatattta tattaaaaaa tttaaattat aattattttt   4320
atagcacgtg atgaaaagga cccaggtggc acttttcggg gaaatgtgcg cggaacccct   4380
atttgtttat ttttctaaat acattcaaat atgtatccgc tcatgagaca ataaccctga   4440
taaatgcttc aataaattgg tcacccggcc agcgacatgg aggcccagaa taccctcctt   4500
gacagtcttg acgtgcgcag ctcaggggca tgatgtgact gtcgcccgta catttagccc   4560
atacatcccc atgtataatc atttgcatcc atacattttg atggccgcac ggcgcgaagc   4620
aaaaattacg gctcctcgct gcagacctgc gagcagggaa acgctcccct cacagacgcg   4680
ttgaattgtc cccacgccgc gcccctgtag agaaatataa aaggttagga tttgccactg   4740
aggttcttct ttcatatact tccttttaaa atcttgctag gatacagttc tcacatcaca   4800
tccgaacata aacaaccatg ggtaaggaaa agactcacgt ttcgaggccg cgattaaatt   4860
ccaacatgga tgctgattta tatgggtata aatgggctcg cgataatgtc gggcaatcag   4920
gtgcgacaat ctatcgattg tatgggaagc ccgatgcgcc agagttgttt ctgaaacatg   4980
gcaaaggtag cgttgccaat gatgttacag atgagatggt cagactaaac tggctgacgg   5040
aatttatgcc tcttccgacc atcaagcatt ttatccgtac tcctgatgat gcatggttac   5100
tcaccactgc gatccccggc aaaacagcat tccaggtatt agaagaatat cctgattcag   5160
gtgaaaatat tgttgatgcg ctggcagtgt tcctgcgccg gttgcattcg attcctgttt   5220
gtaattgtcc ttttaacagc gatcgcgtat ttcgtctcgc tcaggcgcaa tcacgaatga   5280
ataacggttt ggttgatgcg agtgattttg atgacgagcg taatggctgg cctgttgaac   5340
aagtctggaa agaaatgcat aagcttttgc cattctcacc ggattcagtc gtcactcatg   5400
gtgatttctc acttgataac cttatttttg acgaggggaa attaataggt tgtattgatg   5460
ttggacgagt cggaatcgca gaccgatacc aggatcttgc catcctatgg aactgcctcg   5520
gtgagttttc tccttcatta cagaaacggc tttttcaaaa atatggtatt gataatcctg   5580
atatgaataa attgcagttt catttgatgc tcgatgagtt tttctaatca gtcctcggag   5640
atccgtcccc cttttccttt gtcgatatca tgtaattagt tatgtcacgc ttacattcac   5700
gccctccccc cacatccgct ctaaccgaaa aggaaggagt tagacaacct gaagtctagg   5760
tccctattta ttttttata gttatgttag tattaagaac gttatttata tttcaaattt   5820
```

-continued

```
ttcttttttt tctgtacaga cgcgtgtacg catgtaacat tatactgaaa accttgcttg   5880

agaaggtttt gggacgctcg aaggctttaa tttgcaagct ggggtctcgc ggtcggtatc   5940

attgcagcac tggggccaga tggtaagccc tcccgtatcg tagttatcta cacgacgggc   6000

agtcaggcaa ctatggatga acgaaataga cagatcgctg agataggtgc ctcactgatt   6060

aagcattggt aactgtcaga ccaagtttac tcatatatac tttagattga tttaaaactt   6120

catttttaat ttaaaaggat ctaggtgaag atcctttttg ataatctcat gaccaaaatc   6180

ccttaacgtg agttttcgtt ccactgagcg tcagaccccg tagaaaagat caaaggatct   6240

tcttgagatc ctttttttct gcgcgtaatc tgctgcttgc aaacaaaaaa accaccgcta   6300

ccagcggtgg tttgtttgcc ggatcaagag ctaccaactc tttttccgaa ggtaactggc   6360

ttcagcagag cgcagatacc aaatactgtc cttctagtgt agccgtagtt aggccaccac   6420

ttcaagaact ctgtagcacc gcctacatac ctcgctctgc taatcctgtt accagtggct   6480

gctgccagtg gcgataagtc gtgtcttacc gggttggact caagacgata gttaccggat   6540

aaggcgcagc ggtcgggctg aacggggggt tcgtgcacac agcccagctt ggagcgaacg   6600

acctacaccg aactgagata cctacagcgt gagcattgag aaagcgccac gcttcccgaa   6660

gggagaaagg cggacaggta tccggtaagc ggcagggtcg gaacaggaga gcgcacgagg   6720

gagcttccag ggggaaacgc ctggtatctt tatagtcctg tcgggtttcg ccacctctga   6780

cttgagcgtc gatttttgtg atgctcgtca ggggggccga gcctatggaa aaacgccagc   6840

aacgcggcct ttttacggtt cctggccttt tgctggcctt ttgctcacat gttctttcct   6900

gcgttatccc ctgattctgt ggataaccgt attaccgcct ttgagtgagc tgataccgct   6960

cgccgcagcc gaacgaccga gcgcagcgag tcagtgagcg aggaagcgga agagcgccca   7020

atacgcaaac cgcctctccc cgcgcgttgg ccgattcatt aatgcagctg gcacgacagg   7080

tttcccgact ggaaagcggg cagtgagcgc aacgcaatta atgtgagtta gctcactcat   7140

taggcacccc aggctttaca ctttatgctt ccggctcgta tgttgtgtgg aattgtgagc   7200

ggataacaat ttcacacagg aaacagctat gaccatgatt acgccaagct cgaaattaac   7260

cctcactaaa gggaacaaaa gctggtaccg ggccccccct cgaaattc                 7308
```

```
<210> SEQ ID NO 62
<211> LENGTH: 289
<212> TYPE: DNA
<213> ORGANISM: Artificial
<220> FEATURE:
<223> OTHER INFORMATION: clone BGF05 with first open reading frame
<220> FEATURE:
<221> NAME/KEY: CDS
<222> LOCATION: (1)..(165)

<400> SEQUENCE: 62

atg ggt aag cct atc cct aac cct ctc ctc ggt ctc gat tct aca caa       48
Met Gly Lys Pro Ile Pro Asn Pro Leu Leu Gly Leu Asp Ser Thr Gln
1               5                   10                  15

gct atg ggt gct cct cca aaa aag aag aga aag gta gct gaa ttc gca       96
Ala Met Gly Ala Pro Pro Lys Lys Lys Arg Lys Val Ala Glu Phe Ala
            20                  25                  30

agg acg acg acg aca agg ctt atc aat caa tca gtg gtt aga aaa ata      144
Arg Thr Thr Thr Thr Arg Leu Ile Asn Gln Ser Val Val Arg Lys Ile
        35                  40                  45

tgg cta tat cga gat gca agg taacgaaacg ttcaaattgg cagttcgtga         195
Trp Leu Tyr Arg Asp Ala Arg
    50                  55
```

-continued

```
actttcaaat gtggtggaag aaacactttt agccaataat ttagataaaa aagatttaga    255

ctggcttgtc gtcgtcgtcc ttgtagtctg acct                                289


<210> SEQ ID NO 63
<211> LENGTH: 55
<212> TYPE: PRT
<213> ORGANISM: Artificial
<220> FEATURE:
<223> OTHER INFORMATION: Synthetic Construct

<400> SEQUENCE: 63

Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Ala
            20                  25                  30

Arg Thr Thr Thr Thr Arg Leu Ile Asn Gln Ser Val Val Arg Lys Ile
        35                  40                  45

Trp Leu Tyr Arg Asp Ala Arg
    50                  55


<210> SEQ ID NO 64
<211> LENGTH: 196
<212> TYPE: DNA
<213> ORGANISM: clone BGF05 H. influenzae insertion

<400> SEQUENCE: 64

gcaaggacga cgacgacaag gcttatcaat caatcagtgg ttagaaaaat atggctatat     60

cgagatgcaa ggtaacgaaa cgttcaaatt ggcagttcgt gaactttcaa atgtggtgga    120

agaaacactt ttagccaata atttagataa aaaagattta gactggcttg tcgtcgtcgt    180

ccttgtagtc tgacct                                                    196


<210> SEQ ID NO 65
<211> LENGTH: 24
<212> TYPE: PRT
<213> ORGANISM: Artificial
<220> FEATURE:
<223> OTHER INFORMATION: SCL-E47 antagonist encoded by BGF05 A. aeolicus
      insertion

<400> SEQUENCE: 65

Ala Arg Thr Thr Thr Thr Arg Leu Ile Asn Gln Ser Val Val Arg Lys
1               5                   10                  15

Ile Trp Leu Tyr Arg Asp Ala Arg
            20


<210> SEQ ID NO 66
<211> LENGTH: 419
<212> TYPE: DNA
<213> ORGANISM: Artificial
<220> FEATURE:
<223> OTHER INFORMATION: clone BGF06 with first open reading frame
<220> FEATURE:
<221> NAME/KEY: CDS
<222> LOCATION: (1)..(165)
<220> FEATURE:
<221> NAME/KEY: misc_feature
<222> LOCATION: (307)..(307)
<223> OTHER INFORMATION: N at position 307 is any nucleotide residue
<220> FEATURE:
<221> NAME/KEY: misc_feature
<222> LOCATION: (355)..(355)
<223> OTHER INFORMATION: N at position 355 is any nucleotide residue
<220> FEATURE:
```

-continued

<221> NAME/KEY: misc_feature
<222> LOCATION: (357)..(357)
<223> OTHER INFORMATION: N at position 357 is any nucleotide residue

<400> SEQUENCE: 66

```
atg ggt aag cct atc cct aac cct ctc ctc ggt ctc gat tct aca caa       48
Met Gly Lys Pro Ile Pro Asn Pro Leu Leu Gly Leu Asp Ser Thr Gln
1               5                   10                  15

gct atg ggt gct cct cca aaa aag aag aga aag gta gct gaa ttc agg       96
Ala Met Gly Ala Pro Pro Lys Lys Lys Arg Lys Val Ala Glu Phe Arg
            20                  25                  30

tca gac tac aag gac gac gac gac aag gct tat cac ata att gct gtt      144
Ser Asp Tyr Lys Asp Asp Asp Asp Lys Ala Tyr His Ile Ile Ala Val
        35                  40                  45

tgt ttt tta atc aag gta tca tgacatgtcc caacctcgcc cactgctctc         195
Cys Phe Leu Ile Lys Val Ser
    50                  55

tcctcccgaa actgaagaac agttgttagc gcaagcacag caactttctg gttatacatt    255

gggagaactg gcggcacttg tcgggctggt tacgccagag aatttaaaac gngataaagg    315

ctggattggc gtgttactgg agatctggct aggtgccagn gnagggagta aacctgagca    375

agattttgct gttgaataca cctgattgat tgataacctt gtcg                     419
```

<210> SEQ ID NO 67
<211> LENGTH: 55
<212> TYPE: PRT
<213> ORGANISM: Artificial
<220> FEATURE:
<223> OTHER INFORMATION: Synthetic Construct

<400> SEQUENCE: 67

```
Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Arg
            20                  25                  30

Ser Asp Tyr Lys Asp Asp Asp Asp Lys Ala Tyr His Ile Ile Ala Val
        35                  40                  45

Cys Phe Leu Ile Lys Val Ser
    50                  55
```

<210> SEQ ID NO 68
<211> LENGTH: 326
<212> TYPE: DNA
<213> ORGANISM: Artificial
<220> FEATURE:
<223> OTHER INFORMATION: clone BGF06 A. aeolicus insertion
<220> FEATURE:
<221> NAME/KEY: misc_feature
<222> LOCATION: (214)..(214)
<223> OTHER INFORMATION: N at position 214 is any nucleotide residue
<220> FEATURE:
<221> NAME/KEY: misc_feature
<222> LOCATION: (262)..(262)
<223> OTHER INFORMATION: N at position 262 is any nucleotide residue
<220> FEATURE:
<221> NAME/KEY: misc_feature
<222> LOCATION: (264)..(264)
<223> OTHER INFORMATION: N at position 264 is any nucleotide residue

<400> SEQUENCE: 68

```
aggtcagact acaaggacga cgacgacaag gcttatcaca taattgctgt ttgtttttta     60

atcaaggtat catgacatgt cccaacctcg cccactgctc tctcctcccg aaactgaaga    120

acagttgtta gcgcaagcac agcaactttc tggttataca ttgggagaac tggcggcact    180
```

-continued

```
tgtcgggctg gttacgccag agaatttaaa acgngataaa ggctggattg gcgtgttact    240

ggagatctgg ctaggtgcca gngnagggag taaacctgag caagattttg ctgttgaata    300

cacctgattg attgataacc ttgtcg                                        326
```

<210> SEQ ID NO 69
<211> LENGTH: 24
<212> TYPE: PRT
<213> ORGANISM: Artificial
<220> FEATURE:
<223> OTHER INFORMATION: SCL-E47 antagonist encoded by clone BGF06 H. influenzae insertion

<400> SEQUENCE: 69

```
Arg Ser Asp Tyr Lys Asp Asp Asp Asp Lys Ala Tyr His Ile Ile Ala
1               5                   10                  15

Val Cys Phe Leu Ile Lys Val Ser
            20
```

<210> SEQ ID NO 70
<211> LENGTH: 220
<212> TYPE: DNA
<213> ORGANISM: Artificial
<220> FEATURE:
<223> OTHER INFORMATION: clone BGF13 with first open reading frame
<220> FEATURE:
<221> NAME/KEY: CDS
<222> LOCATION: (1)..(123)

<400> SEQUENCE: 70

```
atg ggt aag cct atc cct aac cct ctc ctc ggt ctc gat tct aca caa       48
Met Gly Lys Pro Ile Pro Asn Pro Leu Leu Gly Leu Asp Ser Thr Gln
1               5                   10                  15

gct atg ggt gct cct cca aaa aag aag aga aag gta gct gaa ttc gga       96
Ala Met Gly Ala Pro Pro Lys Lys Lys Arg Lys Val Ala Glu Phe Gly
            20                  25                  30

ttt tgc tct aat caa atg aga gaa atg taaaatgaag ccacgaacat           143
Phe Cys Ser Asn Gln Met Arg Glu Met
        35                  40

attaataata gcctaccact gcaaccatta gttcctgatc aggagaacaa aaataagaga    203

aatgaagaga aatccgt                                                   220
```

<210> SEQ ID NO 71
<211> LENGTH: 41
<212> TYPE: PRT
<213> ORGANISM: Artificial
<220> FEATURE:
<223> OTHER INFORMATION: Synthetic Construct

<400> SEQUENCE: 71

```
Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Gly
            20                  25                  30

Phe Cys Ser Asn Gln Met Arg Glu Met
        35                  40
```

<210> SEQ ID NO 72
<211> LENGTH: 127
<212> TYPE: DNA
<213> ORGANISM: Artificial
<220> FEATURE:
<223> OTHER INFORMATION: clone BGF13 H. influenzae insertion

```
<400> SEQUENCE: 72

ggattttgct ctaatcaaat gagagaaatg taaaatgaag ccacgaacat attaataata     60

gcctaccact gcaaccatta gttcctgatc aggagaacaa aaataagaga aatgaagaga    120

aatccgt                                                              127


<210> SEQ ID NO 73
<211> LENGTH: 10
<212> TYPE: PRT
<213> ORGANISM: Artificial
<220> FEATURE:
<223> OTHER INFORMATION: SCL-E47 antagonist encoded by clone BGF13 T.
      maritima insertion

<400> SEQUENCE: 73

Gly Phe Cys Ser Asn Gln Met Arg Glu Met
1               5                   10


<210> SEQ ID NO 74
<211> LENGTH: 273
<212> TYPE: DNA
<213> ORGANISM: Artificial
<220> FEATURE:
<223> OTHER INFORMATION: clone BGF24 with first open reading frame
<220> FEATURE:
<221> NAME/KEY: CDS
<222> LOCATION: (1)..(171)

<400> SEQUENCE: 74

atg ggt aag cct atc cct aac cct ctc ctc ggt ctc gat tct aca caa       48
Met Gly Lys Pro Ile Pro Asn Pro Leu Leu Gly Leu Asp Ser Thr Gln
1               5                   10                  15

gct atg ggt gct cct cca aaa aag aag aga aag gta gct gaa ttc agg       96
Ala Met Gly Ala Pro Pro Lys Lys Lys Arg Lys Val Ala Glu Phe Arg
            20                  25                  30

tca gac tac aag gac gac gac gac aag ctt atc aaa cat cac tgg gtg      144
Ser Asp Tyr Lys Asp Asp Asp Asp Lys Leu Ile Lys His His Trp Val
        35                  40                  45

ctt tca atc atc acc acc gcg tct cgc taacctgttt caaataccac            191
Leu Ser Ile Ile Thr Thr Ala Ser Arg
    50                  55

catgaactcc tctccaccgt atcttgacta caagggatga ttgattgata agccttgtcg    251

tcgtcgtcct tgtagtctga ct                                             273


<210> SEQ ID NO 75
<211> LENGTH: 57
<212> TYPE: PRT
<213> ORGANISM: Artificial
<220> FEATURE:
<223> OTHER INFORMATION: Synthetic Construct

<400> SEQUENCE: 75

Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Arg
            20                  25                  30

Ser Asp Tyr Lys Asp Asp Asp Asp Lys Leu Ile Lys His His Trp Val
        35                  40                  45

Leu Ser Ile Ile Thr Thr Ala Ser Arg
    50                  55
```

-continued

<210> SEQ ID NO 76
<211> LENGTH: 180
<212> TYPE: DNA
<213> ORGANISM: Artificial
<220> FEATURE:
<223> OTHER INFORMATION: clone BGF24 T. maritima insertion

<400> SEQUENCE: 76

```
aggtcagact acaaggacga cgacgacaag cttatcaaac atcactgggt gctttcaatc     60

atcaccaccg cgtctcgcta acctgtttca aataccacca tgaactcctc tccaccgtat    120

cttgactaca agggatgatt gattgataag ccttgtcgtc gtcgtccttg tagtctgact    180
```

<210> SEQ ID NO 77
<211> LENGTH: 26
<212> TYPE: PRT
<213> ORGANISM: Artificial
<220> FEATURE:
<223> OTHER INFORMATION: SCL-E47 antagonist encoded by clone BGF24 T. maritima insertion

<400> SEQUENCE: 77

```
Arg Ser Asp Tyr Lys Asp Asp Asp Asp Lys Leu Ile Lys His His Trp
1               5                   10                  15

Val Leu Ser Ile Ile Thr Thr Ala Ser Arg
            20                  25
```

<210> SEQ ID NO 78
<211> LENGTH: 288
<212> TYPE: DNA
<213> ORGANISM: Artificial
<220> FEATURE:
<223> OTHER INFORMATION: clone BGF35 with first open reading frame
<220> FEATURE:
<221> NAME/KEY: CDS
<222> LOCATION: (1)..(282)

<400> SEQUENCE: 78

```
atg ggt aag cct atc cct aac cct ctc ctc ggt ctc gat tct aca caa       48
Met Gly Lys Pro Ile Pro Asn Pro Leu Leu Gly Leu Asp Ser Thr Gln
1               5                   10                  15

gct atg ggt gct cct cca aaa aag aag aga aag gta gct gaa ttc caa       96
Ala Met Gly Ala Pro Pro Lys Lys Lys Arg Lys Val Ala Glu Phe Gln
            20                  25                  30

gga cga cga cga caa ggc tta tca atc aat cag tgg tta gaa aaa tat      144
Gly Arg Arg Arg Gln Gly Leu Ser Ile Asn Gln Trp Leu Glu Lys Tyr
        35                  40                  45

ggc tat atc gag atg caa ggt aac gaa acg ttc aaa ttg gca gtt cgt      192
Gly Tyr Ile Glu Met Gln Gly Asn Glu Thr Phe Lys Leu Ala Val Arg
    50                  55                  60

gaa ctt tca aat gtg gtg gaa gaa aca ctt tta gcc aat aat tta gat      240
Glu Leu Ser Asn Val Val Glu Glu Thr Leu Leu Ala Asn Asn Leu Asp
65                  70                  75                  80

aaa aaa gat tta gac tgg ctt gtc gtc gtc gtc ctt gta gtc tgacct       288
Lys Lys Asp Leu Asp Trp Leu Val Val Val Val Leu Val Val
                85                  90
```

<210> SEQ ID NO 79
<211> LENGTH: 94
<212> TYPE: PRT
<213> ORGANISM: Artificial
<220> FEATURE:
<223> OTHER INFORMATION: Synthetic Construct

<400> SEQUENCE: 79

-continued

```
Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Gln
            20                  25                  30

Gly Arg Arg Arg Gln Gly Leu Ser Ile Asn Gln Trp Leu Glu Lys Tyr
        35                  40                  45

Gly Tyr Ile Glu Met Gln Gly Asn Glu Thr Phe Lys Leu Ala Val Arg
    50                  55                  60

Glu Leu Ser Asn Val Val Glu Glu Thr Leu Leu Ala Asn Asn Leu Asp
65                  70                  75                  80

Lys Lys Asp Leu Asp Trp Leu Val Val Val Val Leu Val Val
                85                  90
```

<210> SEQ ID NO 80
<211> LENGTH: 195
<212> TYPE: DNA
<213> ORGANISM: Artificial
<220> FEATURE:
<223> OTHER INFORMATION: clone BGF35 H. influenzae insertion

<400> SEQUENCE: 80

```
caaggacgac gacgacaagg cttatcaatc aatcagtggt tagaaaaata tggctatatc     60

gagatgcaag gtaacgaaac gttcaaattg gcagttcgtg aactttcaaa tgtggtggaa    120

gaaacacttt tagccaataa tttagataaa aaagatttag actggcttgt cgtcgtcgtc    180

cttgtagtct gacct                                                     195
```

<210> SEQ ID NO 81
<211> LENGTH: 63
<212> TYPE: PRT
<213> ORGANISM: Artificial
<220> FEATURE:
<223> OTHER INFORMATION: SCL-E47 antagonist encoded by clone BGF35 H. influenzae insertion

<400> SEQUENCE: 81

```
Gln Gly Arg Arg Arg Gln Gly Leu Ser Ile Asn Gln Trp Leu Glu Lys
1               5                   10                  15

Tyr Gly Tyr Ile Glu Met Gln Gly Asn Glu Thr Phe Lys Leu Ala Val
            20                  25                  30

Arg Glu Leu Ser Asn Val Val Glu Glu Thr Leu Leu Ala Asn Asn Leu
        35                  40                  45

Asp Lys Lys Asp Leu Asp Trp Leu Val Val Val Val Leu Val Val
    50                  55                  60
```

<210> SEQ ID NO 82
<211> LENGTH: 10
<212> TYPE: PRT
<213> ORGANISM: Artificial
<220> FEATURE:
<223> OTHER INFORMATION: 2c7pan8 mimotope

<400> SEQUENCE: 82

```
Gly Asp Pro Asn Ser Ser Thr Ser Pro Arg
1               5                   10
```

<210> SEQ ID NO 83
<211> LENGTH: 6
<212> TYPE: PRT
<213> ORGANISM: Artificial
<220> FEATURE:
<223> OTHER INFORMATION: 2c7pan8 mimotope without phage sequence -continued

<400> SEQUENCE: 83

Ser Ser Thr Ser Pro Arg
1 5

<210> SEQ ID NO 84
<211> LENGTH: 10
<212> TYPE: PRT
<213> ORGANISM: Artificial
<220> FEATURE:
<223> OTHER INFORMATION: 2c7pan9 mimotope

<400> SEQUENCE: 84

Gly Asp Pro Asn Ser Ala Ser Gly Thr Ala
1 5 10

<210> SEQ ID NO 85
<211> LENGTH: 6
<212> TYPE: PRT
<213> ORGANISM: Artificial
<220> FEATURE:
<223> OTHER INFORMATION: 2c7pan9 mimotope without phage sequence

<400> SEQUENCE: 85

Ser Ala Ser Gly Thr Ala
1 5

<210> SEQ ID NO 86
<211> LENGTH: 14
<212> TYPE: PRT
<213> ORGANISM: Artificial
<220> FEATURE:
<223> OTHER INFORMATION: 2c7pan14 mimotope

<400> SEQUENCE: 86

Gly Asp Pro Asn Ser Arg Gly Lys Ser Arg Glu Tyr Leu Ser
1 5 10

<210> SEQ ID NO 87
<211> LENGTH: 10
<212> TYPE: PRT
<213> ORGANISM: Artificial
<220> FEATURE:
<223> OTHER INFORMATION: 2c7pan14 mimotope without phage sequence

<400> SEQUENCE: 87

Ser Arg Gly Lys Ser Arg Glu Tyr Leu Ser
1 5 10

<210> SEQ ID NO 88
<211> LENGTH: 7
<212> TYPE: PRT
<213> ORGANISM: Artificial
<220> FEATURE:
<223> OTHER INFORMATION: 2c7pan26 mimotope

<400> SEQUENCE: 88

Gly Asp Pro Arg Thr His Arg
1 5

<210> SEQ ID NO 89
<211> LENGTH: 4
<212> TYPE: PRT
<213> ORGANISM: Artificial
<220> FEATURE:
<223> OTHER INFORMATION: 2c7pan26 mimotope without phage sequence -continued

<400> SEQUENCE: 89

Arg Thr His Arg
1

<210> SEQ ID NO 90
<211> LENGTH: 22
<212> TYPE: PRT
<213> ORGANISM: Artificial
<220> FEATURE:
<223> OTHER INFORMATION: 2c7pan42 mimotope

<400> SEQUENCE: 90

Gly Asp Pro Asn Ser Ser Ser Val Asp Lys Leu Gly Tyr Trp Arg Val
1 5 10 15

Thr Glu Ser Ser Asn Glu
20

<210> SEQ ID NO 91
<211> LENGTH: 18
<212> TYPE: PRT
<213> ORGANISM: Artificial
<220> FEATURE:
<223> OTHER INFORMATION: 2c7pan42 mimotope without phage sequence

<400> SEQUENCE: 91

Ser Ser Ser Val Asp Lys Leu Gly Tyr Trp Arg Val Thr Glu Ser Ser
1 5 10 15

Asn Glu

<210> SEQ ID NO 92
<211> LENGTH: 5562
<212> TYPE: DNA
<213> ORGANISM: Artificial
<220> FEATURE:
<223> OTHER INFORMATION: pYTB vector

<400> SEQUENCE: 92
ctagcgattt tggtcatgag atcagatcaa cttcttttct ttttttttct tttctctctc 60
ccccgttgtt gtctcaccat atccgcaatg acaaaaaaat gatggaagac actaaaggaa 120
aaaattaacg acaaagacag caccaacaga tgtcgttgtt ccagagctga tgaggggtat 180
ctcgaagcac acgaaacttt ttccttcctt cattcacgca cactactctc taatgagcaa 240
cggtatacgg ccttccttcc agttacttga atttgaaata aaaaaaagtt tgctgtcttg 300
ctatcaagta taaatagacc tgcaattatt aatcttttgt ttcctcgtca ttgttctcgt 360
tccctttctt ccttgtttct ttttctgcac aatatttcaa gctataccaa gcatacaatc 420
aactccaagc ttccccggat cggactacta gcagctgtaa tacgactcac tatagggaat 480
attaagctca ccatgggtaa gcctatccct aaccctctcc tcggtctcga ttctacacaa 540
gctatgggtg ctcctccaaa aaagaagaga aaggtagctg aattcgagct cagatctcag 600
ctgggcccgg taccaattga tgcatcgata ccggtactag tcggaccgca tatgcccggg 660
cgtaccgcgg ccgctcgagg catgcatcta gagggccgca tcatgtaatt agttatgtca 720
cgcttacatt cacgccctcc ccccacatcc gctctaaccg aaaaggaagg agttagacaa 780
cctgaagtct aggtccctat ttattttttt atagttatgt tagtattaag aacgttattt 840
atatttcaaa tttttctttt ttttctgtac agacgcgtgt acgcatgtaa cattatactg 900
aaaaccttgc ttgagaaggt tttgggacgc tcgaaggctt taatttgcgg ccctgcatta 960
atgaatcggc caacgcgcgg ggagaggcgg tttgcgtatt gggcgctctt ccgcttcctc 1020

-continued

```
gctcactgac tcgctgcgct cggtcgttcg gctgcggcga gcggtatcag ctcactcaaa   1080
ggcggtaata cggttatcca cagaatcagg ggataacgca ggaaagaaca tgtgagcaaa   1140
aggccagcaa aagcccagga accgtaaaaa ggccgcgttg ctggcgtttt tccataggct   1200
ccgcccccct gacgagcatc acaaaaatcg acgctcaagt cagaggtggc gaaacccgac   1260
aggactataa agataccagg cgtttccccc tggaagctcc ctcgtgcgct ctcctgttcc   1320
gaccctgccg cttaccggat acctgtccgc ctttctccct tcgggaagcg tggcgctttc   1380
tcatagctca cgctgtaggt atctcagttc ggtgtaggtc gttcgctcca agctgggctg   1440
tgtgcacgaa ccccccgttc agcccgaccg ctgcgcctta tccggtaact atcgtcttga   1500
gtccaacccg gtaagacacg acttatcgcc actggcagca gccactggta acaggattag   1560
cagagcgagg tatgtaggcg gtgctacaga gttcttgaag tggtggccta actacggcta   1620
cactagaagg acagtatttg gtatctgcgc tctgctgaag ccagttacct tcggaaaaag   1680
agttggtagc tcttgatccg gcaaacaaac caccgctggt agcggtggtt tttttgtttg   1740
caagcagcag attacgcgca gaaaaaaagg atctcaagaa gatcctttga tcttttctac   1800
ggggtctgac gctcagtgga acgaaaactc acgttaaggg attttggtca tgagattatc   1860
aaaaaggatc ttcacctaga tccttttaaa ttaaaaatga agttttaaat caatctaaag   1920
tatatatgag taaacttggt ctgacagtta ccaatgctta atcagtgagg cacctatctc   1980
agcgatctgt ctatttcgtt catccatagt tgcctgactc cccgtcgtgt agataactac   2040
gatacgggag cgcttaccat ctggccccag tgctgcaatg ataccgcgag acccacgctc   2100
accggctcca gatttatcag caataaacca gccagccgga agggccgagc gcagaagtgg   2160
tcctgcaact ttatccgcct ccatccagtc tattaattgt tgccgggaag ctagagtaag   2220
tagttcgcca gttaatagtt tgcgcaacgt tgttgccatt gctacaggca tcgtggtgtc   2280
acgctcgtcg tttggtatgg cttcattcag ctccggttcc caacgatcaa ggcgagttac   2340
atgatccccc atgttgtgca aaaaagcggt tagctccttc ggtcctccga tcgttgtcag   2400
aagtaagttg gccgcagtgt tatcactcat ggttatggca gcactgcata attctcttac   2460
tgtcatgcca tccgtaagat gcttttctgt gactggtgag tactcaacca agtcattctg   2520
agaatagtgt atgcggcgac cgagttgctc ttgcccggcg tcaacacggg ataataccgc   2580
gccacatagc agaactttaa aagtgctcat cattggaaaa cgttcttcgg ggcgaaaact   2640
ctcaaggatc ttaccgctgt tgagatccag ttcgatgtaa cccactcgtg cacccaactg   2700
atcttcagca tcttttactt tcaccagcgt ttctgggtga gcaaaaacag gaaggcaaaa   2760
tgccgcaaaa aagggaataa gggcgacacg gaaatgttga atactcatac tcttcctttt   2820
tcaatattat tgaagcattt atcagggtta ttgtctcatg agcggataca tatttgaatg   2880
tatttagaaa aataaacaaa taggggttcc gcgcacattt ccccgaaaag tgccacctga   2940
cgtctaagaa accattatta tcatgacatt aacctataaa aataggcgta tcacgaggcc   3000
ctttcgtctt caagaaattc ggtcgaaaaa agaaaaggag agggccaaga gggagggcat   3060
tggtgactat tgagcacgtg agtatacgtg attaagcaca caaaggcagc ttggagtatg   3120
tctgttatta atttcacagg tagttctggt ccattggtga aagtttgcgg cttgcagagc   3180
acagaggccg cagaatgtgc tctagattcc gatgctgact tgctgggtat tatatgtgtg   3240
cccaatagaa agagaacaat tgacccggtt attgcaagga aaatttcaag tcttgtaaaa   3300
gcatataaaa atagttcagg cactccgaaa tacttggttg gcgtgtttcg taatcaacct   3360
```

-continued

```
aaggaggatg ttttggctct ggtcaatgat tacggcattg atatcgtcca actgcacgga   3420
gatgagtcgt ggcaagaata ccaagagttc ctcggtttgc cagttattaa aagactcgta   3480
tttccaaaag actgcaacat actactcagt gcagcttcac agaaacctca ttcgtttatt   3540
cccttgtttg attcagaagc aggtgggaca ggtgaacttt tggattggaa ctcgatttct   3600
gactgggttg gaaggcaaga gagccccgag agcttacatt ttatgttagc tggtggactg   3660
acgccagaaa atgttggtga tgcgcttaga ttaaatggcg ttattggtgt tgatgtaagc   3720
ggaggtgtgg agacaaatgg tgtaaaagac tctaacaaaa tagcaaattt cgtcaaaaat   3780
gctaagaaat aggttattac tgagtagtat ttatttaagt attgtttgtg cacttgcctg   3840
cagcttctca atgatattcg aatacgcttt gaggagatac agcctaatat ccgacaaact   3900
gttttacaga tttacgatcg tacttgttac ccatcattga attttgaaca tccgaacctg   3960
ggagttttcc ctgaaacaga tagtatattt gaacctgtat aataatatat agtctagcgc   4020
tttacggaag acaatgtatg tatttcggtt cctggagaaa ctattgcatc tattgcatag   4080
gtaatcttgc acgtcgcatc cccggttcat tttctgcgtt tccatcttgc acttcaatag   4140
catatctttg ttaacgaagc atctgtgctt cattttgtag aacaaaaatg caacgcgaga   4200
gcgctaattt ttcaaacaaa gaatctgagc tgcattttta cagaacagaa atgcaacgcg   4260
aaagcgctat tttaccaacg aagaatctgt gcttcatttt tgtaaaacaa aaatgcaacg   4320
cgagagcgct aatttttcaa acaaagaatc tgagctgcat tttacagaa cagaaatgca   4380
acgcgagagc gctattttac caacaaagaa tctatacttc tttttgttc tacaaaaatg   4440
catcccgaga gcgctatttt tctaacaaag catcttagat tacttttttt ctcctttgtg   4500
cgctctataa tgcagtctct tgataacttt ttgcactgta ggtccgttaa ggttagaaga   4560
aggctacttt ggtgtctatt ttctcttcca taaaaaaagc ctgactccac ttcccgcgtt   4620
tactgattac tagcgaagct gcgggtgcat tttttcaaga taaaggcatc cccgattata   4680
ttctataccg atgtggattg cgcatacttt gtgaacagaa agtgatagcg ttgatgattc   4740
ttcattggtc agaaaattat gaacggtttc ttctattttg tctctatata ctacgtatag   4800
gaaatgttta cattttcgta ttgttttcga ttcactctat gaatagttct tactacaatt   4860
tttttgtcta aagagtaata ctagagataa acataaaaaa tgtagaggtc gagtttagat   4920
gcaagttcaa ggagcgaaag gtggatgggt aggttatata gggatatagc acagagatat   4980
atagcaaaga gatacttttg agcaatgttt gtggaagcgg tattcgcaat gggaagctcc   5040
accccggttg ataatcagaa aagccccaaa aacaggaaga ttgtataagc aaatatttaa   5100
attgtaaacg ttaatatttt gttaaaattc gcgttaaatt tttgttaaat cagctcattt   5160
tttaacgaat agcccgaaat cggcaaaatc ccttataaat caaaagaata gaccgagata   5220
gggttgagtg ttgttccagt ttccaacaag agtccactat taaagaacgt ggactccaac   5280
gtcaaagggc gaaaaagggt ctatcagggc gatggcccac tacgtgaacc atcaccctaa   5340
tcaagttttt tggggtcgag gtgccgtaaa gcagtaaatc ggaagggtaa acggatgccc   5400
ccatttagag cttgacgggg aaagccggcg aacgtggcga gaaaggaagg gaagaaagcg   5460
aaaggagcgg gggctagggc ggtgggaagt gtaggggtca cgctgggcgt aaccaccaca   5520
cccgccgcgc ttaatggggc gctacagggc gcgtggggat ga                       5562
```

<210> SEQ ID NO 93
<211> LENGTH: 248
<212> TYPE: DNA
<213> ORGANISM: Artificial

-continued

```
<220> FEATURE:
<223> OTHER INFORMATION: clone 4 encoding JUN dimerization inhibitory
      peptide

<400> SEQUENCE: 93

aggtcagact acaaggacga cgacgacaag gcttatcaat ccatgttctg tgaaagccgc      60

ttcctggaca atgcatctgc ccctgccatg aggaatgcaa agaggcgttc cgaagagcgg     120

gtcctgtgta acctgacagt tcatagaaaa cacattttgc acaagatcac aagtgatgac     180

ctcttccgga cggccttctg cagaaatccg tttatctttt atggccacaa gatgatgcgc     240

atgattga                                                              248


<210> SEQ ID NO 94
<211> LENGTH: 83
<212> TYPE: PRT
<213> ORGANISM: Artificial
<220> FEATURE:
<223> OTHER INFORMATION: clone 4 JUN dimerization inhibitory peptide
      with phage sequence

<400> SEQUENCE: 94

Arg Ser Asp Tyr Lys Asp Asp Asp Asp Lys Ala Tyr Gln Ser Met Phe
1               5                   10                  15

Cys Glu Ser Arg Phe Leu Asp Asn Ala Ser Ala Pro Ala Met Arg Asn
            20                  25                  30

Ala Lys Arg Arg Ser Glu Glu Arg Val Leu Cys Asn Leu Thr Val His
        35                  40                  45

Arg Lys His Ile Leu His Lys Ile Thr Ser Asp Asp Leu Phe Arg Thr
    50                  55                  60

Ala Phe Cys Arg Asn Pro Phe Ile Phe Tyr Gly His Lys Met Met Arg
65                  70                  75                  80

Met Ile Asp


<210> SEQ ID NO 95
<211> LENGTH: 73
<212> TYPE: PRT
<213> ORGANISM: Artificial
<220> FEATURE:
<223> OTHER INFORMATION: clone 4 JUN dimerization inhibitory peptide
      without phage sequence

<400> SEQUENCE: 95

Ala Tyr Gln Ser Met Phe Cys Glu Ser Arg Phe Leu Asp Asn Ala Ser
1               5                   10                  15

Ala Pro Ala Met Arg Asn Ala Lys Arg Arg Ser Glu Glu Arg Val Leu
            20                  25                  30

Cys Asn Leu Thr Val His Arg Lys His Ile Leu His Lys Ile Thr Ser
        35                  40                  45

Asp Asp Leu Phe Arg Thr Ala Phe Cys Arg Asn Pro Phe Ile Phe Tyr
    50                  55                  60

Gly His Lys Met Met Arg Met Ile Asp
65                  70


<210> SEQ ID NO 96
<211> LENGTH: 38
<212> TYPE: DNA
<213> ORGANISM: Artificial
<220> FEATURE:
<223> OTHER INFORMATION: clone 5 encoding JUN dimerization inhibitory
      peptide with phage sequence
```

-continued

<400> SEQUENCE: 96
aggtcagact acaaggacga cgacgacaag gcttatca 38

<210> SEQ ID NO 97
<211> LENGTH: 13
<212> TYPE: PRT
<213> ORGANISM: Artificial
<220> FEATURE:
<223> OTHER INFORMATION: clone 5 JUN dimerization inhibitory peptide with phage sequence

<400> SEQUENCE: 97

Arg Ser Asp Tyr Lys Asp Asp Asp Asp Lys Ala Tyr Gln
1 5 10

<210> SEQ ID NO 98
<211> LENGTH: 3
<212> TYPE: PRT
<213> ORGANISM: Artificial
<220> FEATURE:
<223> OTHER INFORMATION: clone 5 JUN dimerization inhibitory peptide without phage sequence

<400> SEQUENCE: 98

Ala Tyr Gln
1

<210> SEQ ID NO 99
<211> LENGTH: 120
<212> TYPE: DNA
<213> ORGANISM: Artificial
<220> FEATURE:
<223> OTHER INFORMATION: clone 8 encoding JUN dimerization inhibitory peptide with phage sequence

<400> SEQUENCE: 99
aggtcagact acaaggacga cgacgacaag gcttatcaat caatcatagc taatgaagag 60
gagagggaga aaaattttgc atccagcaaa aaggacggat cctataccga tctcttgtga 120

<210> SEQ ID NO 100
<211> LENGTH: 39
<212> TYPE: PRT
<213> ORGANISM: Artificial
<220> FEATURE:
<223> OTHER INFORMATION: clone 8 JUN dimerization inhibitory peptide with phage sequence

<400> SEQUENCE: 100

Arg Ser Asp Tyr Lys Asp Asp Asp Asp Lys Ala Tyr Gln Ser Ile Ile
1 5 10 15

Ala Asn Glu Glu Glu Arg Glu Lys Asn Phe Ala Ser Ser Lys Lys Asp
20 25 30

Gly Ser Tyr Thr Asp Leu Leu
35

<210> SEQ ID NO 101
<211> LENGTH: 29
<212> TYPE: PRT
<213> ORGANISM: Artificial
<220> FEATURE:
<223> OTHER INFORMATION: clone 8 JUN dimerization inhibitory peptide without phage sequence

<400> SEQUENCE: 101

Ala Tyr Gln Ser Ile Ile Ala Asn Glu Glu Glu Arg Glu Lys Asn Phe

-continued

```
1               5                   10                  15

Ala Ser Ser Lys Lys Asp Gly Ser Tyr Thr Asp Leu Leu
            20                  25


<210> SEQ ID NO 102
<211> LENGTH: 123
<212> TYPE: DNA
<213> ORGANISM: Artificial
<220> FEATURE:
<223> OTHER INFORMATION: clone 12 encoding JUN dimerization inhibitory
      peptide with phage sequence
<220> FEATURE:
<221> NAME/KEY: misc_feature
<222> LOCATION: (49)..(50)
<223> OTHER INFORMATION: N at nucleotide position 49 or 50 is any
      nucleotide residue

<400> SEQUENCE: 102

aggtcagact acaaggacga cgacgacaag gcttatcaag agtccaccnn agcgctggtg      60

gaaggtggcg cggatctgat cctgattgaa accgttcttg tcgtcgtcgt ccttgtagtc     120

tga                                                                   123


<210> SEQ ID NO 103
<211> LENGTH: 40
<212> TYPE: PRT
<213> ORGANISM: Artificial
<220> FEATURE:
<223> OTHER INFORMATION: clone 12 JUN dimerization inhibitory peptide
      with phage sequence
<220> FEATURE:
<221> NAME/KEY: MISC_FEATURE
<222> LOCATION: (17)..(17)
<223> OTHER INFORMATION: Xaa at position 17 is any amino acid residue

<400> SEQUENCE: 103

Arg Ser Asp Tyr Lys Asp Asp Asp Asp Lys Ala Tyr Gln Glu Ser Thr
1               5                   10                  15

Xaa Ala Leu Val Glu Gly Gly Ala Asp Leu Ile Leu Ile Glu Thr Val
            20                  25                  30

Leu Val Val Val Val Leu Val Val
        35                  40


<210> SEQ ID NO 104
<211> LENGTH: 30
<212> TYPE: PRT
<213> ORGANISM: Artificial
<220> FEATURE:
<223> OTHER INFORMATION: clone 12 JUN dimerization inhibitory peptide
      without phage sequence
<220> FEATURE:
<221> NAME/KEY: MISC_FEATURE
<222> LOCATION: (7)..(7)
<223> OTHER INFORMATION: Xaa at position 7 is any amino acid

<400> SEQUENCE: 104

Ala Tyr Gln Glu Ser Thr Xaa Ala Leu Val Glu Gly Gly Ala Asp Leu
1               5                   10                  15

Ile Leu Ile Glu Thr Val Leu Val Val Val Val Leu Val Val
            20                  25                  30


<210> SEQ ID NO 105
<211> LENGTH: 297
<212> TYPE: DNA
<213> ORGANISM: Artificial
<220> FEATURE:
<223> OTHER INFORMATION: clone 15 encoding JUN dimerization inhibitory
```

-continued

```
      peptide with phage sequence
<220> FEATURE:
<221> NAME/KEY: misc_feature
<222> LOCATION: (247)..(247)
<223> OTHER INFORMATION: N at position 247 is any nucleotide residue

<400> SEQUENCE: 105

aggtcagact acaaggacga cgacgacaag acttatcaat caatcaatgg cccagaaaat     60

aaagtgaaaa tgtatttttt gaatgattta aatttctcta gacgcgatgc tggatttaaa    120

gcaagaaaag atgcacggga cattgcttca gattatgaaa acatttctgt tgttaacatt    180

cctctatggg gtggagtagt ccagagaatt attagttctg ttaagcttag tacatttctc    240

tgcggtnttg aaaataaaga tgttttaatt ttcaatttcc cgatggccaa accattt       297


<210> SEQ ID NO 106
<211> LENGTH: 99
<212> TYPE: PRT
<213> ORGANISM: Artificial
<220> FEATURE:
<223> OTHER INFORMATION: clone 15 JUN dimerization inhibitory peptide
      with phage sequence
<220> FEATURE:
<221> NAME/KEY: MISC_FEATURE
<222> LOCATION: (83)..(83)
<223> OTHER INFORMATION: Xaa at position 83 is any amino acid

<400> SEQUENCE: 106

Arg Ser Asp Tyr Lys Asp Asp Asp Asp Lys Thr Tyr Gln Ser Ile Asn
1               5                   10                  15

Gly Pro Glu Asn Lys Val Lys Met Tyr Phe Leu Asn Asp Leu Asn Phe
            20                  25                  30

Ser Arg Arg Asp Ala Gly Phe Lys Ala Arg Lys Asp Ala Arg Asp Ile
        35                  40                  45

Ala Ser Asp Tyr Glu Asn Ile Ser Val Val Asn Ile Pro Leu Trp Gly
    50                  55                  60

Gly Val Val Gln Arg Ile Ile Ser Ser Val Lys Leu Ser Thr Phe Leu
65                  70                  75                  80

Cys Gly Xaa Glu Asn Lys Asp Val Leu Ile Phe Asn Phe Pro Met Ala
                85                  90                  95

Lys Pro Phe


<210> SEQ ID NO 107
<211> LENGTH: 89
<212> TYPE: PRT
<213> ORGANISM: Artificial
<220> FEATURE:
<223> OTHER INFORMATION: clone 15 JUN dimerization inhibitory peptide
      without phage sequence
<220> FEATURE:
<221> NAME/KEY: MISC_FEATURE
<222> LOCATION: (73)..(73)
<223> OTHER INFORMATION: Xaa at position 73 is any amino acid

<400> SEQUENCE: 107

Thr Tyr Gln Ser Ile Asn Gly Pro Glu Asn Lys Val Lys Met Tyr Phe
1               5                   10                  15

Leu Asn Asp Leu Asn Phe Ser Arg Arg Asp Ala Gly Phe Lys Ala Arg
            20                  25                  30

Lys Asp Ala Arg Asp Ile Ala Ser Asp Tyr Glu Asn Ile Ser Val Val
        35                  40                  45

Asn Ile Pro Leu Trp Gly Gly Val Val Gln Arg Ile Ile Ser Ser Val
    50                  55                  60
```

-continued

Lys Leu Ser Thr Phe Leu Cys Gly Xaa Glu Asn Lys Asp Val Leu Ile
65 70 75 80

Phe Asn Phe Pro Met Ala Lys Pro Phe
85

<210> SEQ ID NO 108
<211> LENGTH: 63
<212> TYPE: DNA
<213> ORGANISM: Artificial
<220> FEATURE:
<223> OTHER INFORMATION: clone 20 encoding JUN dimerization inhibitory peptide with phage sequence

<400> SEQUENCE: 108
aggtcagact acaaggacga cgacgacaag atttattcat caattctatg ggggacaaaa 60
tgg 63

<210> SEQ ID NO 109
<211> LENGTH: 29
<212> TYPE: PRT
<213> ORGANISM: Artificial
<220> FEATURE:
<223> OTHER INFORMATION: clone 20 JUN dimerization inhibitory peptide with phage sequence

<400> SEQUENCE: 109

Arg Ser Asp Tyr Lys Asp Asp Asp Asp Lys Ile Tyr Ser Ser Ile Leu
1 5 10 15

Trp Gly Thr Lys Trp Cys Val Leu Leu Val Ile Thr Pro
20 25

<210> SEQ ID NO 110
<211> LENGTH: 19
<212> TYPE: PRT
<213> ORGANISM: Artificial
<220> FEATURE:
<223> OTHER INFORMATION: clone 20 JUN dimerization inhibitory peptide without phage sequence

<400> SEQUENCE: 110

Ile Tyr Ser Ser Ile Leu Trp Gly Thr Lys Trp Cys Val Leu Leu Val
1 5 10 15

Ile Thr Pro

<210> SEQ ID NO 111
<211> LENGTH: 105
<212> TYPE: DNA
<213> ORGANISM: Artificial
<220> FEATURE:
<223> OTHER INFORMATION: clone 21 encoding JUN dimerization inhibitory peptide with phage sequence
<220> FEATURE:
<221> NAME/KEY: misc_feature
<222> LOCATION: (53)..(53)
<223> OTHER INFORMATION: N at position 52 is any nucleotide residue

<400> SEQUENCE: 111
aggtcagact acaaggacga cgacgacaag atcattattt atattttcct tancatctct 60
aatagcatca aaaacatctt cgacaatatg ggtaaaatca gataa 105

<210> SEQ ID NO 112
<211> LENGTH: 34
<212> TYPE: PRT
<213> ORGANISM: Artificial

-continued

<220> FEATURE:
<223> OTHER INFORMATION: clone 21 JUN dimerization inhibitory peptide
with phage sequence
<220> FEATURE:
<221> NAME/KEY: MISC_FEATURE
<222> LOCATION: (18)..(18)
<223> OTHER INFORMATION: Xaa at position 18 is any amino acid

<400> SEQUENCE: 112

```
Arg Ser Asp Tyr Lys Asp Asp Asp Asp Lys Ile Ile Ile Tyr Ile Phe
1               5                   10                  15

Leu Xaa Ile Ser Asn Ser Ile Lys Asn Ile Phe Asp Asn Met Gly Lys
            20                  25                  30

Ile Arg
```

<210> SEQ ID NO 113
<211> LENGTH: 24
<212> TYPE: PRT
<213> ORGANISM: Artificial
<220> FEATURE:
<223> OTHER INFORMATION: clone 21 JUN dimerization inhibitory peptide
without phage sequence
<220> FEATURE:
<221> NAME/KEY: MISC_FEATURE
<222> LOCATION: (8)..(8)
<223> OTHER INFORMATION: Xaa at position 8 is any amino acid residue

<400> SEQUENCE: 113

```
Ile Ile Ile Tyr Ile Phe Leu Xaa Ile Ser Asn Ser Ile Lys Asn Ile
1               5                   10                  15

Phe Asp Asn Met Gly Lys Ile Arg
            20
```

<210> SEQ ID NO 114
<211> LENGTH: 156
<212> TYPE: DNA
<213> ORGANISM: Artificial
<220> FEATURE:
<223> OTHER INFORMATION: clone 22 encoding JUN dimerization inhibitory
peptide with phage sequence
<220> FEATURE:
<221> NAME/KEY: misc_feature
<222> LOCATION: (49)..(51)
<223> OTHER INFORMATION: N at any one of positions 49 to 51 is any
nucleotide

<400> SEQUENCE: 114

```
aggtcagact acaaggacga cgacgacaag aaggactcca tacggcggnn ncccgagaat      60

atttcctcgc aggaagtcga ggccgtcctc atgtcgcatc ccgaagtcgt caatgccgcg     120

gtctaccccg tacgcggcga tctgcctggt gattga                               156
```

<210> SEQ ID NO 115
<211> LENGTH: 51
<212> TYPE: PRT
<213> ORGANISM: Artificial
<220> FEATURE:
<223> OTHER INFORMATION: clone 24 JUN dimerization inhibitory peptide
with phage sequence
<220> FEATURE:
<221> NAME/KEY: MISC_FEATURE
<222> LOCATION: (17)..(17)
<223> OTHER INFORMATION: Xaa at position 17 is any amino acid

<400> SEQUENCE: 115

```
Arg Ser Asp Tyr Lys Asp Asp Asp Asp Lys Lys Asp Ser Ile Arg Arg
1               5                   10                  15
```

-continued

```
Xaa Pro Glu Asn Ile Ser Ser Gln Glu Val Glu Ala Val Leu Met Ser
            20                  25                  30

His Pro Glu Val Val Asn Ala Ala Val Tyr Pro Val Arg Gly Asp Leu
        35                  40                  45

Pro Gly Asp
    50


<210> SEQ ID NO 116
<211> LENGTH: 41
<212> TYPE: PRT
<213> ORGANISM: Artificial
<220> FEATURE:
<223> OTHER INFORMATION: clone 22 JUN dimerization inhibitory peptide
      without phage sequence
<220> FEATURE:
<221> NAME/KEY: MISC_FEATURE
<222> LOCATION: (7)..(7)
<223> OTHER INFORMATION: Xaa at position 7 is any amino acid

<400> SEQUENCE: 116

Lys Asp Ser Ile Arg Arg Xaa Pro Glu Asn Ile Ser Ser Gln Glu Val
1               5                   10                  15

Glu Ala Val Leu Met Ser His Pro Glu Val Val Asn Ala Ala Val Tyr
            20                  25                  30

Pro Val Arg Gly Asp Leu Pro Gly Asp
        35                  40


<210> SEQ ID NO 117
<211> LENGTH: 111
<212> TYPE: DNA
<213> ORGANISM: Artificial
<220> FEATURE:
<223> OTHER INFORMATION: clone 24 encoding JUN dimerization inhibitory
      peptide with phage sequence

<400> SEQUENCE: 117

aggtcagact acaaggacga cgacgacaag ctatatcaat cactactcac tgctaccaaa     60

gaattgcttt ttgtcgcgcc tgtagcaaaa gcattcacat cgtgtgattg a             111


<210> SEQ ID NO 118
<211> LENGTH: 36
<212> TYPE: PRT
<213> ORGANISM: Artificial
<220> FEATURE:
<223> OTHER INFORMATION: clone 24 JUN dimerization inhibitory peptide
      with phage sequence

<400> SEQUENCE: 118

Arg Ser Asp Tyr Lys Asp Asp Asp Asp Lys Leu Tyr Gln Ser Leu Leu
1               5                   10                  15

Thr Ala Thr Lys Glu Leu Leu Phe Val Ala Pro Val Ala Lys Ala Phe
            20                  25                  30

Thr Ser Cys Asp
        35


<210> SEQ ID NO 119
<211> LENGTH: 26
<212> TYPE: PRT
<213> ORGANISM: Artificial
<220> FEATURE:
<223> OTHER INFORMATION: clone 24 JUN dimerization inhibitory peptide
      without phage sequence

<400> SEQUENCE: 119
```

-continued

```
Leu Tyr Gln Ser Leu Leu Thr Ala Thr Lys Glu Leu Leu Phe Val Ala
1               5                   10                  15

Pro Val Ala Lys Ala Phe Thr Ser Cys Asp
            20                  25


<210> SEQ ID NO 120
<211> LENGTH: 186
<212> TYPE: DNA
<213> ORGANISM: Artificial
<220> FEATURE:
<223> OTHER INFORMATION: clone 30 encoding JUN dimerization inhibitory
      peptide with phage sequence
<220> FEATURE:
<221> NAME/KEY: misc_feature
<222> LOCATION: (50)..(50)
<223> OTHER INFORMATION: N at position 50 is any nucleotide residue

<400> SEQUENCE: 120

aggtcagact acaaggacga cgacgacaag gtctacgcct acttcggtan caccggcgat      60

gttgtcgaag taggcgtaga ccttgtaggt atcgccggcg ttgcccacgc tcaggccgct     120

gacccgcagg gccagcagca acagggccag caggccggcc aggaggaaca ggccgacacc     180

gattga                                                                186


<210> SEQ ID NO 121
<211> LENGTH: 61
<212> TYPE: PRT
<213> ORGANISM: Artificial
<220> FEATURE:
<223> OTHER INFORMATION: clone 30 JUN dimerization inhibitory peptide
      with phage sequence
<220> FEATURE:
<221> NAME/KEY: MISC_FEATURE
<222> LOCATION: (17)..(17)
<223> OTHER INFORMATION: Xaa at position 17 is any amino acid

<400> SEQUENCE: 121

Arg Ser Asp Tyr Lys Asp Asp Asp Asp Lys Val Tyr Ala Tyr Phe Gly
1               5                   10                  15

Xaa Thr Gly Asp Val Val Glu Val Gly Val Asp Leu Val Gly Ile Ala
            20                  25                  30

Gly Val Ala His Ala Gln Ala Ala Asp Pro Gln Gly Gln Gln Gln Gln
        35                  40                  45

Gly Gln Gln Ala Gly Gln Glu Glu Gln Ala Asp Thr Asp
    50                  55                  60


<210> SEQ ID NO 122
<211> LENGTH: 51
<212> TYPE: PRT
<213> ORGANISM: Artificial
<220> FEATURE:
<223> OTHER INFORMATION: clone 30 JUN dimerization inhibitory peptide
      without phage sequence
<220> FEATURE:
<221> NAME/KEY: MISC_FEATURE
<222> LOCATION: (7)..(7)
<223> OTHER INFORMATION: Xaa at position 7 is any amino acid

<400> SEQUENCE: 122

Val Tyr Ala Tyr Phe Gly Xaa Thr Gly Asp Val Val Glu Val Gly Val
1               5                   10                  15

Asp Leu Val Gly Ile Ala Gly Val Ala His Ala Gln Ala Ala Asp Pro
            20                  25                  30

Gln Gly Gln Gln Gln Gln Gly Gln Gln Ala Gly Gln Glu Glu Gln Ala
        35                  40                  45
```

-continued

```
Asp Thr Asp
    50


<210> SEQ ID NO 123
<211> LENGTH: 66
<212> TYPE: DNA
<213> ORGANISM: Artificial
<220> FEATURE:
<223> OTHER INFORMATION: clone 32 encoding JUN dimerization inhibitory
      peptide with phage sequence

<400> SEQUENCE: 123

aggtcagact acaaggacga cgacgacaat accccccact cctccgatgg ccacaataat     60

ccctaa                                                                66


<210> SEQ ID NO 124
<211> LENGTH: 21
<212> TYPE: PRT
<213> ORGANISM: Artificial
<220> FEATURE:
<223> OTHER INFORMATION: clone 32 JUN dimerization inhibitory peptide
      with phage sequence

<400> SEQUENCE: 124

Arg Ser Asp Tyr Lys Asp Asp Asp Asp Asn Thr Pro His Ser Ser Asp
1               5                   10                  15

Gly His Asn Asn Pro
            20


<210> SEQ ID NO 125
<211> LENGTH: 11
<212> TYPE: PRT
<213> ORGANISM: Artificial
<220> FEATURE:
<223> OTHER INFORMATION: clone 32 JUN dimerization inhibitory peptide
      without phage sequence

<400> SEQUENCE: 125

Thr Pro His Ser Ser Asp Gly His Asn Asn Pro
1               5                   10


<210> SEQ ID NO 126
<211> LENGTH: 60
<212> TYPE: DNA
<213> ORGANISM: Artificial
<220> FEATURE:
<223> OTHER INFORMATION: clone 33 encoding JUN dimerization inhibitory
      peptide with phage sequence

<400> SEQUENCE: 126

aggtcagact acaaggacga cgacgacaag gcttatcaat caatcaaatg gccaatgtaa     60


<210> SEQ ID NO 127
<211> LENGTH: 19
<212> TYPE: PRT
<213> ORGANISM: Artificial
<220> FEATURE:
<223> OTHER INFORMATION: clone 33 JUN dimerization inhibitory peptide
      with phage sequence

<400> SEQUENCE: 127

Arg Ser Asp Tyr Lys Asp Asp Asp Asp Lys Ala Tyr Gln Ser Ile Lys
1               5                   10                  15

Trp Pro Met
```

-continued

```
<210> SEQ ID NO 128
<211> LENGTH: 9
<212> TYPE: PRT
<213> ORGANISM: Artificial
<220> FEATURE:
<223> OTHER INFORMATION: clone 33 JUN dimerization inhibitory peptide
      without phage sequence

<400> SEQUENCE: 128

Ala Tyr Gln Ser Ile Lys Trp Pro Met
1               5


<210> SEQ ID NO 129
<211> LENGTH: 120
<212> TYPE: DNA
<213> ORGANISM: Artificial
<220> FEATURE:
<223> OTHER INFORMATION: clone 34 encoding JUN dimerization inhibitory
      peptide with phage sequence

<400> SEQUENCE: 129

aggtcagact acaaggacga cgacgacaag gcttatcaat caataaattc gtcaccagta     60

ttgccagaaa atagtcaaga attatcactt cacttaaagc aacacgtaac aaaatcatga    120


<210> SEQ ID NO 130
<211> LENGTH: 39
<212> TYPE: PRT
<213> ORGANISM: Artificial
<220> FEATURE:
<223> OTHER INFORMATION: clone 34 JUN dimerization inhibitory peptide
      with phage sequence

<400> SEQUENCE: 130

Arg Ser Asp Tyr Lys Asp Asp Asp Asp Lys Ala Tyr Gln Ser Ile Asn
1               5                   10                  15

Ser Ser Pro Val Leu Pro Glu Asn Ser Gln Glu Leu Ser Leu His Leu
            20                  25                  30

Lys Gln His Val Thr Lys Ser
        35


<210> SEQ ID NO 131
<211> LENGTH: 29
<212> TYPE: PRT
<213> ORGANISM: Artificial
<220> FEATURE:
<223> OTHER INFORMATION: clone 34 JUN dimerization inhibitory peptide
      without phage sequence

<400> SEQUENCE: 131

Ala Tyr Gln Ser Ile Asn Ser Ser Pro Val Leu Pro Glu Asn Ser Gln
1               5                   10                  15

Glu Leu Ser Leu His Leu Lys Gln His Val Thr Lys Ser
            20                  25


<210> SEQ ID NO 132
<211> LENGTH: 213
<212> TYPE: DNA
<213> ORGANISM: Artificial
<220> FEATURE:
<223> OTHER INFORMATION: clone 35 encoding JUN dimerization inhibitory
      peptide with phage sequence

<400> SEQUENCE: 132

aggtcagact acaaggacga cgacgacaag gcttatcaat caatcaggtc tggagggata     60
```

-continued

```
gagtcgagtt cgaaaaggga gaaggtaagg gtgggaatga ccctaaggac ttacaatcca    120

aacgaaacct tcttctctat tcttcacgag tttgtgaagt tccttaagag gaggagacta    180

cttcaagagg ccatagactt gtcgtcgtcg tcc                                 213


<210> SEQ ID NO 133
<211> LENGTH: 72
<212> TYPE: PRT
<213> ORGANISM: Artificial
<220> FEATURE:
<223> OTHER INFORMATION: clone 35 JUN dimerization inhibitory peptide
      with phage sequence

<400> SEQUENCE: 133

Arg Ser Asp Tyr Lys Asp Asp Asp Asp Lys Ala Tyr Gln Ser Ile Arg
1               5                   10                  15

Ser Gly Gly Ile Glu Ser Ser Ser Lys Arg Glu Lys Val Arg Val Gly
            20                  25                  30

Met Thr Leu Arg Thr Tyr Asn Pro Asn Glu Thr Phe Phe Ser Ile Leu
        35                  40                  45

His Glu Phe Val Lys Phe Leu Lys Arg Arg Arg Leu Leu Gln Glu Ala
    50                  55                  60

Ile Asp Leu Ser Ser Ser Ser Leu
65                  70


<210> SEQ ID NO 134
<211> LENGTH: 62
<212> TYPE: PRT
<213> ORGANISM: Artificial
<220> FEATURE:
<223> OTHER INFORMATION: clone 35 JUN dimerization inhibitory peptide
      without phage sequence

<400> SEQUENCE: 134

Ala Tyr Gln Ser Ile Arg Ser Gly Gly Ile Glu Ser Ser Ser Lys Arg
1               5                   10                  15

Glu Lys Val Arg Val Gly Met Thr Leu Arg Thr Tyr Asn Pro Asn Glu
            20                  25                  30

Thr Phe Phe Ser Ile Leu His Glu Phe Val Lys Phe Leu Lys Arg Arg
        35                  40                  45

Arg Leu Leu Gln Glu Ala Ile Asp Leu Ser Ser Ser Ser Leu
    50                  55                  60


<210> SEQ ID NO 135
<211> LENGTH: 78
<212> TYPE: DNA
<213> ORGANISM: Artificial
<220> FEATURE:
<223> OTHER INFORMATION: clone 36 encoding JUN dimerization inhibitory
      peptide with phage sequence

<400> SEQUENCE: 135

aggtcagact acaaggacga cgacgacaag ggactacaag gacgacgacg acaaggttat     60

caatcaatca agccatga                                                   78


<210> SEQ ID NO 136
<211> LENGTH: 25
<212> TYPE: PRT
<213> ORGANISM: Artificial
<220> FEATURE:
<223> OTHER INFORMATION: clone 36 JUN dimerization inhibitory peptide
      with phage sequence
```

-continued

<400> SEQUENCE: 136

```
Arg Ser Asp Tyr Lys Asp Asp Asp Asp Lys Gly Leu Gln Gly Arg Arg
1               5                   10                  15

Arg Gln Gly Tyr Gln Ser Ile Lys Pro
            20                  25
```

<210> SEQ ID NO 137
<211> LENGTH: 15
<212> TYPE: PRT
<213> ORGANISM: Artificial
<220> FEATURE:
<223> OTHER INFORMATION: clone 36 JUN dimerization inhibitory peptide without phage sequence

<400> SEQUENCE: 137

```
Gly Leu Gln Gly Arg Arg Arg Gln Gly Tyr Gln Ser Ile Lys Pro
1               5                   10                  15
```

<210> SEQ ID NO 138
<211> LENGTH: 69
<212> TYPE: DNA
<213> ORGANISM: Artificial
<220> FEATURE:
<223> OTHER INFORMATION: clone 39 encoding JUN dimerization inhibitory peptide with phage sequence
<220> FEATURE:
<221> NAME/KEY: misc_feature
<222> LOCATION: (35)..(35)
<223> OTHER INFORMATION: N at position 35 is any nucleotide residue
<220> FEATURE:
<221> NAME/KEY: misc_feature
<222> LOCATION: (42)..(42)
<223> OTHER INFORMATION: N at position 42 is any nucleotide residue
<220> FEATURE:
<221> NAME/KEY: misc_feature
<222> LOCATION: (43)..(43)
<223> OTHER INFORMATION: N at position 43 is any nucleotide residue
<220> FEATURE:
<221> NAME/KEY: misc_feature
<222> LOCATION: (65)..(65)
<223> OTHER INFORMATION: N at position 65 is any nucleotide residue

<400> SEQUENCE: 138

```
aggtcagact acaaggacga cgacgacaag ggacnacaag gnngccgaaa cctggccaac     60

agccnctaa                                                             69
```

<210> SEQ ID NO 139
<211> LENGTH: 22
<212> TYPE: PRT
<213> ORGANISM: Artificial
<220> FEATURE:
<223> OTHER INFORMATION: clone 39 JUN dimerization inhibitory peptide with phage sequence
<220> FEATURE:
<221> NAME/KEY: MISC_FEATURE
<222> LOCATION: (12)..(12)
<223> OTHER INFORMATION: Xaa at position 12 is any amino acid
<220> FEATURE:
<221> NAME/KEY: MISC_FEATURE
<222> LOCATION: (15)..(15)
<223> OTHER INFORMATION: Xaa at position 15 is any amino acid
<220> FEATURE:
<221> NAME/KEY: MISC_FEATURE
<222> LOCATION: (22)..(22)
<223> OTHER INFORMATION: Xaa at position 22 is any amino acid

<400> SEQUENCE: 139

```
Arg Ser Asp Tyr Lys Asp Asp Asp Asp Lys Gly Xaa Gln Gly Xaa Arg
1               5                   10                  15
```

-continued

```
Asn Leu Ala Asn Ser Xaa
            20


<210> SEQ ID NO 140
<211> LENGTH: 12
<212> TYPE: PRT
<213> ORGANISM: Artificial
<220> FEATURE:
<223> OTHER INFORMATION: clone 39 JUN dimerization inhibitory peptide
      without phage sequence
<220> FEATURE:
<221> NAME/KEY: MISC_FEATURE
<222> LOCATION: (2)..(2)
<223> OTHER INFORMATION: Xaa at position 2 is any amino acid residue
<220> FEATURE:
<221> NAME/KEY: MISC_FEATURE
<222> LOCATION: (5)..(5)
<223> OTHER INFORMATION: Xaa at position 5 is any amino acid residue
<220> FEATURE:
<221> NAME/KEY: MISC_FEATURE
<222> LOCATION: (12)..(12)
<223> OTHER INFORMATION: Xaa at position 12 is any amino acid residue

<400> SEQUENCE: 140

Gly Xaa Gln Gly Xaa Arg Asn Leu Ala Asn Ser Xaa
1               5                   10


<210> SEQ ID NO 141
<211> LENGTH: 66
<212> TYPE: DNA
<213> ORGANISM: Artificial
<220> FEATURE:
<223> OTHER INFORMATION: clone 43 encoding JUN dimerization inhibitory
      peptide with phage sequence

<400> SEQUENCE: 141

aggtcagact acaaggacga cgacgacaag gcttatcaat caattcatcc aaggttgact     60

aaatga                                                                66


<210> SEQ ID NO 142
<211> LENGTH: 20
<212> TYPE: PRT
<213> ORGANISM: Artificial
<220> FEATURE:
<223> OTHER INFORMATION: clone 43 JUN dimerization inhibitory peptide
      with phage sequence

<400> SEQUENCE: 142

Ser Asp Tyr Lys Asp Asp Asp Asp Lys Ala Tyr Gln Ser Ile His Pro
1               5                   10                  15

Arg Leu Thr Lys
            20


<210> SEQ ID NO 143
<211> LENGTH: 11
<212> TYPE: PRT
<213> ORGANISM: Artificial
<220> FEATURE:
<223> OTHER INFORMATION: clone 43 JUN dimerization inhibitory peptide
      without phage sequence

<400> SEQUENCE: 143

Ala Tyr Gln Ser Ile His Pro Arg Leu Thr Lys
1               5                   10


<210> SEQ ID NO 144
<211> LENGTH: 216
<212> TYPE: DNA
```

-continued

```
<213> ORGANISM: Artificial
<220> FEATURE:
<223> OTHER INFORMATION: clone 54 encoding JUN dimerization inhibitory
      peptide with phage sequence
<220> FEATURE:
<221> NAME/KEY: misc_feature
<222> LOCATION: (47)..(47)
<223> OTHER INFORMATION: N at position 47 is any nucleotide residue
<220> FEATURE:
<221> NAME/KEY: misc_feature
<222> LOCATION: (49)..(49)
<223> OTHER INFORMATION: N at position 49 is any nucleotide residue
<220> FEATURE:
<221> NAME/KEY: misc_feature
<222> LOCATION: (50)..(50)
<223> OTHER INFORMATION: N at position 50 is any nucleotide residue
<220> FEATURE:
<221> NAME/KEY: misc_feature
<222> LOCATION: (66)..(66)
<223> OTHER INFORMATION: N at position 66 is any nucleotide residue
<220> FEATURE:
<221> NAME/KEY: misc_feature
<222> LOCATION: (67)..(67)
<223> OTHER INFORMATION: N at position 67 is any nucleotide residue

<400> SEQUENCE: 144

aggtcagact acaaggacga cgacgacaag gcttatcaat cattccncnn ggcaggctac      60

cacggnnaca cttcgagaac atttctagtg ggttcggtat ccgcaactgc ccgaaaatta     120

gttgaagcga ctcaagaaac gatgattgat tatacttgtc gtcgtcgtcc ttgtagtctg     180

acctggtacc aattgatgca tcgataccgg tactag                               216


<210> SEQ ID NO 145
<211> LENGTH: 71
<212> TYPE: PRT
<213> ORGANISM: Artificial
<220> FEATURE:
<223> OTHER INFORMATION: clone 54 JUN dimerization inhibitory peptide
      with phage sequence
<220> FEATURE:
<221> NAME/KEY: MISC_FEATURE
<222> LOCATION: (16)..(16)
<223> OTHER INFORMATION: Xaa at position 16 is any amino acid
<220> FEATURE:
<221> NAME/KEY: MISC_FEATURE
<222> LOCATION: (17)..(17)
<223> OTHER INFORMATION: Xaa at position 17 is any amino acid
<220> FEATURE:
<221> NAME/KEY: MISC_FEATURE
<222> LOCATION: (23)..(23)
<223> OTHER INFORMATION: Xaa at position 23 is any amino acid

<400> SEQUENCE: 145

Arg Ser Asp Tyr Lys Asp Asp Asp Asp Lys Ala Tyr Gln Ser Phe Xaa
1               5                   10                  15

Xaa Ala Gly Tyr His Gly Xaa Thr Ser Arg Thr Phe Leu Val Gly Ser
            20                  25                  30

Val Ser Ala Thr Ala Arg Lys Leu Val Glu Ala Thr Gln Glu Thr Met
        35                  40                  45

Ile Asp Tyr Thr Cys Arg Arg Arg Pro Cys Ser Leu Thr Trp Tyr Gln
    50                  55                  60

Leu Met His Arg Tyr Arg Tyr
65                  70


<210> SEQ ID NO 146
<211> LENGTH: 61
<212> TYPE: PRT
<213> ORGANISM: Artificial
<220> FEATURE:
```

-continued

<223> OTHER INFORMATION: clone 54 JUN dimerization inhibitory peptide
      without phage sequence
<220> FEATURE:
<221> NAME/KEY: MISC_FEATURE
<222> LOCATION: (6)..(6)
<223> OTHER INFORMATION: Xaa at position 6 is any amino acid
<220> FEATURE:
<221> NAME/KEY: MISC_FEATURE
<222> LOCATION: (7)..(7)
<223> OTHER INFORMATION: Xaa at position 7 is any amino acid
<220> FEATURE:
<221> NAME/KEY: MISC_FEATURE
<222> LOCATION: (13)..(13)
<223> OTHER INFORMATION: Xaa at position 13 is any amino acid

<400> SEQUENCE: 146

```
Ala Tyr Gln Ser Phe Xaa Xaa Ala Gly Tyr His Gly Xaa Thr Ser Arg
1               5                   10                  15

Thr Phe Leu Val Gly Ser Val Ser Ala Thr Ala Arg Lys Leu Val Glu
            20                  25                  30

Ala Thr Gln Glu Thr Met Ile Asp Tyr Thr Cys Arg Arg Arg Pro Cys
        35                  40                  45

Ser Leu Thr Trp Tyr Gln Leu Met His Arg Tyr Arg Tyr
    50                  55                  60
```

<210> SEQ ID NO 147
<211> LENGTH: 222
<212> TYPE: DNA
<213> ORGANISM: Artificial
<220> FEATURE:
<223> OTHER INFORMATION: clone 58 encoding JUN dimerization inhibitory
      peptide with phage sequence

<400> SEQUENCE: 147

```
aggtcagact acaaggacga cgacgacaag gcttatcaat caatcatggc agtggctgcc      60

cagcagccgg tcgcgttcct ggtaggccgc cagcgtcgcc gcggtcaggt aggaatcgac     120

tccggcgatc agcaccttcg aacacccctg ttccatgagc tttgtcgtcg tcgtccttgt     180

agtctggcct ggtaccaatt gatgcatcga taccggtact ag                        222
```

<210> SEQ ID NO 148
<211> LENGTH: 73
<212> TYPE: PRT
<213> ORGANISM: Artificial
<220> FEATURE:
<223> OTHER INFORMATION: clone 58 JUN dimerization inhibitory peptide
      with phage sequence

<400> SEQUENCE: 148

```
Arg Ser Asp Tyr Lys Asp Asp Asp Asp Lys Ala Tyr Gln Ser Ile Met
1               5                   10                  15

Ala Val Ala Ala Gln Gln Pro Val Ala Phe Leu Val Gly Arg Gln Arg
            20                  25                  30

Arg Arg Gly Gln Val Gly Ile Asp Ser Gly Asp Gln His Leu Arg Thr
        35                  40                  45

Pro Leu Phe His Glu Leu Cys Arg Arg Arg Pro Cys Ser Leu Ala Trp
    50                  55                  60

Tyr Gln Leu Met His Arg Tyr Arg Tyr
65                  70
```

<210> SEQ ID NO 149
<211> LENGTH: 63
<212> TYPE: PRT
<213> ORGANISM: Artificial

-continued

<220> FEATURE:
<223> OTHER INFORMATION: clone 58 JUN dimerization inhibitory peptide without phage sequence

<400> SEQUENCE: 149

```
Ala Tyr Gln Ser Ile Met Ala Val Ala Ala Gln Gln Pro Val Ala Phe
1               5                   10                  15

Leu Val Gly Arg Gln Arg Arg Arg Gly Gln Val Gly Ile Asp Ser Gly
            20                  25                  30

Asp Gln His Leu Arg Thr Pro Leu Phe His Glu Leu Cys Arg Arg Arg
        35                  40                  45

Pro Cys Ser Leu Ala Trp Tyr Gln Leu Met His Arg Tyr Arg Tyr
    50                  55                  60
```

<210> SEQ ID NO 150
<211> LENGTH: 84
<212> TYPE: DNA
<213> ORGANISM: Artificial
<220> FEATURE:
<223> OTHER INFORMATION: clone 60 encoding JUN dimerization inhibitory peptide with phage sequence

<400> SEQUENCE: 150

```
aggtcagact acaaggacga cgacgacaag gctaatcaat tgcccaaaat acttgctgga     60

cggcttatat ttataaagtg ctaa                                            84
```

<210> SEQ ID NO 151
<211> LENGTH: 27
<212> TYPE: PRT
<213> ORGANISM: Artificial
<220> FEATURE:
<223> OTHER INFORMATION: clone 60 JUN dimerization inhibitory peptide with phage sequence

<400> SEQUENCE: 151

```
Arg Ser Asp Tyr Lys Asp Asp Asp Asp Lys Ala Asn Gln Leu Pro Lys
1               5                   10                  15

Ile Leu Ala Gly Arg Leu Ile Phe Ile Lys Cys
            20                  25
```

<210> SEQ ID NO 152
<211> LENGTH: 17
<212> TYPE: PRT
<213> ORGANISM: Artificial
<220> FEATURE:
<223> OTHER INFORMATION: clone 60 JUN dimerization inhibitory peptide without phage sequence

<400> SEQUENCE: 152

```
Ala Asn Gln Leu Pro Lys Ile Leu Ala Gly Arg Leu Ile Phe Ile Lys
1               5                   10                  15

Cys
```

<210> SEQ ID NO 153
<211> LENGTH: 225
<212> TYPE: DNA
<213> ORGANISM: Artificial
<220> FEATURE:
<223> OTHER INFORMATION: clone 66 encoding JUN dimerization inhibitory peptide with phage sequence

<400> SEQUENCE: 153

```
aggtcagact acaaggacga cgacgacaag gcttatcaat caatcatagg ggcgggaaaa     60
```

-continued

```
tcaacgctaa tcaaagcatt aactggcgta taccacgccg atcgcggcac catctggctg    120

gaaggccagg ctatctcacc gaaaaatacc gcccacgcgc aacaatgtcg tcgtcgtcct    180

tgtagtctga cctggtacca attgatgcat cgataccggt actag                    225


<210> SEQ ID NO 154
<211> LENGTH: 74
<212> TYPE: PRT
<213> ORGANISM: Artificial
<220> FEATURE:
<223> OTHER INFORMATION: clone 66 JUN dimerization inhibitory peptide
      with phage sequence

<400> SEQUENCE: 154

Arg Ser Asp Tyr Lys Asp Asp Asp Asp Lys Ala Tyr Gln Ser Ile Ile
1               5                   10                  15

Gly Ala Gly Lys Ser Thr Leu Ile Lys Ala Leu Thr Gly Val Tyr His
            20                  25                  30

Ala Asp Arg Gly Thr Ile Trp Leu Glu Gly Gln Ala Ile Ser Pro Lys
        35                  40                  45

Asn Thr Ala His Ala Gln Gln Cys Arg Arg Arg Pro Cys Ser Leu Thr
    50                  55                  60

Trp Tyr Gln Leu Met His Arg Tyr Arg Tyr
65                  70


<210> SEQ ID NO 155
<211> LENGTH: 64
<212> TYPE: PRT
<213> ORGANISM: Artificial
<220> FEATURE:
<223> OTHER INFORMATION: clone 66 JUN dimerization inhibitory peptide
      without phage sequence

<400> SEQUENCE: 155

Ala Tyr Gln Ser Ile Ile Gly Ala Gly Lys Ser Thr Leu Ile Lys Ala
1               5                   10                  15

Leu Thr Gly Val Tyr His Ala Asp Arg Gly Thr Ile Trp Leu Glu Gly
            20                  25                  30

Gln Ala Ile Ser Pro Lys Asn Thr Ala His Ala Gln Gln Cys Arg Arg
        35                  40                  45

Arg Pro Cys Ser Leu Thr Trp Tyr Gln Leu Met His Arg Tyr Arg Tyr
    50                  55                  60


<210> SEQ ID NO 156
<211> LENGTH: 123
<212> TYPE: DNA
<213> ORGANISM: Artificial
<220> FEATURE:
<223> OTHER INFORMATION: clones 72, 73, 76 and 77 encoding JUN
      dimerization inhibitory peptide with phage sequence

<400> SEQUENCE: 156

gagctcagat ctcagctggg cccggtacca attgatgcat cgataccggt actagtcgga     60

ccgcatatgc ccgggcgtac cgcggccgct cgaggcatgc atctagaggg ccgcatcatg    120

taa                                                                  123


<210> SEQ ID NO 157
<211> LENGTH: 40
<212> TYPE: PRT
<213> ORGANISM: Artificial
<220> FEATURE:
<223> OTHER INFORMATION: clones 72, 73, 76 and 77 JUN dimerization
```

-continued inhibitory peptide with phage sequence

<400> SEQUENCE: 157

Glu Leu Arg Ser Gln Leu Gly Pro Val Pro Ile Asp Ala Ser Ile Pro
1 5 10 15

Val Leu Val Gly Pro His Met Pro Gly Arg Thr Ala Ala Ala Arg Gly
20 25 30

Met His Leu Glu Gly Arg Ile Met
35 40

<210> SEQ ID NO 158
<211> LENGTH: 40
<212> TYPE: PRT
<213> ORGANISM: Artificial
<220> FEATURE:
<223> OTHER INFORMATION: clones 72, 73, 76 and 77 JUN dimerization inhibitory peptide without phage sequence

<400> SEQUENCE: 158

Glu Leu Arg Ser Gln Leu Gly Pro Val Pro Ile Asp Ala Ser Ile Pro
1 5 10 15

Val Leu Val Gly Pro His Met Pro Gly Arg Thr Ala Ala Ala Arg Gly
20 25 30

Met His Leu Glu Gly Arg Ile Met
35 40

<210> SEQ ID NO 159
<211> LENGTH: 60
<212> TYPE: DNA
<213> ORGANISM: Artificial
<220> FEATURE:
<223> OTHER INFORMATION: clone 79 encoding JUN dimerization inhibitory peptide with phage sequence

<400> SEQUENCE: 159
aggtcagact acaaggacga cgacgacaag gcttatcaat caatcaaatg gccaatgtaa 60

<210> SEQ ID NO 160
<211> LENGTH: 19
<212> TYPE: PRT
<213> ORGANISM: Artificial
<220> FEATURE:
<223> OTHER INFORMATION: clone 79 JUN dimerization inhibitory peptide with phage sequence

<400> SEQUENCE: 160

Arg Ser Asp Tyr Lys Asp Asp Asp Asp Lys Ala Tyr Gln Ser Ile Lys
1 5 10 15

Trp Pro Met

<210> SEQ ID NO 161
<211> LENGTH: 9
<212> TYPE: PRT
<213> ORGANISM: Artificial
<220> FEATURE:
<223> OTHER INFORMATION: clone 79 JUN dimerization inhibitory peptide without phage sequence

<400> SEQUENCE: 161

Ala Tyr Gln Ser Ile Lys Trp Pro Met
1 5

<210> SEQ ID NO 162
<211> LENGTH: 111

-continued

<212> TYPE: DNA
<213> ORGANISM: Artificial
<220> FEATURE:
<223> OTHER INFORMATION: clone 80 encoding JUN dimerization inhibitory peptide with phage sequence

<400> SEQUENCE: 162
aggtcagact acaaggacga cgacgacaag gcttatcaat catccactgg tagtgctgcc 60
atcctcttca atttccgtcg aatggggatc gtgataataa ttcagatcta a 111

<210> SEQ ID NO 163
<211> LENGTH: 36
<212> TYPE: PRT
<213> ORGANISM: Artificial
<220> FEATURE:
<223> OTHER INFORMATION: clone 80 JUN dimerization inhibitory peptide with phage sequence

<400> SEQUENCE: 163

Arg Ser Asp Tyr Lys Asp Asp Asp Asp Lys Ala Tyr Gln Ser Ser Thr
1 5 10 15

Gly Ser Ala Ala Ile Leu Phe Asn Phe Arg Arg Met Gly Ile Val Ile
20 25 30

Ile Ile Gln Ile
35

<210> SEQ ID NO 164
<211> LENGTH: 26
<212> TYPE: PRT
<213> ORGANISM: Artificial
<220> FEATURE:
<223> OTHER INFORMATION: clone 80 JUN dimerization inhibitory peptide without phage sequence

<400> SEQUENCE: 164

Ala Tyr Gln Ser Ser Thr Gly Ser Ala Ala Ile Leu Phe Asn Phe Arg
1 5 10 15

Arg Met Gly Ile Val Ile Ile Ile Gln Ile
20 25

<210> SEQ ID NO 165
<211> LENGTH: 6482
<212> TYPE: DNA
<213> ORGANISM: Artificial
<220> FEATURE:
<223> OTHER INFORMATION: pMF4-5 vector

<400> SEQUENCE: 165
cgtacccatt atcttagcct aaaaaaacct tctctttgga actttcagta atacgcttaa 60
ctgctcattg ctatattgaa gtacggatta gaagccgccg agcgggtgac agccctccga 120
aggaagactc tcctccgtgc gtcctcgtct tcaccggtcg cgttcctgaa acgcagatgt 180
gcctcgcgcc gcactgctcc gaacaataaa gattctacaa tactagcttt tatggttatg 240
aagaggaaaa attggcagta acctggcccc acaaaccttc aaatgaacga atcaaattaa 300
caaccatagg atgataatgc gattagtttt ttagccttat ttctggggta attaatcagc 360
gaagcgatga tttttgatct attaacagat atataaatgc aaaaactgca taaccacttt 420
aactaatact ttcaacattt tcggtttgta ttacttctta ttcaaatgta ataaaagtat 480
caacaaaaaa ttgttaatat acctctatac tttaacgtca aggaggaatt aagcttatgg 540
gtgctcctcc aaaaaagaag agaaaggtag ctggtatcaa taaagatatc gaggagtgca 600

-continued

```
atgccatcat tgagcagttt atcgactacc tgcgcaccgg acaggagatg ccgatggaaa    660
tggcggatca ggcgattaac gtggtgccgg gcatgacgcc gaaaaccatt cttcacgccg    720
ggccgccgat ccagcctgac tggctgaaat cgaatggttt tcatgaaatt gaagcggatg    780
ttaacgatac cagcctcttg ctgagtggag atgcctccta cccttatgat gtgccagatt    840
atgcctctcc cgaattccgt tgtgcaggta ccagagtact gagcggccgc aatctcgaga    900
agctttggac ttcttcgcca gaggtttggt caagtctcca atcaaggttg tcggcttgtc    960
taccttgcca gaaatttacg aaaagatgga aaagggtcaa atcgttggta gatacgttgt   1020
tgacacttct aaataagcga atttcttatg atttatgatt tttattatta aataagttat   1080
aaaaaaaata agtgtataca aattttaaag tgactcttag gttttaaaac gaaaattctt   1140
gttcttgagt aactctttcc tgtaggtcag gttgctttct caggtatagc atgaggtcgc   1200
tcttattgac cacacctcta ccggcatgcc gagcaaatgc ctgcaaatcg ctccccattt   1260
cacccaattg tagatatgct aactccagca atgagttgat gaatctcggt gtgtatttta   1320
tgtcctcaga ggacaacacc tgttgtaatc gttcttccac acggatcctc tagagtcgac   1380
tagcggccgc ttcgacctgc agcaattctg aaccagtcct aaaacgagta aataggaccg   1440
gcaattcttc aagcaataaa caggaatacc aattattaaa agataactta gtcagatcgt   1500
acaataaagc tttgaagaaa aatgcgcctt attcaatctt tgctataaaa aatggcccaa   1560
aatctcacat tggaagacat ttgatgacct catttctttc aatgaagggc ctaacggagt   1620
tgactaatgt tgtgggaaat tggagcgata agcgtgcttc tgccgtggcc aggacaacgt   1680
atactcatca gataacagca atacctgatc actacttcgc actagtttct cggtactatg   1740
catatgatcc aatatcaaag gaaatgatag cattgaagga tgagactaat ccaattgagg   1800
agtggcagca tatagaacag ctaaagggta gtgctgaagg aagcatacga taccccgcat   1860
ggaatgggat aatatcacag gaggtactag actacctttc atcctacata aatagacgca   1920
tataagtacg catttaagca taaacacgca ctatgccgtt cttctcatgt atatatatat   1980
acaggcaaca cgcagatata ggtgcgacgt gaacagtgag ctgtatgtgc gcagctcgcg   2040
ttgcattttc ggaagcgctc gttttcggaa acgctttgaa gttcctattc cgaagttcct   2100
attctctaga aagtatagga acttcagagc gcttttgaaa accaaaagcg ctctgaagac   2160
gcactttcaa aaaaccaaaa acgcaccgga ctgtaacgag ctactaaaat attgcgaata   2220
ccgcttccac aaacattgct caaaagtatc tctttgctat atatctctgt gctatatccc   2280
tatataacct acccatccac ctttcgctcc ttgaacttgc atctaaactc gacctctaca   2340
ttttttatgt ttatctctag tattactctt tagacaaaaa aattgtagta agaactattc   2400
atagagtgaa tcgaaaacaa tacgaaaatg taaacatttc ctatacgtag tatatagaga   2460
caaaatagaa gaaaccgttc ataattttct gaccaatgaa gaatcatcaa cgctatcact   2520
ttctgttcac aaagtatgcg caatccacat cggtatagaa tataatcggg gatgccttta   2580
tcttgaaaaa atgcacccgc agcttcgcta gtaatcagta aacgcgggaa gtggagtcag   2640
gcttttttta tggaagagaa aatagacacc aaagtagcct tcttctaacc ttaacggacc   2700
tacagtgcaa aaagttatca agagactgca ttatagagcg cacaaaggag aaaaaaagta   2760
atctaagatg ctttgttaga aaaatagcgc tctcgggatg catttttgta gaacaaaaaa   2820
gaagtataga ttctttgttg gtaaaatagc gctctcgcgt tgcatttctg ttctgtaaaa   2880
atgcagctca gattctttgt ttgaaaaatt agcgctctcg cgttgcattt ttgttttaca   2940
aaaatgaagc acagattctt cgttggtaaa atagcgcttt cgcgttgcat ttctgttctg   3000
```

-continued

```
taaaaatgca gctcagattc tttgtttgaa aaattagcgc tctcgcgttg catttttgtt   3060
ctacaaaatg aagcacagat gcttcgttaa caaagatatg ctattgaagt gcaagatgga   3120
aacgcagaaa atgaaccggg gatgcgacgt gcaagattac ctatgcaata gatgcaatag   3180
tttctccagg aaccgaaata catacattgt cttccgtaaa gcgctagact atatattatt   3240
atacaggttc aaatatacta tctgtttcag ggaaaactcc caggttcgga tgttcaaaat   3300
tcaatgatgg gtaacaagta cgatcgtaaa tctgtaaaac agtttgtcgg atattaggct   3360
gtatctcctc aaagcgtatt cgaatatcat tgagaagctg caggcaagtg cacaaacaat   3420
acttaaataa atactactca gtaataacct atttcttagc atttttgacg aaatttgcta   3480
ttttgttaga gtcttttaca ccatttgtct ccacacctcc gcttacatca acaccaataa   3540
cgccatttaa tctaagcgca tcaccaacat tttctggcgt cagtccacca gctaacataa   3600
aatgtaagct ttcggggctc tcttgccttc caacccagtc agaaatcgag ttccaatcca   3660
aaagttcacc tgtcccacct gcttctgaat caaacaaggg aataaacgaa tgaggtttct   3720
gtgaagctgc actgagtagt atgttgcagt cttttggaaa tacgagtctt ttaataactg   3780
gcaaaccgag gaactcttgg tattcttgcc acgactcatc tccatgcagt tggacgatat   3840
caatgccgta atcattgacc agagccaaaa catcctcctt aggttgatta cgaaacacgc   3900
caaccaagta tttcggagtg cctgaactat ttttatatgc ttttacaaga cttgaaattt   3960
tccttgcaat aaccgggtca attgttctct ttctattggg cacacatata atacccagca   4020
agtcagcatc ggaatctaga gcacattctg cggcctctgt gctctgcaag ccgcaaactt   4080
tcaccaatgg accagaacta cctgtgaaat taataacaga catactccaa gctgcctttg   4140
tgtgcttaat cacgtatact cacgtgctca atagtcacca atgccctccc tcttggccct   4200
ctccttttct tttttcgacc gaatttcttg aagacgaaag ggcctcgtga tacgcctatt   4260
tttataggtt aatgtcatga taataatggt ttcttagacg tcaggtggca cttttcgggg   4320
aaatgtgcgc ggaaccccta tttgtttatt tttctaaata cattcaaata tgtatccgct   4380
catgagacaa taaccctgat aaatgcttca ataatattga aaaaggaaga gtatgagtat   4440
tcaacatttc cgtgtcgccc ttattccctt ttttgcggca ttttgccttc ctgtttttgc   4500
tcacccagaa acgctggtga aagtaaaaga tgctgaagat cagttgggtg cacgagtggg   4560
ttacatcgaa ctggatctca acagcggtaa gatccttgag agttttcgcc ccgaagaacg   4620
ttttccaatg atgagcactt ttaaagttct gctatgtggc gcggtattat cccgtgttga   4680
cgccgggcaa gagcaactcg gtcgccgcat acactattct cagaatgact tggttgagta   4740
ctcaccagtc acagaaaagc atcttacgga tggcatgaca gtaagagaat tatgcagtgc   4800
tgccataacc atgagtgata acactgcggc caacttactt ctgacaacga tcggaggacc   4860
gaaggagcta accgcttttt tgcacaacat gggggatcat gtaactcgcc ttgatcgttg   4920
ggaaccggag ctgaatgaag ccataccaaa cgacgagcgt gacaccacga tgcctgtagc   4980
aatggcaaca acgttgcgca aactattaac tggcgaacta cttactctag cttcccggca   5040
acaattaata gactggatgg aggcggataa agttgcagga ccacttctgc gctcggccct   5100
tccggctggc tggtttattg ctgataaatc tggagccggt gagcgtgggt ctcgcggtat   5160
cattgcagca ctggggccag atggtaagcc ctcccgtatc gtagttatct acacgacggg   5220
gagtcaggca actatggatg aacgaaatag acagatcgct gagataggtg cctcactgat   5280
taagcattgg taactgtcag accaagttta ctcatatata ctttagattg atttaaaact   5340
```

```
tcatttttaa tttaaaagga tctaggtgaa gatccttttt gataatctca tgaccaaaat   5400

cccttaacgt gagttttcgt tccactgagc gtcagacccc gtagaaaaga tcaaaggatc   5460

ttcttgagat cctttttttc tgcgcgtaat ctgctgcttg caaacaaaaa aaccaccgct   5520

accagcggtg gtttgtttgc cggatcaaga gctaccaact ctttttccga aggtaactgg   5580

cttcagcaga gcgcagatac caaatactgt ccttctagtg tagccgtagt taggccacca   5640

cttcaagaac tctgtagcac cgcctacata cctcgctctg ctaatcctgt taccagtggc   5700

tgctgccagt ggcgataagt cgtgtcttac cgggttggac tcaagacgat agttaccgga   5760

taaggcgcag cggtcgggct gaacgggggg ttcgtgcaca cagcccagct tggagcgaac   5820

gacctacacc gaactgagat acctacagcg tgagctatga gaaagcgcca cgcttcccga   5880

agggagaaag gcggacaggt atccggtaag cggcagggtc ggaacaggag agcgcacgag   5940

ggagcttcca gggggaaacg cctggtatct ttatagtcct gtcgggtttc gccacctctg   6000

acttgagcgt cgatttttgt gatgctcgtc aggggggcgg agcctatgga aaaacgccag   6060

caacgcggcc tttttacggt tcctggcctt ttgctggcct tttgctcaca tgttctttcc   6120

tgcgttatcc cctgattctg tggataaccg tattaccgcc tttgagtgag ctgataccgc   6180

tcgccgcagc cgaacgaccg agcgcagcga gtcagtgagc gaggaagcgg aagagcgccc   6240

aatacgcaaa ccgcctctcc ccgcgcgttg gccgattcat taatgcagct ggcacgacag   6300

gtttcccgac tggaaagcgg gcagtgagcg caacgcaatt aatgtgagtt agctcactca   6360

ttaggcaccc caggctttac actttatgct tccggctcgt atgttgtgtg gaattgtgag   6420

cggataacaa tttcacacag gaaacagcta tgacatgatt acgaattaat tcgagctcgg   6480

ta                                                                  6482
```

```
<210> SEQ ID NO 166
<211> LENGTH: 2648
<212> TYPE: DNA
<213> ORGANISM: Plasmodium falciparum
<220> FEATURE:
<221> NAME/KEY: exon
<222> LOCATION: (626)..(687)
<220> FEATURE:
<221> NAME/KEY: exon
<222> LOCATION: (1042)..(1162)
<220> FEATURE:
<221> NAME/KEY: exon
<222> LOCATION: (1347)..(2525)

<400> SEQUENCE: 166

atatatatat atatatttgt acagaaaata ttttaataaa aaaaaaaaaa aattttaagc     60

atttcatatt tatatacact tgttttttta tgtgttgaaa gaaaaaaaaa aattatgcta    120

tatcatattt atatgaccat tttaatgata ctgtgaaagt atacatatat aattaattat    180

ataataataa taatatatat atacatatat atataatact ctgtttttct tttttttttt    240

ctttttcttt ttcctttttt tttttttttg cactctaaag gtttgagtaa gtaaatatta    300

tatataatat atataaaagt ataatttttt tacaaataat taatagattt attttataag    360

aattaaaaat aataaaatta aaaaaaaaaa aaagaaaaat ttacatatta ttatatatat    420

atatatatat ttaaatatat atttaaaaaa aaaatatatt ttaatgataa agaagaaata    480

ttcatacaat aattaataat atatatttga tttgtatttt tttttttttt tttatataca    540

tatttatata ttttttttta aatcatcatt taagaaaaga aaaagaaaaa aaaagaatat    600

ttattttaat atatttaaat aaaaa atg aga gaa gta ata agt atc cat gta      652
                            Met Arg Glu Val Ile Ser Ile His Val
```

-continued

```
                           1               5

gga caa gct ggt atc caa gtt gga aat gct tgc tg  gtaaaacgat           697
Gly Gln Ala Gly Ile Gln Val Gly Asn Ala Cys Trp
10                  15                  20

aagcttatat attcttacac attattatat taatatatat atatatatat atatatatat    757

aagaaaaaaa aattatatca tatttattgt gttttcattc ataaaagtta aaatcatatg    817

tgtgtgtgta atgttctaaa gaatacataa atatatatat atatatatat atatatatat    877

atatatatat aatacataat aaattcataa tatatatatg tatatattat cgatgtatgt    937

atacacacct gttttaaatg tatatatatc tataaaaagt tatgcatact tatgaataca    997

tcttttcttt attcttttta taaataattt gttgaatttt ttag g gaa ttg ttt      1051
                                                   Glu Leu Phe

tgc cta gag cat gga ata cag ccc gat ggt caa atg ccc tct gac aag     1099
Cys Leu Glu His Gly Ile Gln Pro Asp Gly Gln Met Pro Ser Asp Lys
25                  30                  35                  40

gct tct aga gct aat gat gat gct ttt aat aca ttc ttt tca gaa acg     1147
Ala Ser Arg Ala Asn Asp Asp Ala Phe Asn Thr Phe Phe Ser Glu Thr
                45                  50                  55

ggg gca gga aaa cat gtaagaaata atatacgctg atataatata atatatatat     1202
Gly Ala Gly Lys His
            60

atatatatat atatatttgt aacttataaa aagttgtcct ttatataaca gttaaagaac   1262

atatataaca atatagcata tttattaaaa taagtatata catatatata tatatatata   1322

ttttttttt tttttccttt ttag gta cca cgt tgt gtt ttt gtc gat tta      1373
                          Val Pro Arg Cys Val Phe Val Asp Leu
                                      65                  70

gag cca acc gtt gtt gat gaa gtc aga aca gga act tat cgt caa tta     1421
Glu Pro Thr Val Val Asp Glu Val Arg Thr Gly Thr Tyr Arg Gln Leu
                75                  80                  85

ttt cat cct gaa caa tta ata tca gga aaa gaa gat gct gcc aac aat     1469
Phe His Pro Glu Gln Leu Ile Ser Gly Lys Glu Asp Ala Ala Asn Asn
            90                  95                  100

ttt gct aga gga cac tat aca atc ggt aaa gaa gtt ata gat gta tgt     1517
Phe Ala Arg Gly His Tyr Thr Ile Gly Lys Glu Val Ile Asp Val Cys
        105                 110                 115

ttg gac aga att aga aaa tta gct gat aac tgt acc ggt tta caa gga     1565
Leu Asp Arg Ile Arg Lys Leu Ala Asp Asn Cys Thr Gly Leu Gln Gly
    120                 125                 130

ttt tta atg ttc agc gca gtt gga ggt gga aca ggt agt gga ttt ggt     1613
Phe Leu Met Phe Ser Ala Val Gly Gly Gly Thr Gly Ser Gly Phe Gly
135                 140                 145                 150

tgt tta atg tta gaa aga tta tcc gtt gat tat gga aag aaa tcc aaa     1661
Cys Leu Met Leu Glu Arg Leu Ser Val Asp Tyr Gly Lys Lys Ser Lys
                155                 160                 165

ctg aat ttt tgc tgt tgg cca tca cct caa gtt tca act gct gta gtt     1709
Leu Asn Phe Cys Cys Trp Pro Ser Pro Gln Val Ser Thr Ala Val Val
            170                 175                 180

gaa cca tac aat tca gtt ttg tct act cat tca tta tta gaa cat act     1757
Glu Pro Tyr Asn Ser Val Leu Ser Thr His Ser Leu Leu Glu His Thr
        185                 190                 195

gat gta gca ata atg ctt gat aac gaa gct ata tat gat ata tgc aga     1805
Asp Val Ala Ile Met Leu Asp Asn Glu Ala Ile Tyr Asp Ile Cys Arg
    200                 205                 210

aga aat tta gat att gaa aga cca aca tat act aat tta aat aga ttg     1853
Arg Asn Leu Asp Ile Glu Arg Pro Thr Tyr Thr Asn Leu Asn Arg Leu
215                 220                 225                 230
```

-continued

```
att gct caa gtt att tct tcc tta aca gca tct tta aga ttt gat ggt     1901
Ile Ala Gln Val Ile Ser Ser Leu Thr Ala Ser Leu Arg Phe Asp Gly
                235                 240                 245

gct tta aat gtt gat gta aca gaa ttc caa acc aac tta gta cca tac     1949
Ala Leu Asn Val Asp Val Thr Glu Phe Gln Thr Asn Leu Val Pro Tyr
            250                 255                 260

cct cgt att cat ttt atg tta tct tca tat gct cca gtt gtt agt gct     1997
Pro Arg Ile His Phe Met Leu Ser Ser Tyr Ala Pro Val Val Ser Ala
        265                 270                 275

gaa aaa gca tac cat gaa caa ttg tcc gtt tct gaa att acc aac tca     2045
Glu Lys Ala Tyr His Glu Gln Leu Ser Val Ser Glu Ile Thr Asn Ser
    280                 285                 290

gca ttc gaa cca gca aat atg atg gca aaa tgt gat ccg aga cat gga     2093
Ala Phe Glu Pro Ala Asn Met Met Ala Lys Cys Asp Pro Arg His Gly
295                 300                 305                 310

aaa tat atg gct tgt tgt tta atg tat aga ggt gat gta gta cca aag     2141
Lys Tyr Met Ala Cys Cys Leu Met Tyr Arg Gly Asp Val Val Pro Lys
                315                 320                 325

gat gtg aac gca gct gtt gct acc ata aaa aca aaa aga acc att caa     2189
Asp Val Asn Ala Ala Val Ala Thr Ile Lys Thr Lys Arg Thr Ile Gln
            330                 335                 340

ttt gtt gac tgg tgt cct act ggt ttt aaa tgt ggt ata aat tat caa     2237
Phe Val Asp Trp Cys Pro Thr Gly Phe Lys Cys Gly Ile Asn Tyr Gln
        345                 350                 355

cca cca act gtt gta cca gga gga gat tta gcc aaa gtt atg aga gct     2285
Pro Pro Thr Val Val Pro Gly Gly Asp Leu Ala Lys Val Met Arg Ala
    360                 365                 370

gtt tgt atg atc agc aac tca aca gca att gca gaa gta ttc tca aga     2333
Val Cys Met Ile Ser Asn Ser Thr Ala Ile Ala Glu Val Phe Ser Arg
375                 380                 385                 390

atg gat caa aaa ttt gat tta atg tat gca aaa aga gct ttc gtt cat     2381
Met Asp Gln Lys Phe Asp Leu Met Tyr Ala Lys Arg Ala Phe Val His
                395                 400                 405

tgg tat gta ggt gaa ggt atg gaa gaa gga gaa ttt agt gaa gct aga     2429
Trp Tyr Val Gly Glu Gly Met Glu Glu Gly Glu Phe Ser Glu Ala Arg
            410                 415                 420

gaa gat ttg gcc gcc tta gaa aaa gat tat gaa gag gta gga att gaa     2477
Glu Asp Leu Ala Ala Leu Glu Lys Asp Tyr Glu Glu Val Gly Ile Glu
        425                 430                 435

tcc aat gaa gca gaa gga gaa gat gaa gga tat gaa gca gat tat taa     2525
Ser Asn Glu Ala Glu Gly Glu Asp Glu Gly Tyr Glu Ala Asp Tyr
    440                 445                 450

atttgttaat atataaaagc attatatata tgtatatatt tatatattta tttatatatg   2585

tgtgtatgta catacatcta tatatatata tatatatata tatatatata tatatatata   2645

tat                                                                  2648
```

<210> SEQ ID NO 167
<211> LENGTH: 453
<212> TYPE: PRT
<213> ORGANISM: Plasmodium falciparum

<400> SEQUENCE: 167

```
Met Arg Glu Val Ile Ser Ile His Val Gly Gln Ala Gly Ile Gln Val
1               5                   10                  15

Gly Asn Ala Cys Trp Glu Leu Phe Cys Leu Glu His Gly Ile Gln Pro
            20                  25                  30

Asp Gly Gln Met Pro Ser Asp Lys Ala Ser Arg Ala Asn Asp Asp Ala
        35                  40                  45
```

-continued

```
Phe Asn Thr Phe Phe Ser Glu Thr Gly Ala Gly Lys His Val Pro Arg
    50                  55                  60

Cys Val Phe Val Asp Leu Glu Pro Thr Val Val Asp Glu Val Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Phe Ala Arg Gly His Tyr Thr Ile Gly Lys
            100                 105                 110

Glu Val Ile Asp Val Cys Leu Asp Arg Ile Arg Lys Leu Ala Asp Asn
        115                 120                 125

Cys Thr Gly Leu Gln Gly Phe Leu Met Phe Ser Ala Val Gly Gly Gly
    130                 135                 140

Thr Gly Ser Gly Phe Gly Cys Leu Met Leu Glu Arg Leu Ser Val Asp
145                 150                 155                 160

Tyr Gly Lys Lys Ser Lys Leu Asn Phe Cys Cys Trp Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ile Met Leu Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ala Gln Val Ile Ser Ser Leu Thr Ala
225                 230                 235                 240

Ser Leu Arg Phe Asp Gly Ala Leu Asn Val Asp Val Thr Glu Phe Gln
                245                 250                 255

Thr Asn Leu Val Pro Tyr Pro Arg Ile His Phe Met Leu Ser Ser Tyr
            260                 265                 270

Ala Pro Val Val Ser Ala Glu Lys Ala Tyr His Glu Gln Leu Ser Val
        275                 280                 285

Ser Glu Ile Thr Asn Ser Ala Phe Glu Pro Ala Asn Met Met Ala Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Cys Pro Thr Gly Phe Lys
            340                 345                 350

Cys Gly Ile Asn Tyr Gln Pro Pro Thr Val Val Pro Gly Gly Asp Leu
        355                 360                 365

Ala Lys Val Met Arg Ala Val Cys Met Ile Ser Asn Ser Thr Ala Ile
    370                 375                 380

Ala Glu Val Phe Ser Arg Met Asp Gln Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ile Glu Ser Asn Glu Ala Glu Gly Glu Asp Glu Gly
        435                 440                 445

Tyr Glu Ala Asp Tyr
    450
```

-continued

```
<210> SEQ ID NO 168
<211> LENGTH: 47
<212> TYPE: DNA
<213> ORGANISM: Artificial
<220> FEATURE:
<223> OTHER INFORMATION: synthetic oligonucleotide

<400> SEQUENCE: 168

gatcctcgag gaattcatga gagaagtaat aagtatccat gtaggac                  47


<210> SEQ ID NO 169
<211> LENGTH: 43
<212> TYPE: DNA
<213> ORGANISM: Artificial
<220> FEATURE:
<223> OTHER INFORMATION: synthetic oligonucleotide

<400> SEQUENCE: 169

gatcctcgag ttaataatct gcttcatatc cttcatcttc tcc                      43


<210> SEQ ID NO 170
<211> LENGTH: 2833
<212> TYPE: DNA
<213> ORGANISM: Plasmodium falciparum
<220> FEATURE:
<221> NAME/KEY: CDS
<222> LOCATION: (654)..(749)
<220> FEATURE:
<221> NAME/KEY: CDS
<222> LOCATION: (1112)..(2065)
<220> FEATURE:
<221> NAME/KEY: CDS
<222> LOCATION: (2229)..(2513)

<400> SEQUENCE: 170

aattcctagt ttatttaatt taaaaattaa aagatcgaat gctcaacatt ttaaaaagaa     60

atctgtgaaa catatcttaa caagaaatgg tgtaacaaaa gaaacaatat taaatgataa    120

attaccaaag ataaatgatg aaattgacag aacatataat ggacacaaaa tggatgaaaa    180

tttacaggat aaacaaaaaa ggaatcatgg agtaaatata aaattaataa atgaatatga    240

aaatatcatg tgaagaataa attctcaaaa tcattgattg tatgacaaga ttcaagaatt    300

ggttatataa aaatatattt aggaaaagta attttgggtc atatgtatca acatttacag    360

gtgtatttgg aggtgctgca gctgttagct gtttctgcca taagtggagc ttgtataact    420

aaatttagtg ttacattggt tccggtattt gcatgttttg ggggtgtctt tgcgattatt    480

ataatattat taatattagg aacatggatg cttgttacat ggttatggca acacaaagaa    540

gtagtatttt tttttttttt taatttttac ttaatatatc ctcttacaat ataaaatatt    600

tatatattta aaaaaaaaag aaaaaatttt ctttgagatt attttattaa aga atg       656
                                                           Met
                                                           1

aga gaa att gtt cat att caa gct ggc caa tgt gga aat caa ata ggt      704
Arg Glu Ile Val His Ile Gln Ala Gly Gln Cys Gly Asn Gln Ile Gly
            5                   10                  15

gca aag ttt tgg gaa gtc att tct gat gag cat gga ata gat cca          749
Ala Lys Phe Trp Glu Val Ile Ser Asp Glu His Gly Ile Asp Pro
        20                  25                  30

gtaagtttaa aaaaaaaata tatttattta tatgaatctg taaacatatg tatatttata    809

tatatatata tatatatatg gaagaataat tttgtgtgta taatttgggg tccttcccct    869

ttattgtatt ctataaatgc ctcctttata ttgataataa tttatatatg taaaccttta    929

atgacgaggc ttatatataa aaaccttaga tattataaat aaatgtatat tatgtacata    989
```

```
tgacgatatc gctctctcta tatatatata tatatatata tatatatatt tatttattta   1049

tatatttatt tatttattta tttatttatt tttttttttt tttttatttt tatttttttt   1109

ag agt ggt acc tat agt ggg gac agt gac tta cag tta gaa aga gtt      1156
   Ser Gly Thr Tyr Ser Gly Asp Ser Asp Leu Gln Leu Glu Arg Val
           35                  40                  45

gac gtt ttt tac aac gaa gca aca gga ggt aga tat gtt cca aga gct     1204
Asp Val Phe Tyr Asn Glu Ala Thr Gly Gly Arg Tyr Val Pro Arg Ala
        50                  55                  60

ata ttg atg gac ttg gaa cct ggt act atg gat agt gtt cgt gct ggc     1252
Ile Leu Met Asp Leu Glu Pro Gly Thr Met Asp Ser Val Arg Ala Gly
    65                  70                  75

ccc ttt ggt caa tta ttt cgt cca gat aat ttt gtg ttt ggt caa aca     1300
Pro Phe Gly Gln Leu Phe Arg Pro Asp Asn Phe Val Phe Gly Gln Thr
80                  85                  90                  95

ggt gca gga aat aat tgg gct aaa gga cat tat act gaa ggt gct gaa     1348
Gly Ala Gly Asn Asn Trp Ala Lys Gly His Tyr Thr Glu Gly Ala Glu
                100                 105                 110

ttg ata gat gca gtt tta gat gtg ctt aga aaa gaa gca gaa ggt tgt     1396
Leu Ile Asp Ala Val Leu Asp Val Leu Arg Lys Glu Ala Glu Gly Cys
            115                 120                 125

gat tgt tta caa gga ttt cag att act cat tca tta ggt ggt ggt aca     1444
Asp Cys Leu Gln Gly Phe Gln Ile Thr His Ser Leu Gly Gly Gly Thr
        130                 135                 140

ggt agt ggt atg ggt act ttg ttg att agt aaa ata aga gag gag tat     1492
Gly Ser Gly Met Gly Thr Leu Leu Ile Ser Lys Ile Arg Glu Glu Tyr
    145                 150                 155

cct gat cgt att atg gaa aca ttt tct gta ttt cca tca cca aaa gtt     1540
Pro Asp Arg Ile Met Glu Thr Phe Ser Val Phe Pro Ser Pro Lys Val
160                 165                 170                 175

tct gat act gtt gtt gaa cca tat aat gct aca tta tca gtc cat cag     1588
Ser Asp Thr Val Val Glu Pro Tyr Asn Ala Thr Leu Ser Val His Gln
                180                 185                 190

ttg gtt gaa aat gct gat gaa gtt caa gtt atc gat aat gaa gct tta     1636
Leu Val Glu Asn Ala Asp Glu Val Gln Val Ile Asp Asn Glu Ala Leu
            195                 200                 205

tat gac ata tgt ttt agg act ctt aaa tta aca aca cca aca tat gga     1684
Tyr Asp Ile Cys Phe Arg Thr Leu Lys Leu Thr Thr Pro Thr Tyr Gly
        210                 215                 220

gat tta aat cac ctt gta tca gct gca atg tca ggt gta acc tgt tcg     1732
Asp Leu Asn His Leu Val Ser Ala Ala Met Ser Gly Val Thr Cys Ser
    225                 230                 235

tta aga ttt cct ggt caa ctt aac agt gac tta aga aaa tta gct gtt     1780
Leu Arg Phe Pro Gly Gln Leu Asn Ser Asp Leu Arg Lys Leu Ala Val
240                 245                 250                 255

aat ttg atc cca ttc cca cgt tta cat ttc ttt atg tac ggg ttt gct     1828
Asn Leu Ile Pro Phe Pro Arg Leu His Phe Phe Met Tyr Gly Phe Ala
                260                 265                 270

cct tta act agt aga ggc agt caa caa tac aga gcc tta act gtg ccg     1876
Pro Leu Thr Ser Arg Gly Ser Gln Gln Tyr Arg Ala Leu Thr Val Pro
            275                 280                 285

gag tta aca caa caa atg ttc gac gca aaa aat atg atg tgc aca agt     1924
Glu Leu Thr Gln Gln Met Phe Asp Ala Lys Asn Met Met Cys Thr Ser
        290                 295                 300

gat cca aga cat gga aga tat tta acg gca tgt gct atg ttt aga gga     1972
Asp Pro Arg His Gly Arg Tyr Leu Thr Ala Cys Ala Met Phe Arg Gly
    305                 310                 315

aga atg tcc aca aag gaa gtt gac gaa caa atg tta aac gtt caa aat     2020
Arg Met Ser Thr Lys Glu Val Asp Glu Gln Met Leu Asn Val Gln Asn
```

-continued

```
320                 325                 330                 335

aaa aac tca tct tat ttt gtc gaa tgg att cct cac aac aca aag         2065
Lys Asn Ser Ser Tyr Phe Val Glu Trp Ile Pro His Asn Thr Lys
                340                 345                 350

taagaaggaa caattgatac tagtatgcat gttttttgt ttatatgtat ttatatatat   2125

atatatatat atgtattcat ttatatattt tgaaatatac attttacata taaatttttt   2185

tttttctttt ttcttttttt tttttttgt ttttttcttt aga tca agt gtt tgt     2240
                                                Ser Ser Val Cys

gat att cca cca ttg gga tta aaa atg gct gtt act ttt gta gga aac     2288
Asp Ile Pro Pro Leu Gly Leu Lys Met Ala Val Thr Phe Val Gly Asn
355                 360                 365                 370

tca acc gcc att caa gaa atg ttt aaa aga gtt tct gat caa ttt act     2336
Ser Thr Ala Ile Gln Glu Met Phe Lys Arg Val Ser Asp Gln Phe Thr
                375                 380                 385

gct atg ttt aga aga aaa gcc ttt ttg cac tgg tac acc gga gaa ggt     2384
Ala Met Phe Arg Arg Lys Ala Phe Leu His Trp Tyr Thr Gly Glu Gly
            390                 395                 400

atg gac gag atg gaa ttt aca gaa gct gaa tca aat atg aat gat tta     2432
Met Asp Glu Met Glu Phe Thr Glu Ala Glu Ser Asn Met Asn Asp Leu
        405                 410                 415

gtt tca gaa tat caa caa tat caa gat gct aca gca gaa gag gaa gga     2480
Val Ser Glu Tyr Gln Gln Tyr Gln Asp Ala Thr Ala Glu Glu Glu Gly
    420                 425                 430

gaa ttt gaa gaa gaa gaa gga gac gta gaa gcc taaatctatt tatatttatg   2533
Glu Phe Glu Glu Glu Glu Gly Asp Val Glu Ala
435                 440                 445

aaaatatata catattatat atatatgtat atgtaattaa caagaataaa aaataaaaaa   2593

taaaaaaaaa ataaaataaa aaaataaaaa tacataataa aaaagtataa aataaatatc   2653

taatcattaa ttatatataa caatataatt taactctttt tttttttatt attattgaag   2713

ttatgttcgg gtatatataa catatatata aattatatat atgttgcagt ttcttttttt   2773

tttttttttt tttttttct tatcatttga ttttacactc acatatatat gacatatata   2833


<210> SEQ ID NO 171
<211> LENGTH: 445
<212> TYPE: PRT
<213> ORGANISM: Plasmodium falciparum

<400> SEQUENCE: 171

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Ser Gly Thr Tyr Ser Gly Asp Ser Asp Leu Gln Leu Glu Arg Val Asp
        35                  40                  45

Val Phe Tyr Asn Glu Ala Thr Gly Gly Arg Tyr Val Pro Arg Ala Ile
    50                  55                  60

Leu Met Asp Leu Glu Pro Gly Thr Met Asp Ser Val Arg Ala Gly Pro
65                  70                  75                  80

Phe Gly Gln Leu Phe Arg Pro Asp Asn Phe Val Phe Gly Gln Thr Gly
                85                  90                  95

Ala Gly Asn Asn Trp Ala Lys Gly His Tyr Thr Glu Gly Ala Glu Leu
            100                 105                 110

Ile Asp Ala Val Leu Asp Val Leu Arg Lys Glu Ala Glu Gly Cys Asp
        115                 120                 125
```

-continued

```
Cys Leu Gln Gly Phe Gln Ile Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Glu Thr Phe Ser Val Phe Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Ala Asp Glu Val Gln Val Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Ala Met Ser Gly Val Thr Cys Ser Leu
225                 230                 235                 240

Arg Phe Pro Gly Gln Leu Asn Ser Asp Leu Arg Lys Leu Ala Val Asn
                245                 250                 255

Leu Ile Pro Phe Pro Arg Leu His Phe Phe Met Tyr Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Met Phe Asp Ala Lys Asn Met Met Cys Thr Ser Asp
    290                 295                 300

Pro Arg His Gly Arg Tyr Leu Thr Ala Cys Ala Met Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Val Glu Trp Ile Pro His Asn Thr Lys Ser Ser
            340                 345                 350

Val Cys Asp Ile Pro Pro Leu Gly Leu Lys Met Ala Val Thr Phe Val
        355                 360                 365

Gly Asn Ser Thr Ala Ile Gln Glu Met Phe Lys Arg Val Ser Asp Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Phe Glu Glu Glu Glu Gly Asp Val Glu Ala
        435                 440                 445
```

<210> SEQ ID NO 172
<211> LENGTH: 445
<212> TYPE: PRT
<213> ORGANISM: Plasmodium falciparum

<400> SEQUENCE: 172

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Ser Gly Thr Tyr Ser Gly Asp Ser Asp Leu Gln Leu Glu Arg Val Asp
        35                  40                  45

Val Phe Tyr Asn Glu Ala Thr Gly Gly Arg Tyr Val Pro Arg Ala Ile
    50                  55                  60
```

-continued

```
Leu Met Asp Leu Glu Pro Gly Thr Met Asp Ser Val Arg Ala Gly Pro
65                  70                  75                  80

Phe Gly Gln Leu Phe Arg Pro Asp Asn Phe Val Phe Gly Gln Thr Gly
                85                  90                  95

Ala Gly Asn Asn Trp Ala Lys Gly His Tyr Thr Glu Gly Ala Glu Leu
            100                 105                 110

Ile Asp Ala Val Leu Asp Val Leu Arg Lys Glu Ala Glu Gly Cys Asp
        115                 120                 125

Cys Leu Gln Gly Phe Gln Ile Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Glu Thr Phe Ser Val Phe Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Ala Asp Glu Val Gln Val Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Ala Met Ser Gly Val Thr Cys Ser Leu
225                 230                 235                 240

Arg Phe Pro Gly Gln Leu Asn Ser Asp Leu Arg Lys Leu Ala Val Asn
                245                 250                 255

Leu Ile Pro Phe Pro Arg Leu His Phe Phe Met Tyr Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Met Phe Asp Ala Lys Asn Met Met Cys Thr Ser Asp
    290                 295                 300

Pro Arg His Gly Arg Tyr Leu Thr Ala Cys Ala Met Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Val Glu Trp Ile Pro His Asn Thr Lys Ser Ser
            340                 345                 350

Val Cys Asp Ile Pro Pro Leu Gly Leu Lys Met Ala Val Thr Phe Val
        355                 360                 365

Gly Asn Ser Thr Ala Ile Gln Glu Met Phe Lys Arg Val Ser Asp Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Phe Glu Glu Glu Glu Gly Asp Val Glu Ala
        435                 440                 445
```

<210> SEQ ID NO 173
<211> LENGTH: 39
<212> TYPE: DNA
<213> ORGANISM: Artificial
<220> FEATURE:

-continued

<223> OTHER INFORMATION: synthetic oligonucleotide

<400> SEQUENCE: 173
gatcgaattc atgagagaaa ttgttcatat tcaagctgg 39

<210> SEQ ID NO 174
<211> LENGTH: 43
<212> TYPE: DNA
<213> ORGANISM: Artificial
<220> FEATURE:
<223> OTHER INFORMATION: synthetic oligonucleotide

<400> SEQUENCE: 174
gatcctcgag ttaataatct gcttcatatc cttcatcttc tcc 43

<210> SEQ ID NO 175
<211> LENGTH: 1827
<212> TYPE: DNA
<213> ORGANISM: Cryptosporidium parvum
<220> FEATURE:
<221> NAME/KEY: exon
<222> LOCATION: (1)..(1365)

<400> SEQUENCE: 175

```
atg aga gaa gtt att tca att cat gtt ggg cag gca gga ata caa att       48
Met Arg Glu Val Ile Ser Ile His Val Gly Gln Ala Gly Ile Gln Ile
1               5                   10                  15

ggt aat gct tgt tgg gaa tta ttt tgc ctt gaa cat gga ata aat cca       96
Gly Asn Ala Cys Trp Glu Leu Phe Cys Leu Glu His Gly Ile Asn Pro
            20                  25                  30

gat gga aca atg ccc atg tcc gag caa aat atg ggt att tca gat gat      144
Asp Gly Thr Met Pro Met Ser Glu Gln Asn Met Gly Ile Ser Asp Asp
        35                  40                  45

gca ttc aat acg ttc ttc agc gag act gga gct gga aag cat gtg ccc      192
Ala Phe Asn Thr Phe Phe Ser Glu Thr Gly Ala Gly Lys His Val Pro
    50                  55                  60

aga gca gtt ttt gta gat ctg gag cca act gtt gtt gac gaa att cgt      240
Arg Ala Val Phe Val Asp Leu Glu Pro Thr Val Val Asp Glu Ile Arg
65                  70                  75                  80

agt ggg aca tat agg caa ctg ttt cat cca gag cag ctt att aat ggt      288
Ser Gly Thr Tyr Arg Gln Leu Phe His Pro Glu Gln Leu Ile Asn Gly
                85                  90                  95

aag gaa gat gcg gct aac aac ttt gca agg ggc cat tat aca gta ggg      336
Lys Glu Asp Ala Ala Asn Asn Phe Ala Arg Gly His Tyr Thr Val Gly
            100                 105                 110

aaa gag ata ttg gaa gta tgt ttg gat cga att cgt aaa ctt gct gac      384
Lys Glu Ile Leu Glu Val Cys Leu Asp Arg Ile Arg Lys Leu Ala Asp
        115                 120                 125

aat tgt aca gga tta caa ggt ttt ctt atg ttt aat gca gtt gga ggt      432
Asn Cys Thr Gly Leu Gln Gly Phe Leu Met Phe Asn Ala Val Gly Gly
    130                 135                 140

gga aca gga gct ggc ctc ggg aca tta tta cta gaa agg ctt tct gtt      480
Gly Thr Gly Ala Gly Leu Gly Thr Leu Leu Leu Glu Arg Leu Ser Val
145                 150                 155                 160

gac tat ggc aaa aaa tct aaa ttg aat ttc tgt aca tgg cca tct ccg      528
Asp Tyr Gly Lys Lys Ser Lys Leu Asn Phe Cys Thr Trp Pro Ser Pro
                165                 170                 175

cag ctt agc act gca gtg gta gag cca tac aac gcc gtc ctt tcc act      576
Gln Leu Ser Thr Ala Val Val Glu Pro Tyr Asn Ala Val Leu Ser Thr
            180                 185                 190

cac tct ctc ctt gaa cat gca gat gtt gct gtt atg cta gat aat gaa      624
His Ser Leu Leu Glu His Ala Asp Val Ala Val Met Leu Asp Asn Glu
```

-continued

```
        195                 200                 205

gca ata tat gat atc tgt aga cga aat ttg aac att gag cag cct gct      672
Ala Ile Tyr Asp Ile Cys Arg Arg Asn Leu Asn Ile Glu Gln Pro Ala
    210                 215                 220

tat acg aac cta aat aga tta att gcg caa gta ata tcc tcc ttg act      720
Tyr Thr Asn Leu Asn Arg Leu Ile Ala Gln Val Ile Ser Ser Leu Thr
225                 230                 235                 240

gca tct ttg cgt ttc gat ggt gca ttg aat gtc gat atc acc gag ttt      768
Ala Ser Leu Arg Phe Asp Gly Ala Leu Asn Val Asp Ile Thr Glu Phe
                245                 250                 255

caa acc aat ttg gtt cct tac cca agg atc cac ttt atg ctt tca tca      816
Gln Thr Asn Leu Val Pro Tyr Pro Arg Ile His Phe Met Leu Ser Ser
            260                 265                 270

tat gct cca att att tcc gct gaa aaa gct ttt cac gaa caa tta agt      864
Tyr Ala Pro Ile Ile Ser Ala Glu Lys Ala Phe His Glu Gln Leu Ser
        275                 280                 285

gtt gcc gag att act aat gca gtt ttt gaa cct caa aat caa atg gct      912
Val Ala Glu Ile Thr Asn Ala Val Phe Glu Pro Gln Asn Gln Met Ala
    290                 295                 300

aag tgt gac cct aga cac ggt aaa tat atg gca tgc tgc ttg atg tac      960
Lys Cys Asp Pro Arg His Gly Lys Tyr Met Ala Cys Cys Leu Met Tyr
305                 310                 315                 320

aga ggt gat gtt gtt cca aaa gat aca aat gca gca gtt gca aca att     1008
Arg Gly Asp Val Val Pro Lys Asp Thr Asn Ala Ala Val Ala Thr Ile
                325                 330                 335

aaa act aaa aga act att cag ttt gtt gat tgg tgc cca aca ggc ttc     1056
Lys Thr Lys Arg Thr Ile Gln Phe Val Asp Trp Cys Pro Thr Gly Phe
            340                 345                 350

aaa tgt gga att aat tat caa ccg ccg act gtt gtg cct ggc ggg gat     1104
Lys Cys Gly Ile Asn Tyr Gln Pro Pro Thr Val Val Pro Gly Gly Asp
        355                 360                 365

ctc gct aag gtt atg cgt gca tgt tgt atg att tca aac tca act gca     1152
Leu Ala Lys Val Met Arg Ala Cys Cys Met Ile Ser Asn Ser Thr Ala
    370                 375                 380

ata gct gag gtc ttc aat agg atg gat cat aaa ttt gat tta atg tat     1200
Ile Ala Glu Val Phe Asn Arg Met Asp His Lys Phe Asp Leu Met Tyr
385                 390                 395                 400

tca aaa agg gca ttc gtg cat tgg tat gtc ggc gag ggc atg gaa gaa     1248
Ser Lys Arg Ala Phe Val His Trp Tyr Val Gly Glu Gly Met Glu Glu
                405                 410                 415

ggt gaa ttt agc gag gca aga gaa gac tta gct gca tta gag aaa gac     1296
Gly Glu Phe Ser Glu Ala Arg Glu Asp Leu Ala Ala Leu Glu Lys Asp
            420                 425                 430

tat gaa gag gtt gga att gaa att gca gat gga gaa gat gaa gaa gtt     1344
Tyr Glu Glu Val Gly Ile Glu Ile Ala Asp Gly Glu Asp Glu Glu Val
        435                 440                 445

cat tac gag ggc gat ttc tag ttatccttgt tcattgaatt ctctagattt        1395
His Tyr Glu Gly Asp Phe
    450

aggaggtttg gtttaccgcc cggcgggctc gtgtagatta gtatcttaat ctatggaatt   1455

ttccctattt agttatagtc aaaagcggat ccttgctgca ggtgtgttgt ctttattatc   1515

cggatatgtg cttggtgtga ctaacatacc gagggctgtt ttgctcaatt ttttgtcctt   1575

ttcttggatg aaatggtcta tgcatgtccg tggctatcaa attaccaata gttgtataaa   1635

ttttgagagt tttatcatgg ttctcatcaa ttcctcactt ttacttggtg cttccatagg   1695

ctctattgct tctgtgtttg tggaaagata ttttggtaag gttaaaggca ttctctctgc   1755

atattttttg tttggtattg gttctgtatt ttgtttgaac aaggatttag taattttctt   1815
```

-continued aattggaagg gt 1827

<210> SEQ ID NO 176
<211> LENGTH: 454
<212> TYPE: PRT
<213> ORGANISM: Cryptosporidium parvum

<400> SEQUENCE: 176

Met Arg Glu Val Ile Ser Ile His Val Gly Gln Ala Gly Ile Gln Ile
1 5 10 15

Gly Asn Ala Cys Trp Glu Leu Phe Cys Leu Glu His Gly Ile Asn Pro
20 25 30

Asp Gly Thr Met Pro Met Ser Glu Gln Asn Met Gly Ile Ser Asp Asp
35 40 45

Ala Phe Asn Thr Phe Phe Ser Glu Thr Gly Ala Gly Lys His Val Pro
50 55 60

Arg Ala Val Phe Val Asp Leu Glu Pro Thr Val Val Asp Glu Ile Arg
65 70 75 80

Ser Gly Thr Tyr Arg Gln Leu Phe His Pro Glu Gln Leu Ile Asn Gly
85 90 95

Lys Glu Asp Ala Ala Asn Asn Phe Ala Arg Gly His Tyr Thr Val Gly
100 105 110

Lys Glu Ile Leu Glu Val Cys Leu Asp Arg Ile Arg Lys Leu Ala Asp
115 120 125

Asn Cys Thr Gly Leu Gln Gly Phe Leu Met Phe Asn Ala Val Gly Gly
130 135 140

Gly Thr Gly Ala Gly Leu Gly Thr Leu Leu Leu Glu Arg Leu Ser Val
145 150 155 160

Asp Tyr Gly Lys Lys Ser Lys Leu Asn Phe Cys Thr Trp Pro Ser Pro
165 170 175

Gln Leu Ser Thr Ala Val Val Glu Pro Tyr Asn Ala Val Leu Ser Thr
180 185 190

His Ser Leu Leu Glu His Ala Asp Val Ala Val Met Leu Asp Asn Glu
195 200 205

Ala Ile Tyr Asp Ile Cys Arg Arg Asn Leu Asn Ile Glu Gln Pro Ala
210 215 220

Tyr Thr Asn Leu Asn Arg Leu Ile Ala Gln Val Ile Ser Ser Leu Thr
225 230 235 240

Ala Ser Leu Arg Phe Asp Gly Ala Leu Asn Val Asp Ile Thr Glu Phe
245 250 255

Gln Thr Asn Leu Val Pro Tyr Pro Arg Ile His Phe Met Leu Ser Ser
260 265 270

Tyr Ala Pro Ile Ile Ser Ala Glu Lys Ala Phe His Glu Gln Leu Ser
275 280 285

Val Ala Glu Ile Thr Asn Ala Val Phe Glu Pro Gln Asn Gln Met Ala
290 295 300

Lys Cys Asp Pro Arg His Gly Lys Tyr Met Ala Cys Cys Leu Met Tyr
305 310 315 320

Arg Gly Asp Val Val Pro Lys Asp Thr Asn Ala Ala Val Ala Thr Ile
325 330 335

Lys Thr Lys Arg Thr Ile Gln Phe Val Asp Trp Cys Pro Thr Gly Phe
340 345 350

Lys Cys Gly Ile Asn Tyr Gln Pro Pro Thr Val Val Pro Gly Gly Asp
355 360 365

-continued

```
Leu Ala Lys Val Met Arg Ala Cys Cys Met Ile Ser Asn Ser Thr Ala
    370                 375                 380

Ile Ala Glu Val Phe Asn Arg Met Asp His Lys Phe Asp Leu Met Tyr
385                 390                 395                 400

Ser Lys Arg Ala Phe Val His Trp Tyr Val Gly Glu Gly Met Glu Glu
                405                 410                 415

Gly Glu Phe Ser Glu Ala Arg Glu Asp Leu Ala Ala Leu Glu Lys Asp
            420                 425                 430

Tyr Glu Glu Val Gly Ile Glu Ile Ala Asp Gly Glu Asp Glu Glu Val
        435                 440                 445

His Tyr Glu Gly Asp Phe
    450
```

<210> SEQ ID NO 177
<211> LENGTH: 47
<212> TYPE: DNA
<213> ORGANISM: Artificial
<220> FEATURE:
<223> OTHER INFORMATION: synthetic oligonucleotide

<400> SEQUENCE: 177
gatcctcgag gaattcatga gagaagttat ttcaattcat gttgggc 47

<210> SEQ ID NO 178
<211> LENGTH: 34
<212> TYPE: DNA
<213> ORGANISM: Artificial
<220> FEATURE:
<223> OTHER INFORMATION: synthetic oligonucleotide

<400> SEQUENCE: 178
gatcctcgag ctagaaatcg ccctcgtaat gaac 34

<210> SEQ ID NO 179
<211> LENGTH: 1618
<212> TYPE: DNA
<213> ORGANISM: Cryptosporidium parvum

<400> SEQUENCE: 179

```
tgggtaatct tctggctatt ggggaacttg aattatagat tataataagt tgttgattac     60

tataatttgt aggatattca tattaattga ttcctaatta ccattaataa gaaaaagaga    120

atgagagaaa ttgttcatgt tcaaggagga caatgtggga accagattgg tgctaaattc    180

tgggaagtca tttctgatga gcacgggatc gaccctgtaa gttttgaaaa taattgaaat    240

aatttgaact gaataattga cttttttttt ttcttttttt ttctttgaaa tatgaattta    300

gactggtact ggtacttatc atggagaatc agatttacag atggaacgta ttaatgtttt    360

ctacaatgaa gcttcgggtg gaagatacgt tccaagagcg attttggtag atcttgagcc    420

aggaacaatg gattcagtta gagctggtcc ttttggatca ttatttagac ctgataactt    480

catttttggt caaagtggag ctggtaatat ttgggccaaa ggtcattata cagagggagc    540

tgaactctta gatgctgtaa tggatgtagt tagacatgag gcagaatctt gtgattgctt    600

acagggtttc caaatcactc actctttggg aggtggtaca ggatcaggta tgggtacttt    660

gttggttgga aagattcatg aagaattccc agatcgtatt ttgcagacct tttcagtatt    720

cccatctcca aaggtatcag atactgtagt agagccctac aatgcaacct tatcaattca    780

ccagttggtt gaaaattcgg atgctgttca agtaatcgat aatgaagcct tgtatgatat    840
```

-continued

```
ttgctttaga acattgaaac taacaaatcc atcttatgga gatttgaatc acttggtttc    900

agttgctatg tctggcgtaa cttgttgcct acgtttccca ggtcaactaa acagtgactt    960

aagaaagatg tcagttaact tggttccttt cccaagatta cacttcttca tgattgggtt   1020

tgcacctcta acatcaagag gttctcaaca atacagatct ttatcagttg cagagcttac   1080

ccaacaaatg tttgatgcaa agaatatgat gtgtgcttca gaccctcgac atggaagata   1140

tctcacagct agtgtaatgt tcagaggaag aatgtcaaca aaggaagttg atgaacagat   1200

gcttttggtt caaaacagaa actcatctta ttttgttgaa tggattccaa ataatatcaa   1260

gtcatcagtt tgtgatattc ctccaaaagg attgaagatg gcttcaacct ttgttggaaa   1320

ctctactgcc atccaggaaa tgttcagacg tgttgctgag caattcactt ccatgttcag   1380

gagaaaggcc ttcttgcact ggatatctgg agaggggatg gatgagatgg aattcactga   1440

agctgagacg aatatgaacg atttagtttc tgaatatcaa caatatcaag atgttccagt   1500

tgaagaagat gaatacccag atgacgaaca tcatattgag gcttaaactt cttggacata   1560

aatcaaacca ttgggaagct atcctcatgg ggtggctata gtcgatttca tcattttt     1618


<210> SEQ ID NO 180
<211> LENGTH: 446
<212> TYPE: PRT
<213> ORGANISM: Cryptosporidium parvum

<400> SEQUENCE: 180

Met Arg Glu Ile Val His Val Gln Gly Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Gly Thr Tyr His Gly Glu Ser Asp Leu Gln Met Glu Arg
        35                  40                  45

Ile Asn Val Phe Tyr Asn Glu Ala Ser Gly Gly Arg Tyr Val Pro Arg
    50                  55                  60

Ala Ile Leu Val Asp Leu Glu Pro Gly Thr Met Asp Ser Val Arg Ala
65                  70                  75                  80

Gly Pro Phe Gly Ser Leu Phe Arg Pro Asp Asn Phe Ile Phe Gly Gln
                85                  90                  95

Ser Gly Ala Gly Asn Ile Trp Ala Lys Gly His Tyr Thr Glu Gly Ala
            100                 105                 110

Glu Leu Leu Asp Ala Val Met Asp Val Val Arg His Glu Ala Glu Ser
        115                 120                 125

Cys Asp Cys Leu Gln Gly Phe Gln Ile Thr His Ser Leu Gly Gly Gly
    130                 135                 140

Thr Gly Ser Gly Met Gly Thr Leu Leu Val Gly Lys Ile His Glu Glu
145                 150                 155                 160

Phe Pro Asp Arg Ile Leu Gln Thr Phe Ser Val Phe Pro Ser Pro Lys
                165                 170                 175

Val Ser Asp Thr Val Val Glu Pro Tyr Asn Ala Thr Leu Ser Ile His
            180                 185                 190

Gln Leu Val Glu Asn Ser Asp Ala Val Gln Val Ile Asp Asn Glu Ala
        195                 200                 205

Leu Tyr Asp Ile Cys Phe Arg Thr Leu Lys Leu Thr Asn Pro Ser Tyr
    210                 215                 220

Gly Asp Leu Asn His Leu Val Ser Val Ala Met Ser Gly Val Thr Cys
225                 230                 235                 240
```

-continued

```
Cys Leu Arg Phe Pro Gly Gln Leu Asn Ser Asp Leu Arg Lys Met Ser
                245                 250                 255

Val Asn Leu Val Pro Phe Pro Arg Leu His Phe Phe Met Ile Gly Phe
            260                 265                 270

Ala Pro Leu Thr Ser Arg Gly Ser Gln Gln Tyr Arg Ser Leu Ser Val
        275                 280                 285

Ala Glu Leu Thr Gln Gln Met Phe Asp Ala Lys Asn Met Met Cys Ala
    290                 295                 300

Ser Asp Pro Arg His Gly Arg Tyr Leu Thr Ala Ser Val Met Phe Arg
305                 310                 315                 320

Gly Arg Met Ser Thr Lys Glu Val Asp Glu Gln Met Leu Leu Val Gln
                325                 330                 335

Asn Arg Asn Ser Ser Tyr Phe Val Glu Trp Ile Pro Asn Asn Ile Lys
            340                 345                 350

Ser Ser Val Cys Asp Ile Pro Pro Lys Gly Leu Lys Met Ala Ser Thr
        355                 360                 365

Phe Val Gly Asn Ser Thr Ala Ile Gln Glu Met Phe Arg Arg Val Ala
    370                 375                 380

Glu Gln Phe Thr Ser Met Phe Arg Arg Lys Ala Phe Leu His Trp Ile
385                 390                 395                 400

Ser Gly Glu Gly Met Asp Glu Met Glu Phe Thr Glu Ala Glu Thr Asn
                405                 410                 415

Met Asn Asp Leu Val Ser Glu Tyr Gln Gln Tyr Gln Asp Val Pro Val
            420                 425                 430

Glu Glu Asp Glu Tyr Pro Asp Asp Glu His His Ile Glu Ala
        435                 440                 445
```

<210> SEQ ID NO 181
<211> LENGTH: 41
<212> TYPE: DNA
<213> ORGANISM: Artificial
<220> FEATURE:
<223> OTHER INFORMATION: synthetic oligonucleotide

<400> SEQUENCE: 181

```
gatccaattg atgagagaaa ttgttcatgt tcaaggagga c                        41
```

<210> SEQ ID NO 182
<211> LENGTH: 41
<212> TYPE: DNA
<213> ORGANISM: Artificial
<220> FEATURE:
<223> OTHER INFORMATION: synthetic oligonucleotide

<400> SEQUENCE: 182

```
gatcctcgag ttaagcctca atatgatgtt cgtcatctgg g                        41
```

<210> SEQ ID NO 183
<211> LENGTH: 3646
<212> TYPE: DNA
<213> ORGANISM: Trypanosoma brucei
<220> FEATURE:
<221> NAME/KEY: exon
<222> LOCATION: (1961)..(3316)

<400> SEQUENCE: 183

```
atgcgcgaaa tcgtctgcgt tcaggctggc caatgcggta accagatcgg ctcaaagttc     60

tgggaggtga tcagtgacga gcacggtgtg gaccccacag gtacctacca gggtgactct    120

gacctgcagc tggagcgcat caatgtgtac tttgatgagg caacgggagg tcgctatgtg    180
```

-continued

```
ccccgctccg tgctgattga tctggagcca ggtacaatgg actccgtacg tgctggcccc    240

tatggtcaga tcttccgccc cgacaacttc atctttggac agtctggcgc cggcaacaac    300

tgggcaaagg gccactacac ggagggtgcg gaactgatcg actctgtgct cgatgtgtgc    360

tgcaaggagg cggagagctg tgactgcctc caaggcttcc agatctgcca ctcccttggt    420

ggtggtactg gctccggcat gggtacgctg ctcatctcga agcttcgcga gcagtaccct    480

gaccgtatca tgatgacttt ctccatcatc ccatccccca aggtgtccga cactgtcgtc    540

gagccgtaca atacgactct ctccgtgcac caacttgtgg aaaactccga tgagtcgatg    600

tgcattgaca acgaggcact gtacgatatt tgcttccgca ccctgaaact gacaacacca    660

acgttcggtg acctgaacca cttggtgtct gctgttgtgt ccggcgtcac ctgctgcctg    720

cgcttccctg gtcagttgaa ctctgacctc cgtaagttgg ctgtgaacct tgtcccattc    780

ccgcgtctgc acttcttcat gatgggcttc gccccgctga ccagccgcgg ctcgcagcag    840

taccgcggtc tctccgtgcc cgagctaacg cagcagatgt tcgatgcgaa aaacatgatg    900

caagctgcag atcctcgtca cggccgctac ctgacagcgt ctgcactctt ccgcggccgc    960

atgtcgacga aggaggttga tgagcagatg ctgaacgtgc agaacaagaa ctcgtcctac   1020

ttcattgagt ggatcccgaa caacatcaag tcctctgttt gcgatatccc acccaaggga   1080

ctcaagatgg ctgtcacctt cattggcaac aacacctgca tccaggagat gttccgccgt   1140

gtgggagagc agttcaccct catgttccgt cgcaaggcgt tcttgcactg gtacactggc   1200

gagggtatgg acgagatgga attcacggag gcagagtcca acatgaacga tctcgtgtct   1260

gagtaccagc agtaccagga tgccacgatt gaggaggagg gcgagttcga cgaggaggag   1320

caatactaga cgcggacggg gcatttcccg ttcgtcatta gcagtaggta atgaagatgt   1380

ttgtttctcg tccccttttct ccttcgtcct tctgtcattt tgttcttttg tgtttatgtt   1440

ttgttgttgt tttctttaat tttttttttc ttccacgttt gtgtacatcc gcgcgccact   1500

ctattcagag agccacggat agtagaggag gtgggaaggg tatatgaggg acacgcgtac   1560

catgatgtgg gatgtattgg ggtccctgtc tgtccttacg tgactatgta tgaaccgtca   1620

cgtgtaagat gagctagtga gatcaacagt acaactcatc aacacgcctt cttctcgtta   1680

aatgtacaca atcttgatcc tccaccttta tgggtcccat tgtttgcctc ttccgctgtg   1740

tggagtgcgc ctacacgcac ttctcacttc gtaagtggtg gtggcgtaag tattgcctaa   1800

tgttgactct atattctcct ctcctcaccc cctcgcggtg ctgatttctg acagatcttc   1860

aaacactagt ttaagcaaag gactattcat ccgtttatat tagcaacagt aggtactagc   1920

accactaaca acaacaacaa agcacttcta tttatttatc atg cgt gag gct atc      1975
                                            Met Arg Glu Ala Ile
                                            1               5

tgc atc cac att ggt cag gct ggt tgc cag gtt ggt aac gcc tgc tgg      2023
Cys Ile His Ile Gly Gln Ala Gly Cys Gln Val Gly Asn Ala Cys Trp
                10                  15                  20

gaa ttg ttc tgc ctg gaa cac ggc att caa ccc gat ggt gcg atg ccc      2071
Glu Leu Phe Cys Leu Glu His Gly Ile Gln Pro Asp Gly Ala Met Pro
            25                  30                  35

tct gac aag acg att ggc gtt gag gat gat gcg ttc aac acc ttc ttc      2119
Ser Asp Lys Thr Ile Gly Val Glu Asp Asp Ala Phe Asn Thr Phe Phe
        40                  45                  50

tct gag act ggt gct ggc aag cac gtt ccc cgc gcg gtg ttc ttg gac      2167
Ser Glu Thr Gly Ala Gly Lys His Val Pro Arg Ala Val Phe Leu Asp
    55                  60                  65
```

-continued

```
ctg gag cca aca gtg gtg gat gaa gtg cgc act ggc acg tac cgc cag     2215
Leu Glu Pro Thr Val Val Asp Glu Val Arg Thr Gly Thr Tyr Arg Gln
70                  75                  80                  85

ctg ttc cac ccc gag cag ctg atc tcc ggc aag gag gat gcg gcc aac     2263
Leu Phe His Pro Glu Gln Leu Ile Ser Gly Lys Glu Asp Ala Ala Asn
                90                  95                  100

aac tac gct cgt ggc cac tac acc att ggt aag gag atc gtc gac ctc     2311
Asn Tyr Ala Arg Gly His Tyr Thr Ile Gly Lys Glu Ile Val Asp Leu
            105                 110                 115

tgc ctg gac cgc atc cgc aag ctc gct gac aac tgc act ggt ctt cag     2359
Cys Leu Asp Arg Ile Arg Lys Leu Ala Asp Asn Cys Thr Gly Leu Gln
        120                 125                 130

ggc ttc ctc gtg tat cac gcc gtc ggc ggt ggc act ggt tct ggc ctg     2407
Gly Phe Leu Val Tyr His Ala Val Gly Gly Gly Thr Gly Ser Gly Leu
    135                 140                 145

ggt gcg ctg ctc ttg gag cgc ctc tcc gtg gac tat ggc aag aag tcc     2455
Gly Ala Leu Leu Leu Glu Arg Leu Ser Val Asp Tyr Gly Lys Lys Ser
150                 155                 160                 165

aag ctc ggc tac acg gtg tat cca tca ccg cag gtg tcg acg gct gtc     2503
Lys Leu Gly Tyr Thr Val Tyr Pro Ser Pro Gln Val Ser Thr Ala Val
                170                 175                 180

gtg gag ccc tac aac tct gtg ctc tcg aca cac tca ctt ctg gag cac     2551
Val Glu Pro Tyr Asn Ser Val Leu Ser Thr His Ser Leu Leu Glu His
            185                 190                 195

acc gat gtt gct gcg atg ctt gac aat gaa gca att tat gat ttg act     2599
Thr Asp Val Ala Ala Met Leu Asp Asn Glu Ala Ile Tyr Asp Leu Thr
        200                 205                 210

cgc cgc aac ctc gat att gag cgc ccc acg tac acc aac ctg aac cgc     2647
Arg Arg Asn Leu Asp Ile Glu Arg Pro Thr Tyr Thr Asn Leu Asn Arg
    215                 220                 225

ctc atc ggt cag gtg gtt tcc tcg ctg aca gcg tcc ctc cgc ttc gac     2695
Leu Ile Gly Gln Val Val Ser Ser Leu Thr Ala Ser Leu Arg Phe Asp
230                 235                 240                 245

ggt gca ttg aac gtg gat ctg aca gag ttc cag aca aac ctt gtg ccg     2743
Gly Ala Leu Asn Val Asp Leu Thr Glu Phe Gln Thr Asn Leu Val Pro
                250                 255                 260

tac cca cgt atc cac ttc gtg ctg aca agc tat gca cca gtc atc tcc     2791
Tyr Pro Arg Ile His Phe Val Leu Thr Ser Tyr Ala Pro Val Ile Ser
            265                 270                 275

gca gag aag gcc tac cac gag caa ctc tct gtc tct gag atc tcg aac     2839
Ala Glu Lys Ala Tyr His Glu Gln Leu Ser Val Ser Glu Ile Ser Asn
        280                 285                 290

gct gtg ttt gag ccc gcc tcc atg atg aca aag tgc gac ccc cgc cac     2887
Ala Val Phe Glu Pro Ala Ser Met Met Thr Lys Cys Asp Pro Arg His
    295                 300                 305

ggc aag tac atg gcg tgc tgc ctc atg tac cgt ggt gac gtt gtg cca     2935
Gly Lys Tyr Met Ala Cys Cys Leu Met Tyr Arg Gly Asp Val Val Pro
310                 315                 320                 325

aag gat gtg aat gct gcc gtc gcg acc atc aag acg aag cgc acg att     2983
Lys Asp Val Asn Ala Ala Val Ala Thr Ile Lys Thr Lys Arg Thr Ile
                330                 335                 340

cag ttc gtg gac tgg tct ccc aca ggc ttc aag tgc ggt atc aac tac     3031
Gln Phe Val Asp Trp Ser Pro Thr Gly Phe Lys Cys Gly Ile Asn Tyr
            345                 350                 355

cag cca ccc acg gtg gtg cca ggt ggt gac ctt gcc aag gtg cag cgc     3079
Gln Pro Pro Thr Val Val Pro Gly Gly Asp Leu Ala Lys Val Gln Arg
        360                 365                 370

gcg gta tgc atg atc gcc aac tcc acg gcc atc gca gag gtg ttc gcc     3127
Ala Val Cys Met Ile Ala Asn Ser Thr Ala Ile Ala Glu Val Phe Ala
    375                 380                 385
```

-continued

```
cgt att gac cac aaa ttc gat ctc atg tac agc aag cgc gcc ttc gtg     3175
Arg Ile Asp His Lys Phe Asp Leu Met Tyr Ser Lys Arg Ala Phe Val
390                 395                 400                 405

cac tgg tac gtc ggt gag ggt atg gaa gag ggt gag ttc tcc gag gcc     3223
His Trp Tyr Val Gly Glu Gly Met Glu Glu Gly Glu Phe Ser Glu Ala
                410                 415                 420

cgt gaa gac ctt gca gca ctt gag aag gac tac gaa gag gtt ggt gcc     3271
Arg Glu Asp Leu Ala Ala Leu Glu Lys Asp Tyr Glu Glu Val Gly Ala
            425                 430                 435

gag tcc gcg gat atg gac ggt gag gag gat gtg gag gag tac tag         3316
Glu Ser Ala Asp Met Asp Gly Glu Glu Asp Val Glu Glu Tyr
        440                 445                 450

aaagtgtgac aacgtcgcac catgtgtagg ttttcattta tgttctttct ttcttttttt   3376

tgtgaatttg ttttctgtct caaatgtttt taattcgctt gggacctatg tttttcttgt   3436

ttttttgctc accctttgtg taggaggcac cctgtcacgt ctgtggttgc gtgtatgcct   3496

tccttcccct tattcgcttc ttcctgtcgt gtcacacctc tttctctctc tccctttccg   3556

ccttttcttt caatcttgtt ttctcgacca gccctactag aggagaaaga atagtaaccc   3616

tttcatcaaa gaaaatagtt caaacgaatt                                    3646


<210> SEQ ID NO 184
<211> LENGTH: 451
<212> TYPE: PRT
<213> ORGANISM: Trypanosoma brucei

<400> SEQUENCE: 184

Met Arg Glu Ala Ile Cys Ile His Ile Gly Gln Ala Gly Cys Gln Val
1               5                   10                  15

Gly Asn Ala Cys Trp Glu Leu Phe Cys Leu Glu His Gly Ile Gln Pro
            20                  25                  30

Asp Gly Ala Met Pro Ser Asp Lys Thr Ile Gly Val Glu Asp Asp Ala
        35                  40                  45

Phe Asn Thr Phe Phe Ser Glu Thr Gly Ala Gly Lys His Val Pro Arg
    50                  55                  60

Ala Val Phe Leu Asp Leu Glu Pro Thr Val Val Asp Glu Val Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
        115                 120                 125

Cys Thr Gly Leu Gln Gly Phe Leu Val Tyr His Ala Val Gly Gly Gly
    130                 135                 140

Thr Gly Ser Gly Leu Gly Ala Leu Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ala Met Leu Asp Asn Glu Ala
        195                 200                 205

Ile Tyr Asp Leu Thr Arg Arg Asn Leu Asp Ile Glu Arg Pro Thr Tyr
    210                 215                 220
```

-continued

```
Thr Asn Leu Asn Arg Leu Ile Gly Gln Val Val Ser Ser Leu Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Val Leu Thr Ser Tyr
            260                 265                 270

Ala Pro Val Ile Ser Ala Glu Lys Ala Tyr His Glu Gln Leu Ser Val
        275                 280                 285

Ser Glu Ile Ser Asn Ala Val Phe Glu Pro Ala Ser Met Met Thr Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Ser Pro Thr Gly Phe Lys
            340                 345                 350

Cys Gly Ile Asn Tyr Gln Pro Pro Thr Val Val Pro Gly Gly Asp Leu
        355                 360                 365

Ala Lys Val Gln Arg Ala Val Cys Met Ile Ala Asn Ser Thr Ala Ile
    370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ala Glu Ser Ala Asp Met Asp Gly Glu Glu Asp Val
        435                 440                 445

Glu Glu Tyr
    450


<210> SEQ ID NO 185
<211> LENGTH: 32
<212> TYPE: DNA
<213> ORGANISM: Artificial
<220> FEATURE:
<223> OTHER INFORMATION: synthetic oligonucleotide

<400> SEQUENCE: 185

gatcgaattc atgcgtgagg ctatctgcat cc                               32


<210> SEQ ID NO 186
<211> LENGTH: 37
<212> TYPE: DNA
<213> ORGANISM: Artificial
<220> FEATURE:
<223> OTHER INFORMATION: synthetic oligonucleotide

<400> SEQUENCE: 186

gatcctcgag ctagtactcc tccacatcct cctcacc                          37


<210> SEQ ID NO 187
<211> LENGTH: 3646
<212> TYPE: DNA
<213> ORGANISM: Trypanosoma brucei
<220> FEATURE:
<221> NAME/KEY: exon
<222> LOCATION: (1)..(1329)

<400> SEQUENCE: 187
```

-continued

```
atg cgc gaa atc gtc tgc gtt cag gct ggc caa tgc ggt aac cag atc       48
Met Arg Glu Ile Val Cys Val Gln Ala Gly Gln Cys Gly Asn Gln Ile
1               5                   10                  15

ggc tca aag ttc tgg gag gtg atc agt gac gag cac ggt gtg gac ccc       96
Gly Ser Lys Phe Trp Glu Val Ile Ser Asp Glu His Gly Val Asp Pro
            20                  25                  30

aca ggt acc tac cag ggt gac tct gac ctg cag ctg gag cgc atc aat      144
Thr Gly Thr Tyr Gln Gly Asp Ser Asp Leu Gln Leu Glu Arg Ile Asn
        35                  40                  45

gtg tac ttt gat gag gca acg gga ggt cgc tat gtg ccc cgc tcc gtg      192
Val Tyr Phe Asp Glu Ala Thr Gly Gly Arg Tyr Val Pro Arg Ser Val
    50                  55                  60

ctg att gat ctg gag cca ggt aca atg gac tcc gta cgt gct ggc ccc      240
Leu Ile Asp Leu Glu Pro Gly Thr Met Asp Ser Val Arg Ala Gly Pro
65                  70                  75                  80

tat ggt cag atc ttc cgc ccc gac aac ttc atc ttt gga cag tct ggc      288
Tyr Gly Gln Ile Phe Arg Pro Asp Asn Phe Ile Phe Gly Gln Ser Gly
                85                  90                  95

gcc ggc aac aac tgg gca aag ggc cac tac acg gag ggt gcg gaa ctg      336
Ala Gly Asn Asn Trp Ala Lys Gly His Tyr Thr Glu Gly Ala Glu Leu
            100                 105                 110

atc gac tct gtg ctc gat gtg tgc tgc aag gag gcg gag agc tgt gac      384
Ile Asp Ser Val Leu Asp Val Cys Cys Lys Glu Ala Glu Ser Cys Asp
        115                 120                 125

tgc ctc caa ggc ttc cag atc tgc cac tcc ctt ggt ggt ggt act ggc      432
Cys Leu Gln Gly Phe Gln Ile Cys His Ser Leu Gly Gly Gly Thr Gly
    130                 135                 140

tcc ggc atg ggt acg ctg ctc atc tcg aag ctt cgc gag cag tac cct      480
Ser Gly Met Gly Thr Leu Leu Ile Ser Lys Leu Arg Glu Gln Tyr Pro
145                 150                 155                 160

gac cgt atc atg atg act ttc tcc atc atc cca tcc ccc aag gtg tcc      528
Asp Arg Ile Met Met Thr Phe Ser Ile Ile Pro Ser Pro Lys Val Ser
                165                 170                 175

gac act gtc gtc gag ccg tac aat acg act ctc tcc gtg cac caa ctt      576
Asp Thr Val Val Glu Pro Tyr Asn Thr Thr Leu Ser Val His Gln Leu
            180                 185                 190

gtg gaa aac tcc gat gag tcg atg tgc att gac aac gag gca ctg tac      624
Val Glu Asn Ser Asp Glu Ser Met Cys Ile Asp Asn Glu Ala Leu Tyr
        195                 200                 205

gat att tgc ttc cgc acc ctg aaa ctg aca aca cca acg ttc ggt gac      672
Asp Ile Cys Phe Arg Thr Leu Lys Leu Thr Thr Pro Thr Phe Gly Asp
    210                 215                 220

ctg aac cac ttg gtg tct gct gtt gtg tcc ggc gtc acc tgc tgc ctg      720
Leu Asn His Leu Val Ser Ala Val Val Ser Gly Val Thr Cys Cys Leu
225                 230                 235                 240

cgc ttc cct ggt cag ttg aac tct gac ctc cgt aag ttg gct gtg aac      768
Arg Phe Pro Gly Gln Leu Asn Ser Asp Leu Arg Lys Leu Ala Val Asn
                245                 250                 255

ctt gtc cca ttc ccg cgt ctg cac ttc ttc atg atg ggc ttc gcc ccg      816
Leu Val Pro Phe Pro Arg Leu His Phe Phe Met Met Gly Phe Ala Pro
            260                 265                 270

ctg acc agc cgc ggc tcg cag cag tac cgc ggt ctc tcc gtg ccc gag      864
Leu Thr Ser Arg Gly Ser Gln Gln Tyr Arg Gly Leu Ser Val Pro Glu
        275                 280                 285

cta acg cag cag atg ttc gat gcg aaa aac atg atg caa gct gca gat      912
Leu Thr Gln Gln Met Phe Asp Ala Lys Asn Met Met Gln Ala Ala Asp
    290                 295                 300

cct cgt cac ggc cgc tac ctg aca gcg tct gca ctc ttc cgc ggc cgc      960
Pro Arg His Gly Arg Tyr Leu Thr Ala Ser Ala Leu Phe Arg Gly Arg
```

-continued

```
305                 310                 315                 320

atg tcg acg aag gag gtt gat gag cag atg ctg aac gtg cag aac aag     1008
Met Ser Thr Lys Glu Val Asp Glu Gln Met Leu Asn Val Gln Asn Lys
                325                 330                 335

aac tcg tcc tac ttc att gag tgg atc ccg aac aac atc aag tcc tct     1056
Asn Ser Ser Tyr Phe Ile Glu Trp Ile Pro Asn Asn Ile Lys Ser Ser
            340                 345                 350

gtt tgc gat atc cca ccc aag gga ctc aag atg gct gtc acc ttc att     1104
Val Cys Asp Ile Pro Pro Lys Gly Leu Lys Met Ala Val Thr Phe Ile
        355                 360                 365

ggc aac aac acc tgc atc cag gag atg ttc cgc cgt gtg gga gag cag     1152
Gly Asn Asn Thr Cys Ile Gln Glu Met Phe Arg Arg Val Gly Glu Gln
    370                 375                 380

ttc acc ctc atg ttc cgt cgc aag gcg ttc ttg cac tgg tac act ggc     1200
Phe Thr Leu Met Phe Arg Arg Lys Ala Phe Leu His Trp Tyr Thr Gly
385                 390                 395                 400

gag ggt atg gac gag atg gaa ttc acg gag gca gag tcc aac atg aac     1248
Glu Gly Met Asp Glu Met Glu Phe Thr Glu Ala Glu Ser Asn Met Asn
                405                 410                 415

gat ctc gtg tct gag tac cag cag tac cag gat gcc acg att gag gag     1296
Asp Leu Val Ser Glu Tyr Gln Gln Tyr Gln Asp Ala Thr Ile Glu Glu
            420                 425                 430

gag ggc gag ttc gac gag gag gag caa tac tag acgcggacgg ggcatttccc   1349
Glu Gly Glu Phe Asp Glu Glu Glu Gln Tyr
        435                 440

gttcgtcatt agcagtaggt aatgaagatg tttgtttctc gtcccctttc tccttcgtcc   1409

ttctgtcatt ttgttctttt gtgtttatgt tttgttgttg ttttctttaa tttttttttt   1469

cttccacgtt tgtgtacatc cgcgcgccac tctattcaga gagccacgga tagtagagga   1529

ggtgggaagg gtatatgagg gacacgcgta ccatgatgtg ggatgtattg gggtccctgt   1589

ctgtccttac gtgactatgt atgaaccgtc acgtgtaaga tgagctagtg agatcaacag   1649

tacaactcat caacacgcct tcttctcgtt aaatgtacac aatcttgatc ctccaccttt   1709

atgggtccca ttgtttgcct cttccgctgt gtggagtgcg cctacacgca cttctcactt   1769

cgtaagtggt ggtggcgtaa gtattgccta atgttgactc tatattctcc tctcctcacc   1829

ccctcgcggt gctgatttct gacagatctt caaacactag tttaagcaaa ggactattca   1889

tccgtttata ttagcaacag taggtactag caccactaac aacaacaaca aagcacttct   1949

atttatttat catgcgtgag gctatctgca tccacattgg tcaggctggt tgccaggttg   2009

gtaacgcctg ctgggaattg ttctgcctgg aacacggcat tcaacccgat ggtgcgatgc   2069

cctctgacaa gacgattggc gttgaggatg atgcgttcaa caccttcttc tctgagactg   2129

gtgctggcaa gcacgttccc cgcgcggtgt tcttggacct ggagccaaca gtggtggatg   2189

aagtgcgcac tggcacgtac cgccagctgt tccaccccga gcagctgatc tccggcaagg   2249

aggatgcggc caacaactac gctcgtggcc actacaccat tggtaaggag atcgtcgacc   2309

tctgcctgga ccgcatccgc aagctcgctg acaactgcac tggtcttcag ggcttcctcg   2369

tgtatcacgc cgtcggcggt ggcactggtt ctggcctggg tgcgctgctc ttggagcgcc   2429

tctccgtgga ctatggcaag aagtccaagc tcggctacac ggtgtatcca tcaccgcagg   2489

tgtcgacggc tgtcgtggag ccctacaact ctgtgctctc gacacactca cttctggagc   2549

acaccgatgt tgctgcgatg cttgacaatg aagcaattta tgatttgact cgccgcaacc   2609

tcgatattga gcgccccacg tacaccaacc tgaaccgcct catcggtcag gtggtttcct   2669

cgctgacagc gtccctccgc ttcgacggtg cattgaacgt ggatctgaca gagttccaga   2729
```

-continued

```
caaaccttgt gccgtaccca cgtatccact tcgtgctgac aagctatgca ccagtcatct   2789

ccgcagagaa ggcctaccac gagcaactct ctgtctctga gatctcgaac gctgtgtttg   2849

agcccgcctc catgatgaca aagtgcgacc cccgccacgg caagtacatg gcgtgctgcc   2909

tcatgtaccg tggtgacgtt gtgccaaagg atgtgaatgc tgccgtcgcg accatcaaga   2969

cgaagcgcac gattcagttc gtggactggt ctcccacagg cttcaagtgc ggtatcaact   3029

accagccacc cacggtggtg ccaggtggtg accttgccaa ggtgcagcgc gcggtatgca   3089

tgatcgccaa ctccacggcc atcgcagagg tgttcgcccg tattgaccac aaattcgatc   3149

tcatgtacag caagcgcgcc ttcgtgcact ggtacgtcgg tgagggtatg gaagagggtg   3209

agttctccga ggcccgtgaa gaccttgcag cacttgagaa ggactacgaa gaggttggtg   3269

ccgagtccgc ggatatggac ggtgaggagg atgtggagga gtactagaaa gtgtgacaac   3329

gtcgcaccat gtgtaggttt tcatttatgt tctttctttc tttttttgt gaatttgttt    3389

tctgtctcaa atgtttttaa ttcgcttggg acctatgttt ttcttgtttt tttgctcacc   3449

ctttgtgtag gaggcaccct gtcacgtctg tggttgcgtg tatgccttcc ttccccttat   3509

tcgcttcttc ctgtcgtgtc acacctcttt ctctctctcc ctttccgcct tttctttcaa   3569

tcttgttttc tcgaccagcc ctactagagg agaaagaata gtaacccttt catcaaagaa   3629

aatagttcaa acgaatt                                                  3646


<210> SEQ ID NO 188
<211> LENGTH: 442
<212> TYPE: PRT
<213> ORGANISM: Trypanosoma brucei

<400> SEQUENCE: 188

Met Arg Glu Ile Val Cys Val Gln Ala Gly Gln Cys Gly Asn Gln Ile
1               5                   10                  15

Gly Ser Lys Phe Trp Glu Val Ile Ser Asp Glu His Gly Val Asp Pro
            20                  25                  30

Thr Gly Thr Tyr Gln Gly Asp Ser Asp Leu Gln Leu Glu Arg Ile Asn
        35                  40                  45

Val Tyr Phe Asp Glu Ala Thr Gly Gly Arg Tyr Val Pro Arg Ser Val
    50                  55                  60

Leu Ile Asp Leu Glu Pro Gly Thr Met Asp Ser Val Arg Ala Gly Pro
65                  70                  75                  80

Tyr Gly Gln Ile Phe Arg Pro Asp Asn Phe Ile Phe Gly Gln Ser Gly
                85                  90                  95

Ala Gly Asn Asn Trp Ala Lys Gly His Tyr Thr Glu Gly Ala Glu Leu
            100                 105                 110

Ile Asp Ser Val Leu Asp Val Cys Cys Lys Glu Ala Glu Ser Cys Asp
        115                 120                 125

Cys Leu Gln Gly Phe Gln Ile Cys His Ser Leu Gly Gly Gly Thr Gly
    130                 135                 140

Ser Gly Met Gly Thr Leu Leu Ile Ser Lys Leu Arg Glu Gln Tyr Pro
145                 150                 155                 160

Asp Arg Ile Met Met Thr Phe Ser Ile Ile Pro Ser Pro Lys Val Ser
                165                 170                 175

Asp Thr Val Val Glu Pro Tyr Asn Thr Thr Leu Ser Val His Gln Leu
            180                 185                 190

Val Glu Asn Ser Asp Glu Ser Met Cys Ile Asp Asn Glu Ala Leu Tyr
        195                 200                 205
```

```
Asp Ile Cys Phe Arg Thr Leu Lys Leu Thr Thr Pro Thr Phe Gly Asp
    210                 215                 220

Leu Asn His Leu Val Ser Ala Val Val Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Phe Met Met Gly Phe Ala Pro
            260                 265                 270

Leu Thr Ser Arg Gly Ser Gln Gln Tyr Arg Gly Leu Ser Val Pro Glu
        275                 280                 285

Leu Thr Gln Gln Met Phe Asp Ala Lys Asn Met Met Gln Ala Ala Asp
    290                 295                 300

Pro Arg His Gly Arg Tyr Leu Thr Ala Ser Ala Leu Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Ile Glu Trp Ile Pro Asn Asn Ile Lys Ser Ser
            340                 345                 350

Val Cys Asp Ile Pro Pro Lys Gly Leu Lys Met Ala Val Thr Phe Ile
        355                 360                 365

Gly Asn Asn Thr Cys Ile Gln Glu Met Phe Arg Arg Val Gly Glu Gln
    370                 375                 380

Phe Thr Leu Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ile Glu Glu
            420                 425                 430

Glu Gly Glu Phe Asp Glu Glu Glu Gln Tyr
        435                 440


<210> SEQ ID NO 189
<211> LENGTH: 37
<212> TYPE: DNA
<213> ORGANISM: Artificial
<220> FEATURE:
<223> OTHER INFORMATION: synthetic oligonucleotide

<400> SEQUENCE: 189

gatcctcgag ctagtactcc tccacatcct cctcacc                              37


<210> SEQ ID NO 190
<211> LENGTH: 32
<212> TYPE: DNA
<213> ORGANISM: Artificial
<220> FEATURE:
<223> OTHER INFORMATION: synthetic oligonucleotide

<400> SEQUENCE: 190

gatcctcgag ctagtattgc tcctcctcgt cg                                   32


<210> SEQ ID NO 191
<211> LENGTH: 5
<212> TYPE: PRT
<213> ORGANISM: Artificial
<220> FEATURE:
<223> OTHER INFORMATION: sortase A cleavage site
<220> FEATURE:
<221> NAME/KEY: MISC_FEATURE
```

-continued

```
<222> LOCATION: (3)..(3)
<223> OTHER INFORMATION: Xaa at position 3 is any amino acid

<400> SEQUENCE: 191

Leu Pro Xaa Thr Gly
1               5


<210> SEQ ID NO 192
<211> LENGTH: 5
<212> TYPE: PRT
<213> ORGANISM: Artificial
<220> FEATURE:
<223> OTHER INFORMATION: sortase B cleavage site

<400> SEQUENCE: 192

Asn Pro Gln Thr Asn
1               5


<210> SEQ ID NO 193
<211> LENGTH: 765
<212> TYPE: DNA
<213> ORGANISM: Staphylococcus aureus
<220> FEATURE:
<221> NAME/KEY: CDS
<222> LOCATION: (1)..(765)

<400> SEQUENCE: 193

atg ata ttg aaa ttt gat cac atc att cat tat ata gat cag tta gat       48
Met Ile Leu Lys Phe Asp His Ile Ile His Tyr Ile Asp Gln Leu Asp
1               5                   10                  15

cgg ttt agt ttt cca gga gat gtt ata aaa tta cat tca ggt ggg tat       96
Arg Phe Ser Phe Pro Gly Asp Val Ile Lys Leu His Ser Gly Gly Tyr
            20                  25                  30

cat cat aaa tat gga aca ttc aat aaa tta ggt tat atc aat gaa aat      144
His His Lys Tyr Gly Thr Phe Asn Lys Leu Gly Tyr Ile Asn Glu Asn
        35                  40                  45

tat att gag cta cta gat gta gaa aat aat gaa aag ttg aaa aag atg      192
Tyr Ile Glu Leu Leu Asp Val Glu Asn Asn Glu Lys Leu Lys Lys Met
    50                  55                  60

gca aaa acg ata gaa ggc gga gtc gct ttt gct act caa att gtt caa      240
Ala Lys Thr Ile Glu Gly Gly Val Ala Phe Ala Thr Gln Ile Val Gln
65                  70                  75                  80

gag aag tat gag caa ggc ttt aaa aat att tgt ttg cat aca aat gat      288
Glu Lys Tyr Glu Gln Gly Phe Lys Asn Ile Cys Leu His Thr Asn Asp
                85                  90                  95

ata gag gca gtt aaa aat aaa cta caa agt gag cag gtt gaa gta gta      336
Ile Glu Ala Val Lys Asn Lys Leu Gln Ser Glu Gln Val Glu Val Val
            100                 105                 110

ggg ccg att caa atg gaa aga gat aca cat aaa gat ggt aag gta aag      384
Gly Pro Ile Gln Met Glu Arg Asp Thr His Lys Asp Gly Lys Val Lys
        115                 120                 125

tgg caa ttg ctt tat ata atg aat cag gat gat gat gaa att aag cca      432
Trp Gln Leu Leu Tyr Ile Met Asn Gln Asp Asp Asp Glu Ile Lys Pro
    130                 135                 140

cca ttt ttt att caa tgg gaa gaa agt gat tcc atg cgt act aaa aaa      480
Pro Phe Phe Ile Gln Trp Glu Glu Ser Asp Ser Met Arg Thr Lys Lys
145                 150                 155                 160

ttg caa aaa tat ttt caa aaa caa ttt tca att gaa act gtt att gtg      528
Leu Gln Lys Tyr Phe Gln Lys Gln Phe Ser Ile Glu Thr Val Ile Val
                165                 170                 175

aaa agt aaa aac cga tca caa aca gta tcg aat tgg ttg aaa tgg ttt      576
Lys Ser Lys Asn Arg Ser Gln Thr Val Ser Asn Trp Leu Lys Trp Phe
            180                 185                 190
```

-continued

```
gat atg gac att gta gaa gag aat gac cat tac aca gat ttg att tta      624
Asp Met Asp Ile Val Glu Glu Asn Asp His Tyr Thr Asp Leu Ile Leu
        195                 200                 205

aaa aat gat gat att tat ttt aga att gaa gat ggt aaa gtt tca aaa      672
Lys Asn Asp Asp Ile Tyr Phe Arg Ile Glu Asp Gly Lys Val Ser Lys
    210                 215                 220

tat cat tcg gtt atc ata aaa gac gca caa gca act tca cca tat tca      720
Tyr His Ser Val Ile Ile Lys Asp Ala Gln Ala Thr Ser Pro Tyr Ser
225                 230                 235                 240

att ttt atc aga ggt gct att tat cgc ttt gaa cca tta gta taa          765
Ile Phe Ile Arg Gly Ala Ile Tyr Arg Phe Glu Pro Leu Val
                245                 250


<210> SEQ ID NO 194
<211> LENGTH: 254
<212> TYPE: PRT
<213> ORGANISM: Staphylococcus aureus

<400> SEQUENCE: 194

Met Ile Leu Lys Phe Asp His Ile Ile His Tyr Ile Asp Gln Leu Asp
1               5                   10                  15

Arg Phe Ser Phe Pro Gly Asp Val Ile Lys Leu His Ser Gly Gly Tyr
            20                  25                  30

His His Lys Tyr Gly Thr Phe Asn Lys Leu Gly Tyr Ile Asn Glu Asn
        35                  40                  45

Tyr Ile Glu Leu Leu Asp Val Glu Asn Asn Glu Lys Leu Lys Lys Met
    50                  55                  60

Ala Lys Thr Ile Glu Gly Gly Val Ala Phe Ala Thr Gln Ile Val Gln
65                  70                  75                  80

Glu Lys Tyr Glu Gln Gly Phe Lys Asn Ile Cys Leu His Thr Asn Asp
                85                  90                  95

Ile Glu Ala Val Lys Asn Lys Leu Gln Ser Glu Gln Val Glu Val Val
            100                 105                 110

Gly Pro Ile Gln Met Glu Arg Asp Thr His Lys Asp Gly Lys Val Lys
        115                 120                 125

Trp Gln Leu Leu Tyr Ile Met Asn Gln Asp Asp Asp Glu Ile Lys Pro
    130                 135                 140

Pro Phe Phe Ile Gln Trp Glu Glu Ser Asp Ser Met Arg Thr Lys Lys
145                 150                 155                 160

Leu Gln Lys Tyr Phe Gln Lys Gln Phe Ser Ile Glu Thr Val Ile Val
                165                 170                 175

Lys Ser Lys Asn Arg Ser Gln Thr Val Ser Asn Trp Leu Lys Trp Phe
            180                 185                 190

Asp Met Asp Ile Val Glu Glu Asn Asp His Tyr Thr Asp Leu Ile Leu
        195                 200                 205

Lys Asn Asp Asp Ile Tyr Phe Arg Ile Glu Asp Gly Lys Val Ser Lys
    210                 215                 220

Tyr His Ser Val Ile Ile Lys Asp Ala Gln Ala Thr Ser Pro Tyr Ser
225                 230                 235                 240

Ile Phe Ile Arg Gly Ala Ile Tyr Arg Phe Glu Pro Leu Val
                245                 250


<210> SEQ ID NO 195
<211> LENGTH: 621
<212> TYPE: DNA
<213> ORGANISM: Staphylococcus aureus
<220> FEATURE:
```

-continued

```
<221> NAME/KEY: CDS
<222> LOCATION: (1)..(207)

<400> SEQUENCE: 195

atg aaa aaa tgg aca aat cga tta atg aca atc gct ggt gtg gta ctt       48
Met Lys Lys Trp Thr Asn Arg Leu Met Thr Ile Ala Gly Val Val Leu
1               5                   10                  15

atc cta gtg gca gca tat ttg ttt gct aaa cca cat atc gat aat tat       96
Ile Leu Val Ala Ala Tyr Leu Phe Ala Lys Pro His Ile Asp Asn Tyr
            20                  25                  30

ctt cac gat aaa gat aaa gat gaa aag att gaa caa tat gat aaa aat      144
Leu His Asp Lys Asp Lys Asp Glu Lys Ile Glu Gln Tyr Asp Lys Asn
        35                  40                  45

gta aaa gaa cag gcg agt aaa gat aaa aag cag caa gct aaa cct caa      192
Val Lys Glu Gln Ala Ser Lys Asp Lys Lys Gln Gln Ala Lys Pro Gln
    50                  55                  60

att ccg aaa gat aaa tcgaaagtgg caggctatat tgaaattcca gatgctgata      247
Ile Pro Lys Asp Lys
65

ttaaagaacc agtatatcca ggaccagcaa cacctgaaca attaaataga ggtgtaagct    307

ttgcagaaga aaacgaatca ctagatgatc aaaatatttc aattgcagga cacactttca    367

ttgaccgtcc gaactatcaa tttacaaatc ttaaagcagc caaaaaaggt agtatggtgt    427

actttaaagt tggtaatgaa acacgtaagt ataaaatgac aagtataaga gatgttaagc    487

ctacagatgt agaagttcta gatgaacaaa aaggtaaaga taaacaatta acattaatta    547

cttgtgatga ttacaatgaa aagacaggcg tttgggaaaa acgtaaaatc tttgtagcta    607

cagaagtcaa ataa                                                       621


<210> SEQ ID NO 196
<211> LENGTH: 69
<212> TYPE: PRT
<213> ORGANISM: Staphylococcus aureus

<400> SEQUENCE: 196

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
    50                  55                  60

Ile Pro Lys Asp Lys
65


<210> SEQ ID NO 197
<211> LENGTH: 735
<212> TYPE: DNA
<213> ORGANISM: Staphylococcus aureus
<220> FEATURE:
<221> NAME/KEY: CDS
<222> LOCATION: (1)..(243)

<400> SEQUENCE: 197

atg aga atg aag cga ttt tta act att gta caa att tta ttg gtt gta       48
Met Arg Met Lys Arg Phe Leu Thr Ile Val Gln Ile Leu Leu Val Val
1               5                   10                  15

att att atc att ttt ggt tac aaa att gtt caa aca tat att gaa gac       96
Ile Ile Ile Ile Phe Gly Tyr Lys Ile Val Gln Thr Tyr Ile Glu Asp
```

-continued

```
            20                  25                  30

aag caa gaa cgc gca aat tat gag aaa tta caa caa aaa ttt caa atg       144
Lys Gln Glu Arg Ala Asn Tyr Glu Lys Leu Gln Gln Lys Phe Gln Met
        35                  40                  45

ctg atg agc aaa cat caa gca cat gtg aga cca caa ttt gaa tca ctt       192
Leu Met Ser Lys His Gln Ala His Val Arg Pro Gln Phe Glu Ser Leu
    50                  55                  60

gaa aaa ata aat aaa gac att gtt gga tgg ata aaa tta tca gga aca       240
Glu Lys Ile Asn Lys Asp Ile Val Gly Trp Ile Lys Leu Ser Gly Thr
65                  70                  75                  80

tca ttaaattatc cagtactaca aggtaagaca aatcacgatt atttaaattt            293
Ser

agattttgag cgagaacatc gacgtaaagg tagtattttt atggatttta gaaatgaatt    353

gaagaattta aatcataata ctattttata cgggcaccat gtcggtgata atacgatgtt    413

tgatgtgtta gaagattatt taaagcaatc gttttatgaa aaacacaaga taattgaatt    473

tgacaataaa tatggtaaat atcaattgca agtatttagt gcatataaaa ctactactaa    533

agataattac atacgtacag attttgaaaa tgatcaagat tatcaacaat ttttagatga    593

aacaaaacgt aaatctgtaa ttaattcaga tgttaatgta acggtaaaag atagaataat    653

gactttatca acgtgcgaag atgcatatag tgaaacaacg aaaagaattg ttgttgtcgc    713

aaaaataatt aaggtaagtt aa                                               735


<210> SEQ ID NO 198
<211> LENGTH: 81
<212> TYPE: PRT
<213> ORGANISM: Staphylococcus aureus

<400> SEQUENCE: 198

Met Arg Met Lys Arg Phe Leu Thr Ile Val Gln Ile Leu Leu Val Val
1               5                   10                  15

Ile Ile Ile Ile Phe Gly Tyr Lys Ile Val Gln Thr Tyr Ile Glu Asp
            20                  25                  30

Lys Gln Glu Arg Ala Asn Tyr Glu Lys Leu Gln Gln Lys Phe Gln Met
        35                  40                  45

Leu Met Ser Lys His Gln Ala His Val Arg Pro Gln Phe Glu Ser Leu
    50                  55                  60

Glu Lys Ile Asn Lys Asp Ile Val Gly Trp Ile Lys Leu Ser Gly Thr
65                  70                  75                  80

Ser
```

METHODS OF CONSTRUCTING BIODIVERSE GENE FRAGMENT LIBRARIES AND BIOLOGICAL MODULATORS ISOLATED THEREFROM

RELATED APPLICATION DATA

This application is a 371 of PCT/AU2004/000214 filed Feb. 20, 2004 which claims priority to Ser. No. 10/372,003 filed Feb. 21, 2003 and which is a continuation-in-part application of U.S. Ser. No. 09/568,229 filed May 5, 2000 which claims the benefit of priority under 35 USC §119(e) from U.S. Provisional Application No. 60/132,711 filed May 5, 1999, each of which are herein incorporated by reference in their entirety.

FIELD OF THE INVENTION

The present invention relates generally to methods for the production and of nucleic acid fragment libraries that express highly diverse peptides, polypeptides or protein domains and, in particular, methods for producing nucleic acid fragment libraries wherein the nucleic acid fragments of the libraries are derived from one and preferably from two or more prokaryote genomes or compact eukaryote genomes, such as, for example, organisms having diverse characterized genomes. In another embodiment, the nucleic acid fragments are expressed as protein domains capable of assuming a conformation that binds to a target protein or nucleic acid during library screening. The present invention further provides methods of screening such libraries to identify peptides, polypeptides or protein domains that bind to a target protein or nucleic acid such as, for example, to modulate the activity of the target protein or nucleic acid. Also provided are methods for identifying nucleic acid encoding such peptides, polypeptides or protein domains. The present invention extends to the nucleic acids, peptides, polypeptides and protein domains identified by the methods described herein.

BACKGROUND OF THE INVENTION

1. General Information

This specification contains nucleotide and amino acid sequence information prepared using PatentIn Version 3.1, presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (eg. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied *mutatis mutandis* to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts:

1. Sambrook, Fritsch & Maniatis, whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactiva, Germany);
10. Sakakibara, D., Teichman, J., Lien, E. Land Fenichel, R. L. (1976). *Biochem. Biophys. Res. Commun.* 73 336-342
11. Merrifield, R. B. (1963). *J. Am. Chem. Soc.* 85, 2149-2154.
12. Barany, G. and Merrifield, R. B. (1979) in *The Peptides* (Gross, E. and Meienhofer, J. eds.), vol. 2, pp. 1-284, Academic Press, New York.

13. Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart.
14. Bodanszky, M. (1984) *Principles of Peptide Synthesis*, Springer-Verlag, Heidelberg.
15. Bodanszky, M. & Bodanszky, A. (1984) *The Practice of Peptide Synthesis*, Springer-Verlag, Heidelberg.
16. Bodanszky, M. (1985) *Int. J. Peptide Protein Res.* 25, 449-474.
17. Handbook of Experimental Immunology, Vols. I-IV (D. M. Weir and C. C. Blackwell, eds., 1986, Blackwell Scientific Publications).
18. McPherson et al., In: *PCR A Practical Approach*., IRL Press, Oxford University Press, Oxford, United Kingdom, 1991.
19. Methods in Yeast Genetics: A Cold Spring Harbor Laboratory Course Manual (D. Burke et al., eds) Cold Spring Harbor Press, New York, 2000 (see whole of text).
20. Guide to Yeast Genetics and Molecular Biology. In: Methods in Enzymology Series, Vol. 194 (C. Guthrie and G. R. Fink eds) Academic Press, London, 1991 2000 (see whole of text).

2. Description of the Related Art

As a response to the increasing demand for new lead compounds and new target identification and validation reagents, the pharmaceutical industry has increased its screening of various sources for new lead compounds having a unique activity or specificity in therapeutic applications, such as, for example, in the treatment of neoplastic disorders, infection, modulating immunity, autoimmunity, fertility, etc.

It is known that proteins bind to other proteins, antigens, antibodies, nucleic acids, and carbohydrates. Such binding enables the protein to effect changes in a wide variety of biological processes in all living organisms. As a consequence, proteins represent an important source of natural modulators of phenotype. Accordingly, peptides that modulate the binding activity of a protein represent attractive lead compounds (drug candidates) in primary or secondary drug screening. For example, the formation of a target biological interaction that has a deleterious effect (eg. replication of a pathogen or of a cancer cell), can be assayed to identify lead compounds that antagonize the biological interaction.

Similarly, the activity or expression of an antimicrobial target (eg., a protein produced by a particular microbe that is required for its survival or propagation), can be screened for novel compounds that modulate the survival or propagation of the microbe by antagonizing an activity or function of the antimicrobial target. Peptides that block the function of specific membrane channels, or disrupt cytoplasmic membranes of some organisms is represent attractive candidates for antimicrobial drugs. Antimicrobial effects have been demonstrated for certain natural peptides produced by animals and insects, and for synthetic cationic peptides (eg., azurocidin, cathepsin G, Cationic Antimicrobial Peptides CAP57 and CAP37, defensin, bactenecin and magainin).

A virulence determinant of a pathogen also presents an attractive target for identifying lead compounds having antimicrobial activity. For example, a peptide antagonist of an autoinducer of virulence in *Staphylococcus aureus* that controls the production of bacterial toxins involved in pathogenesis has been determined. The antagonist, designated RIP (RNAIII inhibiting peptide) is produced by a non-pathogenic strain of *Staphylococcus aureus* and appears to inhibit the RNAIII gene that is induced by a threshold concentration of an endogenous protein, RNA III Activating Protein (RAP), in virulent strains.

In another example, differential gene expression between normal and diseased (eg., neoplastic or apoptotic) cells, such as, for example, differential expression of cellular receptors, and/or differential signal transduction processes between normal and diseased cells, implicate those differential patterns of gene expression in disease. Accordingly, the genes or proteins that are differentially expressed in diseased and normal cells, or the differential cellular processes between normal and diseased cells, form attractive targets for therapy. Similarly, cyclin proteins such as Cdc2, Cdc25, and cyclin-dependent kinases (CDKs) are attractive targets for cellular proliferation. Peptides that agonize or antagonize the expression of such target genes or target processes are suitable lead compounds for therapeutic applications.

In yet another example, certain allergen proteins (eg., Der p 1) are attractive targets for screens to identify anti-allergenic compounds that prevent or inhibit immune responses to the allergen protein.

It is widely recognized that there is a need to develop methods for determining novel compounds, including nucleic acid-based products and peptide-based products, that modulate an activity or function of a particular target. In such approaches, an activity of a target protein or nucleic acid is screened in the absence and presence of a potential lead compound, which is a peptide, and modified activity of the target is determined.

Similarly, peptides can be used as dominant negative inhibitors or the validation of prospective drug targets using assays such as observing the phenotype resulting from over-expression of the peptides in ex-vivo assays or in transgenic mice.

In one known approach to identify novel lead compounds, random peptide (synthetic mimetic or mimotope) libraries are produced using short random oligonucleotides produced by synthetic combinatorial chemistry. The DNA sequences are cloned into an appropriate vehicle for expression and the encoded peptide is then screened using one of a variety of approaches. However, the ability to isolate active peptides from random fragment libraries can be highly variable with low affinity interactions occurring between the peptide-binding partners. Moreover, the expressed peptides often show little or none of the secondary or tertiary structure required for efficient binding activity, and/or are unstable. This is not surprising, considering that biological molecules appear to recognise shape and charge rather than primary sequence (Yang and Horng *J. Mol. Biol.* 301(3), 691-711 2000) and that such random peptide aptamers are generally too small to comprise a protein domain or to form the secondary structure of a protein domain. The relatively unstructured 'linear' nature of these peptide aptamers also leads to their more rapid degradation and clearance following administration to a subject in vivo, thereby reducing their appeal as therapeutic agents.

To enhance the probability of obtaining useful bioactive peptides or proteins from random peptide libraries, peptides have previously been constrained within scaffold structures, eg., thioredoxin (Trx) loop (Blum et al. *Proc. Natl. Acad. Sci. USA,* 97, 2241-2246, 2000) or catalytically inactive staphylococcal nuclease (Norman et al, *Science,* 285, 591-595, 1999), to enhance their stability. Constraint of peptides within such structures has been shown, in some cases, to enhance the affinity of the interaction between the expressed peptides and its target, presumably by limiting the degrees of conformational freedom of the peptide, and thereby minimizing the entropic cost of binding.

It is also known to tailor peptide expression libraries for identifying specific peptides involved in a particular process, eg., antigen-antibody-binding activity. For example U.S. Pat. No. 6,319,690 (Dade Behring Marburg GmBH) teaches a PCR-based method of amplifying cDNA sequences encoding a population of antibodies, wherein oligonucleotide primers that are homologous to conserved regions of antibody-encoding cDNAs derived from a mixture of non-activated B-lymphocytes are used to amplify nucleic acids that encode antibody variable regions. The amplified sequences are expressed using a bacterial display system, for screening with selected antigens to determine those antibody fragments that bind the antigens. However, the expression libraries described in U.S. Pat. No. 6,319,690 show limited diversity, because the amplified fragments were all antibody-encoding fragments derived from a single complex eukaryote. Additionally, the antibody-encoding libraries described in U.S. Pat. No. 6,319,690 were screened for antigen-binding activity rather than for a novel bioactivity (ie. the expressed peptides were not mimotopes).

Several attempts have been made to develop libraries based on naturally occurring proteins (eg genomic expression libraries). Libraries of up to several thousand polypeptides or peptides have been prepared by gene expression systems and displayed on chemical supports or in biological systems suitable for testing biological activity. For example, genome fragments isolated from *Escherichia coli* MG1655 have been expressed using phage display technology, and the expressed peptides screened to identify peptides that bind to a polyclonal anti-Rec A protein antisera (Palzkill et al. *Gene,* 221 79-83, 1998). Such expression libraries are generally produced using nucleic acid from single genomes, and generally comprise nucleic acid fragments comprising whole genes and/or multiple genes or whole operons, including multiple linked protein domains of proteins. Additionally, as many bacteria comprise recA-encoding genes, the libraries described by Palzkill et al., were screened for an activity that was known for the organism concerned, rather than for a novel bioactivity (ie. the expressed peptides were not necessarily mimotopes).

U.S. Pat. No. 5,763,239 (Diversa Corporation) describes a procedure for producing normalized genomic DNA libraries from uncharacterized environmental samples containing a mixture of uncharacterized genomes. The procedure described by Diversa Corp. comprises melting DNA isolated from an environmental sample, and allowing the DNA to reanneal under stringent conditions. Rare sequences, that are less likely to reanneal to their complementary strand in a short period of time, are isolated as single-stranded nucleic acid and used to generate a gene expression library. However, total normalization of each organism within such uncharacterized samples is difficult to achieve, thereby reducing the biodiversity of the library. Such libraries also tend to be biased toward the frequency with which a particular organism is found in the native environment. As such, the library does not represent the true population of the biodiversity found in a particular biological sample. In cases where the environmental sample includes a dominant organism, there is likely to be a significant species bias that adversely impacts on the sequence diversity of the library. Furthermore, as many of the organisms found in such samples are uncharacterized, very little information is known regarding the constitution of the genomes that comprise such libraries. Accordingly, it is not possible to estimate the true diversity of such libraries. Additionally, since the Diversa Corp. process relies upon PCR using random primers to amplify uncharacterized nucleic acids, there is no possibility of accounting for biasing factors, such as, for example, a disproportionate representation of repeated sequences across genomes of the organisms in the environmental sample.

Accordingly, there remains a need to produce improved methods for constructing highly diverse and well characterized expression libraries wherein the expressed peptides are capable of assuming a secondary structure or conformation sufficient to bind to a target protein or nucleic acid, such as, for example, by virtue of the inserted nucleic acid encoding a protein domain.

SUMMARY OF THE INVENTION

The present invention is based upon the understanding of the present inventors that, in contrast to random synthetic peptide libraries produced by combinatorial approaches, or short random peptides produced by expression of PCR products, amino acids are not randomly distributed in nature (Pande et al., *Proc Natl Acad. Sci. USA* 91 12972-12975, 1994). Proteins that fold well in nature have non-random hydrophobicity distributions (Irback et al., *Proc Natl Acad. Sci. USA* 93, 9533-9538, 1996). In any native peptide, the distribution of amino acid residues according to their chemical properties (eg hydrophobicity, polarity, etc) is also non-random (Baud and Karlin, *Proc Natl Acad. Sci. USA* 96, 12494-12499, 1999). Accordingly, the present inventors realized that random peptide libraries have a low frequency of naturally occurring or native peptide conformational structures or secondary structures, such as, for example, those structures formed by protein domains.

In work leading up to the present invention, the inventors sought to take advantage of diverse and well-characterized prokaryotic genomes and/or compact eukaryotic genomes in the construction of highly diverse expression libraries for isolating bioactive peptides or proteins. In particular, the use of combinations of nucleic acid fragments from one or two or more well characterized genomes has allowed the inventors to control the degree the diversity of peptides/proteins expressed in their expression libraries, to enhance the possibility of isolating novel peptides having the ability to bind to a desired protein or nucleic acid. It will be understood from the disclosure herein that the bioactive peptides or proteins expressed by individual library clones of such libraries are screened for an activity of the encoded peptide, particularly a binding activity, which said encoded protein has not been shown to possess in the context of the protein from which it was derived (ie in its native environment). In the screening process, any library clone encoding a peptide that has the same activity as it would have in its native environment is excluded during the screening process, since an objective of the present invention is to isolate novel bioactive peptides or proteins.

Peptides encoded by genomes which differ from the genome of the drug target organism (eg. humans) are a particularly rich source of high affinity target binding agents. This is because in the evolution of the target organism itself, such high affinity peptide domains have been selected against other than the interaction interfaces which may exist in that organism for functional dimerization with natural partners.

Accordingly, in a preferred embodiment, nucleic acid fragments are selected that are encoded by genomes that are distinct from the genome encoding a target protein or nucleic acid.

In one embodiment, the libraries described in the present invention are constructed from nucleic acid fragments comprising genomic DNA, cDNA, or amplified nucleic acid derived from one or two or more well-characterized genomes.

Preferably, one or more well-characterized genomes is a compact genome of a eukaryote (ie. protist, dinoflagellate, alga, plant, fungus, mould, invertebrate, vertebrate, etc) such as, for example, a eukaryote selected from the group consisting of *Arabidopsis thaliana, Anopheles gambiae, Caenorhabditis elegans, Danio rerio, Drosophila melanogaster, Takifugu rubripes, Cryptosporidium parvum, Trypanosoma cruzii, Saccharomyces cerevesiae*, and *Schizosaccharomyces pombe.*

In another embodiment, one or more well-characterized genomes is a compact genome of a prokaryote (ie. bacteria, eubacteria, cyanobacteria, etc) such as, for example a prokaryote selected from the group consisting of *Archaeoglobus fulgidis, Aquifex aeolicus, Aeropyrum pernix, Bacillus subtilis, Bordetella pertussis* TOX6, *Borrelia burgdorferi, Chlamydia trachomatis, Escherichia coli* K12, *Haemophilus influenzae* (rd), *Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium* and *Thermotoga maritima.*

In a further embodiment, combinations of nucleic acid fragments from one or more eukaryote genomes and/or one or more prokaryote genomes are used.

In a particularly preferred embodiment, the nucleic acid fragments are derived from an organism selected from the group consisting of: *Aeropyrum pernix, Aquifex aeolicus, Archaeoglobus fulgidis, Bacillus subtilis, Bordetella pertussis, Borrelia burgdorferi, Chlamydia trachomatis, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium* and *Thermotoga maritima.*

In another particularly preferred embodiment, the nucleic acid fragments are derived from an organism selected from the group consisting of: *Archaeoglobus fulgidis, Aquifex aeliticus, Aeropyrum pernix, Aquifex aeolicus, Bacillus subtilis, Bordatella pertussis* TOX6, *Borrelia burgdorferi, Chlamydia trachomatis, Escherichia coli, Haemophilus influenzae, Helicobacter pylori, Methanobacterium thermoautotrophicum, Methanococcus jannaschii, Methanothermobacter thermoautotrophicus, Mycoplasma pneumoniae, Neisseria meningitidis, Pirellula species, Pyrococcus horikoshii, Pseudomonas aeruginosa, Synechosistis* sp., *Thermoplasma volcanium* and *Thermotoga maritima.*

Wherein the nucleic acid fragments are from mixtures of organisms, it is preferred that those organisms are not normally found together in nature. In accordance with this embodiment of the invention, the process of combining nucleic acid fragments derived from diverse organisms not normally found together in nature enhances and controls diversity of the expression library produced using such nucleic acid fragments.

It is to be understood that the nucleic acid fragments used in the production of the expression libraries of the present invention are generated using art-recognized methods such as, for example, a method selected from the group consisting mechanical shearing, digestion with a nuclease and digestion with a restriction endonuclease. Combinations of such methods can also be used to generate the genome fragments. In a particularly preferred embodiment, copies of nucleic acid fragments from one or two or more genomes are generated using polymerase chain reaction (PCR) using random oligonucleotide primers.

The nucleic acid fragments or cDNA or amplified DNA derived therefrom are inserted into a suitable vector or gene construct in operable connection with a suitable promoter for expression of each peptide in the diverse nucleic acid sample.

The construct used for the expression of the diverse nucleic acid fragment library is determined by the system that will be used to screen for those peptides that have a conformation sufficient for binding to a target protein or nucleic acid. Thus, consideration is generally given to an expression format suitable for screening the library.

In one embodiment, the vector or gene construct is suitable for in vitro display of an expressed peptide. Preferred in vitro display formats include, ribosome display, mRNA display or covalent display.

In another embodiment, the vector or gene construct is suitable for expressing a peptide in a cellular host. Preferred cellular hosts in this context are capable of supporting the expression of exogenous or episomal DNA such as, for example, a cellular host selected from the group consisting of a bacterial cell, yeast cell, insect cell, mammalian cell, and plant cell.

In another embodiment, the vector or gene construct is suitable for expressing a peptide in a multicellular organism. Preferred multicellular organisms for this purpose will include organisms having a compact genome and/or short life cycle to facilitate rapid high throughput screening, such as, for example, a plant (eg., *Arabidopsis thaliana* or *Nicotiana tabacum*) or an animal selected from the group consisting of *Caenorhabditis elegans, Danio rerio, Drosophila melanogaster, Takifugu rubripes, Mus* sp. and *Rattus* sp.

Accordingly, one aspect of the present invention provides a method of constructing an expression library for expressing a peptide having a conformation sufficient for binding to a target protein or nucleic acid, said method comprising:

(a) producing nucleic acid fragments from nucleic acids derived from two or more microorganisms and/or eukaryotes containing compact genomes, each of said microorganisms or eukaryotes having a substantially sequenced genome; and (b) inserting the nucleic acid fragments at (a) into a suitable expression construct thereby producing recombinant constructs, wherein each fragment is in operable connection with a promoter sequence that is capable of conferring expression of that fragment.

Preferably, the present invention provides a method of constructing an expression library for expressing a peptide having a conformation sufficient for binding to a target protein or nucleic acid, said method comprising:

(a) producing nucleic acid fragments from nucleic acids derived from two or more microorganisms or eukaryotes containing compact genomes, each of said microorganisms or eukaryotes having a substantially sequenced genome; and (b) inserting the nucleic acid fragments at (a) into a suitable expression construct thereby producing recombinant constructs, wherein each fragment is in operable connection with a promoter sequence that is capable of conferring expression of that fragment.

Preferably, the present invention provides a method of constructing an expression library for expressing a peptide having a conformation sufficient for binding to a target protein or nucleic acid, said method comprising:

(a) producing nucleic acid fragments from nucleic acids derived from two or more microorganisms and eukaryotes containing compact genomes, each of said microorganisms or eukaryotes having a substantially sequenced genome; and (b) inserting the nucleic acid fragments at (a) into a suitable expression construct thereby producing recombinant constructs, wherein each fragment is in operable connection with a promoter sequence that is capable of conferring expression of that fragment.

By way of exemplification, FIG. 1 shows one embodiment of the method of generating the expression library of the present invention, wherein nucleic acid fragments are isolated from multiple evolutionary diverse organisms and pooled in such a way as to ensure about equal representation of each of the genomes. Nested PCR using degenerate PCR primers amplifies sequences from the pooled genomes in a first round, and specific PCR amplifies the nucleic acid fragments so as to permit their direct cloning into an expression vector.

Preferably, the poor representation of low copy number sequences is reduced or minimized by normalizing the nucleic acid according to the complexity and size of the genome of the microorganism or compact eukaryote (ie., relative genome size of content of each contributing genome of the expression library). Thus, where genomes from more than one organism are used in the construction of the library, each of those contributing genomes is preferably used in an amount that is proportional to that complexity and size of the genome (or transcriptome), such as, for example, in comparison to the complexity and size of another genome in the mixture of genomes. This process results in about equal representation of the genome fragments in the biodiverse nucleic acid fragment library.

Accordingly, a preferred embodiment of the present invention provides a method of constructing an expression library for expressing a polypeptide having a conformation sufficient for binding to a target protein or nucleic acid, said method comprising:

(a) producing nucleic acid fragments from nucleic acids derived from two or more microorganisms and/or eukaryotes containing compact genomes, each of said microorganisms or eukaryotes having a substantially sequenced genome; and (b) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

Preferably, the nucleic acid fragments are selected such that the encoded peptides have an average length that is about the length of a protein domain, eg., at least about 12-15 amino acids in length and more preferably at least about 15 amino acids in length or at least about 20 amino acids in length or at least about 30 amino acids in length.

Alternatively, or in addition, the nucleic acid fragments will preferably encode peptides that, on average, comprise or consist of a protein domain. As used herein, the term "protein domain" shall be taken to mean a discrete portion of a protein that assumes a secondary structure or conformation sufficient to permit said portion to perform a specific function in the context of a target protein or target nucleic acid and, in particular, to bind with high affinity to the target protein or nucleic acid. Preferred protein domains are not required to be constrained within a scaffold structure to bind to the target nucleic acid or target protein, or for said binding to be enhanced.

The term "protein domain" or "domain" or similar shall be taken to include an independently folding peptide structure (ie. a "subdomain") unless the context requires otherwise. For example, protein subdomain consisting of a 19-residue fragment from the C-loop of the fourth epidermal growth factor-like domain of thrombomodulin has been described by Alder et al, *J. Biol. Chem.,* 270: 23366-23372, 1995. Accordingly, the skilled artisan is aware of the meaning of the term "protein subdomain".

Accordingly, it is particularly preferred that nucleic acid fragments used in the generation of the expression libraries of the present invention encode peptides that form stable secondary structures or conformations in the absence of a Trx loop or catalytically inactive staphylococcal nuclease peptide.

It is also preferred for the nucleic acid fragments of the expression libraries of the invention to encode a single protein domain. Accordingly, in a particularly preferred embodiment, the nucleic acid fragments of the expression libraries of the present invention will encode a peptide having an upper length of about 50 amino acid residues.

Accordingly, a preferred embodiment of the present invention provides a method of constructing an expression library for expressing a polypeptide having a conformation sufficient for binding to a target protein or nucleic acid, said method comprising:

(a) producing nucleic acid fragments from nucleic acids derived from one or two or more microorganisms or eukaryotes containing compact genomes, each of said microorganisms or eukaryotes having a substantially sequenced genome;

(b) selecting nucleic acid fragments from the fragments at (a) that encode a peptide having an average length of at least about 12-15 amino acid residues and/or encode a protein domain; and (c) inserting the selected fragments at (b) into a suitable expression vector thereby producing recombinant constructs, wherein each fragment is in operable connection with a promoter sequence that is capable of conferring expression of that fragment.

In an alternative embodiment, the present invention provides a method of constructing an expression library for expressing a polypeptide having a conformation sufficient for binding to a target protein or nucleic acid, said method comprising:

(a) producing nucleic acid fragments from nucleic acids derived from two or more microorganisms and/or eukaryotes containing compact genomes, each of said microorganisms or eukaryotes having a substantially sequenced genome;

(b) selecting nucleic acid fragments from the fragments at (a) that encode a peptide having an average length of at least about 12-15 amino acid residues and/or encode a protein domain; and (c) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

In a further preferred embodiment, nucleic acid fragments are selected having sufficiently different nucleotide sequences to thereby enhance the nucleotide sequence diversity between the selected nucleic acid fragments, prior to or following their insertion into an expression vector or gene construct. Preferably, such a selection is performed prior to insertion of the nucleic acid fragments into a vector or gene construct.

In one embodiment, selecting nucleic acid fragments having sufficiently different nucleotide sequences comprises subjecting a base nucleic acid fragment to mutagenesis to produce a mutated fragment and optionally combining the mutated fragment with the base nucleic acid fragment.

In another embodiment, selecting nucleic acid fragments having sufficiently different nucleotide sequences comprises mutating a nucleic acid fragment thereby permitting the nucleic acid fragment to be read in any one or more of three forward reading frames. By "mutating" in this context is meant that one or more nucleotide residues are added to the 5'-end or 3'-end of a nucleic acid fragment. Alternatively, or in addition, "mutating" in this context means that the nucleotide sequence of a nucleic acid fragment is subjected to mutation by the insertion of one or more nucleotides into an internal region of the fragment, or by deleting one or more nucleotides from the fragment, or by substituting one or more nucleotides of the nucleic acid fragment. For example, by adding or deleting one or two or three nucleotides from the 5'-end of a base nucleic acid fragment and inserting the base fragment and each mutated fragment produced therefrom into an expression vector, the first codon becomes positioned at different locations relative to the translation start site such that each three forward reading frame is used.

In another embodiment, selecting nucleic acid fragments having sufficiently different nucleotide sequences comprises cloning a nucleic acid fragment in a reverse orientation relative to the orientation of the fragment in the context of the gene from which it was derived. In accordance with this embodiment, a reverse open reading frame is used.

In another embodiment, selecting nucleic acid fragments having sufficiently different nucleotide sequences comprises deleting a nucleic acid fragment having a sequence that is over represented in the genome or in the expression library. For example, it is preferred to delete or remove nucleic acid fragments comprising highly repetitive nucleotide sequences, or additional copies of nucleic acid fragments that are repeated in a genome (ie., to remove nucleic acid fragments comprising redundant nucleotide sequences of multiple copy or high copy number genes). It is to be understood that "redundant nucleotide sequences" does not include each and every copy of a repeated sequence, since it is preferred to leave at least one copy of such sequences in the nucleic acid fragment pool used to construct the expression library of the present invention.

Accordingly, a preferred embodiment of the present invention provides a method of constructing an expression library for expressing a polypeptide having a conformation sufficient for binding to a target protein or nucleic acid, said method comprising:

(a) producing nucleic acid fragments from nucleic acids derived from one or two or more microorganisms or eukaryotes containing compact genomes, each of said microorganisms or eukaryotes having a substantially sequenced genome;
(b) selecting nucleic acid fragments from the fragments at (a) that have sufficiently different nucleotide sequences thereby enhancing nucleotide sequence diversity among the selected fragments compared to the diversity of sequences in the genome; and
(c) inserting the selected fragments at (b) into a suitable expression construct thereby producing recombinant constructs, wherein each fragment is in operable connection with a promoter sequence that is capable of conferring expression of that fragment.

In an alternative embodiment, the present invention provides a method of constructing an expression library for expressing a polypeptide having a conformation sufficient for binding to a target protein or nucleic acid, said method comprising:

(a) producing nucleic acid fragments from nucleic acids derived from two or more microorganisms and/or eukaryotes containing compact genomes, each of said microorganisms or eukaryotes having a substantially sequenced genome;
(b) selecting nucleic acid fragments from the fragments at (a) that have sufficiently different nucleotide sequences thereby enhancing nucleotide sequence diversity among the selected fragments compared to the diversity of sequences in the genome; and
(c) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

In a particularly preferred embodiment, the present invention provides a method of constructing an expression library for expressing a polypeptide having a conformation sufficient for binding to a target protein or nucleic acid, said method comprising:

(a) producing nucleic acid fragments from nucleic acids derived from one or two or more microorganisms or eukaryotes containing compact genomes, each of said microorganisms or eukaryotes having a substantially sequenced genome;
(b) selecting nucleic acid fragments from the fragments at (a) that have sufficiently different nucleotide sequences thereby enhancing nucleotide sequence diversity among the selected fragments compared to the diversity of sequences in the genome and selecting nucleic acid fragments from the fragments at (a) that encode a peptide having an average length of at least about 12-15 amino acid residues and/or encode a protein domain; and
(c) inserting the selected fragments at (b) into a suitable expression construct thereby producing recombinant constructs, wherein each fragment is in operable connection with a promoter sequence that is capable of conferring expression of that fragment.

In an alternative particularly preferred embodiment, the present invention provides a method of constructing an expression library for expressing a polypeptide having a conformation sufficient for binding to a target protein or nucleic acid, said method comprising:

(a) producing nucleic acid fragments from nucleic acids derived from two or more microorganisms and/or eukaryotes containing compact genomes, each of said microorganisms or eukaryotes having a substantially sequenced genome;
(b) selecting nucleic acid fragments from the fragments at (a) that have sufficiently different nucleotide sequences thereby enhancing nucleotide sequence diversity among the selected fragments compared to the diversity of sequences in the genome and selecting nucleic acid fragments from the fragments at (a) that encode a peptide having an average length of at least about 12-15 amino acid residues and/or encode a protein domain; and
(c) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

Preferably, if the library is to be expressed in either a cellular system or in an organism then the method of producing an expression library in accordance with the present invention further comprises introducing the recombinant vector or recombinant gene construct into a host cell such that a nucleic acid fragment contained therein is capable of being expressed as a peptide or protein domain having a conformation sufficient for binding to target protein or nucleic acid.

A second aspect of the present invention relates to an expression library described according to the procedures described herein. Such libraries will comprise isolated nucleic acid fragments from one or two or more prokaryote or compact eukaryote genomes, wherein said fragments comprise, on average, an open reading frame of about 36 to about 150 nucleotides or about 250 nucleotides in length or sufficient to encode a single protein domain having a conformation sufficient to bind to a target nucleic acid or target protein. Preferably, the fragments comprise nucleotide sequences that are non-redundant or alternatively, encode peptides or protein domains comprising non-redundant amino acid sequences.

Preferably, expression libraries comprising mixtures of nucleic acid fragments from 2 or 3 or 4 or 5 or 6 or 7 or 8 or 9 or 10 or 11 or 12 or 13 or 14 or 15 or 16 or 17 or 18 or 19 or 20 prokaryote or compact eukaryote genomes. Preferably, such mixed libraries are normalized.

In one embodiment, the expression library, or peptides expressed by the library are immobilised on a solid support, such as for example a glass slide (eg. to produce a protein array).

The present invention also relates to the use of the expression libraries to isolate a nucleic acid that encodes a peptide or protein domain, in particular a peptide having a conformation sufficient for binding to a target protein or target nucleic acid. In accordance with this aspect of the invention, the expression library of the present invention is screened to identify a peptide encoded by an inserted nucleic acid fragment of the library that binds to a target protein or target nucleic acid, such as, for example to modulate a specific protein:DNA or protein:protein interaction or a structure such as a cell wall or a membrane transport component.

Accordingly, a further aspect of the present invention provides a method of determining a peptide that binds to a target nucleic acid or target protein comprising:

(a) screening an expression library of the present invention to identify a peptide expressed by the library that binds to the target protein or target nucleic acid; and (b) selecting a peptide from (a) that does not bind to said target protein or nucleic acid in its native environment.

Screening approaches suitable for performing the invention include for example, a method selected from the group consisting of yeast-2-hybrid, n-hybrid, reverse-2-hybrid, reverse n-hybrid, split two hybrid, bacterial display, phage display, retroviral display, covalent display and in vitro display. In a particularly preferred embodiment, the expression library is screened using a phage display method.

Another aspect of the present invention provides an isolated peptide or protein domain that binds to an immunoglobulin, wherein said immunoglobulin was not raised against the peptide or protein domain and wherein said peptide or protein domain does not have a native function of the protein against which the immunoglobulin was prepared (ie., it is not functionally homologous and does not have the same primary structure as the peptide against which the immunoglobulin was prepared). In one particularly preferred embodiment, the peptide or protein domain binds to antibodies against an allergen, more preferably a pollen allergen or a cat allergen and even more preferably against a Der p 1 allergen.

In a particularly preferred embodiment, the peptide or protein domain comprises an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91

This aspect of the present invention clearly extends to any isolated nucleic acid encoding the peptide or protein domain that binds to the immunoglobulin.

In another embodiment, the isolated peptide or protein domain that binds to an antibody against a D15 protein of *H. influenzae*. Clearly, this embodiment of the invention also extends to nucleic acid encoding such an isolated peptide or protein domain.

Another aspect of the present invention provides an isolated peptide or protein domain that partially or completely inhibits or antagonizes or blocks an interaction between two or more proteins in a cell. Preferably, the isolated peptide or protein domain blocks an interaction between SCL and another protein, or between E47 and another protein. Even more preferably, the isolated peptide or protein domain blocks an interaction between SCL and E47 in a cell. In a particularly preferred embodiment, the isolated peptide comprises an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 79 and SEQ ID NO: 81.

This aspect of the present invention clearly extends to any isolated nucleic acid encoding the peptide or protein domain that partially or completely inhibits or antagonizes or blocks an interaction between two or more proteins in a cell. Exemplary nucleic acids provided herein comprise a nucleotide sequence selected from the group consisting of: SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 78 and SEQ ID NO: 80.

In another embodiment, the isolated peptide or protein domain blocks an interaction between two c-Jun proteins, ie c-Jun self-dimerization. Even more preferably, the isolated peptide or protein domain blocks c-Jun self dimerization in a cell. In a particularly preferred embodiment, the isolated peptide comprises an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165.

This aspect of the present invention clearly extends to any isolated nucleic acid encoding the peptide or protein domain that partially or completely inhibits or antagonizes or blocks c-Jun homo-dimerization in a cell. Exemplary nucleic acids provided herein comprise a nucleotide sequence selected from the group consisting of: SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO:

147, SEQ ID NO: 150, SEQ ID NO: 153, SEQ ID NO: 156, SEQ ID NO: 159 and SEQ ID NO: 162.

Another aspect of the present invention provides an isolated peptide or protein domain that is capable of binding to a cell surface protein a bacterium. Preferably, the cell surface protein is a FemABX family of proteins. Preferably, a FemABX protein of *S. aureus*. Preferably, the isolated peptide or protein domain is additionally antibacterial.

Another aspect of the present invention provides an isolated peptide or protein domain that binds to a tubulin protein of a parasite. Preferably, the parasite is selected from the group consisting of *P. falciparum, C. parvum* and *T. brucei rhodesience.*

Another aspect of the present invention provides a database comprising the nucleotide sequences of nucleic acid fragments of an expression library of the present invention in computer readable form.

A related embodiment provides a database comprising amino acid sequences of peptides encoded by nucleic acid fragments of the present invention. Preferably, the database incorporates information regarding the secondary structure of the peptides, including predicted structure or a structure as determined by X-ray crystallography or other empirical means.

A further aspect of the present invention provides a method for determining or validating a target comprising (a) screening an expression library of the present invention to identify a peptide expressed by the library that binds to a target protein or target nucleic acid;
(b) selecting a peptide from (a) that does not bind to said target protein or nucleic acid in its native environment; and
(c) expressing the selected peptide in an organism and determining a phenotype of the organism that is modulated by the target protein or target nucleic acid.

In a preferred embodiment, the target comprises a therapeutic or prophylactic target (eg., an oncoprotein or interaction between oncoproteins, a protein or nucleic acid associated with cancer (eg., a cancer marker) or other disease of an animal or human, or an antibacterial target, antihelminthic target, antiparasitic target, or antiviral target.

For example, the phenotype of an organism that expresses a tumor is assayed in the presence and absence of a peptide or protein domain that blocks an interaction between SCL and E47 in a screen of the expression library of the invention. Amelioration of the oncogenic phenotype by the expressed peptide indicates that the SCL/E47 is a suitable target for intervention, wherein the peptide is then suitably formulated for therapeutic intervention directly, or alternatively, small molecules are identified that are mimetics of the identified peptide or protein domain.

Accordingly, a further aspect of the present invention provides a method for identifying a therapeutic or prophylactic compound comprising (a) screening an expression library of the present invention to identify a peptide expressed by the library that binds to a target protein or target nucleic acid;
(b) selecting a peptide from (a) that does not bind to said target protein or nucleic acid in its native environment;
(c) expressing the selected peptide in an organism and determining a phenotype of the organism that is modulated by the target protein or target nucleic acid; and
(d) identifying a mimetic compound of a peptide that modulated the phenotype of the organism.

Another embodiment of the invention provides a method for the diagnosis and/or prognosis of a disease and/or disorder comprising contacting a biological sample derived from a subject with a peptide of identified by the method of the invention for a time and under conditions sufficient for said peptide to bind to the target protein in the biological sample and detecting said binding.

Preferably, the method diagnoses and/or prognoses an allergic response to a Der p 1 polypeptide in a subject comprising contacting a biological sample derived from the subject with a mimotope of Der p 1 for a time and under conditions sufficient for an antibody/peptide complex to form and detecting the complex, wherein detection of the complex indicates the presence of an allergic response to a Der p 1 polypeptide.

In a preferred embodiment, the present invention provides a method of for the diagnosis and/or prognosis of a disease and/or disorder comprising contacting a biological sample derived from a subject with a peptide comprises an amino acid sequence selected from the group consisting of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93 for a time and under conditions sufficient for said peptide to bind to Der p 1 in the biological sample and detecting said binding.

The present invention further provides a method for determining a subject that has raised an immune response against a Der p 1 polypeptide comprising contacting a biological sample derived from the subject with a mimotope of Der p 1 for a time and under conditions sufficient for an antibody/peptide complex to form and detecting the complex, wherein detection of the complex indicates that the subject that has raised an immune response against a Der p 1 polypeptide. Preferably, the mimotope of Der p 1 comprises an amino acid sequence selected from the group consisting of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

In another embodiment, the present invention provides a method for detecting an antibody against a Der p 1 polypeptide in a biological sample derived from a subject comprising contacting the biological sample with a mimotope of Der p 1 for a time and under conditions sufficient for an antibody/peptide complex to form and detecting the complex. Preferably, the mimotope of Der p 1 comprises an amino acid sequence selected from the group consisting of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

In another embodiment, the present invention provides a method for diagnosing and/or prognosing an allergic response to a D15 protein from *H. influenzae* in a subject comprising contacting a biological sample derived from the subject with a mimotope of D15 protein from *H. influenzae* for a time and under conditions sufficient for an antibody/peptide complex to form and detecting the complex wherein detection of the complex indicates that the subject suffers from an allergic response against D15 protein from *H. influenzae.*

Additionally, the present invention provides a method for detecting an antibody against a D15 protein from *H. influenzae* in a biological sample derived from a subject comprising contacting the biological sample with a mimotope of D15 protein from *H. influenzae* for a time and under conditions sufficient for an antibody/peptide complex to form and detecting the complex.

In another embodiment, the present invention provides a method for determining a subject that has been infected with *S. aureus* comprising contacting a biological sample derived from the subject with a peptide capable of binding to a FemX protein, a Sortase A protein and/or a Sortase B protein from *S.*

*aureus* identified by the method of the present invention for a time and under conditions sufficient for an antibody/peptide complex to form and detecting the complex, wherein presence of the complex indicates that the subject has been infected with *S. aureus*.

In yet another embodiment, the present invention provides a method for determining the presence of *S. aureus* in a biological sample comprising contacting a biological sample derived from the subject with a peptide capable of binding to a FemX protein, a Sortase A protein and/or a Sortase B protein from *S. aureus* identified by the method of the present invention for a time and under conditions sufficient for an antibody/peptide complex to form and detecting the complex, wherein presence of the complex indicates that *S. aureus* is present in the biological sample.

In one embodiment, the present invention provides a method of treatment of a disease or disorder comprising administering an effective amount of a peptide identified by a screening method of the present invention to a subject suffering from the disease and/or disorder or at risk of developing and/or suffering from the disease and/or disorder.

In a preferred embodiment, the present invention provides a method of treatment of an allergic disease or disorder comprising administering an effective amount mimotope of a Der p 1 antibody to a subject suffering from an allergic disease or disorder or at risk of developing and/or suffering from an allergic disease or disorder. Preferably, the mimotope of a Der p 1 antibody comprises an amino acid sequence selected from the group consisting of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

In another embodiment, the present invention provides a method for desensitizing a subject to a Der p 1 polypeptide comprising administering an effective amount mimotope of a Der p 1 antibody to a subject, wherein the mimotope of Der p 1 desensitizes the subject to Der p 1 polypeptide. Preferably, the mimotope of a Der p 1 antibody comprises an amino acid sequence selected from the group consisting of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

In yet another embodiment, the present invention provides a method of inducing a specific antibody response in a subject to a Der p 1 polypeptide comprising administering an effective amount mimotope of a Der p 1 antibody to a subject, wherein the mimotope of Der p 1 induces a specific antibody response in the subject to Der p 1 polypeptide. Preferably, the mimotope of a Der p 1 antibody comprises an amino acid sequence selected from the group consisting of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

In a further embodiment, the present invention provides a method for treating a neurodegenerative disease comprising administering a peptide inhibitor of c-Jun homodimerization to a subject in need of treatment. Preferably the neurodegenerative disease is Huntington's disease.

In a preferred embodiment, the present invention provides a method for treating Huntington's disease comprising administering to a subject in need of treatment a peptide that comprises an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165.

In another preferred embodiment, the present invention provides a method for treating Huntington's disease comprising administering to a subject in need of treatment a peptide encoded by a nucleic acid that comprises a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162.

Another embodiment of the invention provides a method for the treatment of a cancer or a tumor or a malignancy comprising administering an effective amount of a peptide that inhibits the interaction of a SCL and E47 proteins. Preferably, the cancer is a leukemia. Preferably, the peptide comprises an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79 and SEQ ID NO: 81.

Alternatively, the peptide is encoded by a nucleic acid that comprises a nucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 and SEQ ID NO: 80.

A still further embodiment of the invention provides method of treating a *S. aureus* infection comprising administering an effective amount of a peptide that is capable of specifically binding a protein from the FemABX family of proteins of *S. aureus* identified by a screening method of the invention, and wherein said peptide has antibacterial activity. Preferably, the peptide is capable of specifically binding to a FemX polypeptide of *S. aureus* and has antibacterial activity.

In another embodiment, the peptide that is capable of specifically binding to a Sortase A polypeptide of *S. aureus* and has antibacterial activity.

In yet another embodiment, the peptide is capable of specifically binding to a Sortase B polypeptide of *S. aureus* and has antibacterial activity.

In another aspect, the present invention provides a method for treating an infection by an protozoan selected from the group consisting of *P. falciparum, C. parvum* and *T. brucei* comprising administering an effective amount of a peptide that is capable of specifically binding a tubulin protein of *P. falciparum, C. parvum* or *T. brucei* identified by the method of any one of claims 102 to 106, and wherein said peptide has antimicrobial activity.

Preferably, the peptide is capable of specifically binding a tubulin polypeptide of *P. falciparum, C. parvum* or *T. brucei* and has antiparasitic activity.

In one embodiment, the present invention provides a method of treating malaria comprising administering an effective amount of a peptide that is capable of specifically binding a tubulin polypeptide of *P. falciparum* that has antiparasitic activity.

In one embodiment, the present invention provides a method of treating a diarrheal disease and/or inflammatory bowel disease comprising administering an effective amount of a peptide that is capable of specifically binding a tubulin polypeptide of *C. parvum* that has antiparasitic activity.

In another embodiment, the present invention provides a method of treating sleeping sickness comprising administering an effective amount of a peptide that is capable of specifically binding a tubulin polypeptide of *T. brucei rhodesience* that has antimicrobial activity.

In another aspect, the present invention provides a method for immunizing a subject against *H. influenzae* comprising administering a mimotope a D15 polypeptide or nucleic acid encoding same to a subject, wherein said peptide induces an immune response against *H. influenzae.*

In a preferred embodiment, the present invention provides a method for immunizing a subject against a disease selected from the group consisting of sinusitis, pneumonia, bronchitis, bacteremia and meningitis) comprising administering a mimotope of a D15 polypeptide or nucleic acid encoding same to a subject, wherein said peptide induces an immune response against *H. influenzae.*

In another aspect, the present invention provides for the use of a mimotope of Der p 1 in the manufacture of a medicament for use in the treatment of an allergic disease.

A preferred embodiment of the invention provides for the use of a peptide comprising an amino acid sequence set forth in any one of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93. in the manufacture of a medicament for the treatment of an allergic disease.

Preferably, the allergic disease is associated with an allergy to Der p 1.

Another aspect of the invention provides for the use of a peptide that comprising an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165 in the manufacture of a medicament for the treatment of Huntington's disease.

In another embodiment, the present invention provides for the use of a peptide encoded by a nucleic acid that comprises a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162. in the manufacture of a medicament for the treatment of Huntington's disease Another aspect of the invention provides for the use of a peptide comprising an amino acid sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 and SEQ ID NO: 80 in the manufacture of a medicament for the treatment of a cancer.

Another embodiment, of the invention provides for the use of a nucleic acid comprising a nucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 and SEQ ID NO: 80 in the manufacture of a medicament for the treatment of a cancer.

Preferably, the cancer is a leukemia.

The present invention also provides for the use of a peptide capable of specifically binding a tubulin polypeptide of *P. falciparum* identified by the screening methods of the present invention in the manufacture of a medicament for the treatment of malaria.

In another embodiment, the present invention provides for the use of a peptide capable of specifically binding a tubulin polypeptide of *C. parvum* identified by a screening method of the present invention in the manufacture of a medicament for the treatment of diarrheal disease and/or inflammatory bowel disease.

Yet another embodiment provides for the use of a peptide capable of specifically binding a tubulin polypeptide of *T. brucei rhodesience* identified using a screening method of the present invention in the manufacture of a medicament for the treatment of sleeping sickness.

Another embodiment of the invention provides for the use of a mimotope of a D15 polypeptide or nucleic acid encoding same in the manufacture of a medicament for the treatment of a disease selected from the group consisting of sinusitis, pneumonia, bronchitis, bacteremia and meningitis.

DETAILED DESCRIPTION OF THE PREFERRED EMBODIMENTS

Figure 1:
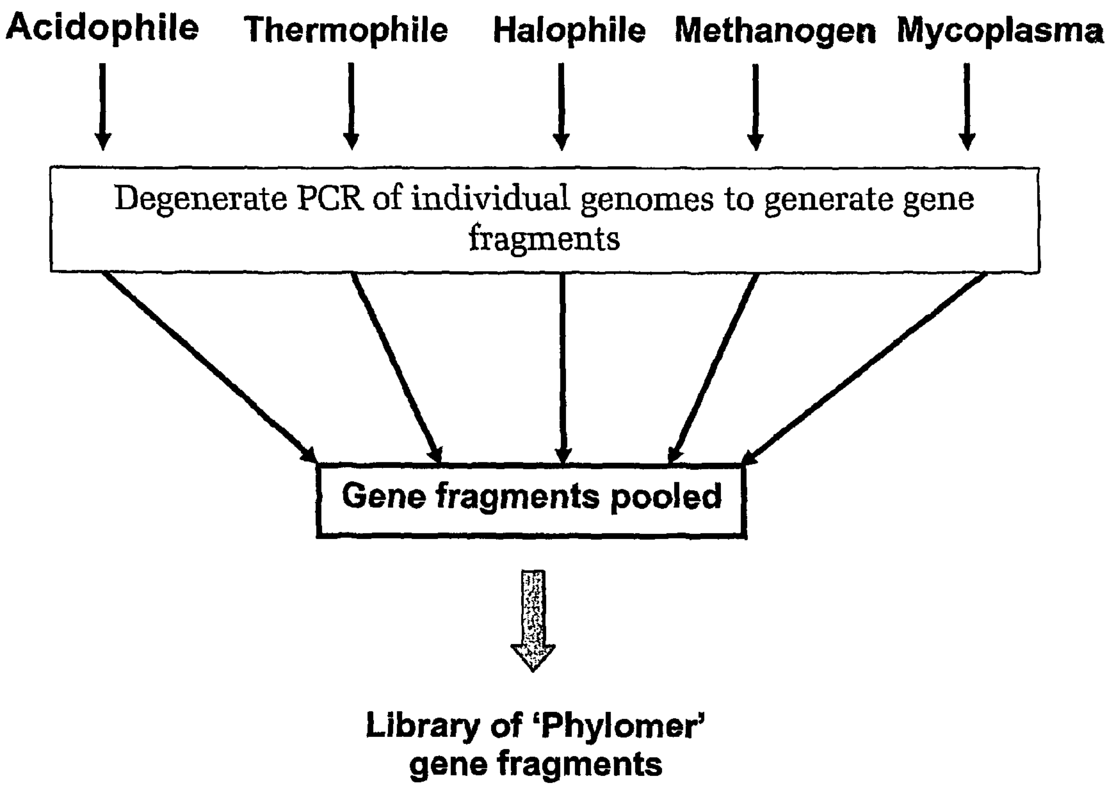
FIG. 1 is a schematic representation showing a simplified method of generating an expression library of the present invention, said library comprising nucleic acid fragments from multiple evolutionary diverse organisms. Initially nucleic acids are isolated from such organisms and pooled in such a way as to ensure equal representation of each of the genomes. Degenerate PCR is then used to amplify sequences from the pool of the genomes, before specific PCR is used to further amplify these nucleic acid fragments in such a way that they may be cloned into an expression vector.

One aspect of the present invention provides a method of constructing an expression library for expressing a polypeptide having a conformation sufficient for binding to a target protein or nucleic acid.

As used herein, the term "expression library" shall be taken to mean a plurality of nucleic acids cloned into a recombinant expression vector such that the cloned DNA fragments are expressed to produce peptides or proteins. As used herein, the terms "expression", "expressed" or "express" shall be taken to mean at least the transcription of a nucleotide sequence to produce a RNA molecule. The term "expression" "expressed" or "express" further means the translation of said RNA molecule to produce a peptide, polypeptide or protein.

As used herein, the term "having a conformation sufficient for binding to a target protein or nucleic acid" shall be taken to mean that an expressed peptide is capable of achieving a secondary structure or conformation sufficient for it to bind to a particular target protein or peptide or polypeptide, or alternatively, a target nucleic acid, preferably in the absence of a constraining peptide such as, for example a Trx loop. Such an affinity is to be interpreted in its broadest context to include, for example, the formation of a peptide:peptide complex, a peptide:protein complex, an antigen:antibody complex, and a peptide:nucleic acid complex.

One preferred embodiment of the present invention relates to the production of nucleic acid fragments from the genome of one or two or more prokaryotes or compact eukaryotes, each of said microorganisms or compact eukaryotes having a substantially sequenced genome.

The term "fragment" as used herein, shall be understood to mean a nucleic acid that is the same as part of, but not all of a nucleic acid that forms a gene.

As used herein, the term "gene" means the segment of nucleic acid, specifically DNA, capable of encoding a peptide or polypeptide, in the present context, a "nucleic acid fragment" is include regions preceding and/or following the coding region of a naturally occurring gene, eg. 5' untranslated or 3' untranslated sequences, as well as intervening sequences between individual coding sequences.

It will be apparent from the disclosure herein that the nucleic acid fragments used to produce the expression libraries in accordance with the present invention do not necessarily encode the same protein or peptide as in their native context (ie. the gene from which they were derived). In fact, the nucleic acid fragments will generally encode a hitherto unknown peptide, particularly if derived from a non-coding region of a native gene. All that is required is an open reading frame of sufficient length to encode a peptide or protein domain.

Nucleic acid fragments are generated by one or more of a variety of methods known to those skilled in the art. Such methods include, for example, a method of producing nucleic acid fragments selected from the group consisting of mechanical shearing (eg by sonication or passing the nucleic acid through a fine gauge needle), digestion with a nuclease (eg Dnase 1), digestion with one or more restriction enzymes, preferably frequent cutting enzymes that recognize 4-base restriction enzyme sites and treating the DNA samples with radiation (eg. gamma radiation or ultra-violet radiation).

In another embodiment, copies of nucleic acid fragments isolated from one or two or more organisms are generated by polymerase chain reaction (PCR) using, for example, random or degenerate oligonucleotides. Such random or degenerate oligonucleotides include restriction enzyme recognition sequences to allow for cloning of the amplified nucleic acid into an appropriate nucleic acid vector. Methods of generating oligonucleotides are known in the art and are described, for example, in Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151. Methods of performing PCR are also described in detail by McPherson et al., In: *PCR A Practical Approach.*, IRL Press, Oxford University Press, Oxford, United Kingdom, 1991.

In a preferred embodiment, the nucleic acid fragment comprises or consists of an open reading frame of nucleotides having a length sufficient to encode a protein domain and preferably, a single protein domain. Examples of protein domains include, for example protein domains selected from the group comprising, helix-loop helix (HLH), leucine zipper, zinc finger, SH2 domain, SH3 domain, WW domain, C2 domain, and proline rich region (PRR), amongst others.

Several studies have shown that the smallest natural domains that are able to fold autonomously consist of about 19 amino acids to about 87 amino acids in length (Gegg et al., *Protein Science,* 6: 1885-1892, 1997, Yang, *Biochemistry* 38, 465, 1999, Alder et al., *J. Biol. Chem.,* 270: 23366-23372, 1995, Horng. *Biochemistry,* 41:13360, 2002, Neidigh, *Nature Structural Biology,* 9:425, 2002). In this context, the term "autonomous" means independent of controlling factors, thus a protein that is able to fold autonomously does so in the absence of factors such as, for example disulphide bonds, ligand binding, or the use of a constraint such as, for example a Trx loop. Accordingly, in one preferred embodiment of the present invention, the nucleic acid fragments of the expression library will consist of an open reading frame sufficient to encode a peptide of about 30-50 amino acids in length.

It is also known that factors such as disulphide bonds control the folding of the peptides. U.S. Pat. No. 6,361,969 and U.S. Pat. No. 6,083,715 describe the expression of protein disulphide isomerases to induce disulphide bond formation in proteins. Studies by Vranken (In: *Proteins,* 47:14-24, 2002) have suggested that natural protein domains stabilized by disulphide bonding can be as small as 15 to 25 amino acids in length. Accordingly, an alternative embodiment of the present invention uses nucleic acid fragments that consist of an open reading frame sufficient to encode a peptide of about 15 amino acids to about 25 amino acids in length.

It will be apparent from the preceding description that the present invention preferably utilizes nucleic acid fragments having a length of about 45 to about 150 nucleotides in length or about 250 nucleotides in length. However, it is to be understood that some variation from this range is permitted, the only requirement being that, on average, nucleic acid fragments generated encode a protein domain or a peptide comprising about 15 to about 50 amino acids in length, and more preferably about 20 to about 50 amino acids in length and still more preferably about 30 to about 50 amino acids in length.

Methods of producing nucleic acid fragments and separating said fragments according to their molecular weight are known in the art and include, for example, the fragmentation methods supra and a method of separation selected from the group comprising, agarose gel electrophoresis, pulse field gel electrophoresis, polyacrylamide gel electrophoresis, density gradient centrifugation and size exclusion chromatography. A number of other methods for separating DNA fragments by their size are known in the art and are described, for example in Sambrook et al (In:).

The genomic nucleic acid is isolated from a variety of sources. In one preferred embodiment, genomic DNA is isolated from a prokaryotic organism. Exemplary prokaryotic sources of nucleic acid fragments include, *Aeropyrum pernix, Agrobacterium tumefaciens, Aquifex aeolicus, Archeglobus fulgidis, Bacillus halodurans, Bacillus subtilis, Borrelia burgdorferi, Brucella melitensis, Brucella suis, Bruchnera* sp., *Caulobacter crescentus, Campylobacter jejuni, Chlamydia pneumoniae, Chlamydia pneumoniae, Chlamydia trachomatis, Chlamydia muridarum, Chlorobium tepidum, Clostridium acetobutylicum, Deinococcus radiodurans, Escherichia coli, Haemophilus influenzae* Rd, *Halobacterium* sp., *Helicobacter pylori, Methanobacterium thermoautotrophicum, Lactococcus lactis, Listeria innocua, Listeria monocytogenes, Methanococcus jannaschii, Mesorhizobium loti, Mycobacterium leprae, Mycobacterium tuberculosis, Mycoplasma genitalium, Mycoplasma penetrans, Mycoplasma pneumoniae, Mycoplasma pulmonis, Neisseria meningitidis, Oceanobacillus iheyensis, Pasteurella multocida, Pseudomonas aeruginosa, Pseudomonas putida, Pyrococcus horikoshii, Rickettsia conorii, Rickettsia prowazekii, Salmonella typhi, Salmonella typhimurium, Shewanella oneidensis* MR-1, *Shigella flexneri* 2a, *Sinorhizobium meliloti, Staphylococcus aureus, Streptococcus agalactiae, Streptococcus agalactiae, Streptococcus mutans, Streptococcus pneumoniae, Streptococcus pyogenes, Streptomyces avermitilis, Streptomyces coelicolor, Sulfolobus solfataricus, Sulfolobus tokodaii, Synechocystis* sp., *Thermoanaerobacter tengcongensis, Thermoplasma acidophilum, Thermoplasma volcanium, Thermotoga maritima, Treponema pallidum, Ureaplasma urealyticum, Vibrio cholerae, Xanthomonas axonopodis* pv., *Citri, Xanthomonas campestris* pv., *Campestris, Xylella fastidiosa*, and *Yersinia pestis.*

Methods of isolating genomic DNA from prokaryotic organisms are known in the art and are described in, for example, Ausubel et al (In: Current Protocols in Molecular Biology. Wiley Interscience, ISBN 047 150338, 1987) or (Sambrook et al., In:).

In an alternative embodiment, genomic nucleic acid is from a compact eukaryote. As used herein the term "compact eukaryote" shall be taken to mean any organism of the superkingdom Eukaryota that has a haploid genome size of less than about 1700 mega base pairs (Mbp), and preferably, less than 100 Mbp. Exemplary compact eukaryotes that are suitable for this purpose include *Arabidopsis thaliana, Anopheles gambiae, Brugia malayi, Caenorhabditis elegans, Danio rerio, Drosophila melanogaster, Eimeria tenella, Eimeria acervulina, Entamoeba histolytica, Oryzias latipes, Oryza sativa, Plasmodium falciparum, Plasmodium vivax, Plasmodium yoelii, Sarcocystis cruzi, Saccharomyces cerevesiae, Schizosaccharomyces pombe, Schistosoma mansoni, Takifugu rubripes, Theileria parva, Tetraodon fluviatilis, Toxoplasma gondii, Tryponosoma brucei*, and *Trypanosoma cruzi.*

Furthermore, it is preferred that said compact eukaryotes contain genomes have less repetitive nucleotide than, for example humans. Such information can be determined from information from NCBI or TIGR.

As used herein the term "NCBI" shall be taken to mean the database of the National Center for Biotechnology Information at the National Library of Medicine at the National Institutes of Health of the Government of the United States of America, Bethesda, Md., 20894.

As used herein the term "TIGR" shall be taken to mean the database of The Institute of Genomic Research, Rockville, Md., 20850.

A preferred example of an organism having a compact genome is the Japanese puffer fish, *Takifugu rubripes*. *T. rubripes* has a haploid genome size of approximately 400 Mbp, with a gene density of about 16%. This is compared to the human genome, which has a size in excess of 3000 Mbp of which only about 3% of nucleotide sequences encode proteins. The absolute number of native genes in the *T. rubripes* genome is comparable to that in the human genome, suggesting fewer repetitive sequences occur in *T. rubripes*. This feature makes *T. rubripes* particularly useful as a source of nucleic acid fragments of the expression libraries of the present invention. This is because a nucleic acid fragment derived from the genome of a compact eukaryote has an increased probability of encoding a protein domain that is contained within a naturally occurring protein in its native context, compared to a sequence derived from a non-compact eukaryote.

It is to be understood that, whilst such native domains of proteins is expressed by the libraries of the invention, the invention is not limited to the expression of known protein domains. Moreover, it is to be understood that the expression libraries of the invention are screened using a process that excludes the selection of clones that encode a known protein domain having its native function. Accordingly, the present invention is directed to products and processes for isolating peptides having new or enhanced functions.

Methods of isolating genomic DNA from eukaryotic organisms are known in the art and are described in, for example, Ausubel et al (In: Current Protocols in Molecular Biology. Wiley Interscience, ISBN 047 150338, 1987) or (Sambrook et al (In:).

In a further embodiment of the present invention, the nucleic acid fragments are derived from complimentary DNA (cDNA). Those skilled in the art will be aware that cDNA is generated by reverse transcription of RNA using, for example, avian reverse transcriptase (AMV) reverse transcriptase or Moloney Murine Leukemia Virus (MMLV) reverse transcriptase. Such reverse transcriptase enzymes and the methods for their use are known in the art, and are obtainable in commercially available kits, such as, for example, the Powerscript kit (Clontech), the Superscript II kit (Invitrogen), the Thermoscript kit (Invitrogen), the Titanium kit (Clontech), or Omniscript (Qiagen).

Methods of isolating mRNA from a variety of organisms are known in the art and are described for example in, Ausubel et al (In: Current Protocols in Molecular Biology. Wiley Interscience, ISBN 047 150338, 1987) or Sambrook et al (In:).

Methods of generating cDNA from isolated RNA are also commonly known in the art and are described in for example, Ausubel et al (In: Current Protocols in Molecular Biology. Wiley Interscience, ISBN 047 150338, 1987) or (Sambrook et al (In:).

In a preferred embodiment, the nucleic acid fragments generated from RNA or cDNA are normalized to reduce any bias toward more highly expressed genes. Methods of normalizing nucleic acids are known in the art, and are described for example in, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001) and Soares et al *Curr. Opinion Biotechnol* 8, 542-546, 1997, and references cited therein. One of the methods described by Soares uses reassociation-based kinetics to reduce the bias of the library toward highly expressed sequences. Alternatively, cDNA is normalized through hybridization to genomic DNA that has been bound to magnetic beads, as described in Kopczynski et al, *Proc. Natl. Acad. Sci. USA,* 95(17), 9973-9978, 1998. This provides an approximately equal representation of cDNA sequences in the eluant from the magnetic beads. Normalized expression libraries produced using cDNA from one or two or more prokaryotes or compact eukaryotes are clearly contemplated by the present invention.

In a particularly preferred embodiment, the nucleic acid fragments are derived from a prokaryote and/or compact eukaryote having a substantially sequenced genome. An advantage of using such fragments is that bioinformatic data can be assembled and used to provide more complete information about the composition of a library than would be possible using uncharacterized libraries. This facilitates the generation of DNA arrays containing sequences derived from many or all of the nucleic acid fragments of the library. Methods used in the generation and screening of DNA arrays are known in the art and are described in for example, Schena (In: Microarray Analysis, John Wiley and Sons, ISBN: 0471414433, 2002). The use of DNA arrays in the high-throughput analysis of the screening of a biodiverse nucleic acid fragment to determine the sequences of positive clones is particularly contemplated.

As used herein "substantially sequenced genome" shall be taken to mean that at least about 60% of the genome has been sequenced. More preferably at least about 70% of the genome has been sequenced, and more preferably at least about 75% of the genome has been sequenced. Even more preferably at least about 80% of the genome has been sequenced.

Methods for determining the amount of a genome that has been sequenced are known in the art. Furthermore, information regarding those sequences that have been sequenced is readily obtained from publicly available sources, such as, for example, the databases of NCBI or TIGR, thereby facilitating determination of the diversity of the genome.

Organisms having a substantially sequenced genome include, for example, an organism selected from the group consisting of *Actinobacillus pleuropneumoniae serovar, Aeropyrum pernix, Agrobacterium tumeficians, Anopheles gambiae, Aquifex aeolicus, Arabidopsis thaliana, Archeglobus fulgidis, Bacillus anthracis, Bacillus cereus, Bacillus halodurans, Bacillus subtilis, Bacteroides thetaiotaomicron, Bdellovibrio bacteriovorus, Bifidobacterium longum, Bordetella bronchiseptica, Bordetella parapertussis, Borrelia burgdorferi, Bradyrhizobium japonicum; Brucella melitensis, Brucella suis, Bruchnera aphidicola, Brugia malayi, Caenorhabditis elegans, Campylobacter jejuni, Candidatus blochmannia floridanus, Caulobacter crescentus, Chlamydia muridarum, Chlamydia trachomatis, Chlamydophilia caviae, Chlamydia pneumoniae, Chlorobium tepidum, Chromobacterium violaceum, Clostridium acetobutylicum, Clostridium perfringens, Clostridium tetani, Corynebacterium diphtheriae, Corynebacterium efficiens, Corynebacterium glutamicum, Coxiella burnetii, Danio rerio, Dechloromonas aromatica, Deinococcus radiodurans, Drosophila melanogaster, Eimeria tenella, Eimeria acervulina, Entamoeba histolytica, Enterococcus faecalis, Escherichia coli, Fusobacterium nucleatum, Geobacter sulfurreducens, Gloeobacter violaceus, Haemophilis ducreyi, Haemophilus influenzae, Halobacterium, Helicobacter hepaticus, Helicobacter pylori, Lactobacillus johnsonii, Lactobacillus plantarum, Lactococcus lactis, Leptospira interrogans serovar lai, Listeria innocua, Listeria monocytogenes, Mesorhizobium loti, Methanobacterium thermoautotrophicum, Methanocaldocossus jannaschii, Methanococcoides burtonii,*

*Methanopyrus kandleri, Methanosarcina acetivorans, Methanosarcina mazei Goel, Methanothermobacter thermautotrophicus, Mycobacterium avium, Mycobacterium bovis, Mycobacterium leprae, Mycobacterium tuberculosis, Mycoplasma gallisepticum* strain R, *Mycoplasma genitalium, Mycoplasma penetrans, Mycoplasma pneumoniae, Mycoplasma pulmonis, Nanoarchaeum equitans, Neisseria meningitidis, Nitrosomonas europaea, Nostoc, Oceanobacillus iheyensis*, Onion yellows phytoplasma, *Oryzias latipes, Oryza sativa, Pasteurella multocida, Photorhabdus luminescens, Pirellula, Plasmodium falciparum, Plasmodium vivax, Plasmodium yoelii, Porphyromonas gingivalis, Prochlorococcus marinus, Prochlorococcus marinus, Prochlorococcus, Pseudomonas aeruginosa, Pseudomonas putida, Pseudomonas syringae, Pyrobaculum aerophilum, Pyrococcus abyssi, Pyrococcus furiosus, Pyrococcus horikoshii, Ralstonia solanacearum, Rhodopseudomonas palustris, Rickettsia conorii, Rickettsia prowazekii, Rickettsia rickettsii, Saccharomyces cerevisiae, Salmonella enterica, Salmonella typhimurium, Sarcocystis cruzi, Schistosoma mansoni, Schizosaccharomyces pombe, Shewanella oneidensis, Shigella flexneri, Sinorhizobium meliloti, Staphylococcus aureus, Staphylococcus epidermidis, Streptococcus agalactiae, Streptococcus agalactiae, Streptococcus mutans, Streptococcus pneumoniae, Streptococcus pyogenes, Streptomyces avermitilis, Streptomyces coelicolor, Sulfolobus solfataricus, Sulfolobus tokodaii, Synechocystis* sp., *Takifugu rubripes, Tetraodon fluviatilis, Theileria parva, Thermoanaerobacter tengcongensis, Thermoplasma acidophilum, Thermoplasma volcanium, Thermosynechococcus elongatus, Thermotoga maritima, Toxoplasma gondii, Treponema denticola, Treponema pallidum, Tropheryma whipplei, Tryponosoma brucei, Trypanosoma cruzi, Ureaplasma urealyticum, Vibrio cholerae, Vibro parahaemolyticus, Vibro vulnificus, Wigglesworthia brevipalpis, Wolbachia endosymbiont* of *Drosophilia melanogaster, Wolinella succinogenes, Xanthomonas axonopodis* pv. *Citri, Xanthomonas campestris* pv. *Campestris, Xylella fastidiosa*, and *Yersinia pestis.*

In an alternate or additional embodiment, nucleic acid fragments are derived from a virus having a substantially sequenced genomes. Virus' with a substantially sequenced genomes are known in the art and include, for example, a virus selected from the group consisting of T7 phage, HIV, equine arteritis virus, lactate dehydrogenase-elevating virus, lelystad virus, porcine reproductive and respiratory syndrome virus, simian hemorrhagic fever virus, avian nephritis virus 1, turkey astrovirus 1, human asterovirus type 1, 2 or 8, mink astrovirus 1, ovine astrovirus 1, avian infectious bronchitis virus, bovine coronavirus, human coronavirus, murine hepatitis virus, porcine epidemic diarrhea virus, SARS coronavirus, transmissible gastroenteritis virus, acute bee paralysis virus, aphid lethal paralysis virus, black queen cell virus, cricket paralysis virus, *Drosophila* C virus, himetobi P virus, kashmir been virus, *plautia stali* intestine virus, *rhopalosiphum padi* virus, taura syndrome virus, triatoma virus, alkhurma virus, apoi virus, cell fusing agent virus, deer tick virus, dengue virus type 1, 2, 3 or 4, Japanese encephalitis virus, Kamiti River virus, kunjin virus, langat virus, louping ill virus, modoc virus, Montana myotis leukoencephalitis virus, Murray Valley encephalitis virus, omsk hemorrhagic fever virus, powassan virus, Rio Bravo virus, Tamana bat virus, tick-borne encephalitis virus, West Nile virus, yellow fever virus, yokose virus, Hepatitis C virus, border disease virus, bovine viral diarrhea virus 1 or 2, classical swine fever virus, pestivirus giraffe, pestivirus reindeer, GB virus C, hepatitis G virus, hepatitis GB virus, bacteriophage M11, bacteriophage Q beta, bacteriophage SP, enterobacteria phage MX1, enterobacteria NL95, bacteriophage AP205, enterobacteria phage fr, enterobacteria phage GA, enterobacteria phage KU1, enterobacteria phage M12, enterobacteria phage MS2, pseudomonas phage PP7, pea enation mosaic virus-1, barley yellow dwarf virus, barley yellow dwarf virus-GAV, barley yellow dwarf virus-MAW, barley yellow dwarf virus-PAS, barley yellow dwarf virus-PAV, bean leafroll virus, soybean dwarf virus, beet chlorosis virus, beet mild yellowing virus, beet western yellows virus, cereal yellow dwarf virus-RPS, cereal yellow dwarf virus-RPV, cucurbit aphid-borne yellows virus, potato leafroll virus, turnip yellows virus, sugarcane yellow leaf virus, equine rhinitis A virus, foot-and-mouth disease virus, encephalomyocarditis virus, theilovirus, bovine enterovirus, human enterovirus A, B, C, D or E, poliovirus, porcine enterovirus A or B, unclassified enterovirus, equine rhinitis B virus, hepatitis A virus, aichi virus, human parechovirus 1, 2 or 3, ljungan virus, equine rhinovirus 3, human rhinovirus A and B, porcine teschovirus 1, 2-7, 8, 9, 10 or 11, avian encephalomyelitis virus, kakugo virus, simian picornavirus 1, aura virus, barmah forest virus, chikungunya virus, eastern equine encephalitis virus, igbo ora virus, mayaro virus, ockelbo virus, onyong-nyong virus, Ross river virus, sagiyama virus, salmon pancrease disease virus, semliki forest virus, sindbis virus, sindbus-like virus, sleeping disease virus, Venezuelan equine encephalitis virus, Western equine encephalomyelitis virus, rubella virus, grapevine fleck virus, maize rayado lino virus, oat blue dwarf virus, chayote mosaic tymovirus, eggplant mosaic virus, erysimum latent virus, kennedya yellow mosaic virus, ononis yellow mosaic virus, physalis mottle virus, turnip yellow mosaic virus and poinsettia mosaic virus.

Information regarding those viral sequences that have been sequenced is readily obtained from publicly available sources, such as, for example, the databases of VirGen and/or NCBI, thereby facilitating determination of the diversity of the genome.

As used herein, the term "VirGen" shall be taken to mean the vial genome resource of the Bioinformatics Centre, University of Pune, Pune 411 007, India.

In a particularly preferred embodiment, nucleic acid fragments are selected that have sufficiently different or divergent nucleotide sequences to thereby enhance nucleotide sequence diversity among the selected fragments compared to the diversity of sequences in the genome from which they were derived.

In one embodiment a nucleic acid fragment is selected such that the encoded polypeptide varies by one or more amino acids with regard to the amino acid sequence of the polypeptide encoded by another fragment in the library, a process that is facilitated using genomes that are substantially sequenced.

In an alternative embodiment, the nucleotide sequence of a nucleic acid fragment is mutated by a process such that the encoded peptide varies by one or more amino acids compared to the "template" nucleic acid fragment. The "template" may have the same nucleotide sequence as the original nucleic acid fragment in its native context (ie. in the gene from which it was derived). Alternatively, the template may itself be an intermediate variant that differs from the original nucleic acid fragment as a consequence of mutagenesis. Mutations include at least one nucleotide difference compared to the sequence of the original fragment. This nucleic acid change may result in for example, a different amino acid in the encoded peptide, or the introduction or deletion of a stop codon. Accordingly, the diversity of the nucleic acids of the expression library and the encoded polypeptides is enhanced by such mutation processes.

In one embodiment, the nucleic acid fragments are modified by a process of mutagenesis selected from the group consisting of, mutagenic PCR, expressing the nucleic acid fragment in a bacterial cell that induces a random mutation, site directed mutagenesis and expressing a nucleic acid fragment in a host cell exposed to a mutagenic agent such as for example radiation, bromo-deoxy-uridine (BrdU), ethylnitrosurea (ENU), ethylmethanesulfonate (EMS) hydroxylamine, or trimethyl phosphate amongst others.

In a preferred embodiment, the nucleic acid fragments are modified by amplifying a nucleic acid fragment using mutagenic PCR. Such methods is include a process selected from the group consisting of: (i) performing the PCR reaction in the presence of manganese; and (ii) performing the PCR in the presence of a concentration of dNTPs sufficient to result in misincorporation of nucleotides.

Methods of inducing random mutations using PCR are known in the art and are described, for example, in Dieffenbach (ed) and Dveksler (ed) (In: PCR Primer: A Laboratory Manual, Cold Spring Harbour Laboratories, NY, 1995). Furthermore, commercially available kits for use in mutagenic PCR are obtainable, such as, for example, the Diversify PCR Random Mutagenesis Kit (Clontech) or the GeneMorph Random Mutagenesis Kit (Stratagene).

In one embodiment, PCR reactions are performed in the presence of at least about 200 μM manganese or a salt thereof, more preferably at least about 300 μM manganese or a salt thereof, or even more preferably at least about 500 μM or at least about 600 μM manganese or a salt thereof. Such concentrations manganese ion or a manganese salt induce from about 2 mutations per 1000 base pairs (bp) to about 10 mutations every 1000 by of amplified nucleic acid (Leung et al *Technique* 1, 11-15, 1989).

In another embodiment, PCR reactions are performed in the presence of an elevated or increased or high concentration of dGTP. It is preferred that the concentration of dGTP is at least about 25 μM, or more preferably between about 50 μM and about 100 μM. Even more preferably the concentration of dGTP is between about 100 μM and about 150 μM, and still more preferably between about 150 μM and about 200 μM. Such high concentrations of dGTP result in the misincorporation of nucleotides into PCR products at a rate of between about 1 nucleotide and about 3 nucleotides every 1000 by of amplified nucleic acid (Shafkhani et al *BioTechniques* 23, 304-306, 1997).

PCR-based mutagenesis is preferred for the mutation of the nucleic acid fragments of the present invention, as increased mutation rates is achieved by performing additional rounds of PCR.

In another preferred embodiment, the nucleic acid of the expression library is mutated by inserting said nucleic acid into a host cell that is capable of mutating nucleic acid.

Such host cells are deficient in one or more enzymes, such as, for example, one or more recombination or DNA repair enzymes, thereby enhancing the rate of mutation to a rate that is rate approximately 5,000 to 10,000 times higher than for non-mutant cells. Strains particularly useful for the mutation of nucleic acids carry alleles that modify or inactivate components of the mismatch repair pathway. Examples of such alleles include alleles selected from the group consisting of mutY, mutM, mutD, mutT, mutA, mutC and mutS. Bacterial cells that carry alleles that modify or inactivate components of the mismatch repair pathway are known in the art, such as, for example the XL-1Red, XL-mutS and XL-mutS-Kan$^r$ bacterial cells (Stratagene).

Alternatively the nucleic acid fragments are cloned into a nucleic acid vector that is preferentially replicated in a bacterial cell by the repair polymerase, Pol I. By way of exemplification, a Pol I variant strain will induce a high level of mutations in the introduced nucleic acid vector, thereby enhancing sequence diversity of the nucleic acid used to generate the expression library of the present invention. Such a method is described by Fabret et al (In: *Nucl Acid Res,* 28, 1-5 2000), which is incorporated herein by reference.

In a further preferred embodiment the mutated nucleic acid fragments are combined with the non-mutated fragments from which they were derived, for subcloning into an expression vector. In this way, the nucleotide diversity of the expression library of the present invention is enhanced, as is the diversity of the conformations of the expressed peptides and proteins.

In another embodiment, the sequence diversity of a nucleic acid fragment is increased, such as, for example, using a synthetic shuffling technique, such as, for example, the process described by Ness et al, *Nature Biotechnology,* 20, 1251-1255, 2002, which is incorporated herein by reference. In adapting such a technique to the present invention, functionally homologous nucleic acid fragments are selected from the expression library, using methods described herein. By "functionally homologous" in this context means that the selected fragments bind to the same target protein or target nucleic acid. The amino acid sequence of each peptide that binds to the target is determined using methods known in the art, and the sequences are aligned using an algorithm known in the art. A consensus sequence is determined from the alignment that provides for highly conserved residues, as well as elucidating those residues that are structurally similar albeit not strictly conserved. The structural features of the peptides are also derived using X-ray crystallography and/or computer-based modelling procedures. Accordingly, the divergence in the identified peptides from an individual screen permits the identification of both primary and secondary structural features that are required for binding to the target protein or target nucleic acid to occur. Based upon the bioinformatic data obtained, oligonucleotides (eg., degenerate oligonucleotides or non-degenerate oligonucleotides as appropriate) are designed that encode all of the possible peptides that bind to the target protein or target nucleic acid. These oligonucleotides are then assembled using PCR employing multiple rounds of amplification, to generate a plurality of nucleic acids encoding all possible peptide combinations. Accordingly, an amino acid sequence that is not normally found in nature is produced.

In a further embodiment, a significant proportion of the nucleic acid fragments are cloned into a gene construct in at least two forward open reading frames, and preferably three forward open reading frames, to thereby enhance the number of divergent peptides or proteins that are encoded by a particular nucleic acid fragment. In this context, the term "significant proportion" means at least about 30% to 50%, preferably at least about 40% to 60%, more preferably at least about 50% to 70%, still more preferably at least about 60% to 80% and still more preferably greater than about 70% or 80% of the total nucleic acid fragments that are subcloned successfully into a suitable gene construct such that more than one open reading frame can be utilized for expression. As will be known to those skilled in the art, procedures for cloning a single nucleic acid into a gene construct in multiple reading frames are known.

Particularly preferred methods of subcloning a nucleic acid fragment in multiple three reading frames comprise a process selected from the group consisting of:

(a) ligating the nucleic acid fragment to a linker or adaptor, such as for example, one or more linkers modified to contain an additional one or two or three base pairs, or a multiple of one or two or three nucleotides;

(b) Placing each nucleic acid fragment operably under the control of a Kozak consensus sequence and at different distances therefrom (eg. one or two or three nucleotides or a multiple of one or two or three nucleotides) from said Kozak consensus sequence;

(c) Placing a fragment under control of sequences that confer transcriptional and/or translational slippage.

By ligating the nucleic acid fragment to a linker or adaptor, the number of introduced nucleotides can be varied such that a significant proportion of the nucleic acid fragments are introduced into an expression vector or gene construct in at least two and preferably three reading frames. Linkers or adaptors are ligated to the 5'-end of the nucleic acid fragment such that, on average, a different length linker or adaptor is added to each nucleic acid fragment having the same sequence. This is generally achieved by varying the relative proportions of each linker/adaptor to the nucleic acid fragments. Naturally, each linker/adaptor of differing length is generally in equimolar concentration in the ligation reaction, and the total concentration of linker/adaptor 3'-ends is held in equimolar concentration to the total concentration of 5'-ends of the nucleic acid fragments being ligated. Methods of ligating adaptors to nucleic acids are known in the art and are described in for example, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

As an alternative to separately adding the linkers/adaptors to the nucleic acid fragments prior to subcloning into a suitable gene construct, a suitable gene construct is used that comprises additional nucleotides 3' of a translation initiation signal, and provides for sub-cloning of nucleic acid fragments in each reading frame. As will be known to those skilled in the art, each reading frame in a gene construct is generally accessed by digesting the gene construct with a different restriction endonuclease and then sub-cloning nucleic acid fragments into the digested, linearized vector. By "sub-cloning" means a process involving or comprising a ligation reaction.

Alternatively, site directed mutagenesis is used to introduce additional nucleotides after the translation initiation site of the gene construct. Methods of site-directed mutagenesis are known in the art, and are described for example, in Dieffenbach (eds) and Dveksler (ed) (In: PCR Primer: A Laboratory Manual, Cold Spring Harbour Laboratories, NY, 1995). Furthermore, kits containing instruction and reagents necessary for site-directed mutagenesis are commercially available, such as, for example, the Quikchange site directed mutagenesis kit (Stratagene).

Furthermore, expression vectors are commercially available that have been modified to include an additional one or two nucleotides after the transcription start codon to allow for cloning of a nucleic acid in at least two and preferably three reading frames. Such vectors include, for example, the pcDNA (A, B, or C) vector suite (Invitrogen).

By positioning each nucleic acid fragment so that expression is placed operably under the control of a Kozak consensus sequence and at different distances therefrom, a significant proportion of the nucleic acid fragments is inserted into the vector in at least two and preferably three reading frames. A preferred Kozak sequence has the core sequence RNNATG (SEQ ID NO: 1), wherein R is a purine (ie. A or G) and N is any nucleotide. A particularly preferred Kozak sequence for expression of a polypeptide in eukaryotic cells comprises the sequence CCRCCATG (SEQ ID NO: 2) or GCCAGCCATGG (SEQ ID NO: 3). A preferred Kozak sequence for the expression of polypeptides in plants is CTACCATG (SEQ ID NO: 4).

A Kozak consensus sequence is generated using synthetic oligonucleotides in a process that is known in the art and described, for example, in, Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151. Alternatively a Kozac sequence is isolated from a natural or recombinant source using methods known in the art, such as for example using from the group, restriction enzyme digestion or PCR.

In one embodiment, the Kozak sequence is generated as an oligonucleotide or nucleic acid fragment and then ligated 5' of the nucleic acid fragment (ie. the nucleic acid fragment being sub-cloned). Methods of ligating such oligonucleotides or fragments are known in the art and are described in for example, Ausubel et al (In: Current Protocols in Molecular Biology. Wiley Interscience, ISBN 047 150338, 1987) or (Sambrook et al (In: Molecular Cloning: Molecular Cloning: A Laboratory Manual, Cold Spring Harbor Laboratories, New York, Third Edition 2001). As with other ligations, the total concentration of nucleic acid of each ligating species (ie. the Kozak containing fragment and the nucleic acid) should preferably be equimolar. Naturally to ensure that a significant proportion of nucleic acid fragments are ligated in each reading frame, the Kozak-containing fragments of differing length should also be present in approximately equimolar concentration.

As an alternative to separately adding the Kozak consensus sequence oligonucleotide or fragment to the nucleic acid fragment prior to subcloning into a suitable vector, an expression vector is used that comprises a translation start site and provides for subcloning of nucleic acid fragments in each reading frame. As will be known to those skilled in the art, each reading frame in such a vector is generally accessed by digesting the vector with a different restriction enzyme and then subcloning fragments into the digested, linearized vector.

When the nucleic acid fragment of the present invention is to be expressed in prokaryotic cells, it is particularly preferred that the Kozak sequence of the above embodiments is replaced with a ribosome binding sequence, or Shine Dalgarno sequence. A particularly preferred Shine Dalgarno sequence consists of nucleic acids having the nucleotide sequence GAAGAAGATA (SEQ ID NO: 5).

By placing a fragment under control of sequences that confer transcriptional and/or translational slippage is meant that the fidelity of the start site for transcription and/or translation is reduced such that translation is initiated at different sites. Accordingly, such a sequence is cause the expression of several different polypeptides.

In one embodiment translational slippage (or translational frameshifting) is induced using nucleic acid comprising of the consensus sequence $N_1N_1N_1N_2N_2N_2N_3$, wherein N represents any nucleotide and all nucleotides represented by $N_1$ are the same nucleotide, all nucleotides represented by $N_2$ are the same nucleotide. In accordance with this embodiment, $N_1$ and/or $N_2$ and/or $N_3$ are the same or different. A particularly preferred translational slippage sequence for use in a eukaryote will comprise a sequence selected from the group consisting of: AAAAAAC (SEQ ID NO: 6), AAATTTA (SEQ ID NO: 7), AAATTTT (SEQ ID NO: 8), GGGAAAC (SEQ ID NO: 9), GGGCCCC (SEQ ID NO: 10), GGGTTTA (SEQ ID NO: 11), GGGTTTT (SEQ ID NO: 12), TTTAAAC (SEQ ID NO: 13), TTTAAAT (SEQ ID NO: 14), TTTTTA (SEQ ID NO: 15), and GGATTTA (SEQ ID NO: 16). In an alternative embodiment, a sequence that induces translational slippage in yeast is CTTAGGC (SEQ ID NO: 17) or GCGAGTT (SEQ ID NO: 18). In yet another embodiment a sequence that induces translational slippage in mammals is TCCTGAT (SEQ ID NO: 19).

In another embodiment, a translational slippage sequences for use in prokaryotic organisms includes, but is not limited to s sequence selected from the group consisting of AAAAAAG (SEQ ID NO: 20), AAAAAAA (SEQ ID NO: 21), AAAAAAC (SEQ ID NO: 22), GGGAAAG (SEQ ID NO: 23), AAAAGGG (SEQ ID NO: 24), GGGAAAA (SEQ ID NO: 25), TTTAAAG (SEQ ID NO: 26) and AAAGGGG (SEQ ID NO: 27). It is particularly preferred that this translational slippage sequence is positioned about 7 to about 19 nucleotides downstream of a Shine Dalgarno sequence. In an alternative embodiment, a nucleic acid that induces translational slippage in bacterial cells comprises the nucleotide sequence CTT (SEQ ID NO: 28), and is positioned 3 nucleotides upstream of a Shine Dalgarno sequence controlling the expression of the nucleic acid fragment.

A translational slippage sequence is generated using synthetic oligonucleotides, or isolated from a natural or recombinant source, for example the prfB gene, the dnaX gene, the mammalian ornithine decarboxylase antizyme, in addition to various retroviruses, coronaviruses, retrotransposons, virus-like sequences in yeast, bacterial genes and bacteriophage genes. Such a sequence is isolated using a method that is known in the art, such as for example, restriction enzyme digestion or PCR.

It is preferred that sequences that confer translational slippage are ligated to the 5'-end of the nucleic acid fragment in the same manner as for adaptor addition. Methods of ligating adaptors are known in the art and are described in for example, Ausubel et al (In: Current Protocols in Molecular Biology. Wiley Interscience, ISBN 047 150338, 1987) or (Sambrook et al (In: Molecular Cloning: Molecular Cloning: A Laboratory Manual, Cold Spring Harbor Laboratories, New York, Third Edition 2001).

It is also preferred that the sequences that confer transcriptional or translational slippage are incorporated into the expression vector or gene construct into which the nucleic acid fragment is inserted, such that it is positioned upstream (ie. 5') of the translational start site in the fragment.

In another embodiment, transcriptional slippage is induced by the introduction of a stretch of nucleotides with a sequence such as, for example, $T_9$ or $A_9$. Transcriptional slippage sequences are preferably cloned downstream (ie. 3') of the site of initiation of transcription. It is also preferred to position a transcriptional slippage sequence upstream (5') of a translational start site in the nucleic acid fragment. Accordingly, the transcriptional slippage sequence is included in the expression vector or gene construct into which the nucleic acid fragment is inserted.

Accordingly, the nucleic acids that form the transcriptional slippage sequence is ligated to the 5' end of a nucleic acid fragment, in conjunction with a translation start site.

It will be apparent from the preceding description that the transcriptional slippage sequence is incorporated into the expression vector or gene construct upstream of the translation start site, and downstream of the site of initiation of transcription.

Preferably, the nucleic acid fragments derived from the prokaryote or compact eukaryote genome are inserted into a gene construct in both the forward and/or reverse orientation, such that 1 or 2 or 3 or 4 or 5 or 6 open reading frames of said nucleic acid fragments are utilized. Methods of bi-directionally inserting fragments into vectors are known in the art.

It will be apparent to the skilled artisan that, by sub-cloning the nucleic acid fragments in multiple reading frames into a suitable expression vector, it is possible to encode a peptide or protein domain that does not occur in nature, as well as producing a variety of natural peptide domains. Accordingly, the diversity of the nucleic acids of the expression library and their encoded peptides are greatly enhanced in these modified nucleic acid fragment expression libraries.

In a preferred embodiment, the expression libraries of the present invention are normalized to remove any redundant nucleic acid from the genome. As cited herein the term "redundant nucleic acid" shall be taken to mean those nucleic acid fragments having the same sequence, such as, for example, high copy number or repetitive sequences. Nucleic acid fragments derived from multiple homologous sequences, whether derived from the same or a different species can be subject to normalization to reduce the presence of redundant sequences in the expression library. Similarly, nucleic acid fragments derived from repetitive DNA and nucleic acid fragments derived from pseudogenes can be subject conveniently to normalization. Methods of normalizing libraries to remove redundant nucleic acid are known in the art and are described, for example, by Ausubel et al., In: Current Protocols in Molecular Biology. Wiley Interscience, ISBN 047 150338, 1987, or Diversa Corporation (U.S. Pat. No. 5,763,239), or Sambrook et al., In: Molecular Cloning: Molecular Cloning: A Laboratory Manual, Cold Spring Harbor Laboratories, New York, Third Edition 2001, or Bonaldo et al., *Genome Res.* 6(9), 791-806, 1997. In one embodiment, the nucleic acid fragments are subjected to hydroxyapatite chromatography to remove redundant or highly repetitive sequences. The success of such a normalization process can be determined, for example, by hybridizing labelled non-normalized and normalized DNA to Southern blots of genomic DNA and comparing the amount of label bound to each blot. The amount of bound label is comparable to the amount of hybridized DNA. A reduced hybridization signal for normalized libraries indicates that iterative sequences have been reduced in the normalized pool.

In one embodiment the nucleic acids used to produce the expression libraries of the present invention are isolated from a single organism. In this case, nucleic acid fragments are generated from nucleic acid derived from a distinct prokaryote or compact eukaryote.

In another embodiment of the present invention the nucleic acids are derived from two or more prokaryotes and/or compact eukaryotes including any and all combinations thereof.

It is especially preferred that the prokaryote(s) and/or compact eukaryote(s) used to produce expression libraries from combined genomes are evolutionally diverse organisms. As used herein the term "evolutionary diverse" shall be taken to mean those organisms that when compared at the genetic level, show a significant degree of genetic diversity. As used herein the term "significant degree of genetic diversity" shall be taken to mean, that the genes of the prokaryotes or compact eukaryotes differ, by at least about 10% to 30% at the nucleic acid level. More preferably the genetic sequences of the prokaryotes or compact eukaryotes differ by at least about 30% to 40% at the nucleic acid level. More preferably the genetic sequences of the prokaryotes or compact eukaryotes differ by at least about 50% at the nucleic acid level. More preferably the genetic sequences of the prokaryote or compact eukaryotes differ by at least about 70% at the nucleic acid level, or more preferably at least about 80% at the nucleic acid level or 90% at the nucleic acid level.

In determining whether or not two nucleotide sequences fall within these defined percentage identity limits, those skilled in the art will be aware that it is possible to conduct a side-by-side comparison of the nucleotide sequences. In such comparisons or alignments, differences will arise in the positioning of non-identical residues depending upon the algorithm used to perform the alignment. In the present context, references to percentage identities and similarities between two or more nucleotide sequences shall be taken to refer to the number of identical and similar residues respectively, between said sequences as determined using any standard algorithm known to those skilled in the art. In particular, nucleotide identities and similarities are calculated using software of the Computer Genetics Group, Inc., University Research Park, Maddison, Wis., United States of America, eg., using the GAP program of Devereaux et al., *Nucl. Acids Res.* 12, 387-395, 1984, which utilizes the algorithm of Needleman and Wunsch, J. Mol. Biol. 48, 443-453, 1970. Alternatively, the CLUSTAL W algorithm of Thompson et al., *Nucl. Acids Res.* 22, 4673-4680, 1994, is used to obtain an alignment of multiple sequences, wherein it is necessary or desirable to maximize the number of identical/similar residues and to minimize the number and/or length of sequence gaps in the alignment. Nucleotide sequence alignments can also be performed using a variety of other commercially available sequence analysis programs, such as, for example, the BLAST program available at NCBI.

In an alternative embodiment, the genetic sequences of the prokaryotes or compact eukaryotes fail to cross hybridize in a standard Cot analysis. The skilled artisan will be aware that standard Cot analyzes determine the similarity between two nucleotide sequences at the nucleotide level by using renaturation-kinetics of the corresponding nucleic acids (eg., Britten and Kohne *Science,* 161, 529-540, 1968).

Where more than one substantially sequenced genome used to produce the expression library of the present invention, it is also preferred that the fragments from each distinct prokaryote or compact eukaryote are used in an amount proportional to the complexity and size of the genome of said prokaryote or compact eukaryote. As the genomes of the prokaryotes and/or compact eukaryotes are substantially sequenced the approximate size of said genome's is determined. Accordingly, library is normalized to ensure that the amount of nucleic acids from all of the incorporated genomes to the final expression library is equal. In a particularly preferred embodiment, the nucleic acid fragment expression libraries are normalized such that nucleic acid fragments from each of the prokaryotes or compact eukaryotes are incorporated in equimolar amounts. In one exemplified embodiment, the sizes (in Mbp or molecular weight) of the genomes to be used in the expression library are compared and nucleic acid from each genome is used in an amount that is proportional to the ration of genome size to the size of the smallest contributing genome for the library. For example, the genome of *T. rubripes* is about 400 Mb in size, compared to the genome of *A. thaliana*, which is only about 120 Mb. Accordingly, for a combination of genomic *T. rubripes* and *A. thaliana* nucleic acid fragments, the ration of *T. rubripes* nucleic acid fragments to *A. thaliana* nucleic acid fragments would be about 4:1.2 (w/w). The relative contributions of nucleic acid fragments for constructing expression libraries from multiple genomes are readily calculated from the information presented in Table 1.

TABLE 1

Sizes of genomes of organisms from which nucleic acid fragments are derived for construction of expression libraries

| Source of nucleic acid fragments | Approx. genome size (Mb) |
|---|---|
| *Actinobacillus pleuropneumoniae* | 2.2 |
| *Aeropyrum pernix* | 1.6-1.7 |
| *Agrobacterium pernix* | 1.67 |
| *Anopheles gambiae* | 26-27 |
| *Arabidopsis thaliana* | 120 |
| *Aquifex aeolicus* | 1.5-1.6 |
| *Archaeoglobus fulgidis* | 1.7 |
| *Bacillus anthracis* | 5.09 |
| *Acillus cereus* | 5.4 |
| *Bacillus halodurans* | 4.2 |
| *Bacillus subtilis* | 4.2 |
| *Bacteroides thetaiotaomicron* | 6.2 |
| *Bdellovibrio bacteriovorus* | 3.8 |
| *Bifidobacterium longum* | 2.3 |
| *Bordetella bronchiseptica* | 5.34 |
| *Bordetall parapertusis* | 4.77 |
| *Bordetella pertussis* | 3.91 |
| *Borellia afzelii* | 0.95 |
| *Borellia garinii* | 0.95 |
| *Borrelia burgdorferi* | 0.91-0.96 |
| *Bradyrhizobium japonicum* | 9.11 |
| *Brucella melitensis* | 3.2 |
| *Brucella suis* | 3.29 |
| *Brugia malayi* | 100 |
| *Buchnera aphidicola* | 0.64 |
| *Caenorhabditis elegans* | 97-102 |
| *Campylobacter jejuni* | 1.64 |
| *Candidatus blochmannia floridanus* | 0.7 |
| *Caulobacter crescentus* | 4.01 |
| *Chlamydia muridarum* | 1.07 |
| *Chlamydia pneumoniae* | 1.22 |
| *Chlamydia trachomatis* | 1.0-1.1 |
| *Chlamydophila caviae* | 3.53 |
| *Chlamydophila pneumoniae* | 1.23 |
| *Chlorobium tepidum* | 2.1 |
| *Chlostridium acetobutylicum* | 4.1 |
| *Chromobacterium violaceum* | 4.8 |
| *Clostridium acetobutylicum* | 3.94 |
| *Clostridium perfringens* | 3.03 |
| *Clostridium tetani* | 4.1 |
| *Corynebacterium diphtheriae* | 2.49 |
| *Corynebacterium efficiens* | 3.15 |
| *Corynebacterium glutamicum* | 3.31 |
| *Coxiella burnetii* | 2.0 |
| *Danio rerio* | 1700 |
| *Dechloromonas aromatica* | 4.50 |
| *Deinococcus radiodurans* | 3.28 |
| *Drosophila melanogaster* | 120 |
| *Eimeria acervulina* | 70 |
| *Eimeria tenella* | 70 |
| *Entamoeba hystolitica* | 40 |
| *Enterococcus faecalis* | 3.36 |
| *Escherichia coli* | 4.6-5.6 |
| *Fusobacterium nucleatum* | 4.33 |
| *Geobacter sulfurreducens* | 3.85 |
| *Gloebacter violaceus* | 4.7 |
| *Haemophilus ducreyi* | 1.7 |
| *Haemophilus influenzae* | 1.83 |
| *Halobacterium* sp. | 2.57 |
| *Helicobacter hepaticus* | 1.8 |
| *Helicobacter pylori* | 1.66 |
| *Lactobacillus johnsonii* | 2.0 |
| *Lactobacillus plantarum* | 3.3 |
| *Lactococcus lactis* | 2.36 |
| *Leptospira interrogans serovar lai* | 4.6 |
| *Listeria innocua* | 3.01 |
| *Listeria monocytogenes* | 2.94 |
| *Mesorhizobium loti* | 7.59 |
| *Methanobacterium thermoautotrophicum* | 1.75 |
| *Methanocaldococcus jannaschii* | 1.66 |
| *Methanococcoides burtonii* | 2.6 |
| *Methanopyrus kandleri* | 1.69 |
| *Methanosarcina acetivorans* | 5.75 |

TABLE 1-continued

| Sizes of genomes of organisms from which nucleic acid fragments are derived for construction of expression libraries | |
|---|---|
| Source of nucleic acid fragments | Approx. genome size (Mb) |
| *Methanosarcina mazei Goel* | 4.1 |
| *Methanothermobacter thermautotrophicus* | 1.75 |
| *Mycobacterium avium* sp. | 4.96 |
| *Mycobacterium bovis* | 4.35 |
| *Mycobacterium leprae* | 2.8 |
| *Mycobacterium tuberculosis* | 4.4 |
| *Mycoplasma gallisepticum* strain R | 1.0 |
| *Mycoplasma genitalium* | 0.58 |
| *Mycoplasma penetrans* | 1.36 |
| *Mycoplasma pneumoniae* | 0.81 |
| *Mycoplasma pulmonis* | 0.96 |
| *Nanoarchaeum equitans* Kin4 | 0.49 |
| *Neisseria meningitidis* | 2.18-2.27 |
| *Nitrosomonas europaea* | 2.81 |
| *Nostoc* sp. | 6.41 |
| *Oceanobacillus iheyensis* | 3.6 |
| Onion yellows phytoplasma | 0.86 |
| *Oryza sativa* | 400 |
| *Pasturella multocida* | 2.4 |
| *Photorhabdus luminescens* sp. | 5.7 |
| *Pirellula* sp. | 7.1 |
| *Porphyromonas gingivalis* | 2.34 |
| *Plasmodium berghei* | 25 |
| *Plasmodium falciparum* | 25 |
| *Plasmodium yoelii* | 23 |
| *Plasmodium vivax* | 30 |
| *Prochlorococcus marinus* str. | 2.41 |
| *Pseudomonas aeruginosa* | 6.3 |
| *Pseudomonas putida* | 6.1 |
| *Pseudomonas syringae* | 6.4 |
| *Pyrobaculum aerophilum* | 2.2 |
| *Pyrococcus abyssi* | 1.77 |
| *Pyrococcus furiosus* | 1.91 |
| *Pyrococcus horikoshii* | 1.74 |
| *Ralstonia solanacearum* | 5.80 |
| *Rhodopseudomonas palustris* | 5.46 |
| *Ricketsia conorii* | 1.27 |
| *Ricketsia prowazekii* | 1.1 |
| *Ricketsia rickettsii* | 1.3 |
| *Saccharomyces cerevesiae* | 13.0 |
| *Salmonella enterica* | 4.8 |
| *Salmonella typhimurium* | 4.8 |
| *Sarcocystis cruzi* | 201 |
| *Schizosaccharomyces pombe* | 13.8-14.0 |
| *Schistosoma mansoni* | 270 |
| *Shewanalla oneidensis* | 5.14 |
| *Shigella flexneri* | 4.7 |
| *Sinorhizobium meliloti* | 6.7 |
| *Staphylococcus aureus* | 2.8 |
| *Staphylococcus epidermidis* | 2.6 |
| *Streptococcus agalactiae* | 2.21 |
| *Streptococcus mutans* | 2.03 |
| *Streptococcus pneumoniae* | 2.2 |
| *Streptococcus pyogenes* | 1.85 |
| *Streptomyces avermitilis* | 9 |
| *Streptomyces coelicolor* | 8.7 |
| *Sulfolobus solfataricus* | 2.99 |
| *Sulfolobus tokodaii* | 2.81 |
| *Synechococcus* sp. | 2.43 |
| *Synechocystis* PCC 6803 | 3.57 |
| *Takifugu rubripes* | 400 |
| *Thermoplasma volcanium* | 1.56-1.58 |
| *Thermoanaerobacter tengcongensis* | 2.69 |
| *Thermoplasma acidophilum* | 1.56 |
| *Thermoplasma volcanium* | 1.58 |
| *Thermotoga maritima* | 1.80 |
| *Thermotoga pallidum* | 1.14 |
| *Toxoplasma gondii* | 89 |
| *Treponema denticola* | 3.06 |
| *Treponema pallidum* | 1.14 |
| *Tropheryma whipplei* | 0.93 |
| *Trypanosoma brucei* | 35 |
| *Trypanosoma cruzi* | 40 |

TABLE 1-continued

| Sizes of genomes of organisms from which nucleic acid fragments are derived for construction of expression libraries | |
|---|---|
| Source of nucleic acid fragments | Approx. genome size (Mb) |
| *Ureaplasma urealyticum* | 0.75 |
| *Vibrio cholerae* | 4 |
| *Vibro parahaemolyticus* | 5.2 |
| *Vibrio vulnificus* | 5.1 |
| *Wigglesworthia brevipalpis* | 0.7 |
| *Wolbachia endosymbiont* of *Drosophila melanogaster* | 1.27 |
| *Wolinella succinogenes* | 2.1 |
| *Xanthomonas axonopodis* | 5.17 |
| *Xanthomonas campestris* | 5.07 |
| *Xylella fastidiosa* | 2.68 |
| *Yersinia pestis* | 4.65 |

Preferred combinations of genomes are selected from the group consisting of:

a) nucleic acid fragments derived from two organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* b) nucleic acid fragments derived from three organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* c) nucleic acid fragments derived from four organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* d) nucleic acid fragments derived from five organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster,*

*Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* e) nucleic acid fragments derived from six organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* f) nucleic acid fragments derived from seven organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* g) nucleic acid fragments derived from eight organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* h) nucleic acid fragments derived from nine organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* i) nucleic acid fragments derived from ten organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* j) nucleic acid fragments derived from eleven organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* k) nucleic acid fragments derived from twelve organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* l) nucleic acid fragments derived from thirteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* m) nucleic acid fragments derived from fourteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* n) nucleic acid fragments derived from fifteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertus-*

*sis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* o) nucleic acid fragments derived from sixteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* p) nucleic acid fragments derived from seventeen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* q) nucleic acid fragments derived from eighteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* r) nucleic acid fragments derived from nineteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* s) nucleic acid fragments derived from twenty organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* t) nucleic acid fragments derived from twenty one organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* u) nucleic acid fragments derived from twenty two organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* v) nucleic acid fragments derived from twenty three organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* w) nucleic acid fragments derived from twenty four organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* x) nucleic acid fragments derived from twenty five organisms selected from the group consisting of: *Aeropyrum pernix,*

*Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima;* y) nucleic acid fragments derived from twenty six organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima*; and z) nucleic acid fragments derived from twenty seven organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima.*

In a particularly preferred embodiment, the nucleic acid fragments are derived from the organisms *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium*, and *Thermotoga maritima.*

In a particularly preferred embodiment, nucleic acid fragments derived from the following bacteria are combined into a single expression library: *Aeropyrum pernix, Aquifex aeolicus, Archaeoglobus fulgidis, Bacillus subtilis, Bordetella pertussis, Borrelia burgdorferi, Chlamydia trachomatis, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium* and *Thermotoga maritima.*

In another particularly preferred embodiment, nucleic acid fragments derived from the following bacteria are combined into a single expression library: *Archaeoglobus fulgidis, Aquifex aeliticus, Aeropyrum pernix, Aquifex aeolicus, Bacillus subtilis, Bordatella pertussis* TOX6, *Borrelia burgdorferi, Chlamydia trachomatis, Escherichia coli, Haemophilus influenzae, Helicobacter pylori, Methanobacterium thermoautotrophicum, Methanococcus jannaschii, Methanothermobacter thermoautotrophicus, Mycoplasma pneumoniae, Neisseria meningitidis, Pirellula species, Pyrococcus horikoshii, Pseudomonas aeruginosa, Synechosistis* sp., *Thermoplasma volcanium* and *Thermotoga maritima.*

The nucleic acid fragments, unmodified or modified by the addition of one or more linkers, adaptors, Kozak containing oligonucleotides, Kozak containing fragments, or nucleic acids comprising a sequence that confers transcriptional or translational slippage, are placed in operable connection with a promoter sequence, thereby producing a recombinant gene construct.

The term "gene construct" is to be taken in its broadest context and includes a promoter sequence that is placed in operable connection with a nucleic acid fragment of the present invention. The nucleic acid comprising the promoter sequence is isolated using techniques known in the art, such as for example PCR or restriction digestion. Alternatively the nucleic acid comprising the promoter sequence is synthetic, that is an oligonucleotide. The methods of producing oligonucleotides are known in the art and are described, for example, in Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151.

The term "promoter" is to be taken in its broadest context and includes the transcriptional regulatory sequences of a genomic gene, including the TATA box or initiator element, which is required for accurate transcription initiation, with or without additional regulatory elements (ie. upstream activating sequences, transcription factor binding sites, enhancers and silencers) which alter gene expression in response to developmental and/or external stimuli, or in a tissue specific manner. In the present context, the term "promoter" is also used to describe a recombinant, synthetic or fusion molecule, or derivative which confers, activates or enhances the expression of a nucleic acid molecule to which it is operably linked, and which encodes the peptide or protein. Preferred promoters can contain additional copies of one or more specific regulatory elements to further enhance expression and/or alter the spatial expression and/or temporal expression of said nucleic acid molecule.

Placing a nucleic acid molecule under the regulatory control of, ie., "in operable connection with", a promoter sequence means positioning said molecule such that expression is controlled by the promoter sequence. Promoters are generally positioned 5' (upstream) to the coding sequence that they control. To construct heterologous promoter/structural gene combinations, it is generally preferred to position the promoter at a distance from the gene transcription start site that is approximately the same as the distance between that promoter and the gene it controls in its natural setting, ie., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, ie., the gene from which it is derived. Again, as is known in the art, some variation in this distance can also occur.

Typical promoters suitable for expression in viruses of bacterial cells and bacterial cells such as for example a bacterial cell selected from the group comprising *E. coli, Staphylococcus* sp, *Corynebacterium* sp., *Salmonella* sp., *Bacillus* sp., and *Pseudomonas* sp., include, but are not limited to, the lacz promoter, the Ipp promoter, temperature-sensitive $\lambda_L$ or $\lambda_R$ promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001).

Typical promoters suitable for expression in yeast cells such as for example a yeast cell selected from the group comprising *Pichia pastoris, S. cerevisiae* and *S. pombe*, include, but are not limited to, the ADH1 promoter, the GAL1 promoter, the GAL4 promoter, the CUP1 promoter, the PHOS promoter, the nmt promoter, the RPR1 promoter, or the TEF1 promoter.

Typical promoters suitable for expression in insect cells, or in insects, include, but are not limited to, the OPE12 promoter, the insect actin promoter isolated from *Bombyx muri*, the *Drosophila* sp. dsh promoter (Marsh et al *Hum. Mol. Genet.* 9, 13-25, 2000) and the inducible metallothionin promoter. Preferred insect cells for expression of the recombinant polypeptides include an insect cell selected from the group comprising, BT1-TN-5B1-4 cells, and *Spodoptera frugiperda* cells (eg., sf19 cells, sf21 cells). Suitable insects for the expression of the nucleic acid fragments include but are not limited to *Drosophila* sp. The use of *S. frugiperda* is also contemplated. Promoters for expressing peptides in plant cells are known in the art, and include, but are not limited to, the *Hordeum vulgare* amylase gene promoter, the cauliflower mosaic virus 35S promoter, the nopaline synthase (NOS) gene promoter, and the auxin inducible plant promoters P1 and P2.

Typical promoters suitable for expression in a virus of a mammalian cell, or in a mammalian cell, mammalian tissue or intact mammal include, for example a promoter selected from the group consisting of, retroviral LTR elements, the SV40 early promoter, the SV40 late promoter, the cytomegalovirus (CMV) promoter, the CMV IE (cytomegalovirus immediate early) promoter, the $EF_{1\alpha}$ promoter (from human elongation factor 1$\alpha$), the EM7 promoter, the UbC promoter (from human ubiquitin C).

Preferred mammalian cells for expression of the nucleic acid fragments include epithelial cells, fibroblasts, kidney cells, T cells, or erythroid cells, including a cell line selected from the group consisting of COS, CHO, murine 10T, MEF, NIH3T3, MDA-MB-231, MDCK, HeLa, K562, HEK 293 and 293T. The use of neoplastic cells, such as, for example, leukemic/leukemia cells, is also contemplated herein.

Preferred mammals for expression of the nucleic acid fragments include, but are not limited to mice (ie., *Mus* sp.) and rats (ie., *Rattus* sp.).

In one embodiment, nucleic acid comprising a promoter sequence is ligated to a nucleic acid fragment from the prokaryote or compact eukaryote, or a modified form thereof, using techniques known in the art.

In another embodiment, nucleic acid comprising a promoter sequence is modified by the addition of one or more linkers, adaptors, Kozak containing oligonucleotides, Kozak containing fragments, or nucleic acids comprising a sequence that confers transcriptional or translational slippage and ligated to a nucleic acid fragment from the prokaryote or compact eukaryote using techniques known in the art.

In yet another embodiment, nucleic acid comprising a promoter sequence is incorporated into an oligonucleotide with or without another nucleic acid comprising one or more spacers, Kozak sequences, or nucleic acids comprising a sequence that confers transcriptional or translational slippage.

Preferably, the oligonucleotide comprises a nucleotide sequence that is complementary or homologous to a region flanking the nucleic acid fragment from the prokaryote or compact eukaryote, such as, for example, an adaptor. Such a complementary or homologous sequence permits oligonucleotide primers to be used for amplifying nucleic acid comprising a promoter region and means for ribosome binding (such as for example a Kozak sequence or Shine-Dalgarno sequence) and the nucleic acid fragment as a single fragment. In this manner, a gene construct comprising a promoter sequence, means for ribosome binding and a nucleic acid fragment is readily constructed using the amplified nucleic acid.

In an alternative embodiment, a nucleic acid comprising a promoter sequence is incorporated into an oligonucleotide with or without another nucleic acid comprising one or more spacers, Kozak sequences, or nucleic acids comprising a sequence that confers transcriptional or translational slippage, and said oligonucleotide is operably linked to a nucleic acid fragment of the present invention by, for example, ligation.

As will be known to the skilled artisan, the promoter is also be positioned in the expression vector or gene construct into which the prokaryote or eukaryote nucleic acid fragment is inserted.

In one embodiment, the nucleic acid fragments are expressed in vitro. According to this embodiment, the gene construct preferably comprises a nucleic acid fragment of the prokaryote or compact eukaryote, and a promoter sequence and appropriate ribosome binding site which is both be present in the expression vector or added to said nucleic acid fragment before it is inserted into the vector. Typical promoters for the in vitro expression of the nucleic acid fragments of the present invention include, but are not limited to the T3 or T7 (Hanes and Plückthun *Proc. Natl. Acad. Sci. USA,* 94 4937-4942 1997) bacteriophage promoters.

In another embodiment, the gene construct optionally comprises a transcriptional termination site and/or a translational termination codon. Such sequences are known in the art, and is incorporated into oligonucleotides used to amplify the nucleic acid fragment of the prokaryote or compact eukaryote, or alternatively, present in the expression vector or gene construct before the nucleic acid fragment is inserted.

In another embodiment, the gene construct is an expression vector. The term "expression vector" refers to a nucleic acid molecule that has the ability confer expression of a nucleic acid fragment to which it is operably connected, in a cell or in a cell free expression system. Within the context of the present invention, it is to be understood that an expression vector may comprise a promoter as defined herein, a plasmid, bacteriophage, phagemid, cosmid, virus sub-genomic or genomic fragment, or other nucleic acid capable of maintaining and or replicating heterologous DNA in an expressible format. Many expression vectors are commercially available for expression in a variety of cells. Selection of appropriate vectors is within the knowledge of those having skill in the art.

Typical expression vectors for in vitro expression or cell-free expression have been described and include, but are not limited to the TNT T7 and TNT T3 systems (Promega), the pEXP1-DEST and pEXP2-DEST vectors (Invitrogen).

Numerous expression vectors for expression of recombinant polypeptides in bacterial cells and efficient ribosome binding sites have been described, such as for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer nc., CT, USA); the pQE series of expression vectors (QIAGEN, CA, USA), or the pL series of expression vectors (Invitrogen), amongst others.

Expression vectors for expression in yeast cells are preferred and include, but are not limited to, the pACT vector (Clontech), the pDBleu-X vector, the pPIC vector suite (Invitrogen), the pGAPZ vector suite (Invitrogen), the pHYB vector (Invitrogen), the pYD1 vector (Invitrogen), and the pNMT1, pNMT41, pNMT81 TOPO vectors (Invitrogen), the pPC86-Y vector (Invitrogen), the pRH series of vectors (Invitrogen), pYESTrp series of vectors (Invitrogen). Particularly preferred vectors are the pACT vector, pDBleu-X vector, the pHYB vector, the pPC86 vector, the pRH vector and the pYES vectors, which are all of use in various 'n'-hybrid assays described herein.

Furthermore, the pYD1 vector is particularly useful in yeast display experiments in *S. cerevesiae*. A number of other gene construct systems for expressing the nucleic acid fragment of the invention in yeast cells are well-known in the art and are described for example, in Giga-Hama and Kumagai (In: Foreign Gene Expression in Fission Yeast: *Schizosaccharomyces Pombe*, Springer Verlag, ISBN 3540632700, 1997) and Guthrie and Fink (In: Guide to Yeast Genetics and Molecular and Cell Biology Academic Press, ISBN 0121822540, 2002).

A variety of suitable expression vectors, containing suitable promoters and regulatory sequences for expression in insect cells are known in the art, and include, but are not limited to the pAC5 vector, the pDS47 vector, the pMT vector suite (Invitrogen) and the pIB vector suite (Invitrogen).

Furthermore, expression vectors comprising promoters and regulatory sequences for expression of polypeptides in plant cells are also known in the art and include, for example, a promoter selected from the group, pSS, pB1121 (Clontech), pZ01502, and pPCV701 (Kuncz et al, *Proc. Natl. Acad. Sci. USA,* 84 131-135, 1987).

Expression vectors that contain suitable promoter sequences for expression in mammalian cells or mammals include, but are not limited to, the pcDNA vector suite supplied by Invitrogen, the pCI vector suite (Promega), the pCMV vector suite (Clontech), the pM vector (Clontech), the pSI vector (Promega), the VP16 vector (Clontech) and the pDISPLAY vectors (Invitrogen). The pDISPLAY vectors are of particular use in mammalian display studies with the expressed nucleic acid fragment targeted to the cell surface with the Igκ leader sequence, and bound to the membrane of the cell through fusion to the PDGFR transmembrane domain. The pM and VP16 vectors are of particular use in mammalian two-hybrid studies.

Methods of cloning DNA into nucleic acid vectors for expression of encoded polypeptides are known in the art and are described for example in, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

The nucleic acid fragments of the present invention is also be expressed in the cells of other organisms, or entire organisms including, for example, nematodes (eg *C. elegans*) and fish (eg *D. rerio*, and *T. rubripes*). Promoters for use in nematodes include, but are not limited to osm-10 (Faber et al *Proc. Natl. Acad. Sci. USA* 96, 179-184, 1999), unc-54 and myo-2 (Satyal et al *Proc. Natl. Acad. Sci. USA,* 97 5750-5755, 2000). Promoters for use in fish include, but are not limited to the zebrafish OMP promoter, the GAP43 promoter, and serotonin-N-acetyl transferase gene regulatory regions In a preferred embodiment, the expression library of the present invention is transcribed and translated in vitro. Methods of transcribing nucleic acid fragments and translating the resulting mRNA are known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001), for example the use of *E. coli* S30 lysate (available in kit for from Promega).

In a preferred embodiment the gene construct contains a second nucleic acid in operable connection with a nucleic acid fragment of the present invention. This second nucleic acid encodes a fusion partner. As used herein the term "fusion partner" shall be understood to mean a polypeptide sequence that is associated with a peptide encoded by a nucleic acid fragment of the present invention. Such a fusion partner confers a common function or ability upon all polypeptides encoded by the expression library. Suitable fusion partners include, but are not limited to, presentation structures, polypeptides that facilitate the uptake of peptides into target cells, polypeptides that cause nuclear localisation, polypeptides that cause secretion, polypeptides that cause mitochondrial localisation, polypeptides that cause membrane localisation, or a combination of any of these sequences.

Without suggesting that such a process is essential to the invention, a peptide encoded by the expression library of the present invention can also be expressed such that it is conformationally constrained, or expressed in a "presentation structure". Such constraint, whilst not generally necessary for expressing protein domains or peptides having a conformation sufficient to bind to a target protein or target nucleic acid, is useful for displaying peptides that comprise more highly flexible sequences, or to enhance stability against proteolytic enzymes (Humphrey et al, *Chem Rev* 97, 2243-2266, 1997).

A presentation structure will generally comprise a first component, ie. polypeptide, that is fused to the amino terminus of the polypeptide and a second component fused to the carboxyl-terminus of the peptide. Examples of such presentation structures include, but are not limited to, cysteine-linked (disulfide) structures, zinc-finger domains, cyclic peptides, and transglutaminase linked structures.

In a preferred embodiment, the presentation structure is a sequence that contains at least two cysteine residues, such that a disulphide bond is formed between the cysteine residues, resulting in a conformationally constrained peptide.

In another embodiment, a peptide encoded by an expression library of the present invention is expressed within a second polypeptide as a fusion protein. Polypeptides used for such purposes are capable of reducing the flexibility of another protein's amino and/or carboxyl termini. Preferably, such proteins provide a rigid scaffold or platform for the protein. In addition, such proteins preferably are capable of providing protection from proteolytic degradation and the like, and/or are capable of enhancing solubility. Preferably, conformation-constraining proteins are small in size (generally, less than or equal to about 200 amino acids in length), rigid in structure, of known three-dimensional configuration, and are able to accommodate insertions of proteins without undue disruption of their structures. A key feature of such proteins is the availability, on their solvent exposed surfaces, of locations where peptide insertions can be made (eg., the Trx loop). It is also preferable that conformation-constraining protein producing genes be highly expressible in various prokaryotic and eukaryotic hosts, or in suitable cell-free systems, and that the proteins be soluble and resistant to protease degradation.

Examples of conformation-constraining proteins include the active site of thioredoxin or Trx loop and other thioredoxin-like proteins, nucleases (eg., RNase A), proteases (eg., trypsin), protease inhibitors (eg., bovine pancreatic trypsin inhibitor), antibodies or structurally rigid fragments thereof, conotoxins, and the pleckstrin homology domain. A conformation-constraining peptide can be of any appropriate length and can even be a single amino acid residue.

This technique has been successfully used for bacterial display of peptides in bacteria using a Trx scaffold (Blum et al *Proc. Natl. Acad. Sci. USA* 97, 2241-2246 2000) in addition to the use in yeast 2 hybrid screening using either a catalytically inactive form of staphylococcal nuclease, or Trx (Norman et al, *Science,* 285, 591-595, 1999; and Colas et al, *Nature* 380, 548-550, 1996).

In another embodiment the expression vector or gene construct is optionally comprise a transcriptional terminator that is operative in the expression system. Furthermore, the gene construct is also comprise a nucleic acid comprising the sequence of a polyadenylation signal operative in the expression system.

It is preferred that when the gene constructs are to be introduced to and/or maintained and/or propagated and/or expressed in bacterial cells, either during generation of said gene constructs, or screening of said gene constructs, that the gene constructs contain an origin of replication that is operable at least in a bacterial cell. A particularly preferred origin of replication is the ColE1 origin of replication. A number of gene construct systems containing origins of replication are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001).

It is also preferred that when the gene constructs are to be introduced to and/or maintained and/or propagated and/or expressed in yeast cells, either during generation of said gene constructs, or screening of said gene constructs, that the gene constructs contain an origin of replication that is operable at least in a yeast cell. One preferred origin of replication is the CEN/ARS4 origin of replication. Another particularly preferred origin of replication is the 2-micron origin of replication. A number of gene construct systems containing origins of replication are well-known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

In another embodiment, the gene construct containing the nucleic acid fragments of the present invention comprise another nucleic acid cassette comprising a promoter sequence in operable connection with a polynucleotide sequence encoding a selectable marker.

As used herein the term "selectable marker" shall be taken to mean a protein or peptide that confers a phenotype on a cell expressing said selectable marker that is not shown by those cells that do not carry said selectable marker. Examples of selectable markers include, but are not limited to the dhfr resistance gene, which confers resistance to methotrexate (Wigler, et al., 1980, Natl. Acad. Sci. USA 77:3567; O'Hare, et al., 1981, Proc. Natl. Acad. Sci. USA 78:1527); the gpt resistance gene, which confers resistance to mycophenolic acid (Mulligan & Berg, 1981, Proc. Natl. Acad. Sci. USA 78:2072); the neomycin phosphotransferase gene, which confers resistance to the aminoglycoside G-418 (Colberre-Garapin, et al., 1981, J. Mol. Biol. 150:1); and the hygromycin resistance gene (Santerre, et al., 1984, Gene 30:147). Alternatively, marker genes is catalyse reactions resulting in a visible outcome (for example the production of a blue color when β galactosidase is expressed in the presence of the substrate molecule 5-bromo-4-chloro-3-indoyl-β-D-galactoside) or confer the ability to synthesise particular amino acids (for example the HIS3 gene confers the ability to synthesize histidine).

In one embodiment the peptide encoded by the nucleic acid fragment of the present invention is expressed as a fusion protein with a peptide sequence capable of enhancing, increasing or assisting penetration or uptake of the peptide by cells either in vitro or in vivo. For example, the peptide sequence capable of enhancing, increasing or assisting penetration or uptake is the *Drosophila* penetratin targeting sequence. This peptide sequence at least comprises the amino acid sequence:

(SEQ ID NO. 29)
CysArgGlnIleLysIleTrpPheGlnAsnArgArgMetLysTrpLysLys further comprising (Xaa)n after the final Lys residue and followed by Cys wherein Xaa is any amino acid and n has a value greater than or equal to 1. Alternatively, a homologue, derivative or analogue of said sequence is used. The use of said sequence is particularly useful when peptides encoded by the nucleic acid fragment of the present invention are synthesised in vitro or secreted from a host cell, and must be taken up by a cell for screening said peptide encoded by the nucleic acid fragment of the present invention.

Those skilled in the art will also be aware of an analogous use of signals such as for example, the tat sequence of HIV to drive import of peptides into cells.

In an alternative embodiment, the peptide encoded by the nucleic acid fragment of the present invention is mixed with a peptide capable of enhancing, increasing or assisting penetration or uptake by cells in vitro or in vivo. A peptide sequence that is able to increase or assist penetration or uptake of cells is the synthetic peptide Pep 1, which at least comprises the amino acid sequence:

LysGluThrTrpTrpGluThrTrpTrpThrGluTrpSerGlnLysLysLysLysArgLysVal. (SEQ ID NO. 30)

The Pep1 peptide does not need to be conjugated to the peptide encoded by the nucleic acid fragments of the present invention. Furthermore, Pep1 dissociates from the peptide encoded by the expression library of the present invention. Thus Pep1 will not interfere with the peptide forming a conformation sufficient for binding to a target protein or nucleic acid. Pep1 is only useful when the peptides encoded by the expression library of the present invention are isolated prior to the addition to a cell or organism for screening. Thus Pep1 is particularly useful when in vitro libraries are screened.

Other protein transduction domains are known in the art, and are clearly useful in the present invention. For example, amino acids 43-58 of *Drosophila* antennapedia, poly-arginine, PTD-5, Transportan and KALA (reviewed in Kabouridis, TRENDS in Biotechnology, 21: 498-503, 2003).

In one embodiment, the expression library of the present invention are introduced to and preferably expressed within a cellular host or organism to generate the expression library, it is preferred that the gene constructs are introduced into said cellular host or said organism. Methods of introducing the gene constructs into a cell or organism for expression are known to those skilled in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001). The method chosen to introduce the gene construct in depends upon the cell type in which the gene construct is to be expressed.

In one embodiment, the cellular host is a bacterial cell. Means for introducing recombinant DNA into bacterial cells include, but are not limited to electroporation or chemical transformation into cells previously treated to allow for said transformation.

In another embodiment, the cellular host is a yeast cell. Means for introducing recombinant DNA into yeast cells include a method chosen from the group consisting of electroporation, and PEG mediated transformation.

In another embodiment, the cellular host is a plant cell. Means for introducing recombinant DNA into plant cells include a method selected from the group consisting of *Agrobacterium* mediated transformation, electroporation of protoplasts, PEG mediated transformation of protoplasts, particle mediated bombardment of plant tissues, and microinjection of plant cells or protoplasts.

In yet another embodiment, the cellular host is an insect cell. Means for introducing recombinant DNA into plant cells include a method chosen from the group consisting of, infection with baculovirus and transfection mediated with liposomes such as by using cellfectin (Invitrogen).

In yet another embodiment, the cellular host is a mammalian cell. Means for introducing recombinant DNA into mammalian cells include a means selected from the group comprising microinjection, transfection mediated by DEAE-dextran, transfection mediated by calcium phosphate, transfection mediated by liposomes such as by using Lipofectamine (Invitrogen) and/or cellfectin (Invitrogen), PEG mediated DNA uptake, electroporation, transduction by Adenoviruses, Herpesviruses, Togaviruses or Retroviruses and microparticle bombardment such as by using DNA-coated tungsten or gold particles (Agacetus Inc., Wis., USA).

In an alternative embodiment, the expression library is an in vitro display library (ie., the peptides encoded by the prokaryote or compact eukaryote nucleic acid fragments of the expression library are displayed using in vitro display wherein the expressed peptide is linked to the nucleic acid from which it was expressed such that said peptide is presented in the absence of a host cell). Accordingly, expression libraries produced by in vitro display technologies are not limited by transformation or transfection efficiencies. Accordingly any such library is of much higher complexity than an in vivo display library. Examples of methods of in vitro display include a method selected from the group comprising but not limited to, ribosome display, covalent display and mRNA display.

In one embodiment, the in vitro display library is a ribosome display library. The skilled artisan will be aware that a ribosome display library directly links mRNA encoded by the expression library to the peptide that it encodes. Means for producing a ribosome display library require that the nucleic acid fragment be placed in operable connection with an appropriate promoter sequence and ribosome binding sequence, ie. form a gene construct. Preferred promoter sequences are the bacteriophage T3 and T7 promoters.

Preferably, the nucleic acid fragment is placed in operable connection with a spacer sequence and a modified terminator sequence with the terminator sequence removed.

As used herein the term "spacer sequence" shall be understood to mean a series of nucleic acids that encode a peptide that is fused to the peptide. The spacer sequence is incorporated into the gene construct, as the peptide encoded by the spacer sequence remains within the ribosomal tunnel following translation, while allowing the peptide to freely fold and interact with another protein or a nucleic acid.

A preferred spacer sequence is, for example, a nucleic acid that encodes amino acids 211-299 of gene III of filamentous phage M13 mp19.

The display library is transcribed and translated in vitro using methods known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

Examples of systems for in vitro transcription and translation include, for example, the TNT in vitro transcription and translation systems from Promega. Cooling the expression reactions on ice generally terminates translation. The ribosome complexes are stabilized against dissociation from the peptide and/or its encoding mRNA by the addition of reagents such as, for example, magnesium acetate or chloroamphenicol. Such in vitro display libraries are screened by a variety of methods, as described herein.

In another embodiment, the expression library of the present invention is a ribosome inactivation display library. In accordance with this embodiment, a nucleic acid fragment is operably linked to a nucleic acid encoding a first spacer sequence. It is preferred that this spacer sequence is a glycine/serine rich sequence that allows a peptide encoded by the expression library of the present invention to freely fold and interact with a target protein or nucleic acid.

The first spacer sequence is linked to a nucleic acid that encodes a toxin that inactivates a ribosome. It is preferred that the toxin comprises the ricin A chain, which inactivates eukaryotic ribosomes and stalls the ribosome on the translation complex without release of the mRNA or the encoded peptide.

The nucleic acid encoding the toxin is linked to another nucleic acid that encodes a second spacer sequence. The second spacer is required as an anchor to occupy the tunnel of the ribosome, and allow both the peptide and the toxin to correctly fold and become active. Examples of such spacer sequences are sequences derived from gene III of M13 bacteriophage.

Ribosome inactivation display libraries are generally transcribed and translated in vitro, using a system such as the rabbit reticulocyte lysate system available from Promega. Upon translation of the mRNA encoding the toxin and correct folding of this protein, the ribosome is inactivated while still bound to both the encoded polypeptide and the mRNA from which it was translated.

In another embodiment, the expression library of the present invention is an mRNA display library. In accordance with this embodiment, a nucleic acid fragment is operably linked to a nucleic acid encoding a spacer sequence, such as a glycine/serine rich sequence that allows a peptide encoded by the expression library of the present invention to freely fold and interact with a target protein or nucleic acid.

The nucleic acid encoding the spacer sequence is operably linked to a transcription terminator.

mRNA display libraries are generally transcribed in vitro, using methods known in the art, such as, for example, the HeLaScribe Nuclear Extract in vitro Transcription System available from Promega. Encoded mRNA is subsequently covalently linked to a DNA oligonucleotide that is covalently linked to a molecule that binds to a ribosome, such as, for example, puromycin, using techniques known in the art and are described in, for example, Roberts and Szostak, *Proc. Natl. Acad. Sci. USA,* 94, 12297-12302 (1997). Preferably, the oligonucleotide is covalently linked to a psoralen moiety, whereby the oligonucleotide is photo-crosslinked to a mRNA encoded by the expression library of the present invention.

The mRNA transcribed from the expression library is then translated using methods known in the art and are described for example, in Ausubel et at (In: Current Protocols in Molecular Biology. Wiley Interscience, ISBN 047 150338, 1987) and (Sambrook et at (In: Molecular Cloning: Molecular Cloning: A Laboratory Manual, Cold Spring Harbor Laboratories, New York, Third Edition 2001). When the ribosome reaches the junction of the mRNA and the oligonucleotide the ribosome stalls and the puromycin moiety enters the phosphotransferase site of the ribosome and thus covalently links the encoded polypeptide to the mRNA from which it was expressed.

In yet another embodiment, the expression library of the present invention is a covalent display library. In accordance with this embodiment, the nucleic acid fragment is operably linked to a second nucleic acid fragment that encodes a protein that interacts with the DNA from which it was encoded. Examples of a protein that interacts with the DNA from which it interacts include, but are not limited to, the *E. coli* bacteriophage P2 viral A protein (P2A) and equivalent proteins isolated from phage 186, HP1 and PSP3.

The P2A protein is particularly preferred. The P2A protein recognizes a defined initiator sequence TCGGA (SEQ ID NO 31) positioned within the nucleic acid encoding the P2A protein and nicks one of the strands while forming a covalent bond with one of the free end nucleotides. Accordingly, it is preferred that at least the sequence TCGGA (SEQ ID NO 31) is included in the gene construct containing the expression library of the present invention.

It is particularly preferred that the protein attachment site is positioned such that a nucleic acid fragment is covalently linked to the peptide that it encodes.

A covalent display gene construct is transcribed and translated in vitro, using a system such as the rabbit reticulocyte lysate system available from Promega. Upon translation of the fusion of the peptide and the P2A protein, the P2A protein nicks the nucleic acid of the sequence of SEQ ID NO: 31 and forms a covalent bond therewith. Accordingly, a nucleic acid fragment is covalently linked to the peptide that it encodes.

In yet another embodiment, the expression library is a phage display library wherein the expressed peptides or protein domains are displayed on the surface of a bacteriophage, as described, for example, in U.S. Pat. No. 5,821,047 and U.S. Pat. No. 6,190,908. The basic principle described relates to the fusion of a first nucleic acid comprising a sequence encoding a peptide or protein to a second nucleic acid comprising a sequence encoding a phage coat protein, such as, for example a phage coat proteins selected from the group, M13 protein-3, M13 protein-7, or M13, protein-8. These sequences are then inserted into an appropriate vector, ie. one that is able to replicate in bacterial cells. Suitable host cells, such as, for example *E. coli*, are then transformed with the recombinant vector. Said host cells are also infected with a helper phage particle encoding an unmodified form of the coat protein to which a nucleic acid fragment is operably linked. Transformed, infected host cells are cultured under conditions suitable for forming recombinant phagemid particles comprising more than one copy of the fusion protein on the surface of the particle. This system has been shown to be effective in the generation of virus particles such as, for example, a virus particle selected from the group comprising λ phage, T4 phage, M13 phage, T7 phage and baculovirus. Such phage display particles are then screened to identify a displayed protein having a conformation sufficient for binding to a target protein or nucleic acid.

In yet another embodiment, the expression library is a retroviral display library wherein the expressed peptides or protein domains are displayed on the surface of a retroviral particle. Retroviral display is of particular use as the proteins and peptides displayed in such a system are generated in eukaryotic cells that can carry out a number of post-translational modifications to the peptides or protein domains that are required for activity. Such a retroviral display system is described in U.S. Pat. No. 6,297,004 (Cambridge Drug Discovery Holding, Limited). In adapting such a system to the present invention, a nucleic acid fragment is placed in operable connection with an envelope protein of a retrovirus, more preferably a spike glycoprotein. An example of such a protein is the mature envelope protein of Moloney Murine leukemia virus. A gene construct comprising a nucleic acid fragment of the present invention in operable connection with a retroviral envelope protein is also placed in operable connection with long terminal repeat sequences, a tRNA binding site and a polypurine tract to ensure reverse transcription and integration of the encapsid RNA in an infected mammalian cell. Furthermore, such a gene construct should comprise an encapsidated signal sequence. An encapsidated signal sequence is a nucleic acid that is recognised by a component of the viral particle that mediates the inclusion of the nucleic acid into the viral particle. Such a gene construct is then expressed in an appropriate host cell, such as, for example, a COS cell or NIH3T3 cell, that has been previously infected with a retrovirus encoding an unmodified spike glycoprotein. In such a system chimeric retroviral particles are generated, carrying a mixture of modified and unmodified forms of the spike glycoprotein. These recombinant retrovirus particles are used to identify a displayed peptide that binds to a target protein or nucleic acid.

In yet another embodiment, the expression library is a bacterial display library wherein the expressed peptides or protein domains are displayed on the surface of a bacterial cell. The cells displaying the expressed peptides or protein domains are then used for biopanning as described, for example, in U.S. Pat. No. 5,516,637. Bacterial display is based on the finding that heterologous proteins is expressed as a fusion with bacterial surface proteins and assayed for the ability to bind to a target protein or nucleic acid. Accordingly, in such systems a nucleic acid fragment is placed in operable connection with a second nucleic acid that encodes an anchoring motif, or amino acid sequence that directs the incorporation of the encoded peptide on the surface of the bacterial cell surface. Preferred amino acid sequences that direct incorporation of a peptide onto the surface of a bacterial cell include, but are not limited to, the flagella major subedit FliC for localizing a protein on the flagellum of *E. coli*, the cell sorting signal of the cell wall proteinase PrtP of *Lactobacillus casei*, the OmpS maltoprotein of *Vibrio cholerae*, Protein A of *Bacillus subtilis*, LysA of *B. subtilis*, and ActA of *B. subtilis*. Expression libraries comprising such gene constructs are then introduced into an appropriate host cell, such as for example *E. coli* or *B. subtilis* and the expressed peptides displayed on the surface of the bacterial cell. Such displayed libraries are of particular use in screening for peptides that have a conformation sufficient for binding a target protein or nucleic acid.

In an alternative embodiment, the peptides encoded by the nucleic acid fragments of the present invention is also be fused to a second nucleic acid comprising a sequences that encodes a peptide that directs the incorporation of the encoded peptide on the surface of a bacterial spore. Such methods are particularly useful in the display of peptides that are toxic to bacteria when expressed intracellularly, or when screening conditions are particularly harsh, such as, for example in the presence of organic solvents, or high temperatures.

In yet another embodiment, the expression library is a display library wherein the expressed peptides or protein domains are displayed on the surface of a yeast cell. This method is particularly useful for the display of peptides encoded by nucleic acid derived from eukaryotes, as prokaryotic species are unable to form some structures encoded by eukaryotic sequences. Such a yeast display method is described in U.S. Pat. No. 6,423,538. In adapting this method to the present invention, a nucleic acid fragment is operably linked to a second nucleic acid fragment encoding the membrane-associated alpha-agglutinin yeast adhesion receptor, encoded by the aga2 gene. The expression library is introduced into an appropriate host cell, such as for example *S. cerevisiae* or *S. pombe*. Following introduction into an appropriate host cell the fusion protein is secreted from the cell. The fusion protein then binds to the Aga1 protein on the surface of the cell by forming disulfide bonds. Such a yeast cell is screened to determine whether or not it expresses a peptide having a conformation sufficient for binding to a target protein or nucleic acid.

In yet another embodiment, the expression library is a display library wherein the expressed peptides or protein domains are displayed on the surface of a mammalian cell. Such a system is described for example in Strenglin et al *EMBO J*, 7, 1053-1059, 1988. Mammalian display is particularly useful for the display of peptides derived from eukaryotes, as prokaryotic species and some lower eukaryotic species are unable to form some structures encoded by eukaryotic sequences. The mechanism behind mammalian display relates to the fusion of a nucleic acid fragment to a second nucleotide sequence encoding a peptide leader sequence, which directs the protein to be secreted, such as for example the Ig κ secretion signal. Furthermore, the nucleic acid fragment is placed in operable connection with another nucleic acid, which encodes a peptide that anchors the peptide to the membrane, such as, for example the sequence of the transmembrane domain of PDGFR. An example of a vector containing such a sequence is the pDISPLAY vector available from Invitrogen. Proteins expressed by such a vector are displayed upon the surface of the mammalian cell, making these cells particularly useful for screening for peptides that adopt a conformation sufficient for binding to a target protein or nucleic acid.

A second aspect of the present invention provides an expression library comprising nucleic acid fragments from two or more microorganisms or eukaryotes containing compact genomes, each of said microorganisms or eukaryotes having a substantially sequenced genome, wherein said nucleic acid fragments are inserted into a suitable expression construct thereby producing recombinant constructs, wherein each fragment is in operable connection with a promoter sequence that is capable of conferring expression of that fragment.

In a preferred embodiment, the present invention provides an expression library comprising nucleic acid fragments derived from two or more microorganisms or eukaryotes containing compact genomes, each of said microorganisms or eukaryotes having a substantially sequenced genome, wherein the fragments are inserted into a suitable expression vector in an amount proportional to the size of the genome from which the fragments were derived thereby producing recombinant constructs and wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library comprise an open reading frame having an average length of at least about 36-45 nucleotide residues and/or encode a protein domain, and wherein the nucleic acid fragments are inserted into a suitable expression vector thereby producing recombinant constructs wherein each fragment is in operable connection with a promoter sequence that is capable of conferring expression of that fragment.

In an alternative embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library comprise an open reading frame having an average length of at least about 36-45 nucleotide residues and/or encode a protein domain, and wherein the nucleic acid fragments are inserted into a suitable expression vector in an amount proportional to the size of the genome from which the fragments were derived thereby producing recombinant constructs wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and are inserted into a suitable expression vector thereby producing recombinant constructs wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and are inserted into a suitable expression vector in an amount proportional to the size of the genome from which the fragments were derived thereby producing recombinant constructs wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and comprise an open reading frame having an average length of at least about 36-45 nucleotide residues and/or encode a protein domain, and wherein the nucleic acid fragments are inserted into a suitable expression vector thereby producing recombinant constructs wherein each fragment is in operable connection with a promoter sequence that is capable of conferring expression of that fragment.

In an alternative embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and comprise an open reading frame having an average length of at least about 36-45 nucleotide residues and/or encode a protein domain, and wherein the nucleic acid fragments are inserted into a suitable expression vector in an amount proportional to the size of the genome from which the fragments were derived thereby producing recombinant constructs wherein each fragment is in operable connection with a promoter sequence that is capable of conferring expression of that fragment.

Preferably, if the library is to be expressed in either a cellular system or in an organism, the expression library is further comprise a host comprising the recombinant vectors of the expression library. In accordance with this embodiment, the expression library of the present invention further comprises a host cell comprising the nucleic acid fragments inserted into the expression vector.

In a particularly preferred embodiment the present invention provides an expression library produced in accordance with a method described herein (ie., it is a direct product of the method if the present invention).

In another embodiment, the present invention provides an arrayed expression library. As used herein "arrayed expression library" shall be taken to mean that the library is assembled in such a way that an individual peptide and/or nucleic acid encoding same is readily identified. For example, each peptide encoded by the library of the present invention is produced individually (ie. in isolation from other peptides), a number or a plurality of different peptides are then pooled. Two or more of these pools of peptides are then pooled, and if necessary, this process is repeated. Accordingly, pools of several thousands or millions of peptides may be produced. The largest of these pools is then screened to determine whether or not it comprises a peptide with a conformation sufficient for binding to a target protein and/or nucleic acid. Should it comprise such a peptide, one or more groups of smaller pools (ie. sub-pools) of peptides are screened to determine which comprise the peptide of interest. Clearly this process can be iteratively repeated with pools of descending size until the individual peptide of interest is isolated. Alternatively, a pool of a smaller number of peptides (eg 10 or 100) may be directly screened to determine which, if any, of the peptides have a conformation sufficient for binding a target protein and/or nucleic acid and the sequence of said peptide or encoding nucleic acid (for example using a biosensor chip in conjunction with mass spectrometry).

As will be apparent to the skilled artisan the present invention clearly encompasses the production of multiple different libraries. Accordingly, the present invention also includes pooled libraries. For example, the present invention encompasses the pooling of two or more libraries. In one embodiment, the libraries are derived from the same organism/s. In another embodiment, the libraries are derived from different organisms (eg. a library derived from eukaryotes comprising a compact genome, and another library derived from bacteria).

As will be apparent to the skilled artisan an arrayed or pooled library of the present invention may comprise nucleic acid fragments derived from the genome of one or more organisms and/or a vector comprising said fragment and/or the peptides encoded by the nucleic acid fragments and/or cells expressing said peptide.

In another embodiment, an arrayed expression library is produced or bound to or conjugated to a chip for analysis. To produce such a chip, the peptides (and/or nucleic acid encoding said peptide and/or a vector comprising said nucleic acid and/or a cell expressing said peptide) of the present invention are bound to a solid support such as, for example glass, polycarbonate, polytetrafluoroethylene, polystyrene, silicon oxide, gold or silicon nitride. This immobilization is either direct (e.g. by covalent linkage, such as, for example, Schiff's base formation, disulfide linkage, or amide or urea bond formation) or indirect. Methods of generating a protein chip are known in the art and are described in for example U.S. Patent Application No. 20020136821, 20020192654, 20020102617 and U.S. Pat. No. 6,391,625. To bind a protein to a solid support it is often necessary to treat the solid support so as to create chemically reactive groups on the surface, such as, for example, with an aldehyde-containing silane reagent or the calixcrown derivatives described in Lee et al, *Proteomics,* 3: 2289-2304, 2003. A streptavidin chip is also useful for capturing proteins and/or peptides and/or nucleic acid and/or cells that have been conjugated with biotin (eg. as described in Pavlickova et al., *Biotechiques,* 34: 124-130, 2003). Alternatively, a peptide is captured on a microfabricated polyacrylamide gel pad and accelerated into the gel using microelectrophoresis as described in, Arenkov et al. *Anal. Biochem.* 278:123-131, 2000.

A protein chip may comprise only one peptide of the present invention. Preferably, the chip comprises a plurality of peptides of the present invention.

Methods of determining a peptide on the chip capable of binding a target protein and/or nucleic acid will be apparent to the skilled artisan. for example, a sample to be analysed using a protein chip is attached to a reporter molecule, such as, for example, a fluorescent molecule, a radioactive molecule, an enzyme, or an antibody that is detectable using methods known in the art. Accordingly, by contacting a protein chip with a labeled sample and subsequent washing to remove any unbound proteins the presence of a bound protein and/or nucleic acid is detected using methods known in the art, such as, for example using a DNA microarray reader.

Alternatively, biomolecular interaction analysis-mass spectrometry (BIA-MS) is used to rapidly detect and characterise a protein present in complex biological samples at the low- to sub-fmole level (Nelson et al. *Electrophoresis* 21: 1155-1163, 2000 and Needelkov and Nelson, *Biosensors and Bioelectronics,* 16: 1071-1078, 2001). One technique useful in the analysis of a protein chip is surface enhanced laser desorption/ionization-time of flight-mass spectrometry (SELDI-TOF-MS) technology to characterise a protein bound to the protein chip. Alternatively, the protein chip is analysed using ESI as described in U.S. Patent Application 20020139751.

A further aspect of the present invention provides a method of determining a peptide that binds to a target nucleic acid or target protein comprising:

(a) screening an expression library of the present invention to identify a peptide expressed by the library that binds to the target protein or target nucleic acid; and
(b) selecting a peptide from (a) that does not bind to said target protein or nucleic acid in its native environment.

In an alternative embodiment, the present invention provides a method of determining a peptide that binds to a target nucleic acid or target protein comprising:

(a) obtaining an expression library of the present invention;
(b) screening the expression library to identify a peptide that binds to the target protein or nucleic acid; and
(c) selecting a peptide that does not bind to said target protein or nucleic acid in its native environment.

In a further alternative embodiment, the present invention provides a method of determining a peptide that binds to a target nucleic acid or target protein comprising:

(a) producing an expression library of the present invention according to the process described herein;
(b) screening the expression library to identify a peptide that binds to the target protein or nucleic acid; and
(c) selecting a peptide that does not bind to said target protein or nucleic acid in its native environment.

The selection step of the screening process is to identify mimotopes or mimetic peptides, rather than merely selecting peptides that perform a known or expected function. Suitable processes for selecting a peptide that does not bind to the target protein or target nucleic acid in its native environment include, for example, determining the amino acid sequence of the peptide or determining the nucleotide sequence of the corresponding nucleic acid encoding said peptide and deriving the amino acid sequence from said nucleotide sequence, determining a known function of the amino acid sequence and excluding a peptide that binds to a target protein or target nucleic acid associated with the known function. Alternatively, or in addition, the selection involves using an expression library that comprises nucleic acid fragments from organisms that do not possess a particular biochemical pathway or signal transduction pathway relevant to the binding reaction being assayed. Alternatively, or in addition, the selection comprises using an expression library that comprises nucleic acid fragments from organisms that do not express one or more of the binding partners of the binding reaction being assayed. The present invention clearly contemplates the combined use of bioinformatic analysis and selection of library components from organisms that are not known to carry out the binding reaction being assayed, to exclude those peptides from the screening process that merely perform their known function. Accordingly, such selection ensures that the selected peptide or protein domain does not bind to the target protein or target nucleic acid in its native environment.

In one embodiment, the expression library of the present invention is screened using affinity purification. Affinity purification techniques are known in the art and are described in, for example, Scopes (In: Protein purification: principles and practice, Third Edition, Springer Verlag, 1994). Methods of affinity purification typically involve contacting the peptides encoded by the nucleic acid fragment library of the present invention with a specific target protein or nucleic acid, and, following washing, eluting those peptides that remain bound to the target protein or nucleic acid. Said target protein or nucleic acid is bound to another molecule to allow for ease of purification, such as, for example, a molecule selected from the group consisting of protein A, protein G, agarose, biotin, glutathione S-transferase (GST), and FLAG epitope. Accordingly, the target protein or nucleic acid is isolated simply through centrifugation, or through binding to another molecule, eg. streptavidin, or binding of a specific antibody, eg. anti-FLAG antibodies, or anti-GST antibodies. Methods using target proteins or nucleic acids covalently bound to affinity matrices are particularly preferred.

In another embodiment, the expression library of the present invention is expressed so as to allow identification of a bound peptide using FACS analysis. The screening of libraries using FACS analysis is described in U.S. Pat. No. 6,455,63 (Rigel Pharmaceuticals Incorporated). In adapting the protocol to the present invention, it is particularly preferred that the expression libraries of the present invention are expressed in such that they are displayed, such as for example, using in vitro display, bacterial surface display, yeast display, or mammalian display.

Preferably, an in vitro display library is screened by FACS sorting. In vitro displayed proteins are covalently linked to a particle or bead suitable for FACS sorting, such as, for example, glass, polymers such as for example polystyrene, latex or cross-linked dextrans such as Sepharose, cellulose, nylon, teflon, amongst others.

The displayed library bound to particles or beads is added to a target protein or nucleic acid that has been labelled with a labelling moiety, such as for example a fluorescent molecule, or a molecule which is detected by a second fluorescent molecule. Methods of labelling a target protein or nucleic acid are known in the art, and include methods using direct linkage or methods using a linker. The beads are then washed and subjected to sorting by FACS, which allows the beads with bound fluorescent target proteins or nucleic acids, to be separated from the beads that have not bound to a fluorescent target protein or nucleic acid.

Alternatively the library is screened using a biosensor-based assay, such as, for example, Biacore sensor chip technology (Biacore AB, UK). The Biacore sensor chip is a glass surface coated with a thin layer of gold modified with carboxymethylated dextran, to which the target protein or nucleic acid is covalently attached. The peptides encoded by the expression libraries of the present invention are then exposed to the Biacore sensor chip comprising the target protein or nucleic acid. Preferably, the nucleic acid fragment of the present invention and its encoded polypeptide are linked, such as for example using display technology.

The Biacore sensor chip is further used in the analysis of the kinetics of the interaction of the peptide encoded by the expression library of the present invention and the target protein or nucleic acid, such as for example through analyzing binding affinity using surface plasmon resonance. Essentially surface plasmon resonance detects changes in the mass of the aqueous layer close to the chip surface, through measuring changes in the refractive index. Accordingly, when a peptide encoded by the expression library of the present invention binds to the target protein or nucleic acid the refractive index increases.

As will be apparent to the skilled artisan another biosensor, such as, for example, an evanescent biosensor, a membrane based biosensor (as described in AU 623,747, U.S. Pat. No. 5,234,566 and USSN 20030143726) or a microcantilever biosensor (as described in USSN 20030010097) is useful for screening the peptides of the present invention.

The present invention is also be applied to identifying peptides that bind to any protein or nucleic acid, such as for example, a receptor protein, oncogenic protein, growth factor, cytokine, transcription factor, kinase, a promoter region of a gene, a suppressor region of a gene, a splice donor site, or a splice acceptor site. Alternatively, the libraries are screened to determine a peptide that modulates (inhibits, blocks, disrupts, down regulates, antagonizes, enhances, up regulates, agonizes, etc) a cellular process, biochemical reaction, protein: protein interaction, or a protein: nucleic acid interaction.

In one particularly preferred embodiment, the nucleic acid fragment expression libraries are screened for encoded peptides that bind to a target immunoglobulin, and preferably to the antigen binding site of a target immunoglobulin. Using standard affinity purification methods or any of the methods described herein, and appropriate antibodies as the target protein, it is possible to isolate peptide mimetics of both linear and discontinuous protein epitopes, in addition to other non-protein antigens, for example an antigen selected from the group consisting of: a carbohydrate, lipid, phospholipid, and protein (eg., Hi-PAL (P6) protein of *H. influenzae*, D15 protein from *H. influenzae*, the FemX protein from *S. aureus*, the FemA protein from *S. aureus*, or the FemAB protein from *S. aureus*). Using subsequent rounds of screening performed at lower concentrations of the target antibody, those peptides that bind with high affinity are selected.

As exemplified herein, a phage display/immunopanning method has been used to identify several peptides that are capable of binding to a monoclonal antibody that specifically binds to an epitope within the major house dust mite allergen Der p 1. Such mimotopes are particularly useful for determining a subject that has raised a specific immune response against Der p 1, and in particular an IgE response against Der p 1, in addition to providing a therapeutic method for the treatment of an allergic response to Der p 1.

In another particularly preferred embodiment, the nucleic acid fragment expression libraries are screened for encoded peptides that inhibit or antagonize or block an interaction between two oncoproteins, such as, for example, SCL and E47. Such peptide antagonists ("peptide blockers") are particularly useful for validating a cellular target in the therapeutic treatment of cancer or for the therapeutic treatment of an individual suffering from a cancer, tumor or neoplastic illness, or alternatively in the prophylactic treatment of a subject having a predisposition or history of cancer, tumor or neoplastic illness. As exemplified herein, reverse two hybrid screens that assay the interaction between SCL and E47, have successfully been used to identify several specific peptide blockers of the SCL/E47 interaction in yeast cells, in addition to a small number of peptide blockers that are not specific for this interaction.

In yet another particularly preferred embodiment, the nucleic acid fragment expression libraries are screened for encoded peptides that inhibit or antagonize or block self dimerization of a protein, such as for example, JUN. Such peptide antagonists ("peptide blockers") are particularly useful for validating a cellular target in the therapeutic treatment of a neurodegenerative disorder or for the therapeutic treatment of an individual suffering from a neurodegenerative disorder. As exemplified herein, reverse two hybrid screens that assay the interaction between JUN1 and JUNZ (fragments of c-JUN that include the leucine zipper domain), have successfully been used to identify several specific peptide blockers of c-JUN dimerization.

In a further embodiment, the nucleic acid fragments of the present invention are expressed as fusion proteins to form single-chain Fv (scFv) or Fab antibody fragments as described in McCafferty et al, *Nature* 348 552-534 (1990) and Hoogenboom et al, *Nucleic Acids Res* 19, 4133-4137 (1991). In a preferred embodiment the expression library of the present invention is used in the generation of a scFv library. The generation of a scFv library essentially involves generation of a gene construct comprising two or more nucleic acid fragments of the present invention separated by a nucleotide sequence encoding a scFv peptide linker, such as for example $(Gly_4Ser)_3$. The resulting gene construct is then expressed in an appropriate system to produce a single chain fragment of an antibody. It is particularly preferred that the expression library is displayed using a system described herein. The displayed library is screened for antibody fragments having a conformation sufficient for binding a specific antigen using techniques known in the art, such as, for example, affinity purification.

Using techniques known in the art, scFv fragments are isolated that bind to specific antigens or molecules. Such techniques include, for example, affinity chromatography and 'n'-hybrid screening. Furthermore, through selection of increased nucleotide sequence diversity through, for example random mutagenesis, it is possible to select for antibodies with increased affinity for the specific antigen.

In a further embodiment, the present invention provides a method of identifying a peptide or protein domain that binds to a target protein or nucleic acid wherein said binding modulates a biological activity of the target protein or nucleic acid. As used herein, the term "biological activity" is to be taken in its broadest context and shall be taken to mean any activity of a substance that relates to a cellular process, or alternatively is required for a cellular event to occur. Examples of biological activity include, but are not limited to, an activity selected from the group comprising, protein binding to a target protein or nucleic acid, for example antibody and antigen binding, disruption of protein binding, modulation of cell signalling, modulation of gene expression, cell viability, cell proliferation, degradation of a protein or nucleic acid, and/or preservation of a protein or nucleic acid.

As stated supra the present invention has provided several peptides that are useful in the diagnosis of a disease and/or disorder. For example, the present invention has provided peptides that are mimotopes of Der p 1 and are capable of inducing a specific immune response against Der p 1. Furthermore, the present invention has provided methods for determining a peptide that is a mimotope of D15 protein from *H. influenzae*. Such peptides are particularly useful in the diagnosis and/or prognosis of a disease and/or disorder.

Additionally, the present inventors have provided a method for determining a peptide that is capable of specifically binding to a FemX protein and/or a Sortase A protein and/or a Sortase B protein of *S. aureus*. Accordingly, the present invention provides the means for the diagnosis and/or prognosis of a variety of disorders.

Accordingly, another aspect of the present invention provides a method for the diagnosis and/or prognosis of a disease and/or disorder comprising contacting a biological sample derived from a subject with a peptide identified using a method of the present invention for a time and under conditions sufficient for said peptide to bind to a protein in the biological sample and detecting said binding.

In a preferred embodiment, the disease and/or disorder is an allergic disease and/or disorder. Examples of allergic disease include, for example, bronchial asthma, rhinitis, sinusitis, immunodeficiency, mastocytosis or anaphylaxis. Preferably, the allergic disease and/or disorder is allergic asthma, preferably induced by Der p 1.

In another preferred embodiment, the disease and/or disorder is an infectious disease and/or disorder. Examples of infectious diseases and/or disorder include, AIDS, SARS, enteric disease, hepatitis, influenza, pneumonia, *E. coli* infection, Lyme disease, a disease caused by a multidrug resistant bacterial species or malaria. Preferably, the infectious disease and/or disorder is influenza and/or *S. aureus* infection.

Methods for determining the presence of an antibody/peptide and/or protein/peptide complex are known in the art and/or described herein. For example such a complex is detected using an ELISA, wherein the peptide of the invention is immobilized on a solid support, such as, for example an array of polymeric pins, microwells or spots or a polymer, glass or gold support. The biological sample is brought into physical relation with the immobilized peptide for a time and under conditions sufficient for an antibody and/or protein in the biological sample to bind thereto. An antibody bound to the mimotope is then detected with another antibody, for example an anti-human antibody, more preferably an anti-human IgE antibody. The antibody is generally labeled with a fluorescent molecule or conjugated to an enzyme (e.g. horseradish peroxidase), or alternatively, a second labeled antibody can be used that binds to the first antibody. It will be apparent to the skilled person that the assay format described herein is amenable to high throughput screening of samples.

Alternatively, the peptide of the invention is used in an assay such as, for example, a radioimmunoassay (RIA), an enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, eg LC MS/MS), biosensor technology, evanescent fiber-optics technology or protein chip technology. Such methods are known in the art and/or described herein.

In one embodiment, the biological sample is a body fluid that is easily accessed and isolated from a subject. Preferably, the biological sample is and/or comprises whole blood, serum, cerebrospinal fluid (CSF), plasma, peripheral blood mononuclear cells (PBMC), a buffy coat fraction, saliva, urine, a buccal cell, urine, fecal material, sweat, a skin cell and an immunoglobulin fraction.

The present invention encompasses obtaining a cell or biological sample from a subject being tested.

Preferably, the cell or biological sample has been obtained previously from the subject.

In one embodiment, a peptide capable of binding to an antibody against Der p 1 (ie a Der p 1 mimotope) (eg a peptide comprising an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91) is useful for determining a subject that has raised a specific immune response against Der p 1 (eg an IgE response). Such a response is the basis of an allergic reaction to the house dust mite, which causes allergic asthma.

Accordingly, the present invention provides a method for detecting an antibody against a Der p 1 polypeptide in a biological sample derived from a subject comprising contacting the biological sample with a mimotope of Der p 1 for a time and under conditions sufficient for an antibody/peptide complex to form and detecting the complex. Preferably the mimotope of Der p 1 comprises the amino acid sequence set forth in SEQ ID NOs: an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91.

In a related embodiment, the present invention provides a method for diagnosing and/or prognosing an allergic response to a Der p 1 polypeptide in a subject comprising contacting a biological sample derived from the subject with a mimotope of Der p 1 for a time and under conditions sufficient for an antibody/peptide complex to form and detecting the complex. Preferably the mimotope of Der p 1 comprising an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91.

In a further related embodiment, the present invention provides a method for determining a subject that has raised an immune response against a Der p 1 polypeptide comprising contacting a biological sample derived from the subject with a mimotope of Der p 1 for a time and under conditions sufficient for an antibody/peptide complex to form and detecting the complex. Preferably the mimotope of Der p 1 comprising an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91.

In another embodiment, a peptide capable of binding to an antibody against D15 protein from *H. influenzae* (ie a D15 mimotope) is useful for determining a subject that has raised a specific immune response against D15. Such a mimotope is useful for the diagnosis of a subject suffering from an infection by *H. influenzae*, or for determining whether or not a subject is recovering from an infection by *H. influenzae.*

Accordingly, the present invention provides a method for detecting an antibody against a D15 protein from *H. influenzae* in a biological sample derived from a subject comprising contacting the biological sample with a mimotope of D15 protein from *H. influenzae* for a time and under conditions sufficient for an antibody/peptide complex to form and detecting the complex. Preferably the mimotope of D15 protein from *H. influenzae* comprises or is a peptide identified using the methods of the present invention.

In a related embodiment, the present invention provides a method for diagnosing and/or prognosing an allergic response to a D15 protein from *H. influenzae* in a subject comprising contacting a biological sample derived from the subject with a mimotope of D15 protein from *H. influenzae* for a time and under conditions sufficient for an antibody/peptide complex to form and detecting the complex wherein detection of the complex indicates that the subject suffers from an allergic response against D15 protein from *H. influenzae*. Preferably the mimotope of D15 protein from *H. influenzae* comprises or is a peptide identified using the methods of the present invention.

In a further related embodiment, the present invention provides a method for determining a subject that has raised an immune response against a D15 protein from *H. influenzae* comprising contacting a biological sample derived from the subject with a mimotope of D15 protein from *H. influenzae* for a time and under conditions sufficient for an antibody/peptide complex to form and detecting the complex wherein detection of the complex indicates that the subject that has raised an immune response against a D15 protein from *H.*

*influenzae*. Preferably the mimotope of D15 protein from *H. influenzae* comprises or is a peptide identified using the methods of the present invention.

A still further embodiment of the invention provides a method for determining a subject that has been infected with *H. influenzae* comprising contacting a biological sample derived from the subject with a mimotope of D15 protein from *H. influenzae* for a time and under conditions sufficient for an antibody/peptide complex to form and detecting the complex, wherein presence of the complex indicates that the subject has been infected with *H. influenzae*. Preferably the mimotope of D15 protein from *H. influenzae* comprises or is a peptide identified using the methods of the present invention.

In another embodiment, a peptide capable of binding to a FemX protein, a Sortase A protein and/or a Sortase B protein from *S. aureus* is useful for determining a subject that is infected with *S. aureus*, Such a peptide is also useful for determining whether or not a subject is recovering from an infection by *H. influenzae.*

One embodiment of the invention provides a method for determining a subject that has been infected with *S. aureus* comprising contacting a biological sample derived from the subject with a peptide capable of binding to a FemX protein, a Sortase A protein and/or a Sortase B protein from *S. aureus* for a time and under conditions sufficient for an antibody/peptide complex to form and detecting the complex, wherein presence of the complex indicates that the subject has been infected with *S. aureus*. Preferably the peptide capable of binding to a FemX protein, a Sortase A protein and/or a Sortase B protein from *S. aureus* comprises or is a peptide identified using the methods of the present invention.

As will be apparent to the skilled artisan, a method for determining a *S. aureus* infection in a subject is also useful for determining whether or not a subject is responding to treatment for a *S. aureus* infection. In one embodiment, the present invention provides a method for determining whether or not a subject is responding to treatment for a *S. aureus* infection comprising contacting a biological sample derived from the subject with a peptide capable of binding to a FemX protein, a Sortase A protein and/or a Sortase B protein from *S. aureus* for a time and under conditions sufficient for an antibody/peptide complex to form and detecting the complex, wherein presence of the complex indicates that the subject is not responding to treatment for a *S. aureus* infection. Preferably the peptide capable of binding to a FemX protein, a Sortase A protein and/or a Sortase B protein from *S. aureus* comprises or is a peptide identified using the methods of the present invention.

A related embodiment of the present invention provides a method of determining the presence of *S. aureus* in a biological sample comprising contacting a biological sample derived from the subject with a peptide capable of binding to a particular surface protein from *S. aureus* for a time and under conditions sufficient for an antibody/peptide complex to form and detecting the complex, wherein presence of the complex indicates that *S. aureus* is present in the biological sample. Preferably, the peptide is capable of specifically binding to the surface protein from *S. aureus* comprises or is a peptide identified using the methods of the present invention.

As will be apparent to the skilled artisan, this embodiment of the invention encompasses testing of, for example, food products and/or medical products (eg. saline and surgical instruments amongst others) for the presence of *S. aureus*

In another embodiment, the present invention provides a method of identifying a peptide or protein domain that binds to a target protein or nucleic acid wherein said binding inhibits the growth or viability of a microorganism. For example, comparative computer analysis of the genomes of microorganisms is used to identify those gene products that are specific to the microorganisms. Such information and comparative computer analysis software is available from, for example NCBI. The genome data of several microorganisms that are pathogens of the respiratory tract are compared to identify those sequences that are common to all of these species. These data are subtracted from genomic data of similar microorganisms that are not pathogens of the respiratory tract. Those sequences are specific to respiratory tract pathogens. This form of data analysis has been performed by, for example Read et al, *Drug Disc. Today* 6, 887-892 (2001). Any of these sequences that encode proteins is then be expressed and the encoded protein isolated, by methods that are known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001). Such proteins are then used as a target for screening the nucleic acid fragment library of the present invention. Any peptides that are identified as having a conformation sufficient for binding to the target protein or nucleic acid, are tested for microbial toxicity, either through directly exposing the microbes to the peptide, or expressing the peptide in the target microorganisms by methods that are known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001).

In a related embodiment, the present invention provides a method of identifying a peptide or protein domain that binds to a target protein or nucleic acid wherein said binding inhibits the growth or viability of an microorganism. In one form, the present embodiment relates to the insertion of the nucleic acid fragments that encode a polypeptide into a vector containing a conditional protein cleavage site, such as, for example, the temperature sensitive splicing element intein modified from the element found in the *S. cerevesiae* VMA1 gene. Such vectors include the IMPACT T7 system from New England Biolabs, for expression of peptides on the surface of T7 phage. Libraries generated using such vectors must be arrayed, such that each nucleic acid fragment is analyzed in isolation from other nucleic acid fragments, such methods are known in the art, for example arraying individual phage or bacteria clones in a 96 well plate format. Accordingly, the vectors are transformed, transfected or transduced into an appropriate host, and the host cells placed under conditions for cleavage to occur, such as, for example, low temperatures in the case of the intein mutant cleavage. The cleaved peptides are then brought into physical contact with the microorganism. Those peptides that are capable of inhibiting the growth of the microorganism, or killing the microorganism is identified using standard techniques, and directly related to the arrayed nucleic acid fragment library.

The methods described herein above are readily modified to suit other gene expression systems, such as for example those systems that secrete the peptide encoded by the expression library of the present invention, and those systems that lyse the host cell that express the peptide encoded by the expression library of the present invention, such as for example, the expression of the peptides from different open reading frames of the same nucleic acid fragment in the T7 lytic phage.

In a related embodiment, libraries that encode peptides in a secretable form, or libraries wherein a host cell is lyzed in preparation for screening, are screened using an assay employing a filter diffusion assay. Such an assay utilises a double faced Petri dish, with the two faces of the dish are separated by a supported semi-permeable membrane which will allow the diffusion of the peptides encoded by the expression library of the present invention, such as for example a membrane selected from the group comprising, nitrocellulose and nylon. A lawn of the microorganism is grown on one side of said double-faced Petri dish. Host cells expressing the expression library are grown on the opposite side of a double-faced Petri dish. The presence of plaques in the lawn of the microorganism is suggestive of the expression and diffusion of a peptide that can inhibit the growth of or kill said microorganism. The nucleic acid is then be isolated from the equivalent region of the phage overlay, using techniques known in the art.

In a related embodiment, a library of T7 phage expressing free peptides is transferred to a nylon membrane before being placed on a newly seeded lawn of pathogenic bacteria. Plaques appearing in this lawn are correlated by orientating the filter to plaques on the *E. coli*/T7 lawn expressing bacteriostatic or antibacterial peptides.

In another embodiment, the expression library of the present invention is introduced into a plurality of suitable host cells using the methods of introducing recombinant expression vectors described herein. Cells are then monitored for a change in the phenotype such as for example, as described in Xu et al, (In: *Nature Genetics* 27, 23-29, 2001). Examples of phenotypic changes include, but a not limited to a phenotypic change selected from the group comprising, modulation of cellular proliferation, morphological changes, resistance to toxins, susceptibility to toxins, and gene expression changes. In adapting the described technique to the present invention, appropriate host cells are transformed or transfected with the expression libraries of the present invention, using methods known in the art, and described above. Alternatively recombinant peptides isolated from the expression libraries of the present invention is incubated with the host cells, in the presence of a polypeptide that facilitates the uptake of peptides into host cells. Said host cells are then monitored for specific phenotype changes, such as for example gene expression changes monitored using DNA microarrays. The nucleic acid encoding the peptide that induces the phenotypic change is then isolated. Further testing of the peptide that induces the desired change in phenotype is clearly envisaged, such as, for example, two-hybrid analysis to determine which proteins the peptides interacts with, and which cellular pathways it is affect.

Preferably, those peptides that are identified in any of the above-mentioned screens to bind to a target protein or nucleic acid are recovered and analyzed.

In one embodiment, the nucleotide sequence of the nucleic acid encoding the identified peptide or protein domain is determined. Preferably, the sequences of several distinct peptides identified in a specific screen of a library are aligned and compared, and highly conserved primary and/or secondary structures within the peptides or protein domains are determined. Alternatively, or in addition, less conserved structures are also determined. More preferably, the highly conserved structural features are used to design and/or to produce additional peptides having the same or enhanced binding properties as the peptides identified in the initial screening.

In an alternative embodiment, the recovered peptide or protein domain and/or nucleic acid encoding same is recovered and used to validate a therapeutic target (ie. it is used as a target validation reagent). By virtue of its ability to bind to a specific target protein or target nucleic acid, it is well within the ken of a skilled artisan to determine the in vivo effect of modulating the activity of the target protein or target nucleic acid by expressing the identified peptide or protein domain in an organism (eg., a bacterium, plant or animal such as, for example, an experimental animal or a human). In accordance with this aspect of the present invention, a phenotype of an organism that expresses the identified peptide or protein domain is compared to a phenotype of an otherwise isogenic organism (ie. an organism of the same species or strain and comprising a substantially identical genotype however does not express the peptide or protein domain). This is performed under conditions sufficient to induce the phenotype that involves the target protein or target nucleic acid. The ability of the peptide or protein domain to specifically prevent expression of the phenotype, preferably without undesirable or pleiotropic side-effects indicates that the target protein or target nucleic acid is a suitable target for development of therapeutic/prophylactic reagents.

Accordingly, a further aspect of the present invention provides a method for determining a therapeutic or prophylactic target comprising (a) screening an expression library of the present invention to identify a peptide expressed by the library that binds to a target protein or target nucleic acid;

(b) selecting a peptide from (a) that does not bind to said target protein or nucleic acid in its native environment; and (c) expressing the selected peptide in an organism and determining a phenotype of the organism that is modulated by the target protein or target nucleic acid.

Preferably, determining a phenotype of the organism that is modulated by the target protein or target nucleic acid comprises comparing the organism to an otherwise isogenic organism that does not express the selected peptide. For example, the phenotype of an organism that expresses a tumor is assayed in the presence and absence of a peptide or protein domain that blocks an interaction between SCL and E47 in a screen of the expression library of the invention. Amelioration of the oncogenic phenotype by the expressed peptide indicates that the SCL/E47 is a suitable target for intervention, wherein the peptide is then suitably formulated for therapeutic intervention directly, or alternatively, small molecules are identified that are mimetics of the identified peptide or protein domain.

It is to be understood that any use of an expression library of the present invention extends to the obtaining of said expression library, or the production of the expression library.

It will also be apparent from the preceding description that the library can be screened using an selected from the group consisting of yeast-2-hybrid, n-hybrid, reverse-2-hybrid, reverse n-hybrid, split two hybrid, bacterial display, phage display, retroviral display, covalent display and in vitro display, or using an affinity purification, such as, for example, an immunoassay that measures the formation of an antigen-antibody complex.

It will also be apparent from the description herein that the peptide selection may comprise (i) determining the amino acid sequence of the peptide or determining the nucleotide sequence of the corresponding nucleic acid encoding said peptide and deriving the amino acid sequence from said nucleotide sequence or determining a known function of the amino acid sequence; and (ii) excluding a peptide that binds to a target protein or target nucleic acid associated with the known sequence or known function.

In accordance with this embodiment, a selection is applied (eg., using flow cytometry to sort cells with particular surface expression characteristics) to isolate library transformants which have acquired a desired phenotype. The amino acid sequence of the peptide expressed from such positively selected clones is then be determined by PCR cloning and sequencing. Two hybrid screening, as described herein, using the isolated peptide as a bait protein is used to identify the target proteins which the peptide bound to exert its phenotypic effect.

By way of an example, the expression library of the present invention is introduced into a cell line and expression induced. After a time sufficient for expression of the peptides encoded by the expression library to occur, the cells are exposed to a toxin to which the wild type cells are susceptible, such as, for example staurosporine. Following such exposure, those cells that are not resistant to the toxin die by apoptosis. Those cells that survive the selection pressure are analyzed further to determine if their survival is a consequence of their expressing a peptide that enables them to survive exposure to the toxin. Preferably, the nucleic acid encoding this peptide is isolated and sub-cloned for further analysis.

In another embodiment, the expression library of the present invention is arrayed and individual nucleic acid fragments or pools of nucleic acid fragments are introduced into a whole organism, using methods known in the art, and described herein. Particular model organisms include, but are not limited to, *Arabidopsis thaliana, Anopheles gambiae, Caenorhabditis elegans, Danio rerio, Drosophila melanogaster, Mus* sp., *Takifugu rubripes, Rattus* sp., *Saccharomyces cerevesiae*, and *Schizosaccharomyces pombe*. Array methods described in Hogan et al (In: Manipulating the Mouse Embryo. A Laboratory Manual, 2$^{nd}$ Edition. Cold Spring Harbour Laboratory. ISBN: 0879693843, 1994) are preferred. After a time sufficient for the organisms to develop to a suitable stage in the life cycle for a target phenotype to be expressed, transformed organisms are monitored for a change in the phenotype, using methods known in the art, such as for example the SHIRPA protocol described in Rogers et al, *Mamm. Genome* 8(10), 711-713, 1997. Organisms expressing a desired change in phenotype are retained for further analysis. Further testing of the peptide that induces the desired change is clearly encompassed by the present invention.

A similar method is applied to the identification of those nucleic acids that encode a polypeptide that confers resistance to, for example, toxins, pathogens, or specific forms of cancer. By way of example, fertilized mouse ova are microinjected with individual, or pools of gene constructs comprising nucleic acid fragments of the present invention. After implanting the microinjected ova and allowing transgenic mice to be born and to develop beyond weaning (ie. approximately 21 days), mice are exposed to a challenge by a microorganism, such as for example *Plasmodium berghei* (a rodent malaria parasite which is related to *P. falciparum*). Following an exposure to *P. berghei* at high dose, mice that are susceptible to *P. berghei* die. Mice that do not die are retained and nucleic acid used to produce those mice are recovered (eg., by PCR) and the sequences determined.

It will also be appreciated by those skilled in the art that the above described method is adapted to monitor any phenotypic changes, for example through methods selected from the group comprising $^{3}$H incorporation, measures of apoptosis (eg TUNEL staining), secretion of particular hormones/proteins, and morphological changes, amongst others In a related embodiment those peptides that are able to modulate the phenotype are further analyzed to determine those cellular components with which the peptide interacts. Methods used in the analysis of protein interactions are known in the art and are described in Weber (In: Protein interactions. Chapman and Hall, New York, 1992). Through determining the proteins with which the peptides interact, the gene expression libraries of the present invention is used for the validation of potential drug targets or in determining the proteins involved in specific cellular pathways and processes.

A particularly preferred embodiment of the present invention relates to the identification of a peptide or protein domain that is able to modulate the biological activity of a target protein or nucleic acid, wherein the modulated biological activity is the ability of the target protein or nucleic acid to bind to another protein or nucleic acid and wherein the modulated binding is determined using a reporter molecule. As used herein, the term “reporter molecule” shall be taken to mean a molecule that displays a physically measurable property that alters in a way that can be measured and correlated with changes in the biological activity or a target protein or nucleic acid. Reporter molecules are known in the art, and include, but are not limited to, proteins that fluoresce, for example green fluorescence protein, proteins that induce a colour change in the presence of a substrate, for example *E. coli* β-galactosidase, molecules that confer growth characteristics on the host cells, such as for example HIS1, and molecules that induce the death or reduced growth ability of the host cells, such as for example URA3 and CYH2CYH3.

One embodiment of the present invention relates to the identification of nucleic acids that encode peptides having a conformation capable of binding to a DNA sequence. The one-hybrid assay, as described in Chong and Mandel (In: Bartel and Fields, The Yeast Two-Hybrid System, New York, N.Y. pp 289-297, 1997) is used to determine those peptides able to bind to a target DNA sequence. In adapting the standard one-hybrid technique to the present purpose, the target nucleotide sequence is incorporated into the promoter region of a reporter gene(s), the expression of which can be determined as described above. The peptide encoded by the expression library of the present invention is expressed in such a manner that it forms a fusion protein with a transcriptional activation domain (for example from the GAL4 protein, the LexA protein, or the mouse NF κB protein). The transcriptional activation domain is recruited to the promoter through a functional interaction between the expressed peptide and the target nucleotide sequence. The transcriptional activation domain subsequently interacts with the basal transcriptional machinery of the cell, activating expression of the reporter genes.

In another embodiment a polypeptide is identified that is able to bind a target protein or peptide using the two-hybrid assay described in U.S. Pat. No. 6,316,223 to Payan et al and Bartel and Fields, The Yeast Two-Hybrid System, New York, N.Y., 1997. The basic mechanism described requires that the binding partners are expressed as two distinct fusion proteins in an appropriate host cell, such as for example bacterial cells, yeast cells, and mammalian cells. In adapting the standard two-hybrid screen to the present purpose, a first fusion protein consists of a DNA binding domain fused to the target protein, and a second fusion protein consists of a transcriptional activation domain fused to the peptide encoded by the expression library of the present invention. The DNA binding domain binds to an operator sequence which controls expression of one or more reporter genes. The transcriptional activation domain is recruited to the promoter through the functional interaction between the peptide expressed by the expression library of the present invention and the target protein. Subsequently, the transcriptional activation domain interacts with the basal transcription machinery of the cell, thereby activating expression of the reporter gene(s), the expression of which can be determined.

The three hybrid assay as described in Zhang et al (In: Bartel and Fields, The Yeast Two-Hybrid System, New York, N.Y. pp 289-297, 1997) is used to determine those peptides that bind target RNA sequences. In adapting the described 3-hybrid technique to the present invention, a first fusion protein consists of a DNA binding domain which is fused to a known RNA binding protein, eg. the coat protein of bacteriophage MS2. An RNA hybrid molecule is also formed, consisting of a fusion between a RNA molecule known to bind the RNA binding protein, eg. MS2 binding sequences, and a target RNA binding sequence. A second fusion protein consists of a transcriptional activation domain fused to the peptide encoded by the expression library of the present invention. The DNA binding domain of the first fusion protein binds to an operator sequence that controls expression of one or more reporter genes. The RNA fusion molecule is recruited to the first fusion protein through the functional interaction between the RNA binding protein and the RNA molecule known to interact with said RNA binding protein. The transcriptional activation domain is recruited to the promoter of one or more reporter molecules through functional interaction between the target RNA sequence of the peptide encoded by the nucleic acid of the present invention.

Other modifications of the two-hybrid screens are known in the art, such as for example the PolIII two hybrid system, the Tribrid system, the ubiquitin based split protein sensor system and the Sos recruitment system as described in Vidal and Legrain *Nucl. Acid Res.* 27(4), 919-929 (1999). All of these systems are particularly contemplated.

A particularly preferred embodiment of the present invention relates to the identification of peptides that antagonize or inhibit the interaction between the target protein or nucleic acid and another protein or nucleic acid. Accordingly, reverse 'n'-hybrid screens are employed to identify agonist molecules. Reverse hybrid screens differ from the forward hybrid screens supra in that they use a counter selectable reporter marker(s), such as for example the URA3 gene, the CYH2 gene or the LYS2 gene, to select against interactions between the target protein or nucleic acid and another protein or nucleic acid. Cell survival or cell growth is reduced or prevented in the presence of a drug or a toxigenic substrate of the counter selectable reporter gene product, which is converted by the counter selectable marker to a toxic compound, such as for example the URA3 gene product which confers lethality in the presence of the drug 5-FOACYH2. Accordingly, cells in which the interaction between the target protein and another protein or nucleic acid is blocked or inhibited survive in the presence of the substance. This is because the counter selectable reporter molecule will not be expressed, and accordingly, the substrate will not be converted to a toxic product or the drug (in the case of cycloheximide) will not be active against the essential target encoded by the reporter gene. Such a result suggests that the peptide encoded by the expression library of the present invention is an inhibitor of the interaction between the target protein or nucleic acid and another protein or nucleic acid.

In a particularly preferred embodiment, the screening method of the present invention identifies an antagonist of a protein: protein interaction or protein: nucleic acid interaction. In accordance with this embodiment, the present invention provides a reverse two hybrid screening process, such as, for example, essentially as described by Watt et al. (U.S. Ser. No. 09/227,652), for identifying an inhibitory amino acid sequence that partially or completely inhibits a target protein-protein interaction or DNA-protein interaction involving one or more protein binding partners said method comprising:

(i) providing cells that each comprise: (a) a nucleic acid comprising a counter-selectable reporter gene encoding a polypeptide that is capable of reducing cell growth or viability by providing a target for a cytotoxic or cytostatic compound (eg., CYH2 gene that confers susceptibility to cycloheximide) or by converting a substrate to a cytotoxic or cytostatic product (eg., URA3 gene that converts 5-FOA to a toxic product), said gene being positioned downstream of a promoter comprising a cis-acting element such that expression of said gene is operably under the control of said promoter and wherein a protein binding partner of the protein-protein interaction or the DNA-protein interaction being assayed binds to said cis-acting element; and (b) nucleic acid selected from the group consisting of: (i) nucleic acid encoding a protein of the DNA-protein interaction that binds to said cis-acting element to activate expression of the counter-selectable reporter gene; and (ii) nucleic acids encoding two protein binding partners of the protein-protein interaction wherein a protein binding partner binds to the cis-acting element and the protein binding partners interact, said binding to the cis-acting element and said interaction being required to activate expression of the counter-selectable reporter gene;

(ii) transforming or transfecting the cells or a portion of the cells with an expression library of the invention such that a single gene construct of the expression library is present in each transformed or transfected cell;

(iii) culturing the transformed or transfected cells for a time and under conditions sufficient for the protein binding partner(s) to activate expression of the counter-selectable reporter gene in the absence of inhibition of the protein-protein interaction or the DNA-protein interaction by an amino acid sequence encoded by the expression library;

(iv) culturing the transformed or transfected cells under conditions sufficient for an amino acid sequence of the expression library to be expressed in each of said transformed or transfected cells or a proportion of said transformed or transfected cells;

(v) culturing the transformed or transfected cells in the presence of the substrate or the cytotoxic or cytostatic compound such that the expressed counter-selectable reporter gene reduces the growth or viability of the cells unless said expression is reduced by virtue of an amino acid sequence of the expression library inhibiting the target protein-protein interaction or DNA-protein interaction;

(vi) selecting a cell having enhanced growth or viability compared to a cell that does not express the amino acid sequence of the expression library wherein the enhanced growth or viability is indicative of a partial or complete inhibition of the protein-protein interaction or a DNA-protein interaction by the amino acid sequence and (vii) selecting a peptide expressed by the cell at (vi) that does not bind to a protein or nucleic acid of the protein-protein interaction or a DNA-protein interaction in its native environment.

Preferably, wherein a protein-protein interaction is being assayed, the binding of the two protein binding partners reconstitutes a functional transcriptional regulatory protein, such as, for example, by virtue of the binding partners being expressed as fusion proteins wherein each fusion protein comprises a portion of a transcriptional regulatory protein that does not modulate transcription without the other portion (eg., a fusion protein comprising a transcriptional activator domain and a fusion protein comprising a DNA-binding domain). In a particularly preferred embodiment, one fusion protein comprises a Gal4 DNA-binding domain fused to SCL, and another fusion protein comprises the transcriptional activation domain of the LMO2 protein and a domain that interacts with SCL and, in this embodiment, the URA3 counter selectable reporter gene is operably under the control of a promoter comprising a Gal4 upstream activator sequence (Gal4 UAS), such that docking of the Gal4/SCL fusion to the Gal4 UAS and binding between SCL and LMO2 is required to activate transcription of the URA3 gene, thereby conferring lethality on cells grown in the presence of 5-fluoro orotic acid (5-FOA). In screening the expression library, only those cells that survive in the presence of 5-FOA are selected.

For example, a specific receptor is expressed as a DNA binding domain fusion protein, such as with the DNA binding domain of GAL4, and the ligand of said receptor is expressed as an activation domain fusion protein, such as with the GAL4 activation domain. These fusion proteins are expressed in yeast cells in operable connection with the CYH2 counter selectable marker, wherein expression of the CYH2 gene requires a physical interaction between the GAL4 DNA binding domain and the GAL4 activation domain. This physical relation is achieved is achieved, for example, by placing the expression of the marker gene under the control of a promoter comprising nucleotide sequences to which the GAL4 DNA binding domain binds. Cells in which the reporter gene is expressed do not grow in the presence of cycloheximide. The expression libraries of the present invention are expressed in these yeast cells and those cells that then grow in the presence of cycloheximide are further analyzed, such as, for example, analysis of the nucleic acid encoding the candidate peptide inhibitor(s).

In another particularly preferred embodiment, one fusion protein comprises a Gal4 DNA-binding domain fused to JUN1, and another fusion protein comprises the transcriptional activation domain of the LMO2 protein and a domain that interacts with JUN1 (eg JUNZ) and the URA3 counter selectable reporter gene is operably under the control of a promoter comprising a Gal4 upstream activator sequence (Gal4 UAS), such that docking of the Gal4/JUN1 fusion to the Gal4 UAS and binding between JUN1 and JUNZ is required to activate transcription of the URA3 gene, thereby conferring lethality on cells grown in the presence of 5-fluoro orotic acid (5-FOA). In screening the expression library, only those cells that survive in the presence of 5-FOA are selected.

As will be known to the skilled artisan, the reverse 'n'-hybrid technique briefly described above is readily modified for use in 1-hybrid, 2-hybrid or 3-hybrid assays.

In an alternative embodiment, the antagonist is identified using a reverse split two hybrid screening process, such as, for example, essentially as described by Erickson et al. (WO95/26400), wherein a relay gene that is a negative regulator of transcription is employed to repress transcription of a positive readout reporter gene when the interacting proteins (ie., bait and prey) interact, such that reporter gene expression is only induced in the absence of the protein encoded by the relay gene product. In accordance with this embodiment, there is provided a method for identifying an inhibitory amino acid sequence that partially or completely inhibits a target protein-protein interaction or DNA-protein interaction involving one or more protein binding partners said method comprising:

(i) providing cells that each comprise: (a) a nucleic acid encoding a negative regulator of transcription (eg., Gal80 or mdm2 oncoprotein-encoding gene), said nucleic acid being positioned downstream of a promoter comprising a cis-acting element and wherein a protein binding partner of the protein-protein interaction or the DNA-protein interaction being assayed binds to said cis-acting element; (b) nucleic acid selected from the group consisting of: (i) nucleic acid encoding a protein of the DNA-protein interaction that binds to said cis-acting element to activate expression of the negative regulator of transcription; and (ii) nucleic acids encoding two protein binding partners of the protein-protein interaction wherein a protein binding partner binds to the cis-acting element and the protein binding partners interact, said binding to the cis-acting element and said interaction being required to activate expression of the negative regulator of transcription; and (c) nucleic acid comprising a positive reporter gene (eg., an antibiotic resistance gene, herbicide resistance gene, or other resistance gene, or a gene which complements an auxotrophic mutation in the screening cells) operably connected to a cis-acting element (eg., a GALA binding site capable of binding to Gal80, or Gal80, or the transactivation domain of p53 that binds to mdm2 oncoprotein) to which the negative regulator of transcription binds to thereby inhibit or repress expression of the positive reporter gene;

(ii) transforming or transfecting the cells or a portion of the cells with an expression library of the invention such that a single gene construct of the expression library is present in each transformed or transfected cell;

(iii) culturing the transformed or transfected cells for a time and under conditions sufficient for the protein binding partner(s) to activate expression of negative regulator of transcription in the absence of inhibition of the protein-protein interaction or the DNA-protein interaction by an amino acid sequence encoded by the expression library;

(iv) culturing the transformed or transfected cells under conditions sufficient for an amino acid sequence of the expression library to be expressed in each of said transformed or transfected cells or a proportion of said transformed or transfected cells;

(v) culturing the transformed or transfected cells in the presence of a compound to which the positive reporter gene confers resistance on the cells such that the expressed negative regulator of transcription represses expression of the positive reporter gene thereby reducing the growth or viability of the cells unless said expression is reduced by virtue of an amino acid sequence of the expression library inhibiting the target protein-protein interaction or DNA-protein interaction;

(vi) selecting a cell having enhanced growth or viability compared to a cell that does not express the amino acid sequence of the expression library wherein the enhanced growth or viability is indicative of a partial or complete inhibition of the protein-protein interaction or a DNA-protein interaction by the amino acid sequence and (vii) selecting a peptide expressed by the cell at (vi) that does not bind to a protein or nucleic acid of the protein-protein interaction or a DNA-protein interaction in its native environment.

Preferably, wherein a protein-protein interaction is being assayed, the binding of the two protein binding partners reconstitutes a functional transcriptional regulatory protein. In a particularly preferred embodiment, one interacting protein comprises a LexA fusion protein, and another interacting protein comprises a VP16 fusion protein which when they interact induce expression of a GAL80 reporter gene regulated by lexA operators. In this embodiment, the positive reporter gene (eg. a gene complementing an auxotrophic mutation) is placed operably under the control of a promoter comprising a Gal4 upstream activator sequence (Gal4 UAS), such that docking of a Gal80 negative regulator of transcription to the Gal4 UAS and binding between SCL and LMO2 is required to repress transcription of the positive reporter gene, thereby preventing cells from proliferating. Conversely, repression of the interaction between the LexA-fusion and VP16 fusion prevents Gal80 expression allowing expression of the positive reporter gene which complements an auxotrophic mutation in the screening cells, particularly in cells that express endogenous Gal4 protein, allowing those cells to grow in the absence of the nutrient which the corresponding auxotrophic mutation had conferred dependence on.

In a preferred embodiment of the present invention, those nucleic acid fragments that encode a polypeptide that binds to a target protein or nucleic acid are exposed to further rounds of selection using, for example, mutagenic PCR or expression of said fragments in "mutator" strains of bacteria. This increases the diversity of the selected nucleic acid. Said selected nucleic acid is again screened for those that encode a peptide having a conformation sufficient for binding a target protein or nucleic acid. Through multiple rounds of screening and selection with lower concentrations of the target protein or nucleic acid, those peptides with the highest affinity for the target protein or nucleic acid are selected.

In a related embodiment, the sequences of those nucleic acid fragments encoding peptides that bind to the target protein or nucleic acid are optimally aligned and the sequences compared to identify those nucleic acids that encode amino acids that are particularly desired for binding the target protein or nucleic acid. Furthermore, this information is used to generate synthetic nucleotide sequences encoding peptides, or synthetic peptides, containing those amino acids that are particularly desirable for binding to a target protein or nucleic acid.

Preferably, those peptides that bind to the target protein or nucleic acid, are recovered and used in further analysis, such as for example, determining the nucleotide sequence of the nucleic acid encoding the identified peptide or protein domain. Initially, the nucleic acid fragment encoding the peptide is isolated using methods known in the art, such as for example, PCR, RT-PCR, and nucleic acid isolation, amongst others. An isolated nucleic acid fragment is then characterized by methods such as nucleic acid sequencing. Such methods are known in the art.

In one embodiment, an insolated nucleic acid fragment is placed into an expression vector using methods known in the art, and described herein. Such a nucleic acid fragment is only expressed in a single reading frame and only in one direction. This method is repeated until all possible open reading frames of the nucleic acid fragment are tested, and that/those that encode a polypeptide having a conformation sufficient for binding a target protein or nucleic acid are identified. As used herein the term "all possible open reading frames" shall include those open reading frames that include the entire nucleic acid fragment, in addition to those open reading frames that are formed within a nucleic acid fragment, such as for example by the inclusion of a second ATG start codon, a Kozak sequence, a Shine-Dalgarno sequence, or an internal ribosome entry sequence (IRES), amongst others. Preferably, such translational start sites are incorporated in order of increasing strength from the 5' end to the 3' end of the ribosome binding region of the expression construct, to compensate for a disproportionately strong initiation from the first Kozak sequence encountered after the cap site of the mRNA. All of the expressed peptides are then screened in an appropriate screening system to determine those that have a conformation sufficient for binding to a target protein or nucleic acid. Accordingly, analysis of the nucleic acid encoding such a peptide is used to determine the amino acid sequence of the peptide. Using such software as the Translate tool available at ExPasy. As used herein, the term "ExPasy" shall be understood to mean, the ExPasy proteomics server provided by the Swiss Institute of Bioinformatics at CMU-Rue Michel—Servet 1 1211 Genève 4 Switzerland Following isolation of the nucleic acid that encodes a peptide with a conformation sufficient for binding to a target protein or nucleic acid, it is preferred that all homologues of this sequence are isolated from the genomes of the organisms used to generate the expression library of the present invention. Methods of isolating homologous nucleic acid regions are known in the art and are described, for example, in Dieffenbach (ed) and Dveksler (ed) (In: PCR Primer: A Laboratory Manual, Cold Spring Harbour Laboratories, NY, 1995). Such methods include PCR and degenerate PCR. Such homologues are then screened in all possible reading frames using a suitable screening system, as are known in the art and described herein.

It is a further preferred embodiment that an identified nucleotide sequence or amino acid sequence shall be used as a "reference sequence" for a homology search using a database of all known sequences. Such a reference sequence is a nucleotide or amino acid sequence to which all nucleotides or amino acid sequences in a database are compared. A number of source databases are available that contain either a nucleotide sequence and/or a deduced amino acid sequence that are particularly useful to identify all known sequences that are substantially homologous the sequence of nucleic acid or peptide, polypeptide or protein domain identified as positive in the present invention. Such databases are known in the art and include, for example, Genbank (at NCBI) and SWISS-PROT and TrEMBL (available at ExPasy). A number of different methods of performing such sequence searches are known in the art. The sequence data of the clone is then aligned to the sequences in the database or databases using algorithms designed to measure homology between two or more sequences.

In one embodiment, a nucleic acid identified in a homology search of the known nucleic acids is isolated using one of a variety of methods known in the art, such as for example PCR amplification of the specific region of genomic DNA or cDNA of the organism in which the nucleic acid is naturally found. The sequence of the isolated nucleic acid is determined, used to generate a gene construct as described herein, and screened to determine if it encodes a peptide that has a conformation sufficient for binding the target protein or nucleic acid.

In another embodiment a nucleic acid encoding an amino acid sequence identified in a homology search of known amino acid sequences using techniques known in the art, such as for example degenerate PCR. An isolated nucleic acid is then used to generate a gene construct as described herein, and screened to determine if it encodes a peptide that has a conformation sufficient for binding the target protein or nucleic acid.

It is a particularly preferred embodiment of the present invention that those nucleic acids that encode a polypeptide having a conformation that binds to a target protein or nucleic acid are analyzed to select those nucleic acid fragments that encode polypeptides that do not bind to said target protein or nucleic acid in its native environment. As used herein, the term "native environment" of a polypeptide shall be understood to mean the protein encoded by the gene from which the nucleic acid fragment was isolated. Accordingly, it is the aim of the present invention to identify those polypeptides that display a function of the subdomain of the native protein, for example by binding to a target protein or nucleic acid to which it cannot bind in the context of the protein in which it naturally occurs.

The known function/s of the polypeptides isolated in the screening of the libraries of the present invention are determined using sequence analysis software as is available from, for example NCBI, or Prosite. As used herein the term "Prosite" shall be understood to mean the Prosite protein database which is a part of the ExPasy proteomics server provided by the Swiss Institute of Bioinformatics at CMU-Rue Michel—Servet 1 1211 Genève 4 Switzerland. Accordingly, those polypeptides that are known to bind to the target protein or nucleic acid in their native environment are excluded from any further analysis. Furthermore, analysis of the bioinformatic information available, for example, at NCBI aids in determining the native function of a protein. Such analysis will determine if, for example, the pathway being modified exists in an organism from which a peptide is identified or if a target protein or nucleic acid is found in any of the organisms used to generate an expression library.

It is particularly preferred that an expression library of the present invention is generated using nucleic acid fragments isolated from organisms that are distinct from the organism in which the target protein or nucleic acid naturally occurs. For example, to identify a nucleic acid that encodes a peptide that has a conformation sufficient for binding the Hi-PAL (P6) outer membrane protein of *Haemophilus influenzae* an expression library is generated from the organisms *Aeropyrum pernix, Aquifex aeolicus, Archaeoglobus fulgidis, Bacillus subtilis, Bordetella pertussis, Borrelia burgdorferi, Chlamydia trachomatis, Escherichia coli, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium* and *Thermotoga maritima*. This will reduce the likelihood of identifying a peptide that interacts with the Hi-PAL (P6) protein in its native environment. Even more preferably, an expression library is generated using the organisms *Aeropyrum pernix, Aquifex aeolicus, Arabidopsis thaliana, Archaeoglobus fulgidis, Caenorhabditis elegans, Danio rerio, Drosophila melanogaster, Methanobacterium thermoautotrophicum, Methanococcus jannaschii, Pyrococcus horikoshii, Saccharomyces cerevesiae, Takifugu rubripes, Thermoplasma volcanium*, and *Thermotoga maritima* as these organisms are unlikely to occur in the same environment as *Haemophilus influenzae*, and as such, any peptide isolated from such an expression library would be especially unlikely to interact with Hi-PAL (P6) in its native environment.

Another aspect of the present invention is a database of nucleic acids that are found in an expression library of the present invention. As the nucleic acid fragments are derived from organisms with substantially sequenced genomes, it is possible to use this information to generate a database of the nucleotide sequences of nucleic acid fragments that is generated in the construction of an expression library of the present invention.

The utility of the database lies in the ability for a skilled person to search the database for a nucleotide sequence or amino acid sequence determined by screening an expression library of the present invention. In this way, it is possible to identify nucleic acid fragments that encode a peptide that is adopt a conformation sufficient for binding to a specific target protein or nucleic acid. Furthermore, the database allows the user to identify a sequence that is homologous to a nucleic acid, in addition to determining from which species it is derived. Once a sequence is identified, the specific nucleic acid is isolated from the expression library using techniques known in the art, eg. PCR and the expressed peptide analyzed.

Nucleotide sequences of the nucleic acid fragments of the expression library are derived from any one of many publicly known databases, such as for example NCBI or TIGR, as the organisms used in the generation of an expression library of the present invention has a substantially sequenced genome.

Amino acid sequences that are found in the database are derived by conceptual translation of nucleotide sequences that are found in an expression library of the present invention. The conceptual translation of a nucleotide sequence comprises applying the known codon usage rules to obtain hypothetical peptide sequences by translating a nucleotide sequence in both orientations and in all three reading frames for each possible orientation. Software for translation of nucleotide sequence to amino acid sequence is known in the art, and includes, for example, the Translate tool at ExPasy. Care is taken to translate a nucleotide sequence using the known codon usage of the organism in which a nucleic acid fragment is to be expressed. Such codon usage information is known in the art. Amino acid sequences are also derived by sequencing the expressed peptides. Methods of sequencing peptides and proteins are known in the art.

Alternatively or in addition, various comparisons can be made between the Library database sequences and any other sequence database as would be familiar to those practiced in the art.

Additionally, the sequence information is used to generate a highly specific probe for isolating both genomic clones from existing databases, as well as cDNA. Additionally, the probe is used to isolate the homologous nucleic acid fragment from sufficiently related species, including humans. Once isolated, the nucleic acid fragment is inserted into a gene construct and screened as herein described.

In a related embodiment, a database of amino acid sequences of peptides is analyzed to generate a database of potential domain structures, or three-dimensional structures that is formed by a peptide expressed by the expression library of the present invention. Methods for predicting the 3 dimensional structure of a peptide are known in the art, and are described, for example, in US Patent Application No 20020150906 (California Institute of Technology), or using a computer program or algorithm, such as, for example, MODELLER, (Sali and Blundell, *J. Mol. Biol.* 234, 779-815, 1993). These techniques rely upon aligning the sequence of a peptide with the sequences of peptides or proteins that have a characterized structure. Such alignment algorithms are known in the art and are accessed through software packages such as, for example BLAST at NCBI. Structural information, ie. three-dimensional structure, of a query peptide is then be predicted based upon structural information corresponding to the sequence or subsequences aligned in the proteins or peptides that have previously been characterized. In this way it is possible to generate a library of three-dimensional structures of peptides expressed from the expression library of the present invention. This information is used to determine those sequences that is adopt a conformation sufficient for binding to a target protein or nucleic acid. Accordingly, the nucleic acid fragment encoding such a peptide is isolated using methods known in the art, and inserted into a gene construct. The encoded peptide is then screened using the methods described herein.

As will be apparent to the skilled artisan, peptides identified in the method of the present invention are useful as a therapeutic and/or prophylactic treatment of a disease and/or disorder. For example, the present inventors have shown that a peptide mimotope of Der p 1 is capable of inducing an immune response against Der p 1. Accordingly, such a peptide is useful for inducing an antibody (ie. IgG) response upon exposure to Der p 1, rather than a cross linking of IgE on mast cells (ie an allergic response).

Accordingly, another aspect of the present invention provides a method of treatment of a disease or disorder comprising administering an effective amount of a peptide identified by the method of the present invention to a subject suffering from the disease and/or disorder or at risk of developing and/or suffering from the disease and/or disorder and/or in need of treatment.

Clearly the present invention encompasses the use of a peptide identified by a method of the present invention in the manufacture of a medicament for use in medicine. Additionally, the present invention encompasses a peptide identified by the present invention when used in medicine.

As will be apparent to the skilled artisan, the use of a peptide identified by the method of the present invention to treat a disorder may require the peptide be formulated into a compound for administration.

Preferably, the compound is a pharmaceutical compound.

Formulation of a pharmaceutical compound will vary according to the route of administration selected (e.g., solution, emulsion, capsule). An appropriate composition comprising the identified modulator to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

As will be apparent to a skilled artisan, a compound that is active in vivo is particular preferred. A compound that is active in a human subject is even more preferred. Accordingly, when manufacturing a compound that is useful for the treatment of a disease it is preferable to ensure that any components added to the peptide does not inhibit or modify the activity of said peptide.

The present invention clearly encompasses the use of any in silico analytical method and/or industrial process for carrying the screening methods described herein into a pilot scale production or industrial scale production of a compound identified in such screens. This invention also provides for the provision of information for any such production. Accordingly, a further aspect of the present invention provides a process for identifying or determining a compound or modulator supra, said method comprising:

(i) performing a method as described herein to thereby identify or determine a peptide capable of forming a conformation sufficient for binding a target protein and/or nucleic acid;

(ii) optionally, determining the amount of the peptide;

(iii) optionally, determining the structure of the peptide; and (iv) providing the compound or the name or structure of the peptide such as, for example, in a paper form, machine-readable form, or computer-readable form.

As used herein, the term "providing the peptide" shall be taken to include any chemical or recombinant synthetic means for producing said compound (with or without derivitisation) or alternatively, the provision of a compound that has been previously synthesized by any person or means.

In a preferred embodiment, the compound or the name or structure of the compound is provided with an indication as to its use e.g., as determined by a screen described herein.

A further aspect of the present invention provides a process for producing a compound supra, said method comprising:

a process for identifying or determining a compound or modulator supra, said method comprising:

(i) performing a method as described herein to thereby identify or determine a peptide capable of forming a conformation sufficient for binding a target protein and/or nucleic acid;

(ii) optionally, determining the amount of the peptide;

(iii) optionally, determining the structure of the peptide;

(iv) optionally, providing the name or structure of the peptide such as, for example, in a paper form, machine-readable form, or computer-readable form; and (v) providing the peptide.

Preferably, the method further comprises providing a chemical derivative of the peptide by protection of the amino- or carboxy-terminus, cyclisation of the peptide or construction of the peptide as a retroinvertopeptide.

In a preferred embodiment, the synthesized peptide or the name or structure of the peptide is provided with an indication as to its use e.g., as determined by a screen described herein.

A further aspect of the present invention provides a method of manufacturing a peptide identified by a method of the present invention for use in medicine comprising:

(i) performing a method as described herein to thereby identify or determine a peptide capable of forming a conformation sufficient for binding a target protein and/or nucleic acid; and (ii) using the peptide in the manufacture of a therapeutic or prophylactic for use in medicine.

In one embodiment, the method comprises the additional step of isolating the peptide. Alternatively, a compound is identified and is produced for use in the manufacture of a compound for use in medicine.

In one embodiment, the peptide capable of forming a conformation sufficient for binding a target protein and/or nucleic acid is a mimotope of a Der p 1 antibody. More preferably, the peptide is a mimotope of the monoclonal antibody 2C7 that specifically binds to Der p 1. Even more preferably, the peptide capable of forming a conformation sufficient for binding a target protein and/or nucleic acid is a peptide comprising an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91.

Accordingly, a method of treatment comprises, administering to a subject in need of treatment an effective amount of a peptide that is a mimotopes of a structural feature of an allergen, wherein administration of said peptide induces an antibody response against the allergen. Preferably, the antibody response is an IgG response. In a preferred embodiment, a method of treatment comprises, administering to a subject in need of treatment an effective amount of a peptide comprising an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91, wherein the peptide induces an immune response against Der p 1. Preferably the immune response is an IgG response (ie an antibody response).

As will be apparent to the skilled artisan this method of the invention provides a method of inducing desensitization to the dust mite allergen Der p 1, and preferably desensitization to a dust mite. As used herein, the term desensitization shall be taken to mean that the treatment is capable of inhibiting an allergic (IgE) response in a subject to an allergen). Accordingly, the present invention provides a method for desensitizing a subject to an allergen said method comprising administering an effective amount of a peptide that has a conformation sufficient for binding to IgE that specifically binds said allergen, wherein said peptide suppresses an allergic response to the allergen. Preferably, the peptide suppresses or inhibits the ability of IgE to bind to an allergen and cross-link thereby inducing an allergic response. Such suppression may be by virtue of the peptide inducing a specific antibody response against the allergen that inhibits the binding of IgE to the allergen. Alternatively, or in addition, the peptide inhibits allergen binding to the antigen binding site of an IgE thereby inhibiting the ability of the IgE to bind to the allergen. Alternatively, or in addition, the peptide induces the formation and/or activation of suppressor T cells, thereby suppressing an allergic response.

In one embodiment, the present invention provides a method for treating an allergic response and/or allergic disease caused or induced by an environmental allergen, preferably a mite.

In a preferred embodiment, the present invention provides a method for treating a subject that has IgE that binds to Der p 1 comprising administering to a subject in need of treatment an effective amount of a peptide comprising an amino acid sequence selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90 and SEQ ID NO: 91, wherein the peptide induces an immune response against Der p 1. Preferably the immune response is an IgG response (ie an antibody response) (ie. desensitizes the subject).

This embodiment of the invention need not be limited to those subjects that have already raised an immune response against an allergen, but is also useful for "immunising" subjects against allergens (particularly Der p 1).

In accordance with this aspect of the invention the peptide of the invention need only be administered directly to the subject, for example by injection, to induce an immune response against Der p 1. Alternatively, or in addition, the peptide is administered with an adjuvant, such as, for example, aluminium hydroxide, aluminium phosphate, Freund's complete adjuvant, Freund's incomplete adjuvant, the oil emulsion MF59 (Chiron Corporation), RC-529 (Corixa Corporation), an immunostimulatory oligonucleotide (as described in Narayanan et al., *J. Med. Chem.* 46: 5031-5044, 2003 and reviewed in Rothenfusser et al., *Curr. Opin. Mol. Ther.,* 5: 98-106, 2003) or the saponin derivative QS21. Alternatively, or in addition, as exemplified herein, the peptide may be administered while conjugated to the phage from which it is displayed, and thereby induce an immune response against Der p 1. Alternatively, or in addition, the peptide is administered.

Alternatively, or in addition, the peptide is administered with an immunogenic carrier protein such as, for example, keyhole limpet haemocyanin, a tetanus toxin, a diphtheria toxin, an enterobacter toxin A or B subunit, and a hepatitis B coat protein As will be apparent to the skilled artisan, the peptide may also be synthesised or expressed as a fusion with an immunogenic carrier protein such as, for example, a Glutathione-S-transferase protein of a *Schistosomas* species.

As will be apparent to the skilled artisan, the peptide per se need not be administered, rather a cell expressing and/or displaying the peptide may be administered, or a DNA vaccine may be administered, ie a nucleic acid capable of encoding a peptide that induces an immune response against Der p 1. Methods of formulating such compounds are known in the art and/or described herein.

Clearly the present invention encompasses the use of a peptide identified by a method of the present invention that is a mimotope of Der p 1 in the manufacture of a medicament for use in the treatment of an allergic disease, more preferably an allergy to Der p 1, eg allergic asthma. In one embodiment, the present invention provides for the use of a peptide comprising an amino acid sequence set forth in any one of SEQ ID NOs: 84 to 93 in the manufacture of a medicament for the treatment of an allergic disease, more preferably an allergy to Der p 1, eg allergic asthma.

Additionally, the present invention encompasses a peptide of identified by the method of the present invention when used in the treatment of an allergic disease, more preferably an allergy to Der p 1, eg allergic asthma. In one embodiment, the present invention provides a peptide comprising an amino acid sequence set forth in any one of SEQ ID NOs: 84 to 93 when used to treat an allergic disease, more preferably an allergy to Der p 1, eg allergic asthma.

The present inventors have also isolated several peptide inhibitors that are inhibitors of c-Jun self dimerisation. Accordingly, the present invention provides a peptide inhibitor of C-Jun homo-dimerization. Preferably, the peptide inhibitor is a peptide having a conformation sufficient for binding to c-Jun. More preferably, the peptide inhibitor is a peptide having a conformation sufficient for binding to a region of c-Jun required for homo-dimerization, such as, for example, a leucine zipper region of c-Jun.

In one embodiment, the present invention also provides a peptide selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, to SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO:

164 and SEQ ID NO: 165. Preferably, the peptide is capable of inhibiting self-dimerization of c-Jun.

In another embodiment, the present invention provides a peptide encoded by a nucleic acid comprising a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162. Preferably, the peptide is capable of inhibiting self-dimerization of c-Jun.

In another embodiment, the present invention provides a nucleic acid comprising a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162. Preferably, the nucleic acid encodes a peptide that is capable of inhibiting self-dimerization of c-Jun.

In a still further embodiment, the present invention provides a nucleic acid capable of encoding a peptide comprising an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165. Preferably, the nucleic acid encodes a peptide that is capable of inhibiting self-dimerization of c-Jun.

As stated supra the peptides identified by the present inventors are capable of inhibiting the homo-dimerization of c-Jun. Accordingly, in one embodiment, the present invention provides a method for inhibiting self dimerization of c-Jun comprising administering a peptide inhibitor identified by the method of the present invention to a cell or subject comprising or expressing a c-Jun polypeptide. Preferably, the peptide inhibitor has a conformation sufficient for binding a c-Jun polypeptide.

In a particularly preferred embodiment, the present invention provides a method for inhibiting the homo-dimerization of c-Jun comprising administering a peptide that comprises an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165 to a cell and/or subject comprising and/or expressing c-Jun.

In another particularly preferred embodiment, the present invention provides a method for inhibiting the homo-dimerization of c-Jun comprising administering a nucleic acid capable of expressing a peptide that comprises an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165 to a cell and/or subject comprising and/or expressing c-Jun, wherein the nucleic acid is placed in operable connection with a promoter thereby enabling expression of said peptide.

In yet another particularly preferred embodiment, the present invention provides a method for inhibiting the homo-dimerization of c-Jun comprising administering a peptide encoded by a nucleic acid comprising a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, to SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162 to a cell and/or subject comprising and/or expressing c-Jun.

In a still further embodiment, the present invention provides a method provides a method for inhibiting the homo-dimerization of c-Jun comprising administering a nucleic acid comprising a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162 to a cell and/or subject comprising and/or expressing c-Jun, wherein the nucleic acid is placed in operable connection with a promoter thereby enabling expression of said peptide.

A homodimer of c-Jun is required for effective activation of this transcription factor. Active c-Jun has been implicated in cell survival, cell differentiation and neuronal regeneration. Furthermore, c-Jun inhibition has been shown to protect neurons from apoptosis both in vitro and in vivo (Estus et al., *J. Cell Biol.,* 127: 1717-1727, 1994 and Behrens et al., *Nat. Genet.* 21: 326-329, 1999). In fact, studies have shown that inhibition of c-Jun function is neuroprotective in a model of neurodegenerative disease (Garcia et al., *J. Neuroscience,* 22: 2174-2184, 2002.

Accordingly, the present invention provides a method for treating a neurodegenerative disease comprising administering to a subject in need of treatment a peptide that comprises an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165. Preferably, the subject in need of treatment suffers from a neurodegenerative disease, more preferably Huntington's disease.

In another embodiment, the present invention provides a method for treating a neurodegenerative disease comprising administering to a subject in need of treatment a peptide encoded by a nucleic acid that comprises a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162. Preferably, the subject in need of treatment suffers from a neurodegenerative disease, more preferably Huntington's disease.

In a further embodiment, the present invention provides a method for treating a neurodegenerative disease comprising administering to a subject in need of treatment a nucleic acid that comprises a nucleotide sequence selected from the group consisting of SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159 and SEQ ID NO: 162, wherein the nucleic acid is placed in operable connection with a promoter thereby enabling expression of said peptide in a cell of the subject. Preferably, the subject in need of treatment suffers from a neurodegenerative disease, more preferably Huntington's disease.

In a still further embodiment, the present invention provides a method for treating a neurodegenerative disease comprising administering to a subject in need of treatment a nucleic acid capable of encoding a peptide that comprises an amino acid sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165, wherein the nucleic acid is placed in operable connection with a promoter thereby enabling expression of said peptide in a cell of the subject. Preferably, the subject in need of treatment suffers from a neurodegenerative disease, more preferably Huntington's disease.

In yet another preferred embodiment, the present invention provides a method for the treatment of a cancer or a tumor or a malignancy comprising administering an effective amount of a peptide that inhibits the interaction of a SCL and E47 proteins. Preferably, the present invention provides a method of treating leukemia comprising administering a peptide that inhibits the interaction of a SCL and E47 proteins.

In a particularly preferred embodiment, a peptide capable of inhibiting the interaction of SCL and E47 comprises an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79 and SEQ ID NO: 81.

In another particularly preferred embodiment, a peptide capable of inhibiting the interaction of SCL and E47 is encoded by a nucleic acid comprising a nucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 or SEQ ID NO: 80.

For the treatment of cancers it is particularly preferred to target the interaction of SCL and E47 in one or more specific cells or tissues, such as, for example, a cancer tissue or cell, thereby ensuring that the active compound is delivered to that cell-tissue and does not inhibit cell proliferation generally. Antibodies recognizing tumor-specific antigens have been used to deliver cytotoxic drugs to tumors. Antibodies recognizing tumor-specific antigens can be conjugated to the active compound.

Theiss et al, *Exp. Hematol.* 31: 1223-1229, 2003 describe the use of CpG-oligodeoxynucleotides and CD40L to stimulate B-cell chronic lymphocytic leukemia (B-CLL) cells which thereby resulted in increased transduction of these cells with a recombinant adeno-associated virus and increased expression of a transgene carried by the virus.

Alternatively, nucleic acid encoding an inhibitor of SCL and E47 interaction, such as, for example nucleic acid comprising a nucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 or SEQ ID NO: 80, is introduced to a subject in need of treatment and expressed therein operably under the control of a suitable tumor-specific promoter sequence (eg the WT1 promoter and enhancer described in Hosen et al, *Leukemia,* 2004). Tumor-specific promoters/enhancers have also been used in a therapeutic approach called "virus-directed enzyme/prodrug therapy" (VDEPT), wherein tumor-killing efficacy can be enhanced with reduced side effects on normal cells (the so-called "bystander effect"). For example, the alpha-fetoprotein (AFP) promoter/enhancer cassette has been utilized to control E1 expression from an Adenoviral vector, to induce a virus-mediated oncolytic effect on hepatocellular carcinoma. Alternatively, a variation of this system, the "Complementary-Adenoviral Vector System" as described in US Patent Publication No. 20020142989 may be employed.

Clearly the present invention provides for the use of a peptide of identified by the method of the present invention that is capable of inhibiting the interaction of SCL and E47 in the manufacture of a medicament for the treatment of a cancer, preferably a leukemia.

In one embodiment, the present invention provides for the use of a peptide comprising an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79 and SEQ ID NO: 81 in the manufacture of a medicament for the treatment of a cancer, preferably a leukemia.

In another embodiment the present invention provides for the use of a nucleic acid comprising a nucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 or SEQ ID NO: 80 in the manufacture of a medicament for the treatment of a cancer, preferably a leukemia.

In a further embodiment the present invention provides a peptide of identified by the method of the present invention that is capable of inhibiting the interaction of SCL and E47 in the manufacture of a medicament for the treatment of a cancer, preferably a leukemia.

In one embodiment, the present invention provides a peptide comprising an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79 and SEQ ID NO: 81 when used for the treatment of a cancer, preferably a leukemia.

In another embodiment the present invention provides a nucleic acid comprising a nucleotide sequence selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 or SEQ ID NO: 80 when used for the treatment of a cancer, preferably a leukemia.

In another preferred embodiment, the present invention provides a method of treating a *S. aureus* infection comprising administering an effective amount of a peptide of identified by the method of the present invention that is capable of specifically binding a protein from the FemABX family of proteins of *S. aureus*, and wherein said peptide of identified by the method of the present invention has antibacterial activity.

In one embodiment, the protein from the FemABX family of proteins of *S. aureus* is a FemX protein. In another embodiment, the protein from the FemABX family of proteins is a Sortase A protein and/or a Sortase B protein.

In one embodiment, the present invention provides a method of treating a *S. aureus* infection comprising administering an effective amount of a peptide of identified by the method of the present invention that is capable of specifically binding to a FemX polypeptide of *S. aureus*, and wherein said peptide of identified by the method of the present invention has antibacterial activity or antivirulence activity.

In another embodiment, the present invention provides a method of treating a *S. aureus* infection comprising administering an effective amount of a peptide of identified by the method of the present invention that is capable of specifically binding to a Sortase A polypeptide of *S. aureus*, and wherein said a peptide of identified by the method of the present invention has antibacterial activity or antivirulence activity.

In a further embodiment, the present invention provides a method of treating a *S. aureus* infection comprising administering an effective amount of a peptide of identified by the method of the present invention that is capable of specifically binding to a Sortase B polypeptide of *S. aureus*, and wherein said a peptide of identified by the method of the present invention has antibacterial activity or antivirulence activity.

In another embodiment, the method for treating a *S. aureus* infection comprises administering an effective amount of two or more peptides of identified by the method of the present invention that is capable of specifically binding one or more proteins from the FemABX family of proteins of *S. aureus*, and wherein said peptides of identified by the method of the present inventions have antibacterial activity.

Preferably, the peptide of identified by the method of the present invention is identified using a method described herein.

In one embodiment, the subject undergoing treatment has been previously diagnosed with a *S. aureus* infection.

In a still further preferred embodiment, the present invention provides a method for treating an infection by an protozoan selected from the group consisting of *P. falciparum, C. parvum* and *T. brucei* comprising administering an effective amount of a peptide of identified by the method of the present invention that is capable of specifically binding a tubulin protein of *P. falciparum, C. parvum* or *T. brucei*, and wherein said peptide of identified by the method of the present invention has antimicrobial activity.

In one embodiment, the infection is by *P. falciparum*. Commonly such an infection is associated with malaria. Accordingly the present invention provides a method of treating malaria comprising administering a peptide of identified by the method of the present invention that is capable of specifically binding a tubulin polypeptide of *P. falciparum*, and wherein said peptide of identified by the method of the present invention has antimicrobial activity.

In accordance with this embodiment, the peptide of identified by the method of the present invention is capable of binding a tubulin polypeptide of *C. falciparum*. Preferably, the tubulin is an $\alpha_1$-tubulin (SEQ ID NO: 167) and/or a β-tubulin (SEQ ID NO: 171) of *P. falciparum*. Preferably, the peptide is identified, isolated and/or provided using a method described herein.

Clearly, the present invention encompasses the use of a peptide of identified by the method of the present invention capable of specifically binding a tubulin polypeptide of *P. falciparum* in the manufacture of a medicament for the treatment of malaria. Additionally the present invention encompasses a peptide of identified by the method of the present invention capable of specifically binding a tubulin polypeptide of *P. falciparum* when used to treat malaria.

In another embodiment, the infection is by *C. parvum*. Such infection is commonly associated with an acute and/or persistent diarrheal disease and/or inflammatory bowel disease. Accordingly the present invention provides a method of treating a diarrheal disease and/or inflammatory bowel disease comprising administering an effective amount of a peptide identified by the method of the present invention that is capable of specifically binding a tubulin polypeptide of *C. parvum*, and wherein said peptide of identified by the method of the present invention has antimicrobial activity.

In accordance with this embodiment, the peptide of identified by the method of the present invention is capable of binding a tubulin polypeptide of *C. parvum*. Preferably, the tubulin is an α-tubulin (SEQ ID NO: 175) and/or a β-tubulin (SEQ ID NO: 179) of *C. parvum*. Preferably, the peptide of identified by the method of the present invention is identified, isolated and/or provided using a method described herein.

Clearly the present invention encompasses the use of a peptide of identified by the method of the present invention capable of specifically binding a tubulin polypeptide of *C. parvum* in the manufacture of a medicament for the treatment of diarrheal disease and/or inflammatory bowel disease. Additionally the present invention encompasses a peptide of identified by the method of the present invention capable of specifically binding a tubulin polypeptide of *C. parvum* when used to treat diarrheal disease and/or inflammatory bowel disease.

In a still further embodiment, the infection is by *T. brucei*. Preferably, *T. brucei* rhodesience. Such infection is commonly associated with sleeping sickness. Accordingly the present invention provides a method of treating sleeping sickness comprising administering an effective amount of a peptide of identified by the method of the present invention that is capable of specifically binding a tubulin polypeptide of *T. brucei* rhodesience, and wherein said peptide of identified by the method of the present invention has antimicrobial activity.

In accordance with this embodiment, the peptide of identified by the method of the present invention is capable of binding a tubulin polypeptide of *T. brucei rhodesience*. Preferably, the tubulin is an $\alpha$-tubulin (SEQ ID NO: 183) and/or a $\beta$-tubulin (SEQ ID NO: 187) of *T. brucei rhodesience*. Preferably, the peptide of identified by the method of the present invention is identified, isolated and/or provided using a method described herein.

Clearly the present invention encompasses the use of a peptide of identified by the method of the present invention capable of specifically binding a tubulin polypeptide of *T. brucei rhodesience* in the manufacture of a medicament for the treatment of sleeping sickness. Additionally the present invention encompasses a peptide of identified by the method of the present invention capable of specifically binding a tubulin polypeptide of *T. brucei rhodesience* when used to treat sleeping sickness.

In yet another preferred embodiment, the present invention provides a method for immunizing a subject against *H. influenzae* comprising administering a peptide of identified by the method of the present invention that is a mimetic of a D15 polypeptide or nucleic acid encoding same to a subject, wherein said peptide of identified by the method of the present invention induces an immune response against *H. influenzae*.

In accordance with this embodiment, the peptide of identified by the method of the present invention is administered to a subject to induce a specific immune response against the D15 protein of *H. influenzae*. The outer membrane D15 protein is conserved amongst several types of *H. influenzae*, accordingly such a vaccine is useful for vaccination against *H. influenzae* serotypes a, b, c, d, e, and f, NTHI, and *H. parainfluenzae*.

In one embodiment, the present invention provides a method for immunizing a subject against a *H. influenzae* disease (eg a disease selected from the group consisting of sinusitis, pneumonia, bronchitis, bacteremia and meningitis) comprising administering a peptide of identified by the method of the present invention that is a mimetic of a D15 polypeptide or nucleic acid encoding same to a subject, wherein said peptide of identified by the method of the present invention induces an immune response against *H. influenzae*.

Preferably, the peptide of identified by the method of the present invention is identified, isolated and/or provided using a method described herein.

Clearly the present invention encompasses the use of a peptide of identified by the method of the present invention that is a mimetic of a D15 polypeptide or nucleic acid encoding same in the manufacture of a medicament for the treatment of a *H. influenzae* disease (eg a disease selected from the group consisting of sinusitis, pneumonia, bronchitis, bacteremia and meningitis). Additionally the present invention encompasses a peptide of identified by the method of the present invention that is a mimetic of a D15 polypeptide or nucleic acid encoding same when used to treat a *H. influenzae* disease (eg a disease selected from the group consisting of sinusitis, pneumonia, bronchitis, bacteremia and meningitis).

The present invention is further described with reference to the following non-limiting examples.

EXAMPLE 1

The Construction of a Biodiverse Nucleic Acid Fragment Expression Library in the Vector pDEATH-Trp Nucleic acid was isolated from the following bacterial species:

| | |
|---|---|
| 1 | *Archaeoglobus fulgidis* |
| 2 | *Aquifex aeliticus* |
| 3 | *Aeropyrum pernix* |
| 4 | *Bacillus subtilis* |
| 5 | *Bordetella pertussis* TOX6 |
| 6 | *Borrelia burgdorferi* |
| 7 | *Chlamydia trachomatis* |
| 8 | *Escherichia coli* K12 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *S nechosistis* PCC 6803 |
| 18 | *Thermoplasma volcanium* |
| 19 | *Thermotoga maritima* |

Nucleic acid fragments were generated from the genomic DNA of each genome using 2 consecutive rounds of primer extension amplification using tagged random oligonucleotides with the sequence:

5'-GACTACAAGGACGACGACGACAAGGCT-TATCAATCAATCAN$_6$-3' (SEQ ID NO: 33). The PCR amplification was completed using the Klenow fragment of *E. coli* DNA polymerase I in the following primer extension reaction:

| Reagent | Volume |
|---|---|
| DNA (100-200 ng) | |
| Oligonucleotide comprising SEQ ID NO: 33 (25 μM) | 4 μl |
| $H_2O$ | to 17.4 μl. |

Samples were then boiled for 3-5 minutes to denature the nucleic acid isolated from the bacteria, before being snap cooled, to allow the tagged random oligonucleotides to anneal to said nucleic acid. These samples were then added to the following reagents:

| | |
|---|---|
| Klenow buffer | 3 μl |
| dNTP (2 mM) | 3 μl |
| Klenow | 0.6 μl |
| Polyethylene Glycol (8,500) | 6 μl |

Primer extension reactions were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.5 μl of the Klenow fragment of *E. coli* DNA polymerase I was added to each reaction and the samples incubated at 15° C. for 30 minutes, then at room temperature for 2 hours, before being heated to 37° C. for 15 minutes.

Following boiling the samples, following snap cooling another 2 rounds of primer extension were completed using the tagged random oligonucleotide:

(SEQ ID NO: 34)
5'-GACTACAAGGACGACGACGACAAGGCTTATCAATCAATCA$N_9$-3'

To complete this the following reagents were added to the samples of the previous step:

| | |
|---|---|
| Oligonucleotide comprising SEQ ID NO 34 (25 μM) | 4 μl |
| Klenow Buffer | 1 μl |
| dNTP (2 mM) | 3 μl |
| Klenow | 0.5 μl |
| $H_2O$ | to 40 μl |

Samples were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.5 μl of the Klenow fragment of *E. coli* DNA polymerase I was added to each reaction and the samples incubated at 15° C. for 30 minutes, then at room temperature for 2 hours, before being heated to 37° C. for 15 minutes.

Following completion of the primer extension amplification all sample volumes were increased to 500 μl with TE buffer and added to an Amicon spin column. These columns were then centrifuged for 15 minutes at 3,800 rpm in a microcentrifuge. Columns were then inverted and 30 μl of TE buffer was added before the columns were centrifuged for 2 minutes at 3,800 rpm, with this fraction collected for later use. The Klenow amplified DNA was then used in subsequent DNA manipulations.

The now purified primer extension products were then used in a PCR reaction with an oligonucleotide comprising the following sequence: 5'-GAGAGAAT<u>TCA</u>GG<u>TCA</u>GA <u>CTA</u>CAAGGACGACGACGACAAG-3' (SEQ ID NO: 35), wherein an EcoRI restriction endonuclease site is shown in bold text, and three stop codons are underlined. Note that each of the stop codons is in a different reading frame.

Thus, the following PCR reaction was used:

| | |
|---|---|
| Oligonucleotide comprising SEQ ID NO: 35 (10 μM) | 12 μl |
| PCR buffer | 5 μl |
| dNTP (2 mM) | 5 μl |
| Taq polymerase (Boehringer) 5.5 U/μl) | 0.4 μl |
| $H_2O$ | 26.6 μl |
| Klenow amplified DNA | 2 μl |

Reactions were then cycled in a thermocycler using the following program:

95° C. for 2 min; 60° C. for 30 sec; 72° C. for 1 min;

95° C. for 20 sec; 60° C. for 30 sec; 72° C. for 1 min (repeated 29 times); and

72° C. for 5 min.

PCR products were then purified using Amicon spins columns which fractionate on the basis of size.

Figure 2:
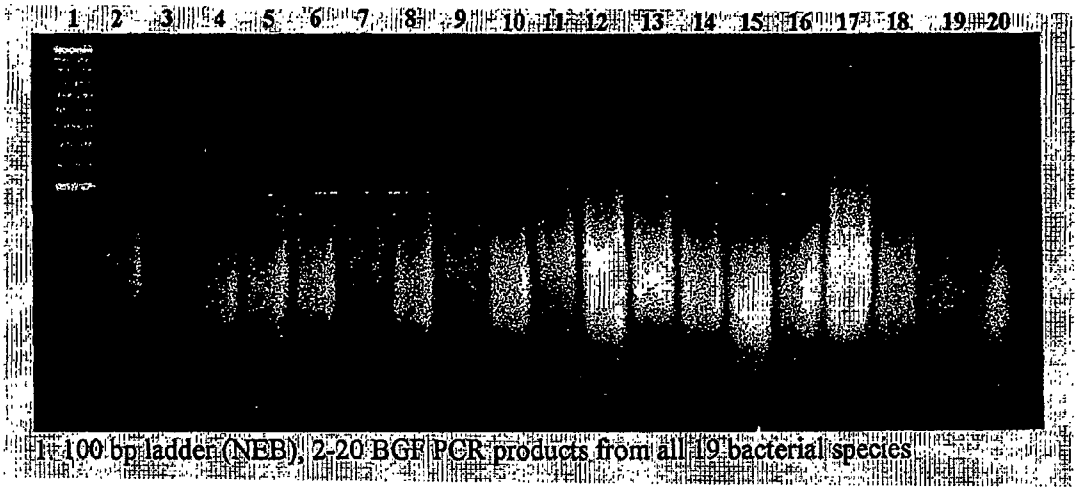
FIG. 2 is a photographic representation showing amplification products of random PCR amplification of genomic DNA isolated from *Archaeoglobus fulgidis, Aquifex aeliticus, Aeropyrum pernix, Bacillus subtilis, Bordetella pertussis* TOX6, *Borrelia burgdorferi, Chlamydia trachomati, Escherichia coli* K12, *Haemophilus influenzae* (rd), *Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium*, and *Thermotoga maritima*. The molecular weight marker is shown on the far left.

The PCR products were then analyzed by electrophoresis on standard TAE-agarose gels to determine the approximate size of the nucleic acid fragments generated as shown in FIG. 2. The nucleic acid concentration of the samples was also determined.

PCR products from each of the 19 bacterial species were then pooled to generate a biodiverse nucleic acid library. To do so, DNA from each organism was added in an equimolar amount when compared to the amount of nucleic acid added to the pool from the organism with the smallest genome. Between 1 μg and 10 μg of DNA from each organism was used, depending on the genome size of the organism from which the DNA was obtained.

Figure 3:
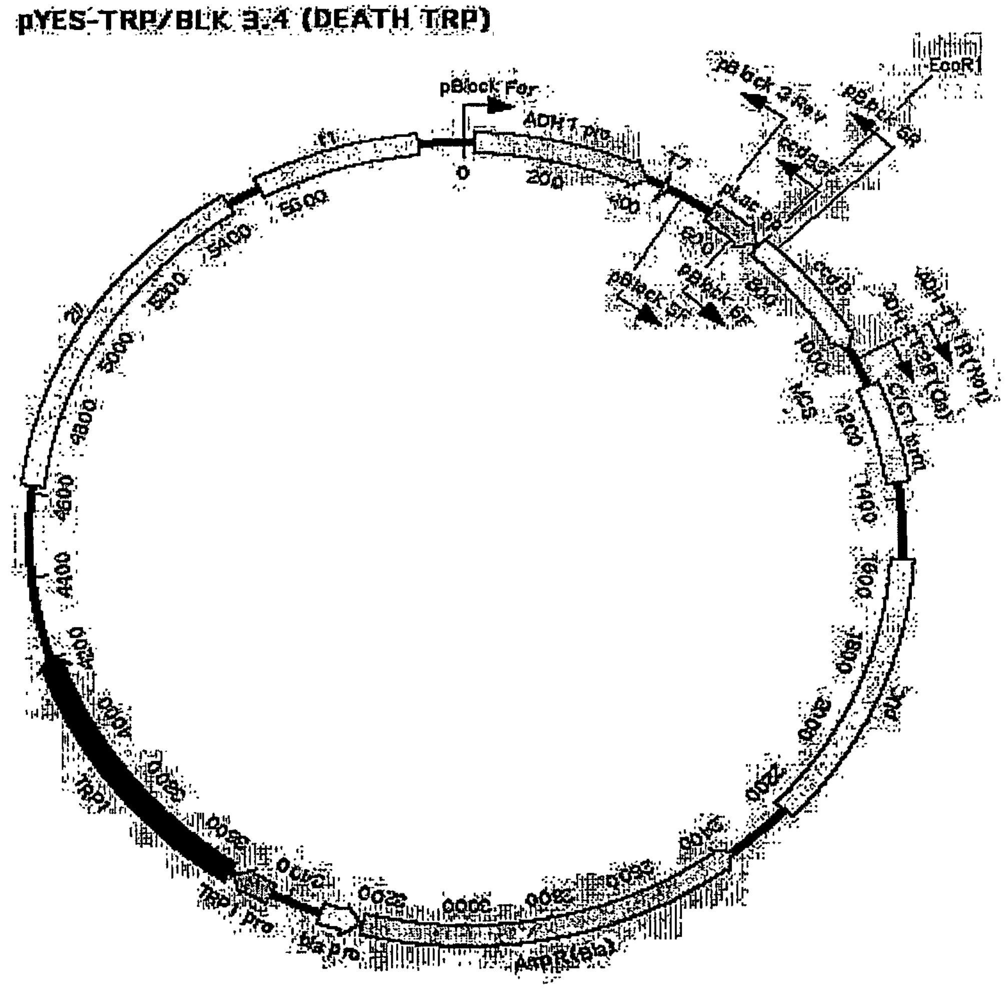
FIG. 3 is a schematic representation of the pDEATH-Trp vector (SEQ ID NO: 36). The pDEATH-Trp vector comprises a minimal ADH promoter for constitutive expression of a nucleic acid inserted into the vector in yeast cells; a T7 promoter for expression of a nucleic acid fragment in bacterial cells; a nucleic acid encoding a SV-40 nuclear localization signal to force any expressed polypeptide into the nucleus of a yeast cell; a CYC1 terminator, for termination of transcription in yeast cells; a nucleic acid encoding a peptide conferring ampicillin resistance, for selection in bacterial cells; a nucleic acid encoding TRP1 which allows auxotrophic yeast to grow in media lacking tryptophan; a pUC origin of replication, to allow the plasmid to replicate in bacterial cells; and a 2μ origin of replication, to allow the plasmid to replicate in yeast cells.

In order to allow efficient cloning of the nucleic acid fragments into the pDEATH-Trp vector (SEQ ID NO: 36; FIG. 3), both the fragments and the vector were digested with the EcoRI restriction endonuclease. Restriction digests were completed in the following reactions:

Digestion of PCR products used the following reaction conditions:

| PCR products (1 μg) | |
|---|---|
| EcoR I Buffer (Promega) | 17 μl |
| BSA (10x) | 17 μl |
| EcoR I enzyme (20 U/μL) (Promega) | 0.9 μl |
| $H_20$ | to 170 μl |

Restriction digests were allowed to proceed for 40 minutes at 37° C. Samples were then purified using QIAquick PCR purification columns as per manufacturer's instructions. Nucleic acid was eluted into 50 μl of $H_2O$.

Digestion of pDEATH-Trp vector used the following reaction conditions:

| pDEATH-Trp (25 μg) | |
|---|---|
| EcoR I Buffer (Promega) | 100 μl |
| BSA (10X) | 100 μl |
| EcoR I enzyme (20 U/μL) | 4 μl |
| $H_20$ | to 1000 μl |

Restriction digests were allowed to proceed for 5 minutes at 37° C. Samples were then purified using 3 QIAquick PCR purification columns as per manufacturer's instructions. Nucleic acid was eluted into 150 μl of $H_2O$.

The fragments generated from the PCR products were then ligated into the pDEATH-Trp vector (SEQ ID NO 36) using the following reaction:

| pDEATH-Trp (2 μg) | |
|---|---|
| BGF-PCR Fragments (1 μg) | |
| Ligation Buffer (10x) (NEB) | 20 μl |
| T4 DNA Ligase (NEB) | 10 μl |
| $H_20$ | to 200 μl |

Ligation reactions were allowed to proceed overnight at 16° C. The ligase was then heat inactivated by incubating the samples at 65° C. for 30 minutes. Following completion of the ligation reaction sample volumes were increased to 500 μl with TE buffer and added to an Amicon spin column. These columns were then centrifuged for 15 minutes at 3,800 rpm in a microcentrifuge. Columns were then inverted and 30 μl of TE buffer was added before the columns were centrifuged for 2 minutes at 3,800 rpm, with this fraction collected for later use.

Figure 4:
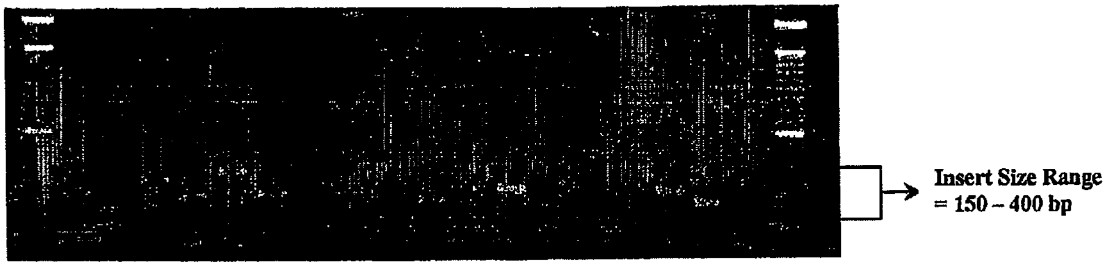
FIG. 4 is a photographic representation showing nucleic acid fragments isolated from bacterial clones carrying the pDEATH-Trp vector. The isolated vector was digested with the restriction endonuclease EcoRI and the resulting fragments electrophoresed. The molecular weight marker is shown on the far left and far right, and the text indicates the size range of the nucleic acid fragments in base pairs.

The pDEATH-Trp vector containing the biodiverse nucleic acid fragment was then transformed into *E. coli* TOP10 cells. Expression vectors were then isolated from bacteria using standard procedures. Restriction enzyme digestion of the isolated vectors using EcoRI was then used to characterise the size of the inserts contained in the library, as shown in FIG. 4.

Vectors were then pooled and transformed into the yeast strain PRT 51. Yeast strain PRT-51 is characterized by the following genotype: MATα, his3, trp1, ura3, 6 LexA-LEU2, lys2:3 clop-LYS2, $CYH2^R$, ade2:G418-pZero-ade2, met15: Zeo-pBLUE-met15, his5::hygro.

The result of this transformation was a library of 61 million clones. The recombinant clones each express a peptide that is fused to another polynucleotide sequence encoding the FLAG epitope or other marker.

EXAMPLE 2

Characterization of a Biodiverse Nucleic Acid Fragment Expression Library in the pDEATH-Trp Vector Sequence analysis of nucleic acids cloned into pDEATH-Trp vector show that the fragments are derived from a variety of organisms, and encode a variety of proteins, as shown in Table 2.

TABLE 2

Characterization of nucleic acid fragment cloned into pDEATH-Trp

| No. | Insert size (bp) | Organism | Genbank ID | Function |
|---|---|---|---|---|
| 1 | 114 | *P. aeruginosa* | AAG05339.1 | Hypothetical Protein |
| 2 | 143 | *Synechocystis* PCC6803 | BAA10184.1 | Fructose |
| 3 | 166 | *E. coli* | AAC73742.1 | Lipoprotein |
| 4 | 180 | *B. subtilis* | CAB12555.1 | methyl-accepting chemotaxis protein |
| 5 | 150 | *N. meningitis* | AAF41991.1 | N utilization substance protein A |
| 6 | 240 | *E. coli* | AAC75637.1 | Hypothetical protein |
| 7 | 357 | *H. pylori* | AAD08555.1 | transcription termination factor NusA |
| 8 | 83 | *Z. maritima* | AAD36283.1 | Hypothetical protein |

EXAMPLE 3

Screening of a Biodiverse Nucleic Acid Fragment Library for Inhibitors of the Interaction Between the Polymyositis-Scleroderma Autoantigen (SCL) and Basic Helix-Loop-Helix Transcription Factor E47

Figure 5:
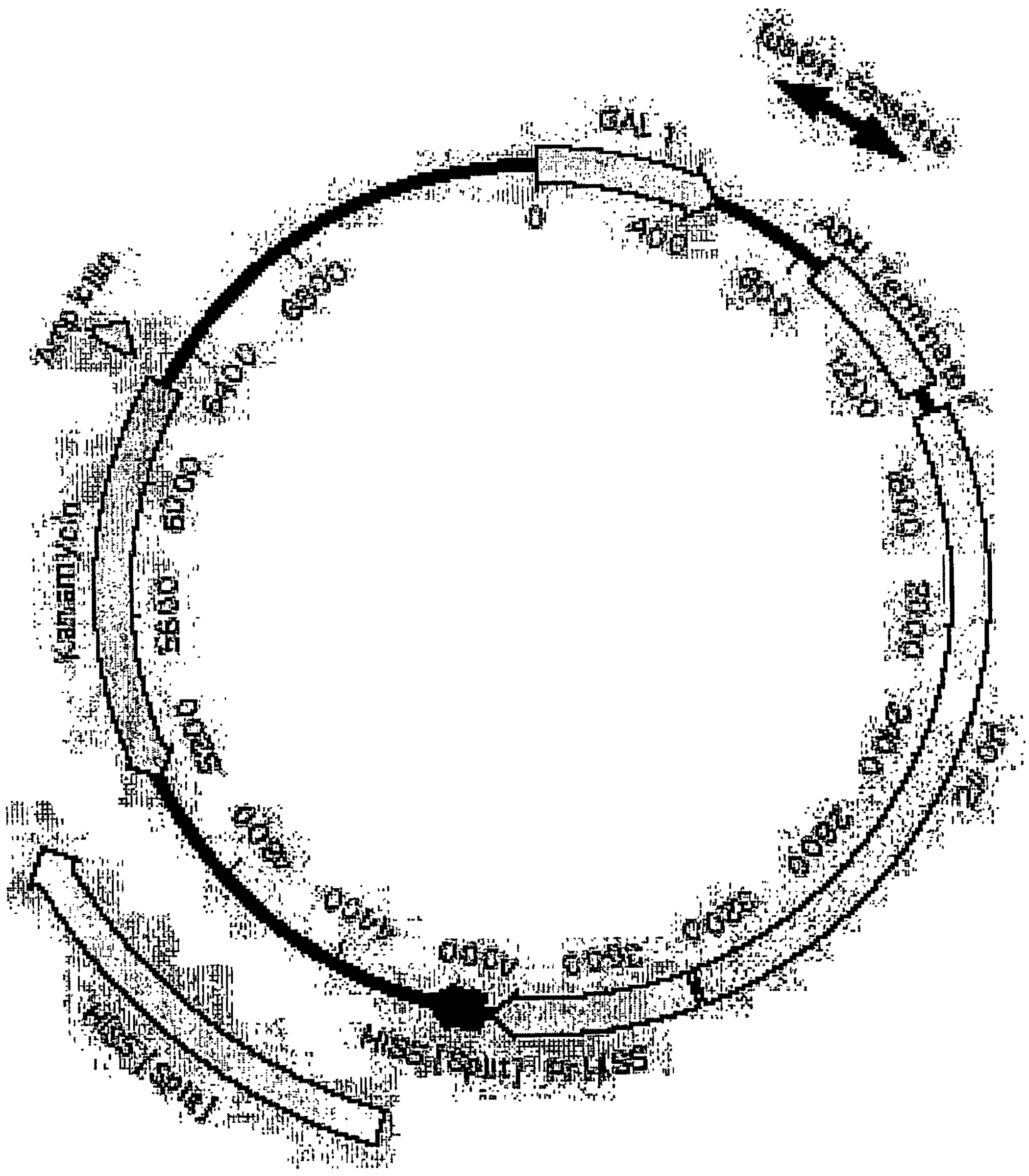
FIG. 5 is a schematic representation of the pJFK vector (SEQ ID NO: 60). The pJFK vector comprises a GAL1 promoter for inducible expression of a nucleic acid fragment in yeast cells; a nuclear localization signal to force any expressed polypeptide into the nucleus of a yeast cell; a nucleic acid encoding an activation domain derived from the B42 protein, to be expressed as a fusion with a polypeptide of interest in a "n"-hybrid screen; an ADH terminator or termination of transcription in yeast cells; a 2μ origin of replication, to allow the plasmid to replicate in yeast cells; an HIS5 gene to allow auxotrophic yeast to grow in media lacking histidine; a nucleic acid encoding a peptide conferring ampicillin resistance, for selection in bacterial cells; and a nucleic acid encoding a peptide conferring kanamycin resistance.
Figure 6:
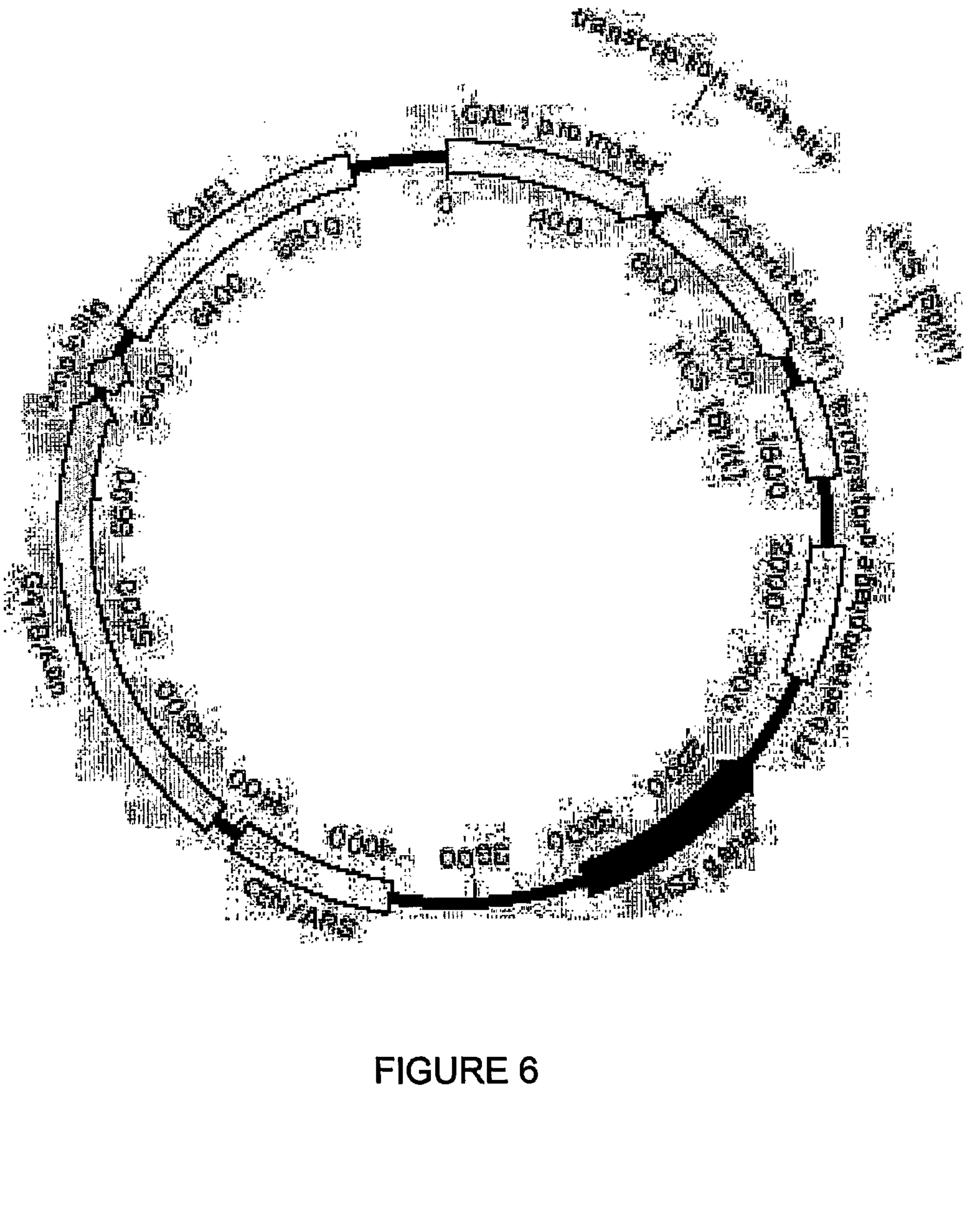
FIG. 6 is a schematic representation of the pDD vector (SEQ ID NO: 61). The pDD vector comprises a GAL1 promoter for inducible expression of a nucleic acid fragment in yeast cells; a nucleic acid encoding a LEXA1 protein, to be expressed as a fusion with a polypeptide of interest in a "n"-hybrid screen; an ADH terminator or termination of transcription in yeast cells; a 2μ origin of replication, to allow the plasmid to replicate in yeast cells; an HIS5 gene to allow auxotrophic yeast to grow in media lacking histidine; a nucleic acid encoding a peptide conferring ampicillin resistance, for selection in bacterial cells; and a nucleic acid encoding a peptide conferring kanamycin resistance.

Nucleic acid encoding the SCL protein was cloned into the prey vector pJFK (SEQ ID NO: 60; FIG. 5) in operable connection with a nuclear localisation signal, and a B42 activation domain. The nucleic acid encoding the E47 protein was cloned into the bait vector pDD (SEQ NO: 61; FIG. 6) in operable connection with the LexA DNA binding domain. The pDD vector also contains a nucleic acid encoding the HIS3 gene (FIG. 6).

These vectors were transformed into the PRT 480 yeast strain (which contains two LexA-CYH2 chimeric reporter genes and two LexA-URA3 counter selectable reporter genes).

Figure 7:
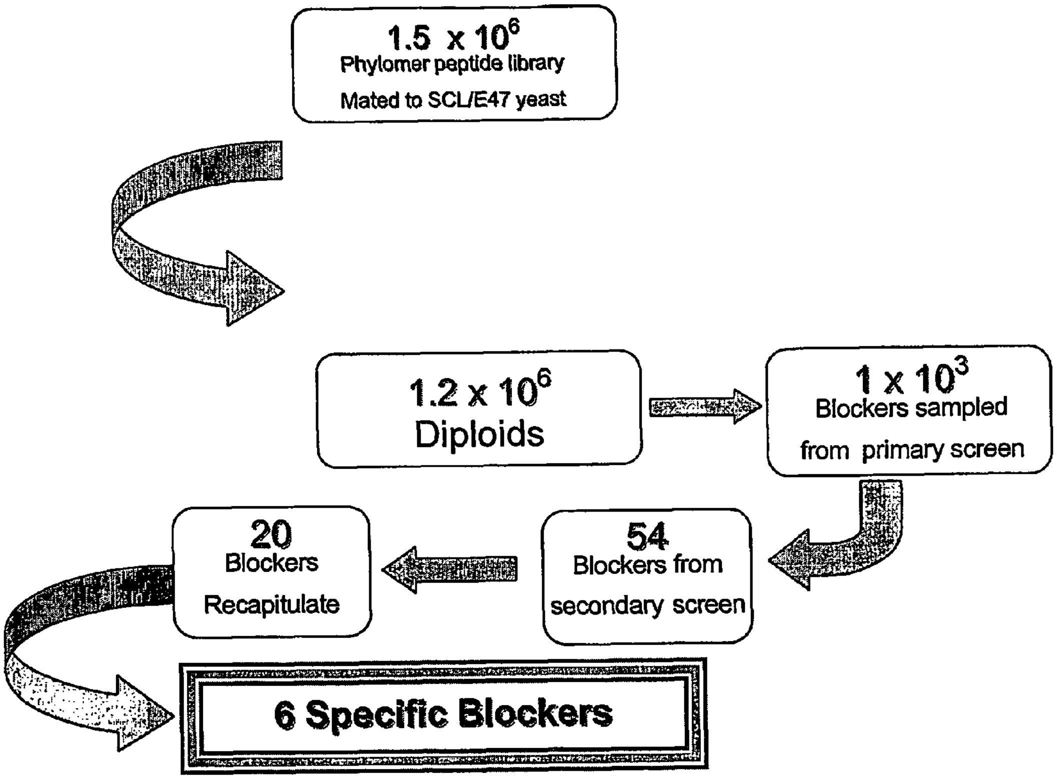
FIG. 7 is a schematic representation of a reverse two-hybrid screen to identify antagonists of the interaction of SCL/E47. Initially, yeast expressing a library of the present invention is mated to a yeast strain expressing E47 and SCL. From this screen 1000 clones were chosen that were able to grow on FOA plates. These were then screened to identify those clones that were not able to grow on LEU-plates. The plasmids that expressed putative antagonists of the SCL/E47 interaction were then isolated and re-transformed into yeast to confirm their ability to block such an interaction.

The process of screening the library is represented schematically in FIG. 7. Briefly, the PRT 480-SCL/E47 bait prey haploid strain was grown to high density in complete synthetic media lacking histidine and uracil (ie., HU media) and supplemented with 0.03% (w/v) galactose/2% (w/v) raffinose and then mass-mated with the PRT 51-library strain produced as described in Example 1. Approximately 300,000 diploids were plated onto 30 cm plates containing complete synthetic media lacking histidine and tryptophan (ie., HW media), and supplemented with 0.06% (w/v) galactose/0.04% 5-FOA and glucose.

After growth of these plates at 30° C. for 2-3 days, 1000 FOA-resistant colonies were isolated and plated onto a master-plate of complete synthetic media lacking histidine and tryptophan (ie., HW media). These cells potentially expressed peptide antagonists (ie., blockers) that prevent the SCL/E47 interaction, however may also include cells that had shut down expression of the URA3 reporter genes, such as, for example, by epigenetic means, including epistasis.

Figure 8:
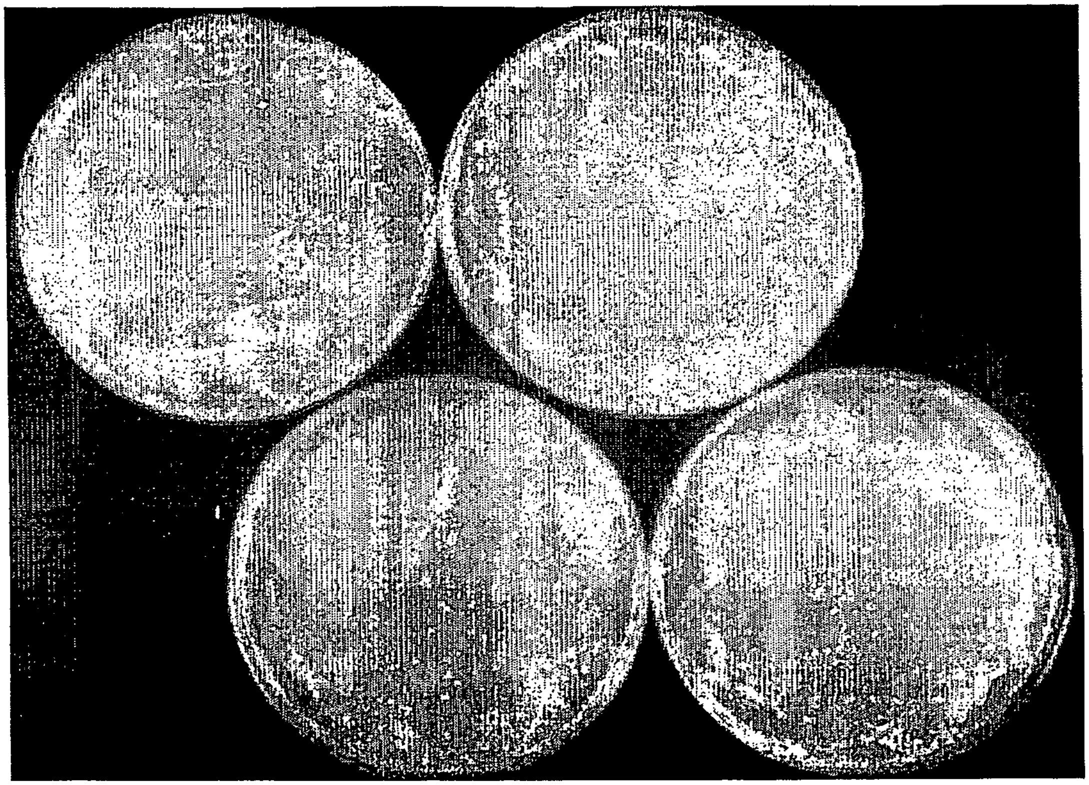
FIG. 8 is a photographic representation showing library clones that have not expressed the URA3 counter selectable marker gene on yeast 0.04% FOA plates, and are able to grow on 5-FOA.

Results of this primary reverse two-hybrid screen are shown in FIG. 8.

The FOA-resistant colonies were replica-plated from the master-plate onto plates containing HWU media, or media lacking histidine, tryptophan and leucine (ie. HWL media). The replica-plate media also contained various concentrations of galactose. By modulating the level of galactose in the media, we were able to discriminate between yeast cells expressing genuine peptide blockers as opposed to those cells that had shut down expression of the URA3 reporter genes, such as, for example, by epigenetic means, including epistasis.

Figure 9:
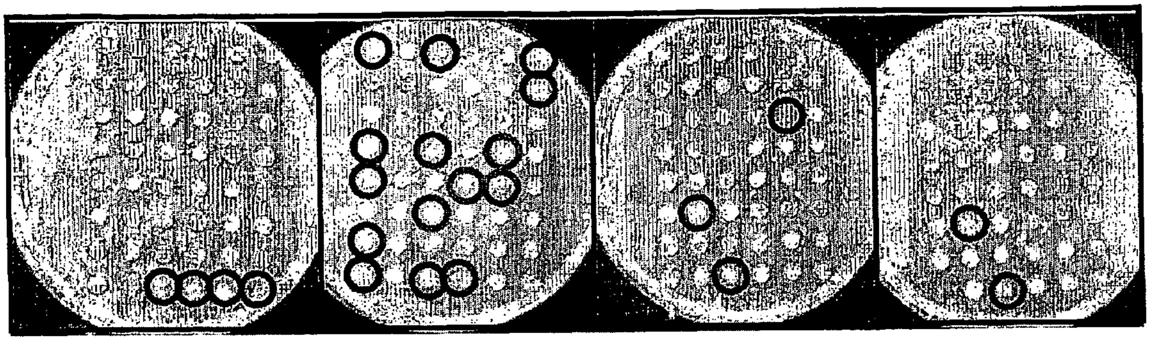
FIG. 9 is a photographic representation showing yeast colonies isolated from an initial reverse two-hybrid screen grown on media lacking leucine. The circled colonies are those that are not expressing the LEU2 selectable marker. Accordingly, it appears that these colonies express a peptide that inhibits the interaction of SCL and E47.

Results of this secondary screen are shown in FIG. 9. In summary, 54 colonies (6% of FOA-resistant colonies) were isolated from this screen.

Yeast colonies that exhibited reduced growth on media lacking leucine were selected, grown out on media containing leucine and selecting for the library plasmid and a library plasmid was subsequently rescued from each colony. Those plasmids that were from cells wherein the SCL/E47 interaction was antagonized or inhibited were sequenced.

Library plasmids were re-transformed into strain PRT51, and the resultant yeast cells were again mated with strain PRT 480 SCL/E47 haploids. Diploids were re-screened for their ability to block the SCL/E47 interaction, by plating in the forward direction on plates containing HWU or HWL media supplemented with various concentrations of galactose. The ability of a particular plasmid to recapitulate the blocked phenotype was determined.

Figure 10:
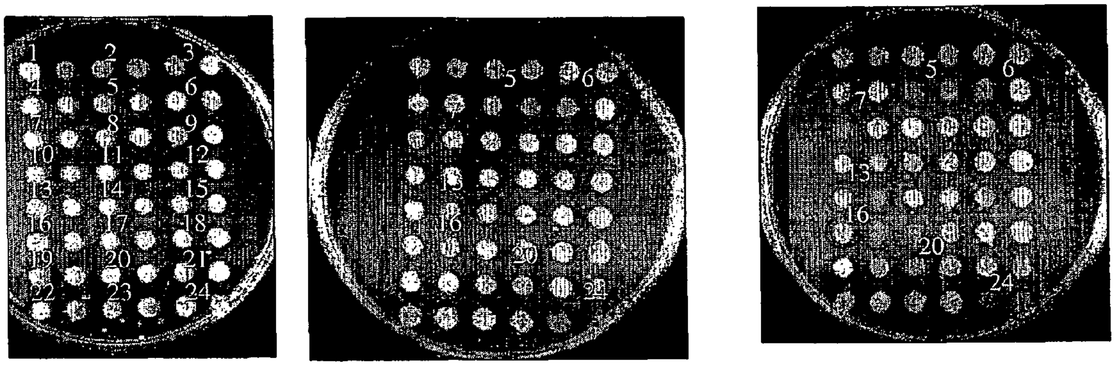
FIG. 10 is a photographic representation of yeast colonies expressing the E47 bait and SCL prey proteins in addition to putative peptide inhibitors identified in a reverse two-hybrid screen. These were tested for blocking of the interaction through growing the colonies on media lacking uracil and media lacking leucine. In this way any putative peptide inhibitors were re-tested for the ability to block the interaction between SCL and E47.

Data shown in FIG. 10 indicate that, for 54 colonies tested, the interaction between SCL and E47 was again inhibited in 26 clones (ie. 2% of FOA-resistant colonies). Seven clones were found to recapitulate the blocking of an interaction between SCL and E47 twice.

Subsequently, the specificity of blocking was assayed, by mating those strains that did recapitulate the blocked phenotype into a strain PRT480 expressing two interacting proteins selected from the group consisting of: (i) E2,2 2F and SCL; and (ii) ID and E47. The E2-22F protein is a helix-loop-helix protein that is capable of forming heterodimers with other helix-loop-helix proteins, such as, for example, SCL. The ID protein is another helix-loop-helix protein, which has been shown to bind E47 and inhibit the ability of E47 to bind DNA.

Of the 26 colonies tested, the interaction between SCL and E47 was specifically blocked in 6 colonies (Table 3).

TABLE 3

Specificity of antagonism of the SCL/E47 interaction

| Clone Number | Predicted fusion peptide size | Target interaction[(1)] SCL/E47 | SCL/E2.22F | Id1/E47 |
|---|---|---|---|---|
| BGF 05 | 55 | + | + | + |
| BGF 06 | 24 | + | − | − |
| BGF 13 | 10 | + | − | − |
| BGF 30 | | + | − | − |
| BGF 24 | 26 | + | − | − |
| BGF 35 | 63 | + | − | − |
| BGF 51 | | + | − | − |

(1)+, the interaction was blocked; −, the interaction was not blocked.

The plasmids were isolated from these clones and either the nucleic acid sequence or the predicted peptide sequence of 4 of these clones was analyzed using the BLAST program available from NCBI.

The results of this analysis are represented in Table 4. Data indicate that we have isolated 6 specific peptide blockers of the interaction of SCL and E47 from a sample screen of a library containing $1\times10^6$ independent clones, there being considerable sequence divergence observed between those peptides blockers. None of the peptide blockers identified was merely performing its native function. Based upon the frequency of peptide blockers identified per library clone, it is estimated that the method described herein is about 100-fold more efficient than a screen of a peptide aptamer library.

EXAMPLE 4

The Construction of a Biodiverse Nucleic Acid Fragment Expression Library in the Vector T7Select415-1

Nucleic acid was isolated from the following bacterial species:

| | |
|---|---|
| 1 | *Archaeoglobus fulgidis* |
| 2 | *Aquifex aeliticus* |
| 3 | *Aeropyrum pernix* |
| 4 | *Bacillus subtilis* |
| 5 | *Bordetella pertussis* TOX6 |
| 6 | *Borrelia burgdorferi* |
| 7 | *Chlamydia trachomatis* |
| 8 | *Escherichia coli* K12 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *Synechosistis* PCC 6803 |
| 18 | *Thermoplasma volcanium* |
| 19 | *Thermotoga maritima* |

Nucleic acid fragments were generated from each of these genomes using multiple consecutive rounds of Klenow primer extension using tagged random oligonucleotides.

In the final round of PCR, the sequence of the oligonucleotide primer comprised the sequence:

(SEQ ID NO: 37)
5'-AGAGGAATTCAGGTCAGACTACAAGGACGACGACGACAAG-3'.

The primer extension products generated were then used as a template for PCR reactions using the following oligonucleotides:

5'-CAGAAGCTTAAGGACGACGACGACAAG-3'; (SEQ ID NO: 38)

5'-CAGGAATTCAAGGACGACGACGACAAG-3'; (SEQ ID NO: 39)

TABLE 4

Characterization of the antagonists of the SCL/E47 interaction

| Clone | Nucleotide sequence of first forward ORF in clone | Amino acid sequence of fusion peptide encoded by first forward ORF in clone | Nucleotide sequence of inserted nucleic acid fragment in clone | Amino acid sequence encoded by fragment | Genome from which fragment was isolated | Protein deduced to be encoded by fragment in native context (1) |
|---|---|---|---|---|---|---|
| BGF 05 | SEQ ID NO: 62 | SEQ ID NO: 63 | SEQ ID NO: 64 | SEQ ID NO: 65 | *H. influenzae* | β-ketoacyl-ACP synthase III |
| BGF 06 | SEQ ID NO: 66 | SEQ ID NO: 67 | SEQ ID NO: 68 | SEQ ID NO: 69 | *A. aeolicus* | glutamyl-tRNA synthetase |
| BGF 13 | SEQ ID NO: 70 | SEQ ID NO: 71 | SEQ ID NO: 72 | SEQ ID NO: 73 | *H. influenzae* | DNA repair protein (radA) |
| BGF 24 | SEQ ID NO: 74 | SEQ ID NO: 75 | SEQ ID NO: 76 | SEQ ID NO: 77 | *T. maritima* | response regulator TM0143 |
| BGF 35 | SEQ ID NO: 78 | SEQ ID NO: 79 | SEQ ID NO: 80 | SEQ ID NO: 81 | *H. influenzae* | beta-ketoacyl-ACP synthase III (fabH) |

(1) Native function was obtained by BLAST analysis of the nucleotide sequence of the nucleic acid fragment in each clone.

-continued

5'-CAGGAATTCCAAGGACGACGACGACAAG-3'; (SEQ ID NO: 40)
and

5'-CAGGAATTCACAAGGACGACGACGACAAG-3', (SEQ ID NO: 41)

wherein the underlined sequence in SEQ ID Nos: 37-41 permits amplification of the PCR products. Furthermore, the sequence shown in bold highlights a HindIII restriction endonuclease recognition site or EcoRI recognition site. Furthermore, note the addition of one or two nucleotides after the EcoRI restriction site in SEQ ID Nos: 40 and 41, respectively (shown in italics). These nucleotides allow expression of amplified nucleic acid in multiple forward reading frames.

Each DNA template was amplified by "one armed" (ie. using only 1 oligonucleotide primer) PCR, with each of the oligonucleotides (ie., SEQ ID Nos: 38-41) in separate reactions (ie. 76 reactions).

Each PCR reaction contained:

| | |
|---|---|
| Template DNA | 1 µl |
| Taq buffer (10x) (Promega) | 5 µl |
| $MgCl_2$ (25 mM) | 4 µl |
| dNTP (2 mM) | 5 µl |
| a primer selected from the group consisting of SEQ ID Nos: 38-41 (10 pmol/µl) | 10 µl |
| Taq DNA polymerase (Promega 5 U/µl) | 0.4 µl |
| $H_2O$ | to 50 µl |

Reactions were then cycled in a Perkin Elmer thermocycler PE 9700 or PE 2400 using the following program:

5 min at 94° C., followed by 30 cycles wherein each cycle consists of 30 sec at 94° C., followed by 30 sec at 55° C., and followed by 1 min at 72° C.], followed by 5 min at 72° C.

A sample of the resulting PCR products was analyzed by electrophoresis using a 2% agarose/TAE gel. The amount of nucleic acid in each of the PCR products was also determined using the picogreen method following instructions provided by the manufacturer.

PCR products generated with each of the oligonucleotides SEQ ID Nos: 38-41 were pooled. DNA from each organism was added in an equimolar amount when compared to the amount of nucleic acid added to the pool from the organism with the smallest genome.

Subsequently, the pools generated from PCR products amplified using the oligonucleotides SEQ ID NO: 39, SEQ ID NO: 40 or SEQ ID NO: 41 were combined in equal ratios (ie. equal amounts of nucleic acid) to form one pool.

The pooled PCR products were then purified using QIAquick PCR purification columns (QIAGEN) as per manufacturer's instructions. This step removes any unincorporated oligonucleotides, dNTPs and contaminating proteins.

Each of the pools of PCR products (6 µg) was then divided into 3 equal parts and each part digested with a different one of the restriction enzymes AluI, HaeII or RsaI (NEB) in the following reaction:

| | |
|---|---|
| PCR product (2 µg) | |
| Restriction endonuclease buffer (10x) (NEB) | 4 µl |
| Restriction endonuclease | 1 µl |
| $H_2O$ | to 40 µl |

Reactions were allowed to proceed for 2 hours at 37° C., before being heat inactivated by incubating at 65° C. for 20 minutes. Restriction digests were then re-pooled and purified using QIAquick PCR purification columns (QIAGEN) as per manufacturer's instructions.

Each of the enzymes AluI, HaeII and RsaI produce blunt ends. Accordingly, it is possible to ligate blunt end adaptors to the restriction digested PCR products to allow directional cloning into the T7Select415-1 vector. Oligonucleotides encoding the blunt-end adaptors were generated comprising the following sequences:

5'-AATTCGAACCCCTTCG-3' (SEQ ID NO: 42)

5'-CGAAGGGGTTCG-3' (SEQ ID NO: 43)

5'-AATTCGAACCCCTTCGC-3' (SEQ ID NO: 44)

5'-GCGAAGGGGTTCG-3' (SEQ ID NO: 45)

5'-AATTCGAACCCCTTCGCG-3' (SEQ ID NO: 46)

5'-CGCGAAGGGGTTCG-3' (SEQ ID NO: 47)

5'-AGCTCGAAGGGGTTCG-3' (SEQ ID NO: 48)

5'-CGAACCCCTTCG-3'. (SEQ ID NO: 49)

The adaptor pairs SEQ ID Nos: 42 and 43; SEQ ID Nos: 44 and 45; SEQ ID NOs: 46 and 47; SEQ ID NOs: 48 and 49 were then annealed to one another. This process was completed in $H_2O$ with each of the oligonucleotides at a concentration of 50 µM. Pairs of adaptors were incubated at 94° C. for 10 minutes and then allowed to cool to room temperature slowly.

The annealed adaptors were then ligated to the pool of amplified PCR products in separate ligation reactions. The adaptor formed through annealing of SEQ ID NOs: 48 and 49 was ligated to the pool of PCR products amplified using the oligonucleotides set forth in SEQ ID NO: 39, SEQ ID NO: 40 and SEQ ID NO: 41.

Ligations were carried out in the following reactions:

| | |
|---|---|
| Pooled PCR product (average length of 200 bp) | 2 pmol |
| Annealed adaptor | 150 pmol |
| Ligation buffer (10x) (Promega) | 1 µl |
| T4 DNA ligase (3 U/µl) (Promega) | 1 µl |
| $H_2O$ | to 10 µl |

Samples were then incubated at 4° C. overnight before being heat inactivated through incubation at 65° C. for 20 minutes.

Samples were then phosphorylated using T4 polynucleotide kinase (Promega) in the following reaction:

| | |
|---|---|
| Ligation buffer (10x) (Promega) | 1 µl |
| rATP (10 mM) | 2 µl |
| T4 polynucleotide kinase (5 U/µl) | 1 µl |
| $H_2O$ | 20 µl |

Samples were incubated at 37° C. for 30 minutes followed by incubation at 65° C. for 20 minutes to heat inactivate the T4 polynucleotide kinase.

Following ligation and phosphorylation each of the three reactions comprising nucleic acid amplified using the oligonucleotide SEQ ID NO: 38 were combined in equal ratios, ie. equal amounts of nucleic acid to form one pool.

The nucleic acids originally amplified with SEQ ID NO: 38 were then digested with the restriction endonuclease HindIII in the following reaction:

| | |
|---|---|
| PCR product (2 μg) | |
| HindIII buffer (10x) (Promega) | 8 μl |
| HindIII (10 U/μl) (Promega) | 1 μl |
| $H_2O$ | to 80 μl |

The nucleic acids in the pool originally amplified by one of SEQ ID Nos: 39-41 were digested with the restriction endonuclease EcoRI in the following reaction:

| | |
|---|---|
| PCR product (2 μg) | |
| EcoRI buffer (10x) (Promega) | 8 μl |
| EcoRI (10 U/μl) (Promega) | 1 μl |
| $H_2O$ | to 80 μl |

Samples were then purified using a QIAquick PCR purification column (QIAGEN) as per manufacturer's instructions. Nucleic acid concentration was then determined by spectrophotometry measuring UV absorption at 260 nm.

Both pools of nucleic acid fragments (ie. those digested with EcoRI and those digested with HindIII) were then combined in equal ratios, ie. equal amounts of nucleic acid, to form one pool. This pool of nucleic acid fragments was then suitable for cloning into the peptide display vector T7Select415-1 (Novagen). The T7415-1 vector is provided in a form for nucleic acids to be ligated into EcoRI and HindIII restriction endonuclease sites.

The nucleic acid fragments were then ligated into the T7Select415-1 vector using the following reaction:

| | |
|---|---|
| Ligation buffer (10x) (Novagen) | 0.5 μl |
| rATP (10 mM) | 0.5 μl |
| DTT (10 mM) | 0.5 μl |
| T7Select415-1 EcoRI/HindIII vector arms (0.02 pmol) | 1 μl |
| Nucleic acid fragments (0; 0.02; and 0.06 pmol in independent reactions) | |
| $H_2O$ | to 5 μl |

Reactions were incubated at 16° C. overnight.

EXAMPLE 5

Packaging and Amplification of a Biodiverse Nucleic Acid Fragment Expression Library The ligation reactions of Example 4 were packaged using commercial packaging extract available from Novagen. These reactions were then titered according to manufacturer's instructions by infection of *E. coli* BL21 cells. By using 1 μl from each of three independent ligations, titers between $1.3\times10^7$ and $7\times10^7$ plaque forming units (pfu)/ml were obtained.

Pooling of three ligation reactions containing a total of 1 μg of T7Select415-1 vector, and packaging, resulted in a library with $2.75\times10^7$ pfu, ie $2.75\times10^7$ initial recombination events. The library was immediately amplified by "plate lysate amplification" (as per manufacturer's instructions) on 180 LB Petri dishes (14 cm diameter). Titers of the amplified lysates varied between 1 and $5\times10^{10}$ pfu/ml. Two liters of lysate were harvested, pooled and the titer determined at $1.5\times10^{10}$ pfu/ml, ie $3\times10^{13}$ pfu in total. The lysate was stored at 4° C. over $CHCl_3$ (as per manufacturer's instructions) and glycerol stocks containing 10% glycerol were stored at −80° C.

EXAMPLE 6

Characterization of a T7-Displayed Biodiverse Nucleic Acid Fragment Library

During the amplification of the library described in Example 5, individual plaques from low-density plates were collected and analyzed by PCR with primers specific to T7Select415-1 of the nucleotide sequence.

Thirty nine plaques with insert sizes larger than 70 bp were analyzed by DNA sequence analysis. The resulting sequences are summarised in the Table 5

DNA from 13 of the 19 bacterial genomes could be identified in the recombinant phage analyzed. In most cases, the homology was between 96 and 100% in the regions that were derived from the genomic starting material. In addition, primers and adapters were identified, however, there were also many cases of strings of adapters and multiple PCR primers in the insert regions. The inserted DNA of the analyzed phage clones was up to 250 bp long.

TABLE 5

Characterization of nucleic acid fragments in T7Select-415-1

| BGF clone | T7for/rev PCR fragment (bp) | Insert homology to organism (% homology in the matching region) | Size of homologous region (bp) | Extra amino Acids after Asn (T7) | Natural reading frame |
|---|---|---|---|---|---|
| 8 | 255 | *B. pertussis* (98%) | 112 | 16 | |
| 14 | 212 | *M. thermoautotrophicum* (98%) | 73 | 12 | |
| 15 | 350 | *B. pertussis* (98%) | 171 | 0 | |
| 16 | 263 | *A. fulgidus* (100%) | 125 | 20 | |
| 18 | 260 | *A. fulgidus* (100%) | 112 | 0 | |
| 31 | 260 | *A. fulgidus* (96%) | 118 | 65 | yes |
| 52 | 240 | *T. volcanicum* (100%) | 39 | 0 | |
| 61 | 272 | *M. jannashii* (100%) | 90 | 12 | |
| 65 | 230 | *N. meningiditis* (100%) | 107 | 0 | |
| 73 | 230 | *C. trachomatis* (98%) | 62 | 10 | |
| 83 | 200 | *B. burgdorferi* (100%) | 46 | 8 | |
| 89 | 411 | *B. subtilis* (98%) | 170 | 15 | |
| 100 | 268 | *P. aeruginosa* | 159 | 11 | |
| 104 | 174 | no match | — | 12 | |

TABLE 5-continued

| Characterization of nucleic acid fragments in T7Select-415-1 | | | | | |
|---|---|---|---|---|---|
| BGF clone | T7for/ rev PCR fragment (bp) | Insert homology to organism (% homology in the matching region) | Size of homologous region (bp) | Extra amino Acids after Asn (T7) | Natural reading frame |
| 125 | 250 | *E. coli* Kl2 (98%) | 109 | 4 | |
| 126 | 220 | *E. coli* Kl2 | 91 | 6 | |
| 139 | 240 | *Synechocystis* PCC 6803 (100%) | 109 | 26 | yes |
| 141 | 250 | *E. coli* Kl2 | 126 | 6 | |
| 144 | 170 | no match | — | 15 | |
| 152 | 160 | *E. coli* Kl2 (100%) | 39 | 13 | |
| 153 | 290 | *C. trachomatis* (100%) | 131 | 7 | |
| 163 | 260 | *C. trachomatis* (100%) | 90 | 5 | |
| 166 | 270 | *E. coli* Kl2 (100%) | 112 | 20 | |
| 169 | 240 | *M. thermoautotrophicum* (100%) | 112 | 6 | |
| 10 | 180 | no match | — | 7 | |
| 17 | 190 | *M. jannashii* | 68 | 13 | |
| 20 | 190 | *E. coli* K12 | 58 | 22 | |
| 25 | 170 | *P. horikoshii* | 40 | 10 | |
| 30 | 200 | *P. aeruginosa* | 54 | 13 | |
| 40 | 190 | no match | — | 24 | |
| 42 | 190 | *B. sublilis* | 44 | 0 | |
| 44 | 250 | *B. burgdorferi* | 130 | 6 | |
| 47 | 210 | *C. trachomatis* | 95 | 13 | |
| 48 | 200 | *Synechocystis* PCC 6803 | 82 | 20 | |
| 55 | 180 | no match | — | 11 | |
| 64 | 190 | *Synechocystis* PCC 6803 | 46 | 16 | |
| 82 | 180 | *M. thermoautotrophicum* | 39 | 8 | |
| 87 | 250 | No match | — | 51 | |
| 134 | 280 | *M. thermoautotrophicum* | | | |

EXAMPLE 7

Screening a T7 Phage Displayed Biodiverse Nucleic Acid Fragment Library for a Mimotope of FLAG The library of Example 5 was screened to isolate phage displaying peptides that bound to monoclonal antibodies in a similar way as natural peptides would. The monoclonal antibody was adsorbed to a Petri dish and a lysate of the amplified phage library was allowed to bind to the antibody immobilised on the Petri dish. After rigorous washing to remove non-specifically bound phage, the remaining phage was eluted and amplified for additional rounds of selection.

Each Petri dish (Nunc, 3.5 cm diameter) was rinsed twice with distilled water. The target antibody in this case was a mouse monoclonal antibody to the FLAG epitope (α-FLAG M2, Sigma Aldrich). The antibody was diluted in TBS buffer to 20 μg/ml and 500 μl was added per dish. The antibody was allowed to adsorb for 3 to 4 hours at room temperature or at 4° C. overnight. The dish was rinsed three times with TBS buffer and filled with 5% skim milk in distilled water. For blocking the skim milk solution was allowed to bind with gentle rocking for 1 hour at room temperature or at 4° C. overnight. The dish was rinsed five times with TBS buffer and filled with TBS buffer until use.

About $3\times10^{10}$ pfu to about $4\times10^{10}$ pfu of amplified T7 phage library (as described in Example 4) was added to the precoated and blocked Petri dish. The volume was increased to 0.5 ml with $ddH_2O$ and 10×TBS buffer to obtain 1×TBS as final concentration. For dilute phage suspensions the total volume can be raised to 1.5 ml without loss of binding, however the volume should be kept as small as possible to avoid spillage of phage. The phage suspension was allowed to bind with gentle rocking for 5 hours at room temperature or at 4° C. overnight. The phage suspension was discarded and the dish was washed twice with TBS buffer containing Tween-20. TBS-Tween (1 ml) was added to the dish, and the dish incubated for 10 minutes with gentle shaking. This wash step was repeated twice more, without shaking. Bound phage were eluted with 0.5 ml of 1% SDS. The 1% SDS was added to the plates and the plates incubated for 30 minutes with gentle shaking. The eluate was transferred into a reaction tube and the phage titer determined.

For further rounds of biopanning the eluate was amplified in a 10-40 ml culture. A fresh culture of *E. coli* BL21 in LB medium was grown at 37° C. to an optical density of 0.5 and infected 1:200 with eluate. The culture was shaken at 37° C. for 1 to 2 hours until lysis was observed. The culture was centrifuged at 8000 g for 10 minutes at 4° C. to pellet remaining *E. coli* cells and cell debris. The supernatant was transferred into a fresh tube, titered and stored over $CHCl_3$ at 4° C. until use.

Three consecutive rounds of biopanning were completed and a binding rate for each round was determined. These binding rates are described in Table 6 below:

TABLE 6

| Panning antibody | Round | Input (pfu) | Output (pfu | Binding rate |
|---|---|---|---|---|
| αFLAG ab | 1 | $4 \times 10^9$ | $5.5 \times 10^5$ | 0.014 |
| αFLAG ab | 2 | $4 \times 10^9$ | $2.3 \times 10^8$ | 5.7 |
| αFLAG ab | 3 | $4 \times 10^9$ | $1.6 \times 10^9$ | 40 |

Figure 11:
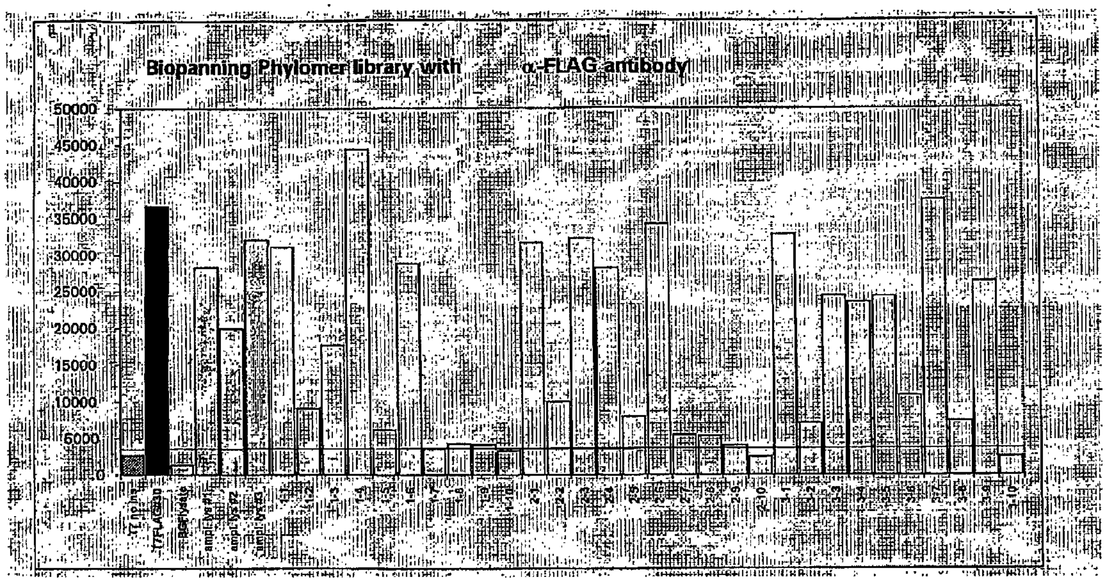
FIG. 11 is a graphical representation of the binding of phage-displayed peptides to the α-FLAG antibody using time resolved fluorescence analysis using a europium detection system. The column marked "T7-no insert" refers to a phage carrying a phage display vector with no insert. "T7 FLAG" refers to a phage displaying the FLAG epitope, ie. a positive control. The column marked "BGF lysate" refers to a pool of random phage from the entire phage displayed library, and the columns marked "Ampl. Lys #1-3 refer to pools of phage isolated following consecutive rounds of biopanning with the α-FLAG antibody. The remaining columns show the ability of individual phage displayed peptides to bind to the α-FLAG antibody, with the first number referring to the round of biopanning from which the phage was isolated, and the second number the clone number.

The binding rate increased from 0.014% in the first round of biopanning to 40% in the third round indicating enrichment of T7 phage clones with a specificity for the panning antibody. Ten individual plaques from each round of biopanning were grown up and analyzed by TRF ELISA with a FLAG antibody coated wells (100 ng/well). Sixty percent of the clones from the first two rounds and 90% of the clones from the third round of biopanning showed a strong positive signal (FIG. 11). The same clones were tested in an ELISA coated with a monoclonal antibody to papain (3D5) and showed no significant signal. This indicates that the isolated phage clones were specific to the α-FLAG antibody.

As a positive control, oligonucleotides were designed to generate a DNA fragment with EcoRI and HindIII overhangs for cloning into T7Select415-1 EcoRI/HindIII vector arms, in addition to encoding the FLAG epitope (Asp-TyrLysAspAspAspAspLys; SEQ ID NO: 50). These oligonucleotides comprised the sequences:

```
5'-                               (SEQ ID NO: 51)
AATTCCGACTACAAGGACGACGATGACAAGA-3'

5'-                               (SEQ ID NO: 52)
AGCTTCTTGTCATGGTCGTCCTTGTAGTCGG-3'
```

The oligonucleotides comprising SEQ ID NO: 51 and SEQ ID NO: 52 were allowed to anneal as previously described before being ligated into the T7Select415-1 EcoRI/HindIII vector arms as described in Example 3.

FIG. 11 shows the binding of phage-displayed peptides to the α-FLAG antibody using time resolved fluorescence analysis using a europium detection system (eg. DELFIA, Perkin Elmer Life Sciences).

EXAMPLE 8

Screening a T7 Phage Displayed Biodiverse Nucleic Acid Fragment Library for a Mimotope of the Dust Mite Allergen Der p 1

The majority of individuals allergic to the house dust mite *D. pteronyssinus* produce IgE to the allergens Der p 1. Protection against house dust mite (HDM) allergy could be achieved by desensitisation with HDM allergens—or representative peptides—skewing the immune response from an atopic IgE to a regulatory IgG response. HDM specific monoclonal antibodies can be used to isolate peptides which mimic the epitopes of complete allergens, (ie a mimotope), from a peptide libraries.

To identify a mimotope of Der p 1 the phage display library described in Example 5 was screened to isolate phage that displayed peptides capable of binding to a monoclonal antibody that specifically binds the major dustmite allergen Der p 1, 2C7 (McElveen et al., *Clin. Exp. Allergy* 28: 1427-1434, 1998). The screening was performed essentially as described in Example 7. The monoclonal antibody (approximately 10 μg) was adsorbed to a Petri dish and the amplified phage display library brought into contact with the adsorbed antibody.

Three consecutive rounds of biopanning were completed and a binding rate for each round was determined. These binding rates are described in Table 7 below:

TABLE 7

Results of a screen to identify a peptide capable of binding monoclonal antibody 2C7.

| Panning antibody | round # | input per dish [pfu] | output [pfu] | recovery rate |
|---|---|---|---|---|
| 2C7 | 1 | $3 \times 1.1 \times 10^{10}$ | $5.5 \times 10^{6}$ | 0.02% |
| 2C7 | 2 | $3 \times 1 \times 10^{10}$ | $1.8 \times 10^{7}$ | 0.06% |
| 2C7 | 3 | $3 \times 0.7 \times 10^{10}$ | $6 \times 10^{8}$ | 2.7% |

As a positive control, oligonucleotides were designed to generate a DNA fragment with EcoRI and HindIII overhangs for cloning into T7Select415-1 EcoRI/HindIII vector arms, in addition to encoding the 2C7 epitope, essentially as described by Furmonaviciene et al., *Clinical and Experimental Allergy* 29:1563-1571, 1999.

The eluate after round three was amplified and ninety-nine individual T7 clones were tested for binding to the panning antibody 2C7 using a dissociation-enhanced ianthinide fluoroimmunoassay (DELFIA) with 500 ng/well 2C7. Assays were performed essentially according to manufacturer's instructions (Perkin Elmer Life Sciences). The first ligand used in the DELFIA was T7lysate (ie the library) (1:2 in assay buffer); second ligand: SIGMA biotinylated anti-T7 monoclonal antibody 1:10,000 (mouse), Strep-Eur+enhancement solution). T7 clones which showed significant binding to 2C7 were named "2C7pan" clones.

Figure 12:
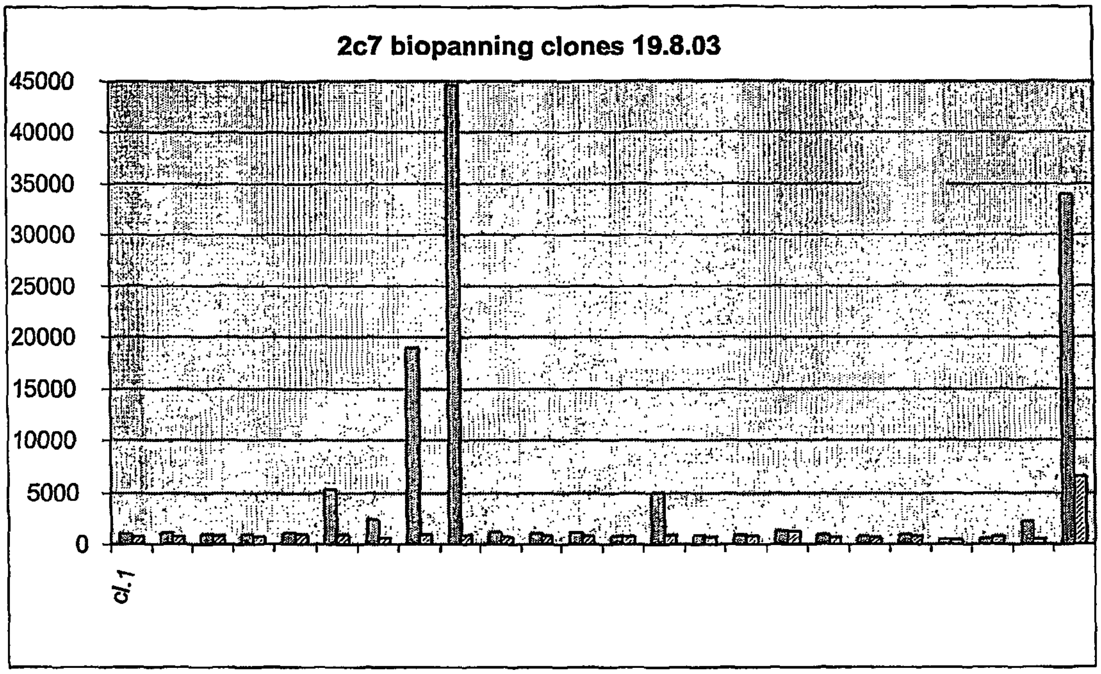
FIG. 12 is a graphical representation of phage displayed peptides to the anti-Der p 1 monoclonal antibody 2C7. The binding affinity of the peptides was determined using time resolved fluorescence analysis using a europium detection system.

FIG. 12 shows the binding of phage-displayed peptides to the α-Der p I monoclonal antibody using time resolved fluorescence analysis using a europium detection system (ie DELFIA).

A total of twenty-three T7 clones were isolated and their DNA insert region sequenced. Surprisingly, only five different insert groups were found and the majority of clones belonged to two of these groups. The length of the displayed amino acid sequence ranged between 4 and 18 amino acids. The amino acid sequence of the peptides identified in the panning screen are shown in Table 9.

TABLE 9

Sequence of mimotopes of Der p 1

| T7clone | No. of clones | TRF[a] | aa sequence displayed at carboxy-terminus |
|---|---|---|---|
| 2c7pan8 | 3 | 1900 | *GDPN* S S T S P R (SEQ ID NO: 82 and 83)[b] |
| 2c7pan9 | 1 | 17000 | *GDPN* S A S G T A (SEQ ID NO: 84 and 85)[b] |
| 2c7pan14 | 2 | 1800 | *GDPN* S R G K S R E Y L S (SEQ ID NO: 86 and 87)[b] |
| 2c7pan26 | 9 | 8500 | *GDP* R T H R (SEQ ID NO: 88 and 89)[b] |
| 2c7pan42 | 8 | 64000 | *GDPN* S S S V D K L G Y W R V T E S S N E (SEQ ID NO: 90 and 91)[b] |

[a]TRF (time resolved fluoroetry) values of 50 μl lysate in the standard T7-DELFIA 17.9.03, comparison: T7wt ~500 TRF. Sequence shon in italics is encoded by the T7-Select vector.

[b]SEQ ID NOs. 84, 86, 88, 90 and 92 provide the peptide sequence with the flanking vector sequence; SEQ ID NOs: 85, 87, 89, 91 and 93 provide the peptide sequence without flanking vector sequence Sequence alignments of the amino acid sequence of the isolated peptides and the amino acid sequence of Der p 1 revealed no obvious regions homology or identity consistent with the representation of discontinuous or conformational epitopes.

Competition DELIFAs were then used to study the interaction between the monoclonal antibody and the peptides identified, using recombinant Der p 1 or the epitope of the 2C7 antibody (GST-P1fragment 98-140 [please provide this sequence]) as a competitor. These assays showed that 2C7 pan clones 8, 9, 14 and 26 were specifically inhibited by the recombinant Der p 1 protein but not by the GST-P1fragment 98-140 peptide. These results indicate that the isolated peptides are capable of forming a conformation that mimics structural features of the native polypeptide, rather than mimicking the sequence of a synthetic peptide to which the 2C7 antibody has been shown to bind.

Figure 13A:
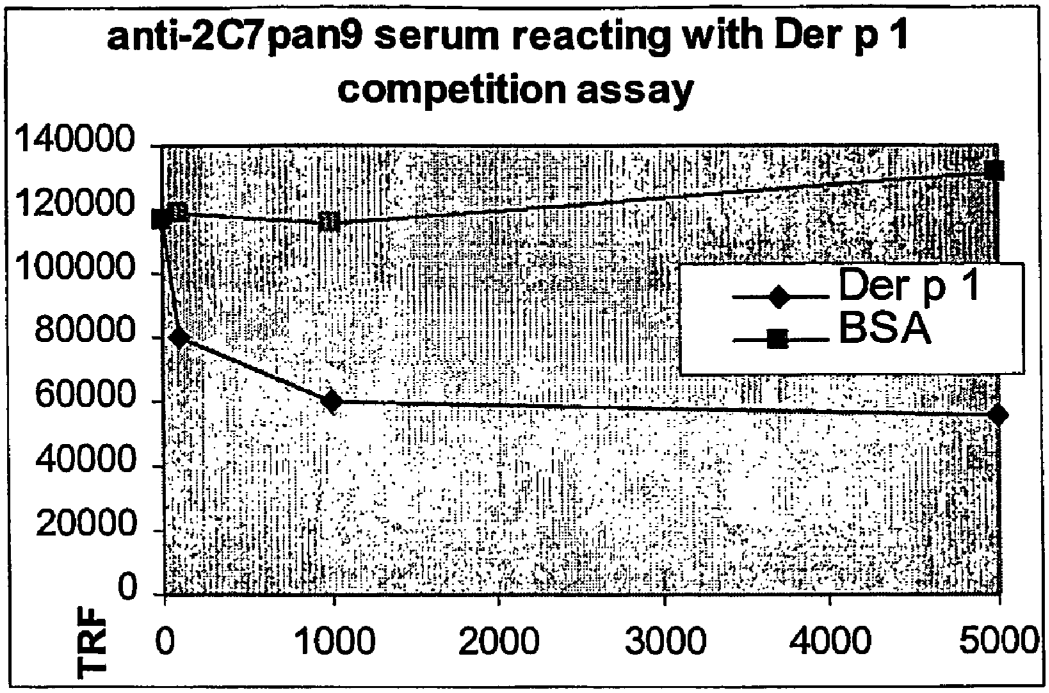
FIG. 13A is a graphical representation showing the inhibition of binding of clone number 9 capable of binding antibody 2C7 (2C7pan9) by recombinant Der p 1. The degree of binding of the peptide to 2C7 was determined using a time resolved fluorescence analysis using a europium detection system. As a negative control BSA was used at increasing concentrations. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).
Figure 13B:
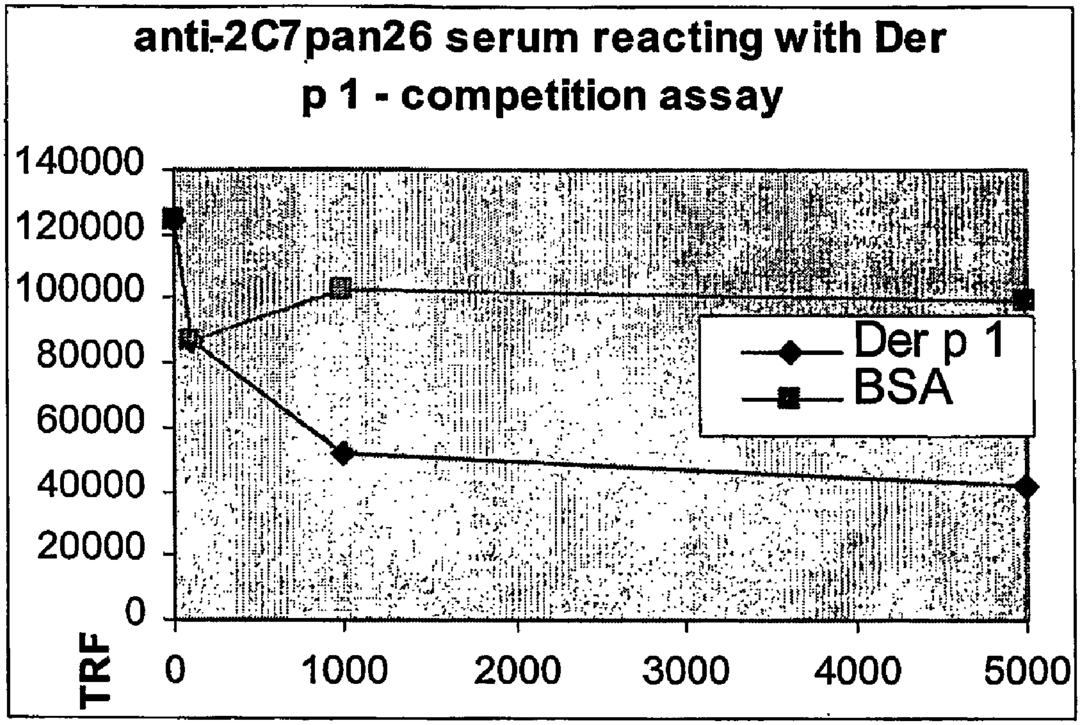
FIG. 13B is a graphical representation showing the inhibition of binding of clone number 26 capable of binding antibody 2C7 (2C7pan26) by recombinant Der p 1. The degree of binding of the peptide to 2C7 was determined using a time resolved fluorescence analysis using a europium detection system. As a negative control BSA was used at increasing concentrations. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).
Figure 13C:
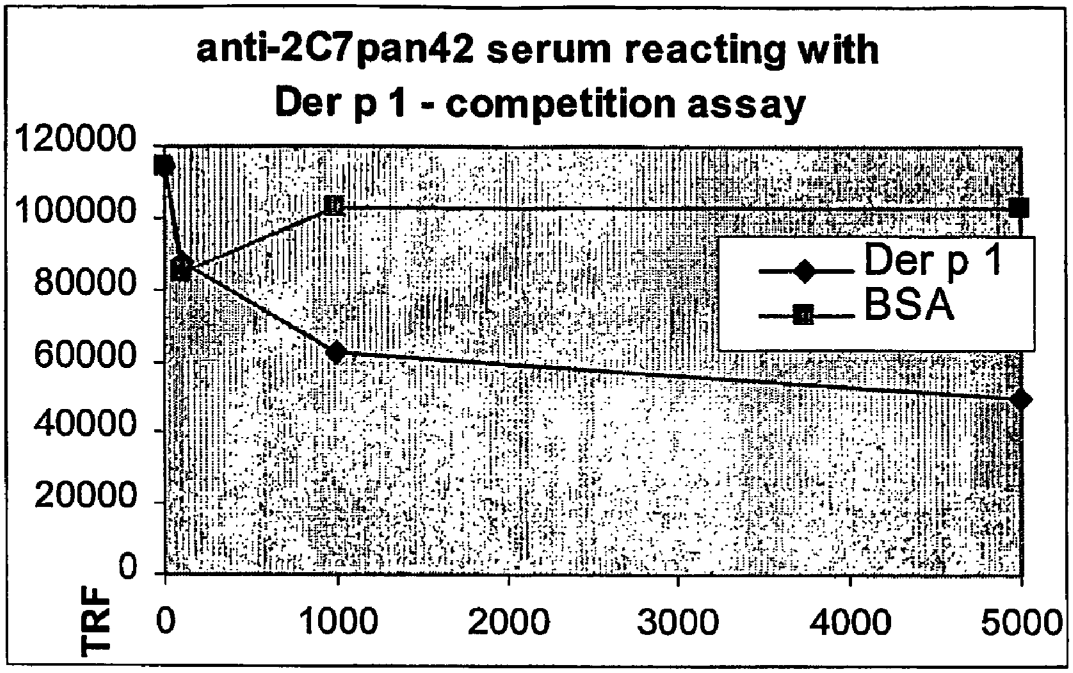
FIG. 13C is a graphical representation showing the inhibition of binding of clone number 42 capable of binding antibody 2C7 (2C7pan42) by recombinant Der p 1. The degree of binding of the peptide to 2C7 was determined using a time resolved fluorescence analysis using a europium detection system. As a negative control BSA was used at increasing concentrations. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).

Interestingly, the binding of 2C7pan42 clone to 2C7 was only partially inhibited by recombinant Der p 1 and higher levels of inhibition occurred with GST-P1fragment 98-140. Results of the competition assays for clones 2C7 pan clones 9, 26 and 42 are shown in FIGS. 13 A-C.

EXAMPLE 9

Use of Mimotopes to Immunize Mice Against Der p 1

Figure 14A:
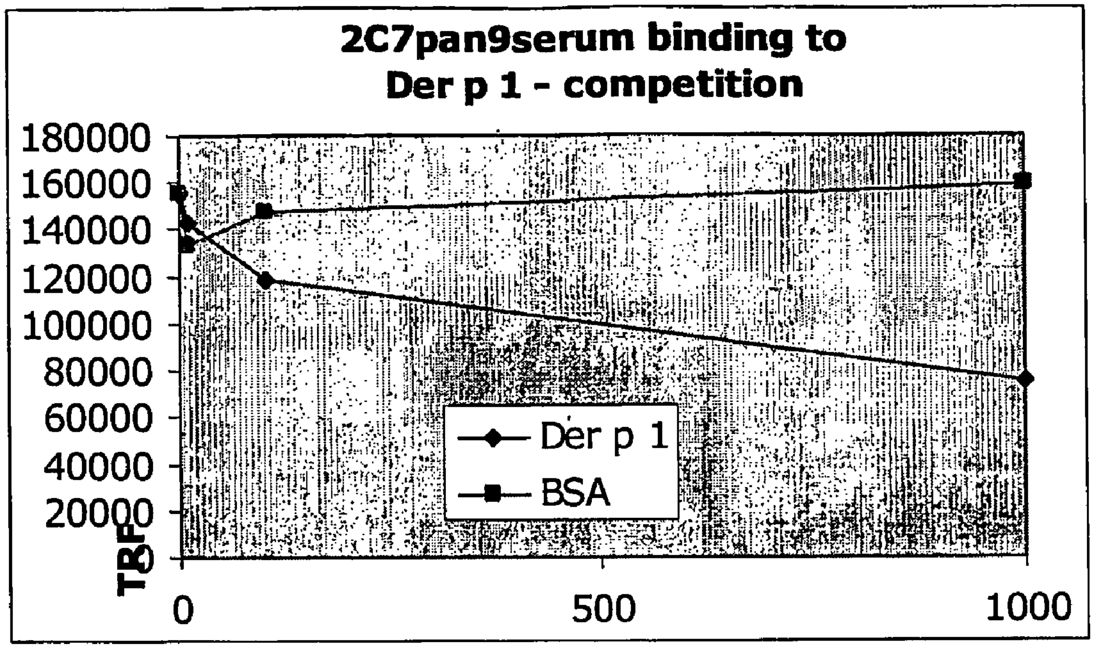
FIG. 14A is a graphical representation showing the binding of mouse antiserum raised against clone number 9 capable of binding antibody 2C7 (2C7pan9) to recombinant Der p 1. The ability of recombinant Der p 1 and BSA to inhibit this binding was also determined to show that the antiserum is specific to Der p 1. Binding was determined using a time resolved fluorescence analysis using a europium detection system. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).
Figure 14B:
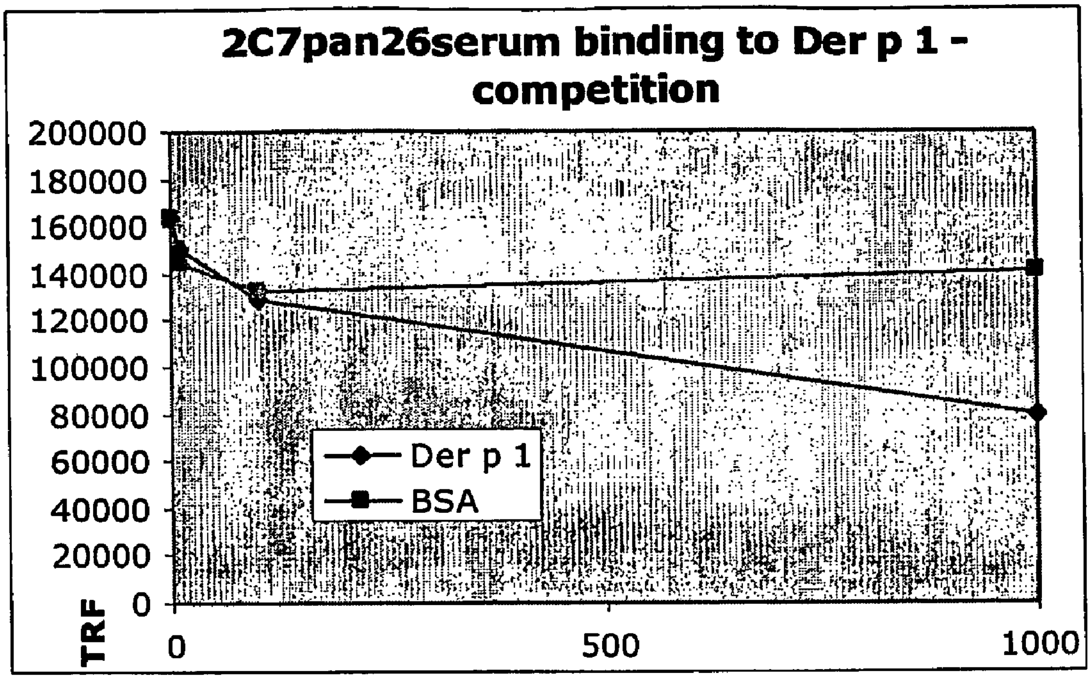
FIG. 14B is a graphical representation showing the binding of mouse antiserum raised against clone number 26 capable of binding antibody 2C7 (2C7pan26) to recombinant Der p 1. The ability of recombinant Der p 1 and BSA to inhibit this binding was also determined to show that the antiserum is specific to Der p 1. Binding was determined using a time resolved fluorescence analysis using a europium detection system. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).
Figure 14C:
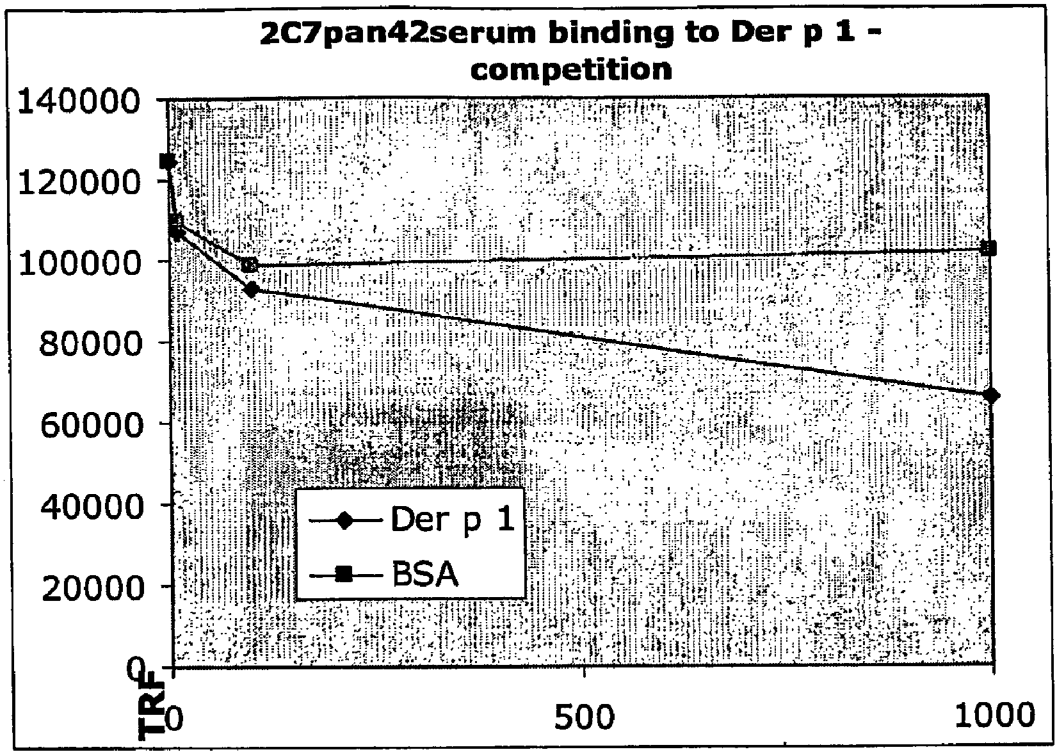
FIG. 14*c* is a graphical representation showing the binding of mouse antiserum raised against clone number 42 capable of binding antibody 2C7 (2C7pan42) to recombinant Der p 1. The ability of recombinant Der p 1 and BSA to inhibit this binding was also determined to show that the antiserum is specific to Der p 1. Binding was determined using a time resolved fluorescence analysis using a europium detection system. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).

The clones, 2C7pan clones 9, 26 and 42, described in Example 8 were then used to immunize mice. Phage were purified by CsCl gradient centrifugation and then used to immunize mice. Each injection consisted of $10^{11}$ phage particles suspended in Freunds complete adjuvant. After the first booster mice were bled and tested by DELFIA for binding to Der p 1. Furthermore, the specificity of the immune response for Der p 1 was tested using competitive DELFIA. As shown in FIGS. 14A-C an anti-Der p 1 immune response was induced in mice injected with each of 2C7pan clones 9, 26 and 42 and the binding of the immune serum to Der p 1 was inhibited by the addition of recombinant Der p 1 (and not by the addition of BSA).

Figure 14D:
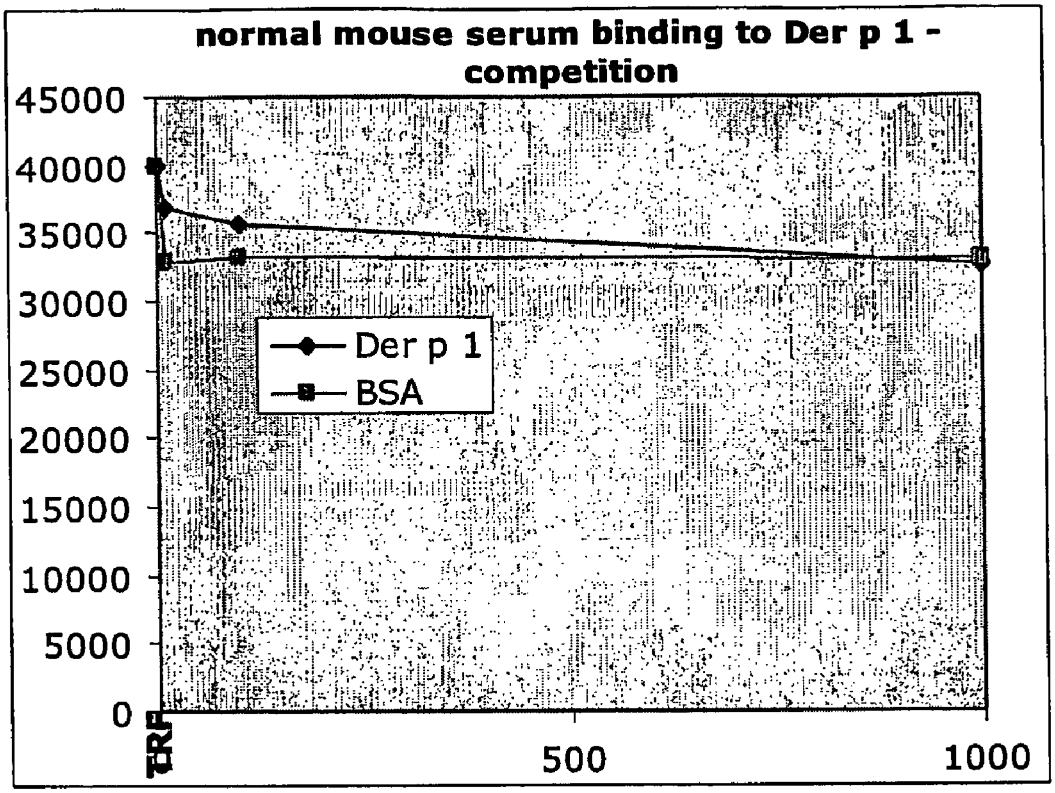
FIG. 14D is a graphical representation showing the binding of normal mouse serum to recombinant Der p 1. The ability of recombinant Der p 1 and BSA to inhibit this binding was also determined to show that any binding is not specific to Der p 1. Binding was determined using a time resolved fluorescence analysis using a europium detection system. Time resolved fluorescence units are indicated on the left hand side of the figure. Concentrations of the test compounds (Der p 1 or BSA) are indicated at the bottom of the drawing. Results attained with Der p 1 are indicated by the black diamonds and results from BSA are indicated by the grey squares (as shown).
Figure 15:
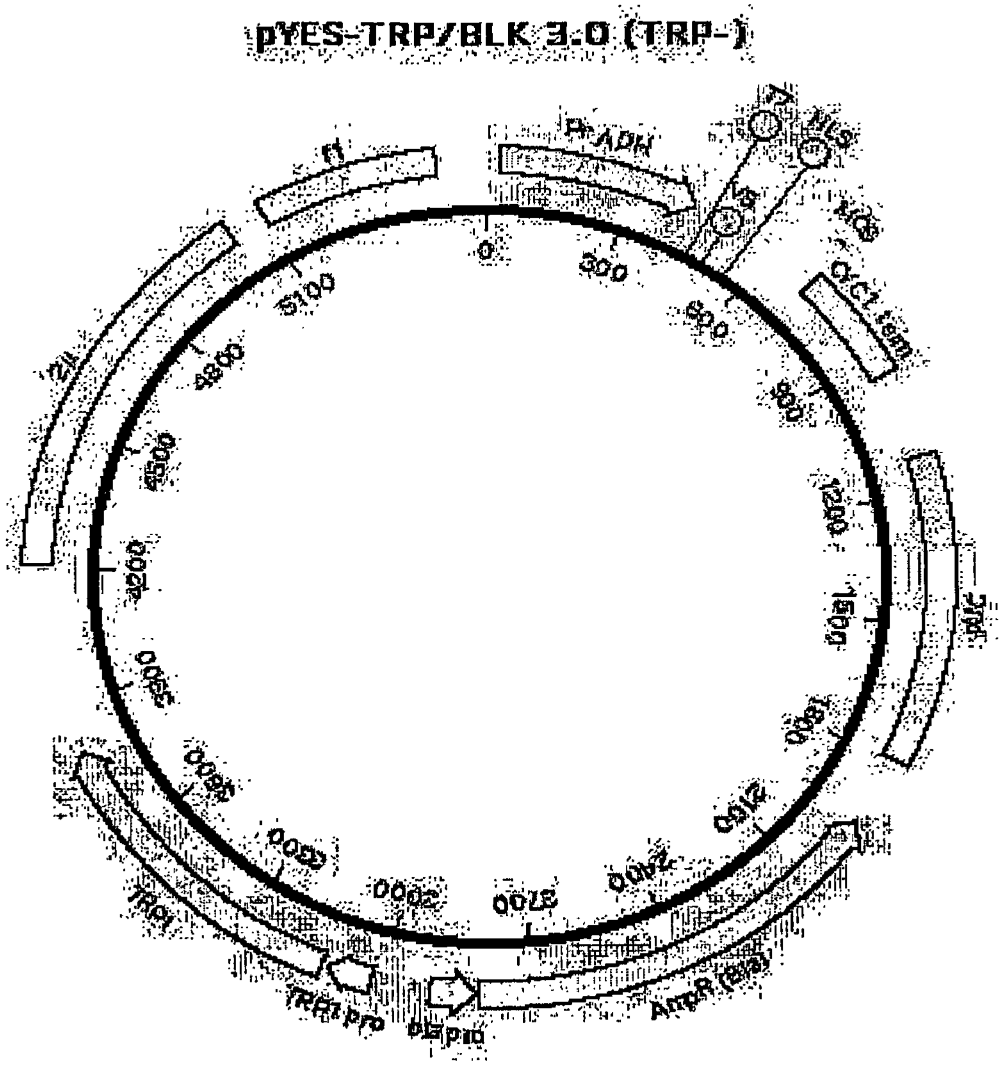
FIG. 15 is a schematic representation of the pYTB3 vector (SEQ ID NO: 92). The pYTB vector comprises a minimal ADH promoter for constitutive expression of a nucleic acid fragment in yeast cells, a nuclear localisation signal, to target an expressed peptide to the nucleus of a yeast cell, a CYC1 terminator for termination of transcription in yeast cells; a 2μ origin of replication, to allow the plasmid to replicate in yeast cells; a TRP1 gene to allow auxotrophic yeast to grow in media lacking tryptophan; a nucleic acid encoding a peptide conferring ampicillin resistance, for selection in bacterial cells; and a pUC origin of replication to allow for replication in bacterial cells. The pYTB3 vector also comprises a T7 promoter to facilitate expression of peptides in bacterial cells and using in vitro transcription/translation systems.

The binding of normal mouse serum to Der p 1 was not inhibited by the addition of recombinant Der p 1 (FIG. 14D).

EXAMPLE 10

Identification of a Peptide Capable of Inhibiting the Self-Dimerization of c-Jun A biodiverse nucleic acid fragment library was produced in the vector pMF4-5 (Phylogica Ltd, Australia) (SEQ ID NO: 165, FIG. 18) essentially as described in Example 1. Amplified fragments were digested with EcoRI and Acc651. The resulting fragments were then purified using a QIAQuick PCR purification column (Qiagen) essentially according to manufacturer's instructions. The expression vector pMF4-5 was also digested with EcoRI and Acc651, treated with shrimp alkaline phosphatase and then purified using a QIAQuick PCR purification column (Qiagen) essentially according to manufacturer's instructions. Ligations were then performed at a molar ratio of 10:1 insert:vector, and transformed into TOP10 electrocompetent cells (Invitrogen).

These vectors were then isolated from bacteria using standard methods and transformed into the PRT51 yeast strain (with the genotype MATa, his3, trp1, ura3, 6 LexA-LEU2, lys2::3 clop-LYS2, CYH2R, ade2::G418-pZero-ade2, met15::Zeo-pBLUE-met15, his5::hygroR). Transformants were then aliquoted and snap frozen in 15% glycerol.

Figure 16:
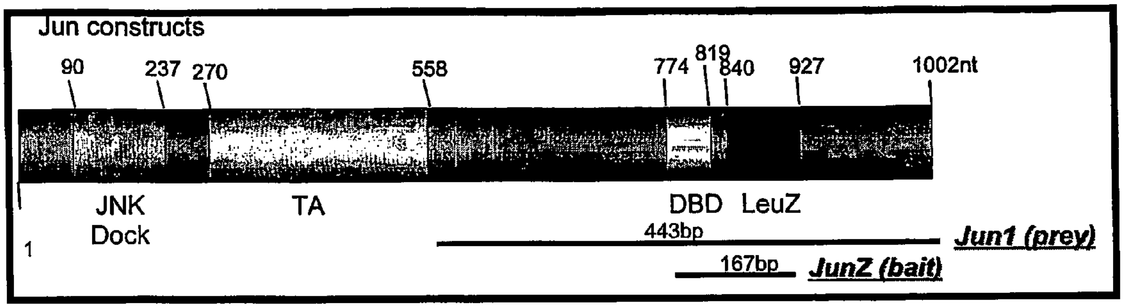
FIG. 16 is a schematic representation of a JUN polypeptide. As shown the constructs JUN1 and JUNZ both encompass the DNA binding domain (DBD) and leucine zipper (LeuZ) domain of JUN. The leucine zipper domain is important for homo-dimerization of JUN.

The bait and prey used in the present screen were JUN1 and JUNZ (these regions of c-Jun are shown in FIG. 16). Briefly, nucleic acid encoding the JUN1 protein was cloned into the prey vector pJFK (SEQ ID NO: 60; FIG. 5) in operable connection with a nuclear localisation signal, and a B42 activation domain. The nucleic acid encoding the JUNZ protein was cloned into the bait vector pDD (SEQ ID NO: 61; FIG. 6) in operable connection with the LexA DNA binding domain. The pDD vector also contains a nucleic acid encoding the HIS3 gene (FIG. 6). These vectors were then transformed into the yeast strain PRT480 (with the genotype MATa, his3, trp1, ura3, 4 LexA-LEU2, lys2::3 clop-LYS2, CANR, CYH2R, ade2::2 LexA-CYH2-ZEO, his5::1 LexA-URA3-G418).

The yeast that carry the bait and prey proteins and the potential blocking peptides were then mass mated, and from approximately 300,000 clones, 95 positives were identified (ie, approximately 1/3000).

Two methods of analysis were used to identify interaction-blocking activity:

The first of these comprised plating approximately 500 cells per half plate onto HTU media containing plates and counting the number of colonies growing after 3 days. In these conditions, an interaction of JUN1 and JUNZ enables the cells to grow. Accordingly, a reduction in the number of colonies indicates that the library being screened comprises peptide inhibitors of the JUNZ/JUNZ interaction.

The second screening method involved isolation and streaking of 10 individual colonies to new HTU media containing plates and analysing for growth of new single colonies. After 3 days, those that express a peptide inhibitor generally have very little or no new growth, while those that do not express a peptide inhibitor have re-grown a streak of single colonies. As a positive control a known inhibitor of JUN1/JUNZ interaction, FosZ was used. As a negative control empty pYTB3 vector (SEQ ID NO: 92) with no peptide insert was used. A score of 1-10 given depending on growth of 10 individual clones of each peptide compared to the two control samples.

The score from method 1 and method 2 was then combined to determine if a specific colony expressed a peptide inhibitor of JUN1/JUNZ interaction. In the present case a cell expressing a peptide inhibitor was one that showed >50% reduction of growth compared to negative control in both tests.

All scoring was performed by two independent individuals and scores of both individuals were combined.

Following screening it was found that 60 of the clones were capable of inhibiting the interaction of JUN1 and JUNZ.

Of the 60 clones identified, 27 were sequenced and analysed to determine their most likely source using BLAST-P. Results of this analysis are set forth in Table 10.

TABLE 10

Characterisation of peptides capable of blocking the interaction of JUNZ and JUN1.

| Peptide # | Length (aa) | Native ORF (Yes/No) | Species |
|---|---|---|---|
| 4 | 75 | No | *Bacillus subtilis* |
| 5 | 12 | No | *Aquifex aeolicus* |
| 8 | 39 | Yes | *Helicobacter pylorii* |
| 12 | 27 | Yes | *Escherichia coli* |
| 15 | 86 | Yes | *Escherichia coli* |
| 20 | 20 | No | *Helicobacter pylorii* |
| 21 | 25 | No | *Borrelia burgdorferi* |
| 22 | 40 | Yes | *Bordatella pertussis* |

TABLE 10-continued

| Characterisation of peptides capable of blocking the interaction of JUNZ and JUN1. | | | |
|---|---|---|---|
| Peptide # | Length (aa) | Native ORF (Yes/No) | Species |
| 24 | 26 | No | *Haemophilus influenzae* |
| 30 | 53 | No | *Pseudomonas aeruginosa* |
| 32 | 13 | No | *Plasmodium falciparum* |
| 33 | 11 | No | *Haemophilus influenzae* |
| 34 | 29 | No | *Aquifex aeolicus* |
| 35 | 62 | Yes | *Pyrococcus horikoshii* |
| 36 | 16 | Yes | *Bacillus subtilis* |
| 39 | 12 | No | *Bordatella pertussis* |
| 43 | 12 | No | *Neisseria meningitidis* |
| 54 | 32 | Yes | *Escherichia coli* |
| 58 | 45 | No | *Bacillus subtilis* |
| 60 | 20 | No | *Bacillus subtilis* |
| 66 | 39 | Yes | *Bacillus subtilis* |
| 72 | 38 | No | *Haemophilus influenzae* |
| 73 | 33 | No | *Pyrococcus horikoshii* |
| 76 | 24 | No | *Thermoplasma volcanium* |
| 77 | 18 | No | *Thermoplasma volcanium* |
| 79 | 12 | No | *Haemophilus influenzae* |
| 80 | 26 | Yes | *Bacillus subtilis* |

Note that 30% of the identified peptides are expressed in their native reading frame (ie they are identical to a region of a protein found in nature). This represents a significantly greater (p<0.009) number than would be expected by chance (as only 1 in 6 fragments would be expected to be in their native reading frame).

The sequence of the peptides identified in this screen are set forth in Table 11.

| Clone number | Source of nucleic acid | Native ORF (Y/N) | Nucleotide sequence | Sequence of peptide encoded by 1st ORF with flanking phage sequence | Sequence of peptide encoded by 1st ORF without flanking phage sequence |
|---|---|---|---|---|---|
| 4 | *B subtilis* | N | SEQ ID NO: 93 | SEQ ID NO: 94 | SEQ ID NO: 95 |
| 5 | *A aeolicus* | N | SEQ ID NO: 96 | SEQ ID NO: 97 | SEQ ID NO: 98 |
| 8 | *H Pylori* | Y | SEQ ID NO: 99 | SEQ ID NO: 100 | SEQ ID NO: 101 |
| 12 | *E. coli* | N | SEQ ID NO: 102 | SEQ ID NO: 103 | SEQ ID NO: 104 |
| 15 | *E. coli* | Y | SEQ ID NO: 105 | SEQ ID NO: 106 | SEQ ID NO: 107 |
| 20 | *H. pylori* | N | SEQ ID NO: 108 | SEQ ID NO: 109 | SEQ ID NO: 110 |
| 21 | *B burgdorferei* | N | SEQ ID NO: 111 | SEQ ID NO: 112 | SEQ ID NO: 113 |
| 22 | *B. pertussis* | Y | SEQ ID NO: 114 | SEQ ID NO: 115 | SEQ ID NO: 116 |
| 24 | *H. influenzae* | N | SEQ ID NO: 117 | SEQ ID NO: 118 | SEQ ID NO: 119 |
| 30 | *P. aeruginosa* | Y | SEQ ID NO: 120 | SEQ ID NO: 121 | SEQ ID NO: 122 |
| 32 | *P. falciparum* | N | SEQ ID NO: 123 | SEQ ID NO: 124 | SEQ ID NO: 125 |
| 33 | *H. influenzae* | N | SEQ ID NO: 126 | SEQ ID NO: 127 | SEQ ID NO: 128 |
| 34 | *A. aeolicus* | Y | SEQ ID NO: 129 | SEQ ID NO: 130 | SEQ ID NO: 131 |
| 35 | *P. horikoshii* | Y | SEQ ID NO: 132 | SEQ ID NO: 133 | SEQ ID NO: 134 |
| 36 | *B. subtilis* | N | SEQ ID NO: 135 | SEQ ID NO: 136 | SEQ ID NO: 137 |
| 39 | *B. pertussis* | N | SEQ ID NO: 138 | SEQ ID NO: 139 | SEQ ID NO: 140 |
| 43 | *P. horikoshii* | N | SEQ ID NO: 141 | SEQ ID NO: 142 | SEQ ID NO: 143 |
| 54 | *Synechocystis* PCC 6803 | Y | SEQ ID NO: 144 | SEQ ID NO: 145 | SEQ ID NO: 146 |
| 58 | *B. pertussis* | Y | SEQ ID NO: 147 | SEQ ID NO: 148 | SEQ ID NO: 149 |
| 60 | *N. meningitidis* | N | SEQ ID NO: 150 | SEQ ID NO: 151 | SEQ ID NO: 152 |
| 66 | *E. coli* | Y | SEQ ID NO: 153 | SEQ ID NO: 154 | SEQ ID NO: 155 |
| 72, 73, 76 and 77 | *B. subtilis* | N | SEQ ID NO: 156 | SEQ ID NO: 157 | SEQ ID NO: 158 |
| 79 | *H. influenzae* | N | SEQ ID NO: 159 | SEQ ID NO: 160 | SEQ ID NO: 161 |
| 80 | *B. subtilis* | N | SEQ ID NO: 162 | SEQ ID NO: 163 | SEQ ID NO: 164 |

Figure 17:
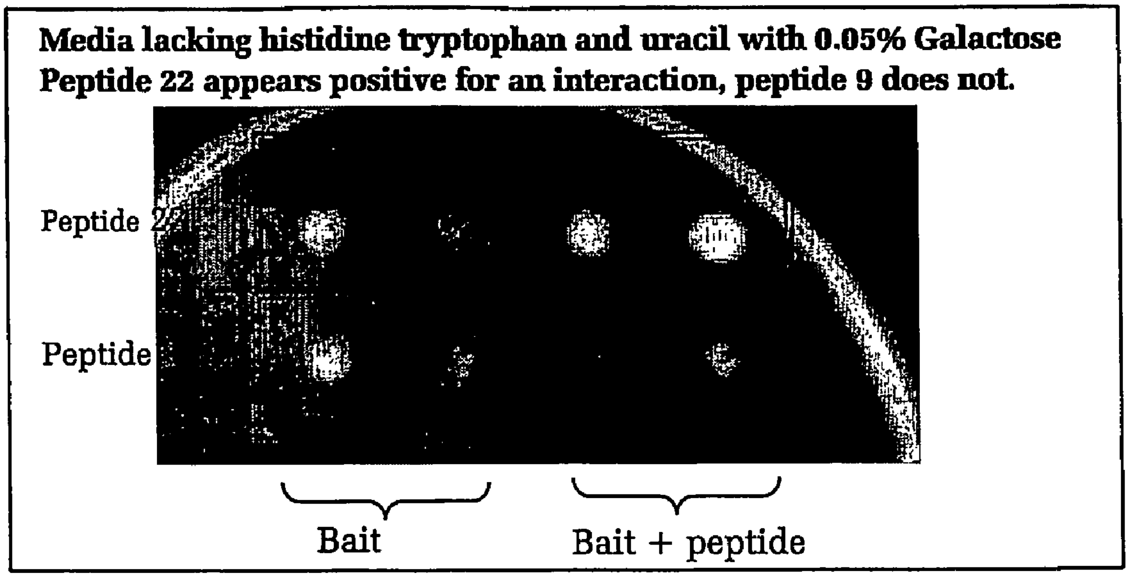
FIG. 17 is a graphical representation of a photograph showing yeast colonies expressing JUN1 and a peptide that interacts with JUN1 (Peptide 22) or JUN1 and a peptide that does not interact with JUN1 (Peptide 9). Also shown are cells expressing only the bait (ie JUN1). Note the increased growth in those cell expressing the interacting polypeptides.

The ability of the peptides to interact with JUN1 was then confirmed with a forward two-hybrid assay. Each of the identified peptides capable of inhibiting the interaction of JUN1 and JUNZ was cloned into the bait vector pDD (SEQ ID NO: 61; FIG. 6). Additionally nucleic acid encoding a peptide known not to inhibit the interaction between JUN1 and JUNZ was also cloned into pDD. The pDD vector and the JUN1 prey vector was transformed into the yeast strain PRT480 and the interaction of the encoded peptide and JUN1 assessed by determining the amount of growth in the absence of uracil. An example of such a screen is shown in FIG. 17.

EXAMPLE 11

Identifying Those Peptides Capable of Inhibiting Neurodegeneration in a Cellular Model of Huntington's Disease Huntington disease is a chronic neuropathological disease characterized by preferential degeneration of striatal neurons. While the disease is known to be caused by a pathological expansion of a polyglutamine repeat in the Huntington protein, the means by which neuronal degeneration occurs is unknown, making it difficult to identify potential therapeutics of this disease.

Chronic 3-nitropropionic acid (3-NP) administration in several model organisms has provided a similar pattern of neurodegeneration as seen in Huntington's disease subjects. Accordingly, 3-NP administration is a useful model for screening compounds for their utility in the treatment of a neurodegenerative disease, and, in particular, Huntington's disease.

The effect of the peptides identified in Example 10 is studied in a cellular model of Huntington's disease using 3-NP. Nucleic acid capable of encoding a peptide that comprises a sequence selected from the group consisting of SEQ ID NO: 94, SEQ ID NO: 95, SEQ ID NO: 97, SEQ ID NO: 98, SEQ ID NO: 100, SEQ ID NO: 101, SEQ ID NO: 103, SEQ ID NO: 104, SEQ ID NO: 106, SEQ ID NO: 107, SEQ ID NO: 109, SEQ ID NO: 110, SEQ ID NO: 112, SEQ ID NO: 113, SEQ ID NO: 115, SEQ ID NO: 116, SEQ ID NO: 118, SEQ ID NO: 119, SEQ ID NO: 121, SEQ ID NO: 122, SEQ ID NO: 124, SEQ ID NO: 125, SEQ ID NO: 127, SEQ ID NO: 128, SEQ ID NO: 130, SEQ ID NO: 131, SEQ ID NO: 133, SEQ ID NO: 134, SEQ ID NO: 136, SEQ ID NO: 137, SEQ ID NO: 139, SEQ ID NO: 140, SEQ ID NO: 142, SEQ ID NO: 143, SEQ ID NO: 145, SEQ ID NO: 146, SEQ ID NO: 148, SEQ ID NO: 149, SEQ ID NO: 151, SEQ ID NO: 152, SEQ ID NO: 154, SEQ ID NO: 155, SEQ ID NO: 157, SEQ ID NO: 158, SEQ ID NO: 160, SEQ ID NO: 161, SEQ ID NO: 163, SEQ ID NO: 164 and SEQ ID NO: 165 is cloned into the pcDNA3.1 mammalian expression vector (Invitrogen).

The model used to study the effect of the peptides is an in vitro striatal neuron culture. To produce such a culture striata of fetal rat (embryonic day 17) from pregnant Sprague Dawley rats are dissected, and tissues dissociated by repeated trituration with a pipette in PBS and 0.6% glucose. After decantation for 5 min, cells are collected by centrifugation at 1000×g for 5 min. Cell pellets are resuspended in Neurobasal media supplemented with B27, glutamine, penicillin-streptomycin (Invitrogen, Gaithersburg, Md.), and β-mercaptoethanol (Sigma). Cells are seeded at 960 cells/$mm^2$ into poly-D-lysine (Sigma)-coated 24-well plates. The cultures are maintained at 37° C. in a humidified incubator with 5% $CO_2$ and 95% air.

Cells are then transiently transfected with the expression construct produced previously with LipofectAMINE 2000 (Invitrogen) as recommended by the manufacturer's protocol. Cells ($1.8\times10^5$) are transfected with 1 μg of enhanced green fluorescent protein (pEGFP-N3; Clontech, Cambridge, UK) alone or in the of an expression vector produced previously. After 6 hr, the cultures are rinsed with fresh medium. Cells are then incubated for an appropriate period. On the seventh day in vitro, the medium is removed and replaced by fresh medium containing 3-NP (Fluka) at 1 mm.

Following the treatment with 3-NP, the cells are fixed using 4% paraformaldehyde in 0.1 M $Na_2HPO_4/NaH_2PO_4$ buffer, pH 7.5.

The degree of cell death is then determined using TUNEL staining. The detection of DNA strand breaks is performed using terminal deoxynucleotidyl transferase-mediated biotinylated UTP nick end-labeling (TUNEL) according to the procedure of the manufacturers (Roche Molecular Biochemicals, Bagnolet, France) with minor modifications. Briefly, sections are mounted on slides and rehydrated. They are then treated with 0.1% sodium citrate and 0.1% Triton X-100 for 30 min at room temperature and rinsed three times in PBS. They are then incubated in proteinase K (1 mg/ml in PBS, pH 7.4) for 5 min, reimmersed in 4% paraformaldehyde for 15 min, and rinsed three times in PBS before TUNEL reactions. Sections are then covered with 50 μl of TUNEL mixture for 30 min at 37° C. in a humidified chamber. After three washes in PBS, the slides are mounted with Vectashield (Vector Laboratories).

Cells are also monitored for changes in neurite outgrowths and changes in the size of the cell body, both of which are measures of neuronal dysfunction.

Those peptides that are inhibit c-Jun homodimerization and reduce or inhibit cell death and/or neuronal dysfunction are selected as these peptides are useful for further study for their utility in the treatment of neurodegenerative disease.

EXAMPLE 12

Identification of a Peptide Capable of Interacting with JUN

The gene fragment expression library in the pYTB3 vector (described in Example 10) is electrotransformed into *E. coli* cells. Cells are plated onto agar plates and grown overnight at 37° C. Approximately 100,000 individual clones are then picked for further growth and plasmids isolated. The plasmids are then pooled to form pools of 10 different plasmids, and these pooled to form pools of 100 plasmids, and these pooled to form pools of 10,000 plasmids. Ten of these pools are then combined to form a pool of 100,000 plasmids. The peptides encoded by the fragments are then transcribed and translated using the TNT in vitro transcription/translation system (Promega) essentially according to manufacturer's instructions.

Recombinant Jun protein is labelled with Biotin using a Biotin-XX Protein Labeling Kit (Molecular Probes, Eugene, Oreg., USA) and attached to a standard surface plasmon resonance streptavidin chip (Sensor Chip SA)(Biacore).

The in vitro translated peptides are injected across the chip at a rate of approximately 5 μl/min in a BiaCore 3000 analyser. This allows detection of interactions between one or more peptides with a JUN protein at the surface of the chip. Following detection of an interaction in the largest pool of samples (ie 100,000), each of the 10,000 sample pools are tested to determine whether or not they contain a peptide capable of interacting with JUN. Those that do are selected, and the pools of 100 samples that make up these pools are then analysed. Following identification of the pools of 100 samples that comprise one or more peptides capable of interacting with JUN, the chip is washed with distilled water and allowed to air dry.

The chip is then prepared for mass spectrometry by applying α-cyano-4-hydroxyxinnamic acid and BIA-MS analysis performed essentially as described in Needelkov and Nelson Biosensors and Bioelectronics, 16: 1071-1078, 2001 to identify the sequence of each of the peptides bound to the chip.

EXAMPLE 13

Identification of a Peptide Capable of Binding a Specific G-Protein Coupled Receptor (GPCR)

The pYTB vector library described in Example 10 is electrotransformed into DH10B *E. coli* cells (Invitrogen, CA, USA) and grown on 100 square Petri dishes on LB agar containing ampicillin. Approximately $1.2\times10^6$ colonies are picked using a robotic colony picker (Q-pix) to a 3000×384 master plate containing LB-amp+15% glycerol. Plates are then grown at 37° C. for 4 hours then stored at 4° C.

Using a liquid handling robot (Corbett Research) 23,040 groups of 50 colonies are pooled each from the master plate to duplicate 60×384-well plates; one containing LB-amp (subpool plate) and the other containing LB-amp media including 15% glycerol (subpool master plates). Following sub-pooling _ the subpool master plates are stored at −80° C. and the subpool plates are grown to stationary phase at 37° C. for plasmid isolation (see below).

Plasmids are then isolated form the bacteria in the subpool plates using miniprep and to the peptide encoded by the cloned genome fragment translated in the presence of a fluorescently labelled puromycin analogue essentially as described by Nemoto et al, *FEBS Lett.,* 462: 43-46, 1996, to produce a fluorescently labelled mRNA-peptide fusion.

A GPCR microarray is then produced using standard robotic pin printing techniques (essentially as described in Fang et al., *Chembiochem.,* 3: 987-991, 2002). The labelled peptides are then brought into direct contact with the microarray and fluorescence detected using a standard microarray reader. Any peptides bound to the GPCR microarray are isolated and the subpool of clones from which it is isolated further divided into a smaller pool. Each of the smaller pools is then screened as described supra, and this process repeated until only a single clone is isolated.

The nucleic acid encoding the peptide capable of binding to the GPCR of interest is then amplified using PCR and cloned into the pYTB3 vector. The peptide encoded by this vector is then re-tested to determine its ability to bind to the GPCR.

EXAMPLE 14

Development and Screening of a Biodiverse Nucleic Acid Fragment Library for Anti-Parasitic Peptides in Drug Resistant *C. elegans*

The modified biodiverse nucleic acid fragment library developed in Example 5 is digested with the restriction enzymes EcoRI and HindIII in the following reaction:

| Biodiverse nucleic acid fragment library (3 μg) | |
|---|---|
| EcoRI buffer (10x) (Promega) | 8 μl |
| BSA (10x) | 8 μl |
| EcoRI (20 U/μl) (Promega) | 3 μl |
| HindIII (10 U/μl) (Promega) | 3 μl |
| $H_2O$ | to 80 μl |

Reactions proceed at 37° C. for 2 hours, before enzymes are heat inactivated by incubating the reactions at 65° C. for 20 minutes. Reactions are then electrophoresed in a 2% TAE/agarose gel and the bands relating to the nucleic acid fragments isolated using a QIAquick gel extraction kit (QIAGEN).

At the same time the pGEMEX-1 bacterial expression vector (Promega) is also digested with EcoRI and HindIII in the following reaction:

| pGEMEX-1 (2 μg) | |
|---|---|
| EcoRI buffer (10x) (Promega) | 3 μl |
| BSA (10x) | 3 μl |
| EcoRI (20 U/μl) (Promega) | 1 μl |
| HindIII (10 U/μl) (Promega) | 1 μl |
| $H_2O$ | to 30 μl |

Reactions are allowed to proceed at 37° C. for 2 hours, before enzymes are heat inactivated by incubating the reactions at 65° C. for 20 minutes. Reactions are then electrophoresed in a 2% TAE/agarose gel and the bands relating to the nucleic acid fragments isolated using a QIAquick gel extraction kit (QIAGEN).

Nucleic acid concentration is then determined by spectrophotometry measuring UV absorption at 260 nm.

The biodiverse nucleic acid fragments are then ligated into the pGEMEX-1 vector in the following reaction:

| pGEMEX-1 (1 μg)<br>BGF-PCR Fragments (1 μg) | |
|---|---|
| Ligation Buffer (10x) (NEB) | 20 μl |
| T4 polynucleotide kinase (5 U/μl) | 10 μL |
| $H_20$ | to 200 μl |

Ligation reactions are allowed to proceed overnight at 16° C. The ligase is then heat inactivated by incubating the samples at 65° C. for 30 minutes. Following completion of the ligation reaction sample volumes are increased to 500 μl with TE buffer and added to an Amicon spin column. These columns are then centrifuged for 15 minutes at 3,800 rpm in a microcentrifuge. Columns are inverted and 30 μl of TE buffer is added before the columns are centrifuged for 2 minutes at 3,800 rpm, with this fraction collected for later use.

The pGEMEX-1 vector containing the biodiverse nucleic acid fragment is then transformed into *E. coli* TOP10 cells.

Individual colonies of bacteria are then individually picked and plated onto a master plate of LB-agar+ampicillin (50 μg/ml). 100 colonies from each plate are grown in a flask containing 10 ml LB broth until confluent. Approximately 5 drops of the broth is then added to a 9 cm plate containing NG agar (as described in Sulston and Hodgkin (In: The Nematode *Caenorhabditis elegans*, Cold Spring Harbour Laboratories, New York, 1988)), and gently spread to cover approximately two thirds of the surface area of the agar. These plates are then incubated at 37° C. overnight or until a bacterial lawn is observed. These plates are then useful for the growth of *C. elegans*, which feed on the bacterial cells and take up any expressed peptides into their cells. *C. elegans* provides a model system for testing an effect of a peptide expressed by an isolated clone of the expression library in vivo, eg., in target validation.

The model system described in Dent et al, *Proc. Natl. Acad. Sci. USA* 97, 2674-267, 1999, showed that *C. elegans* is able to develop resistance to the anti-parasitic antibiotic ivomectin, through mutation of the genes avr-14, avr-15 and glc-1. Such a peptide proves invaluable for the screening of anti-parasitic peptides that act through a pathway that is not affected by these genes.

Approximately 400-500 L4 stage or adult stage *C. elegans* worms that are resistant to ivomectin are seeded onto the plates containing 2 μg/ml Ivomectin (which is not toxic to the mutant strain) and the bacteria expressing an expression library of the present invention. Plates are incubated at 25° C. and scored for live worms every 4-6 hours. A worm is considered dead when it no longer responds to touch.

Plates are scored to determine those that contain a significant portion of dead *C. elegans*, excluding those that have stuck to the side wall. Those plates that have the majority of worms dead are further analyzed.

In further analyzing the peptides that kill the ivomectin resistant worms, single bacterial colonies are used to generate the feeder layer for the worms. An individual colony is picked and grown in a flask containing 10 ml LB broth at 37° C. shaking at 225 rpm, until confluent. Approximately 5 drops of the broth is then added to a 9 cm plate containing NG agar (with 2 μg/ml ivomectin) and gently spread to cover approximately two thirds of the surface area of the agar. Plates are again incubated at 37° C. overnight or until a bacterial lawn is observed.

Again resistant *C. elegans* are seeded onto the plates which are incubated at 25° C. and scored for live worms every 4-6 hours. Bacteria are isolated from those plates containing a significant proportion of dead worms, and cultured for 16 hours in 10 ml LB broth (+50 μg/ml ampicillin). The expression plasmids are then isolated using a QIAprep spin miniprep kit (QIAGEN) using the method described by the manufacturer.

Isolated plasmids are then further analyzed to determine the nucleotide sequence that encodes the peptide that is toxic to ivomectin resistant *C. elegans.*

EXAMPLE 15

Development of a Forward N-Hybrid Gene Fragment Library

Nucleic acid was isolated form the organisms shown in Table 12 and used to produce a biodiverse gene fragment library in the forward N-hybrid vector pMF4-5 (Phylogica Ltd, Australia) (SEQ ID NO: 165, FIG. 18). The pMF4-5 vector is a derivative of pJG4-5 (Ausubel et al Current Protocols in Molecular Biology. Wiley Interscience, ISBN 047 150338, 1987) from which the peptides are expressed as a fusion with a transcriptional activation domain. The nucleic acid fragments are cloned between the Acc651 and EcoRI restriction sites of pMF4-5 essentially as described in Example 1.

TABLE 12 genomes used in the production of a biodiverse gene fragment library

| Number | Species |
|---|---|
| 1 | *Archaeoglobus fulgidis* |
| 2 | *Aquifex aeliticus* |
| 3 | *Aeropyrum pernix* |
| 4 | *Aquifex aeolicus* |
| 5 | *Bacillus subtilis* |
| 6 | *Bordatella pertussis* TOX6 |
| 7 | *Borrelia burgdorferi* |
| 8 | *Chlamydia trachomatis* |
| 9 | *Escherichia coli* |
| 10 | *Haemophilus influenzae* |
| 11 | *Helicobacter pylori* |
| 12 | *Methanobacterium thermoautotrophicum* |
| 13 | *Methanococcus jannaschii* |
| 14 | *Methanothermobacter thermoautotrophicus* |
| 15 | *Mycoplasma pneumoniae* |
| 16 | *Neisseria meningitidis* |
| 17 | *Pirellula species* |
| 18 | *Pyrococcus horikoshii* |
| 19 | *Pseudomonas aeruginosa* |
| 20 | *Synechosistis* |
| 21 | *Thermoplasma volcanium* |
| 22 | *Thermotoga maritima* |

The genome fragments were electroporated into *E. coli* to yield a library with a complexity of approximately $6.3\times10^7$ clones. Sequence analysis of 18 of these clones is shown in Table 13.

TABLE 13

Characterisation of nucleic acid fragments in a biodiverse gene fragment library

| Clone # | Insert Size(bp) | ORF Size(aa) | Species |
|---|---|---|---|
| 1 | 218 | 38 | *Methanobacterium thermoautotrophicum* |
| 2 | 58 | 35 | *Thermoplasma volcanium* |
| 3 | 155 | 14 | *Escherichia coli* |
| 4 | 81 | 36 | *Escherichia coli* |
| 5 | 131 | 40 | *Aerpyrum pernix* |
| 6 | 89 | 43 | *Bordatella pertussis* TOX6 |
| 7 | 113 | 43 | *Thermoplasma volcanium* |
| 8 | 213 | 36 | *Bacillus subtilis* |
| 9 | 81 | 11 | *Pseudomonas aeruginosa* |
| 10 | 100 | 36 | *Methanothermobacter thermoautotrophicus* |

TABLE 13-continued

Characterisation of nucleic acid fragments in a biodiverse gene fragment library

| Clone # | Insert Size(bp) | ORF Size(aa) | Species |
|---|---|---|---|
| 11 | 90 | 25 | *Neisseria meningitidis* |
| 12 | 69 | 19 | *Neisseria meningitidis* |
| 13 | 106 | 29 | *Bacillus subtilis* |
| 14 | 39 | 11 | *Pirellula* sp |
| 15 | 120 | 34 | *Escherichia coli* |
| 16 | 128 | 33 | *Haemophilus influenzae* |
| 17 | 195 | 60 | *Bordatella pertussis* TOX6 |
| 18 | 175 | 25 | *Escherichia coli* |

This analysis confirms that the nucleic acid fragments and their encoded peptides were derived from a variety of bacterial species as expected. The average insert size is 114 bp and the average peptide encoded by the fragments approximately 31 amino acids in length.

EXAMPLE 16

Screening a Biodiverse Gene Fragment Library for an Inhibitor of *Plasmodium falciparum* Tubulins Genomic DNA encoding *P. falciparum* $\alpha_1$-tubulin (SEQ ID NO: 166 encoding the polypeptide set forth in SEQ ID NO: 168) is amplified from genomic DNA by PCR using oligonucleotides comprising the sequence GATCctcgaggaattcATGAGAGAAGTAATAAGTATCCATGTAGGAC (SEQ ID NO: 168) and GATCctcgagTTAATAATCTGCTTCATATCCTTCATCTTCTCC (SEQ ID NO: 169).

The PCR product is then digested with XhoI and cloned into the XhoI site of the pDD vector (FIG. 6, SEQ ID NO: 61).

DNA encoding *P. falciparum* β-tubulin (SEQ ID NO: 170 encoding the polypeptide set forth in SEQ ID NO: 171) is amplified from genomic DNA by PCR using oligonucleotides comprising the sequence GATCgaattcATGAGAGAAATTGTTCATATTCAAGCTGG (SEQ ID NO: 172) and GATCctcgagTTAATAATCTGCTTCATATCCTTCATCTTCTCC (SEQ ID NO: 173). PCR products are digested with EcoRI and XhoI and cloned into the vector pJFK (FIG. 5, SEQ ID NO: 60) that has been previously digested with EcoRI and XhoI.

the pDD and pJFK are independently electrotransformed into *E. coli* Top 10 cells (Invitrogen) and the cells grown on agar with kanamycin. Clones that comprise the vectors are selected using Grunstein and Hogness Hybridization, and plasmids are isolated using miniprep. The isolated plasmids are then rapid transformed into *Saccharomyces cerevisiae* yeast strain PRT480 and the cells grown on HIS selective agar. Transformed yeast cells are mated with PRT51 yeast strain and protein expression tested by Western blotting after gene expression is induced with galactose.

The pMF4-5 gene fragment library (described in Example 13) is then transformed into yeast strain PRT51. These yeast are then mass mated with the haploid transformed PRT480 cells described previously, and cells selected that are capable of growing on selective media, indicating an interaction between the peptide encoded by a gene fragment and either $\alpha_1$-tubulin or β-tubulin.

The peptides found to bind to either α1-tubulin or β-tubulin are then chemically synthesized and tested for *P. falciparum* growth inhibitory activity essentially as described in Rosenthal et al., *Antimicrob. Agents Chemother.* 40:1600-

1603, 1996. Briefly, synchronized W2 strain *P. falciparum* parasites (Lambros et al., *J. Parasitol.* 65:418-420, 1972) are cultured with a peptide previously shown to bind to $\alpha_1$-tubulin or β-tubulin for 48 h beginning at the ring stage (control sample contain no peptide or a peptide shown not to bind $\alpha_1$-tubulin or β-tubulin). The medium is changed after 24 h, with maintenance of the appropriate inhibitor concentration. Giemsa-stained smears are made after 48 h, when control cultures contain nearly all ring-stage parasites. The number of new ring forms per 500 erythrocytes is counted, and counts are compared with those of controls.

EXAMPLE 17

Screening a Biodiverse Gene Fragment Library for an Inhibitor of *Cryptosporidium parvum* Tubulins Genomic DNA encoding *C. parvum* α-tubulin (SEQ ID NO: 174 encoding the polypeptide set forth in SEQ ID NO: 175) is amplified from genomic DNA by PCR using oligonucleotides comprising the sequence GATCctcgaggaattcATGAGAGAAGTTATTTCAATTCATGTTGGGC (SEQ ID NO: 176) and GATCctcgagCTAGAAATCGCCCTCGTAATGAAC (SEQ ID NO: 177).

The PCR product is then digested with XhoI and cloned into the XhoI site of the pDD vector (FIG. 6, SEQ ID NO: 61).

DNA encoding *C. parvum* β-tubulin (SEQ ID NO: 178 encoding the polypeptide set forth in SEQ ID NO: 179) is amplified from cDNA reverse transcribed from *C. parvum* mRNA by PCR using oligonucleotides comprising the sequence GATCcaattgATGAGAGAAATTGTTCATGTTCAAGGAGGAC (SEQ ID NO: 180) and GATCctcgagTTAAGCCTCAATATGATGTTCGTCATCTGGG (Seq ID NO: 181). PCR products are digested with MfeI and XhoI and cloned into the vector pJFK (FIG. 5, SEQ ID NO: 60) that has been previously digested with EcoRI and XhoI.

the pDD and pJFK are independently electrotransformed into *E. coli* Top 10 (Invitrogen) and the cells grown on agar with kanamycin. Clones that comprise the vectors are selected using Grunstein and Hogness Hybridization, and plasmids are isolated using miniprep. The isolated plasmids are then rapid transformed into *Saccharomyces cerevisiae* yeast strain PRT480 and the cells grown on HIS selective agar. Transformed yeast cells are mated with PRT51 yeast strain and protein expression tested by Western blotting after gene expression is induced with galactose.

The pMF4-5 gene fragment library (described in Example 13) is then transformed into yeast strain PRT51. These yeast are then mass mated with the haploid transformed PRT480 cells described previously, and cells selected that are capable of growing on selective media, indicating an interaction between the peptide encoded by a gene fragment and either α-tubulin or β-tubulin.

Peptides identified in these screens are synthesised and then tested for their ability to inhibit the growth of *C. parvum*. $5\times10^4$ HCT-8 cells are incubated at 37° C. for 48 hours, or until confluent. Following this a peptide from the previous experiment is added to the cells, followed by *C. parvum* sporozoites. Samples are then incubated for 4 hours, and the level of growth inhibition of *C. parvum* determined using an immunoassay essentially as described by Gargala et al., *Int. J. Parasitol.* 29:703-709.

EXAMPLE 18

Screening a Biodiverse Gene Fragment Library for an Inhibitor of *Trypanosoma brucei rhodesiense* Tubulins Genomic DNA encoding *T. brucei* α-tubulin (SEQ ID NO: 182 encoding the polypeptide set forth in SEQ ID NO: 183) is amplified from genomic DNA by PCR using oligonucleotides comprising the sequence GATCgaattcATGCGTGAGGCTATCTGCATCC (SEQ ID NO: 184) and GATCctcgagCTAGTACTCCTCCACATCCTCCTCACC (SEQ ID NO: 185).

The PCR product is then digested with EcoRI and XhoI and cloned into the pDD vector (FIG. 6, SEQ ID NO: 61) previously digested with EcoRI and XhoI.

DNA encoding *T. brucei* β-tubulin (SEQ ID NO: 186 encoding the polypeptide set forth in SEQ ID NO: 187) is amplified from genomic DNA by PCR using oligonucleotides comprising the sequence GATCcaattgATGCGCGAAATCGTCTGCGTTCAGGC (SEQ ID NO: 188) and GATCctcgagCTAGTATTGCTCCTCCTCGTCG (Seq ID NO: 189). PCR products are digested with MfeI and XhoI and cloned into the vector pJFK (FIG. 5, SEQ ID NO: 60) that has been previously digested with MfeI and XhoI.

The pDD and pJFK are independently electrotransformed into *E. coli* Top 10 (Invitrogen) and the cells grown on agar with kanamycin. Clones that comprise the vectors are selected using Grunstein and Hogness Hybridization, and plasmids are isolated using miniprep. The isolated plasmids are then rapid transformed into *Saccharomyces cerevisiae* yeast strain PRT480 and the cells grown on HIS selective agar. Transformed yeast cells are mated with PRT51 yeast strain and protein expression tested by Western blotting after gene expression is induced with galactose.

The pMF4-5 gene fragment library (described in Example 13) is then transformed into yeast strain PRT51. These yeast are then mass mated with the haploid transformed PRT480 cells described previously, and cells selected that are capable of growing on selective media, indicating an interaction between the peptide encoded by a gene fragment and either α-tubulin or β-tubulin.

Procyclic forms of *T. brucei rhodesiense* are grown in SDM-79 supplemented with 10% fetal bovine serum (FBS) in the presence or absence of a peptide previously determined to bind to *T. brucei rhodesiense* myosin. As a further control a peptide determined not to bind to *T. brucei rhodesiense* myosin is included. Cells are incubated overnight. Cell densities are determined using a Neubauer chamber. Procyclic forms are diluted to $1\times10^6$ cell/ml. Growth curves are plotted by using the product of the cell density and the dilution factor.

EXAMPLE 19

Development and Screening of a Biodiverse Nucleic Acid Fragment Library from *Takifugu rubripes*

Nucleic acid fragments are generated from genomic DNA from the Japanese puffer fish *T. rubripes* using a restriction enzyme digestion with the enzymes AluI and HaeIII, in the following reaction:

| Genomic DNA (20 μg) | |
|---|---|
| Restriction enzyme buffer (10x) | 5 μl |
| AluI(10 U/μg) | 4 μl |
| HaeIII(10 U/μg) | 4 μl |
| $H_2O$ | to 50 μl |

The DNA fragments are then separated by electrophoresis using a 2% agarose/TAE gel. Fragments in the 90-120 bp range are isolated using the QIAquick Gel Extraction Kit (QIAGEN) following manufacturer's instructions.

The concentration of DNA is determined using spectrophotometry at 260 nm.

The adaptor pairs SEQ ID Nos: 42 and 43; SEQ ID Nos: 44 and 45; SEQ ID NOs: 46 and 47; SEQ ID NOs: 48 and 49 are then annealed to one another. This process is completed in $H_2O$ with each of the oligonucleotides at a concentration of 50 μM. Pairs of adaptors are incubated at 94° C. for 10 minutes and then allowed to cool to room temperature slowly.

The annealed adaptors are then ligated to the isolated nucleic acid fragments in separate ligation reactions.

Ligations are carried out in the following reactions:

| Pooled genomic DNA fragments (average fragment length of 100 bp) | |
|---|---|
| Annealed adaptor | 150 pmol |
| Ligation buffer (10x) (Promega) | 1 μl |
| T4 DNA ligase (3 U/μl) (Promega) | 1 μl |
| $H_2O$ | to 10 μl |

Samples are then incubated at 4° C. overnight before being heat-inactivated through incubation at 65° C. for 20 minutes.

Samples are phosphorylated using T4 polynucleotide kinase (Promega) in the following reaction:

| | |
|---|---|
| Ligation buffer (10x) (Promega) | 1 μl |
| rATP (10 mM) | 2 μl |
| T4 polynucleotide kinase (5 U/μl) | 1 μl |
| $H_2O$ | 20 μl |

Samples are incubated at 37° C. for 30 minutes followed by incubation at 65° C. for 20 minutes to heat inactivate the enzyme.

Nucleic acid fragments from each of the ligation reactions are then combined in equal ratios, ie. equal amounts of nucleic acid, to form one pool. This pool of nucleic acid fragments is then suitable for cloning into the peptide display vector T7Select415-1 (Novagen). However, it is first necessary to digest the T7Select415-1 vector with EcoRI in the following reaction:

| | |
|---|---|
| T7Select415-1 vector (1 μg) | |
| EcoRI buffer (10x) (Promega) | 3 μl |
| BSA (10x) | 3 μl |
| EcoRI (20 U/μl) (Promega) | 2 μl |
| $H_2O$ | to 30 μl |

Reactions proceed at 37° C. for 2 hours, before enzymes are heat inactivated by incubating the reactions at 65° C. for 20 minutes. Samples are then purified using a QIAquick PCR purification column using manufacturer's instructions. Nucleic acid concentration are then determined by spectrophotometry measuring UV absorption at 260 nm, before diluting the DNA to a final concentration of 0.02 μM.

The nucleic acid fragments are then ligated into the T7Select415-1 vector using the following reaction:

| | |
|---|---|
| Ligation buffer (10x) (Novagen) | 0.5 μl |
| rATP (10 mM) | 0.5 μl |
| DTT (10 mM) | 0.5 μl |
| T7Select415-1 (0.02 pmol) | 1 μl |
| Nucleic acid fragments<br>(0; 0.02; and 0.06 pmol in independent reactions) | |
| $H_2O$ | to 5 μl |

Reactions are incubated at 16° C. overnight. Samples are then purified using a QIAquick PCR purification column (QIAGEN), before being diluted in 1 ml of phosphate buffered saline.

The library generated from *T. rubripes* is then screened for mimotopes of epitopes of the D15 protein. The D15 protein is a 80 kDa outer membrane protein of *Haemophilus influenzae*, which are shown to elicit an immune response in rabbits. The antibodies isolated from these rabbits, in turn, are shown to confer resistance to *H. influenzae* to infant rats. Affinity-purified antibodies isolated from rabbits have also been shown to be protective in screens using infant rats (Thomas et al, *Infect Immunol,* 58(6), 1909-1915, 1990).

In an attempt to identify mimotopes of epitopes of the D15 protein, the phage displayed library generated from *T. rubripes*, is screened for those peptides that have a conformation sufficient for binding the affinity purified antibody described in Thomas et al (1990).

The phage display library is added to the affinity purified antibody, which is linked to an antibody coated goat anti-rabbit coupled magnetic beads. These beads are generated by incubating 10 μg of the antibody with 5 mg Dynal beads and incubating at 25° C. for 1 hour, followed by 6 washes with HEG buffer (35 mM HEPES-KOH, pH 7.5/0.1 mM EDTA/100 mM sodium glutamate).

Phage are incubated with these beads at 0° C. for 1 hour, before being washing three times with 5 ml cold HEG buffer/0.1% BSA. Beads are then washed a further three times with HEG buffer using a magnet, such as a tesla magnet (Miltenyi Biotec, Bergish Gladbach, Germany) to immobilise the beads. Bound phage are then eluted with 0.5 ml of 1% SDS. Phage isolated by this method are re-screened, or, alternatively, the nucleic acid fragments encoding the binding peptide are isolated from the phage and analyzed. For example, the amino acid sequences of the peptides are determined.

EXAMPLE 20

Construction of a Biodiverse Nucleic Acid Fragment for Ribosome Display

Nucleic acid is isolated from the following bacterial species:

| | |
|---|---|
| 1 | *Archaeoglobus fulgidis* |
| 2 | *Aquifex aeliticus* |
| 3 | *Aeropyrum pernix* |
| 4 | *Bacillus subtilis* |
| 5 | *Bordetella pertussis* TOX6 |
| 6 | *Borrelia burgdorferi* |

-continued

| | |
|---|---|
| 7 | *Chlamydia trachomatis* |
| 8 | *Escherichia coli* K12 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *Synechosistis* PCC 6803 |
| 18 | *Thermoplasma volcanium* |
| 19 | *Thermotoga maritima* |

Nucleic acid fragments are generated from each of these genomes using 4 consecutive rounds of PCR using tagged random oligonucleotides with the sequence:

```
                                        (SEQ ID NO: 53)
5'-TTTCCCGAATTGTGAGCGGATAACAATAGAAATAATGTTTAACTTTA

    AGAAGGAGATATATCCATGGACTACAAAGAN9-3'.
```

This oligonucleotide introduces a ribosome binding site.

In order to complete this the following reagents are added to the samples:

| | |
|---|---|
| Genomic DNA (100-200 ng) | |
| Oligonucleotide comprising SEQ ID NO: 53 (25 μM) | 4 μl |
| Klenow Buffer | 1 μl |
| dNTP(2 mM) | 3 μl |
| Klenow | 0.5 μl |
| $H_2O$ | to 40 μl |

Samples are incubated at 15° C. for 30 minutes, then at room temperature for 2 hours, before being heated to 37° C. for 15 minutes.

Samples are boiled for 5 minutes to again denature the nucleic acid in said sample, before being snap cooled to allow renaturation of said nucleic acid. Another 0.5 μl of the Klenow fragment of *E. coli* DNA polymerase I is added to each reaction, and the samples incubated at 15° C. for 30 minutes, then at room temperature for 2 hours, before being heated to 37° C. for 15 minutes.

The PCR products generated are then used as a template for PCR reactions using the following oligonucleotide:

```
                                        (SEQ ID NO: 54)
5'GGGGCCAAGCAGTAATAATACGAGTCACTATAGGGAGACCACAAC

GGTTTCCCGAATTGTG-3'.
```

This oligonucleotide comprises a T7 promoter and a region that is homologous a region of to SEQ ID NO: 53).

Each DNA template is amplified by "one armed" PCR, with the oligonucleotide SEQ ID NO: 54 in separate reactions (ie. 19 reactions). Each PCR reaction contains the following:

| | |
|---|---|
| Template DNA | 1 μl |
| Taq buffer (10x) (Promega) | 5 μl |
| $MgCl_2$ (25 mM) | 4 μl |
| dNTP (2 mM) | 5 μl |
| Oligonucleotide comprising SEQ ID NO: 54 (10 pmol/μl) | 10 μl |
| Taq DNA polymerase (Promega 5 U/μl) | 0.4 μl |
| $H_2O$ | to 50 μl |

Reactions are then cycled in a Perkin Elmer thermocycler PE 9700 or PE 2400 using the following program:

5 min 94° C.+30×[30 sec 94° C., 30 sec. 55° C., 1 min 72° C.]+5 min 72° C.

The resulting PCR products are electrophoresed using a 2% agarose/TAE gel, and the nucleic acid fragments between 50 bp to 250 bp extracted using a QIAquick gel extraction kit (QIAGEN) using manufacturer's instructions. Nucleic acid concentration is determined by spectrophotometry measuring UV absorption at 260 nm.

Pools of PCR products derived from each of the 19 bacterial species are produced. To do so, DNA from each organism is added in an equimolar amount when compared to the amount of nucleic acid added to the pool from the organism with the smallest genome.

Nucleic acid fragments are then blunt ended using Munga Bean Nuclease (NEB) in the following reaction:

| | |
|---|---|
| Nucleic acid fragments (2 μg) | |
| Mung bean nuclease buffer (10x) | 3 μl |
| Mung bean nuclease (10 U/μl)(NEB) | 2 μl |
| $H_2O$ | to 30 μl |

The reaction proceeds at 30° C. for 1 hour. The sample is then purified using a QIAquick PCR purification column (QIAGEN) as per manufacturer's instructions.

Oligonucleotides encoding a blunt-end adaptor are generated comprising the following sequences:

```
5'-TTTAAGCAGCTCGATAGCAGCAC-3';    (SEQ ID NO: 55)
and

5'-GTGCTGGTATCGAGCTGCTTAAA-3'.    (SEQ ID NO: 56)
```

The adaptors are annealed to one another. This process is completed in $H_2O$ with each of the oligonucleotides at a concentration of 50 μM. Pairs of adaptors are incubated at 94° C. for 10 minutes and then allowed to cool to room temperature slowly. Annealed adaptors are ligated to the nucleic acid fragments in the following reactions:

| | |
|---|---|
| Pooled PCR product (average length of 150 bp) | 2 pmol |
| Annealed adaptor | 150 pmol |
| Ligation buffer (10x) (Promega) | 1 μl |
| T4 DNA ligase (3 U/μl) (Promega) | 1 μl |
| $H_2O$ | to 10 μl |

Samples are then incubated at 4° C. overnight before being heat inactivated through incubation at 65° C. for 20 minutes. The ligation reaction is then purified using a QIAquick PCR purification kit (QIAGEN)

The modified nucleic acid fragments are then amplified in a PCR reaction with oligonucleotides of the sequence SEQ ID NO: 54 and the following sequence: 5'AGACCCGTTTAGAGGCCCCAAGGGGTTATGGAATTCACCTTTAAGCAGCT C-3' (SEQ ID NO: 57). The oligonucleotide of SEQ ID NO: 57 introduces a modified lipoprotein terminator with the stop codon removed.

The PCR reactions are completed in the following reaction:

| | |
|---|---|
| Template DNA | 1 μl |
| pfu buffer (10x) (Promega) | 5 μl |
| $MgCl_2$ (25 mM) | 4 μl |

-continued

| | |
|---|---|
| dNTP (2 mM) | 5 µl |
| oligonucleotide SEQ ID NO: 54 (10 pmol/µl) | 10 µl |
| oligonucleotide SEQ ID NO: 57 (10 pmol/µl) | 10 µl |
| pfu DNA polymerase (Promega 5 U/µl) | 0.4 µl |
| $H_2O$ | to 50 µl |

The PCR reactions are completed with the following cycling conditions:

5 min 94° C.+30×[30 sec 94° C., 30 sec. 55° C., 1 min 72° C.]+5 min 72° C.

PCR products are then purified using a QIAquick PCR purification column (QIAGEN).

In a separate reaction the amino acids 211-299 of gene III of filamentous phage M13 are amplified using the following oligonucleotides:

```
5'-CGTGAAAAAATTATTATTCGCAATTC-3'    (SEQ ID NO: 58)

5'-                                 (SEQ ID NO: 59)
TTAAGACTCCTTATTACGCAGTATGTTAGC-3'
```

The oligonucleotide SEQ ID NO: 58 is phosphorylated using T4 polynucleotide kinase (Promega), to allow for later directional cloning of the PCR product. The phosphorylation proceeds in the following reaction:

| Oligonucleotide (SEQ ID NO: 58) | |
|---|---|
| Ligation buffer (10x) (Promega) | 1 µl |
| rATP (10 mM) | 2 µl |
| T4 polynucleotide kinase (5 U/µl) | 1 µl |
| $H_2O$ | 20 µl |

Samples are incubated at 37° C. for 30 minutes followed by incubation at 65° C. for 20 minutes to heat inactivate the T4 polynucleotide kinase.

The oligonucleotides are then used in the following PCR reaction:

| | |
|---|---|
| Template DNA | 1 µl |
| pfu buffer (10x) (Promega) | 5 µl |
| $MgCl_2$ (25 mM) | 4 µl |
| dNTP (2 mM) | 5 µl |
| oligonucleotide SEQ ID NO: 58 (10 pmol/µl) | 10 µl |
| oligonucleotide SEQ ID NO: 59 (10 pmol/µl) | 10 µl |
| pfu DNA polymerase (Promega 5 U/µl) | 0.4 µl |
| $H_2O$ | to 50 µl |

Reactions are then cycled in a Perkin Elmer thermocycler PE 9700 or PE 2400 using the following program:

5 min 94° C.+30×[30 sec 94° C., 30 sec. 59° C., 1 min 72° C.]+5 min 72° C.

Reactions are electrophoresed in a 2% TAE/agarose gel and the 1276 bp fragment isolated using a QIAquick gel purification kit (QIAGEN).

The modified nucleic acid fragments and the spacer sequence isolated from M13 phage are then ligated in the following reaction:

| | |
|---|---|
| Modified nucleic acid fragment (2 µg) | |
| Spacer (2 µg) | |
| Ligation buffer (10x) (Promega) | 2 µl |
| T4 DNA ligase (3 U/µl) (Promega) | 1 µl |
| $H_2O$ | to 20 µl |

-continued

Samples are then incubated at 4° C. overnight before being heat inactivated through incubation at 65° C. for 20 minutes. The ligation reaction is then purified using a QIAquick PCR purification kit (Qiagen)

The resulting gene constructs are transcribed and translated in vitro using the Promega *E. coli* S 30 Extract system for linear templates as per manufacturer's instructions, which are a modification of the protocol of Leslie et al, *J. Biol. Chem.* 266, 2632-1991.

The translation reaction is stopped by adding magnesium acetate [$Mg(OAc)_2$] to a final concentration of 50 mM, chloroamphenicol to a final concentration of 50 µM and cooling the samples on ice. The samples are then diluted 8 fold with ice-cold wash buffer (50 mM Tris-HOAc, pH7.5/150 mM NaCl/50 mM $Mg(Oac)_2$/0.1% Tween 20) and centrifuged for 5 minutes at 4° C. at 100,000 g to remove any insoluble components.

The in vitro displayed library is then screened to isolate peptides that bind to α-FLAG monoclonal antibody. The monoclonal antibody is first adsorbed to a microtiter plate. Each well of a microtiter plate is rinsed twice with distilled water. The α-FLAG monoclonal antibody (α-FLAG M2, Sigma Aldrich) is diluted in TBS buffer to 20 µg/ml and 100 µl added per well. The antibody is allowed to adsorb at 4° C. overnight. The microtiter plate is then rinsed three times with TBS buffer and filled with 5% skim milk in distilled water. For blocking the skim milk solution is allowed to bind with gentle rocking for 1 hour at room temperature. The dish is then rinsed five times with double distilled water ($ddH_2O$) and filled with $ddH_2O$ until use.

Prior to use, each well of the microtiter plate is washed with ice-cold wash buffer, and the supernatant from the centrifuged translation mixture applied (200 µl per well). The plate is then gently rocked for 1 hour at room temperature. Each well of the microtiter plate is then washed with ice-cold wash buffer five times, and the bound ribosome displayed peptides eluted using ice cold elution buffer (50 mM Tris-HOAc, pH7.5/150 mM NaCl/10 mM EDTA/50 µg/ml *E. coli* tRNA). Elution buffer (100 µl) is added per well, and the plates gently rocked for 10 minutes at 4° C. The released mRNA is recovered using the RNeasy kit (QIAGEN) using manufacturer's instructions.

Recovered mRNAs are then reverse transcribed using Superscript reverse transcriptase (Invitrogen) according to manufacturer's instructions. The positive nucleic acid fragments are then amplified using PCR with the oligonucleotides (very first ones without random bases). PCR products are electrophoresed in a 2% TAE/agarose gel and the PCR products recovered using QIAquick gel extraction kit. Recovered nucleic acids are then sequenced using a Big Dye Terminator system (Perkin Elmer).

EXAMPLE 21

Identification of Peptides Capable of Binding Bacterial FemX and Sortase Family Proteins Gram-positive cocci, such as pneumococci and staphylococci rely on the synthesis of a branched peptidoglycan for high penicillin resistance. This interpeptide is synthesised by a nonribosomal amino-acid ligase belonging to the FemABX family (Hegde and Schrader, *Journal of Biological Chemistry* 276:6998-7003, 2001). Inactivation of FemABX abolishes penicillin resistance in pneumococci Filipe et al., *Microb. Drug*

Resist., 7: 303-316, 2001), or methicillin resistance in Methicillin Resistant *S. Aureus* (MRSA) (Stranden et al., *J. Bacteriol.* 179: 9-16, 1997). In *S. aureus* FemX catalyses the critical addition of the first glycine to the pentaglycine interpeptide (Rohrer et al., *Proc. Natl. Acad. Sci. USA,* 96: 9351-9356, 1999). FemA and FemB function to add subsequently the glycines 2-3 and 4-5 using glycyl-tRNA (Stranden et al, supra. Accordingly, the FemABX family of proteins provide attractive antibacterial targets, since inactivation of FemX will be lethal to the cell.

The precursors of most surface proteins on Gram-positive bacteria have a C-terminal hydrophobic domain and charged tail, preceded by a conserved motif that signals the anchoring process. This motif is the substrate for an enzyme, termed 'sortase', which has a transpeptidation activity resulting in the cleavage of the protein and its attachment of the protein to the peptidoglycan. The enzymes of interest are sortase A which cleaves polypeptides with a LPXTG (SEQ ID NO: 190) motif and sortase B which cleaves proteins with NPQTN (SEQ ID NO: 191) motif. This pathway is involved in multiple pathogenic determinants and thus represents an attractive target. Mouse models have established that mutation of sortase reduces the virulence of *Staphylococcus* (Mazmanian et al., *Proc. Natl. Acad. Sci.* 97: 5510-5515, 2000), confirming its status as a true virulence factor. Accordingly, a peptide capable of binding to and inhibiting the action of either or both of the sortase family of proteins and FemX represents an attractive target for the treatment of infections by antibiotic resistant bacteria, in particular MRSA.

The biodiverse gene fragment library in pMF4-5 described in Example 13 is used to determine a peptide capable of binding FemX and the sortase family.

Each of the FemX gene (SEQ ID NO: 192), Sortase A gene (SEQ ID NO: 194) OR the Sortase B gene (SEQ ID NO: 196) are cloned into the pDD vector (SEQ ID NO: 61; FIG. 6) in operable connection with the LexA DNA binding domain.

The pMF4-5 library (described in Example 13) is transformed into yeast cells, in addition to one of the bait genes. Colonies of yeast are then screened to determine those that are capable of inducing both the reporter genes, indicating that the peptide encoded by the genome fragment is capable of interacting with the bait protein.

EXAMPLE 22

Characterisation of the Antibacterial Activity or Antivirulence Activity of Identified Peptides Yeast cells that express peptides that interact with FemX, Sortase A and/or Sortase B are lysed, and the plasmid containing the fragment encoding the peptide isolated using the BD YeastMaker™ Yeast Plasmid Isolation Kit (Clontech, Palo Alto, Calif., USA) essentially according to manufacturer's instructions. Inserts from rescued plasmids encoding interactors are released by restriction digestion with EcoR1 and Acc651 and subcloned into the vector pYTB3 digested with EcoR1 and Acc651 as described supra are then electroporated into BL21 *E. coli* cells.

The peptides encoded by the genome fragments are then expressed by virtue of the T7 RNA polymerase promoter in the pYTB3 expression vector. Expression is induced by growing transformed bacterial cells in the presence of IPTG.

Following growth of bacterial cells and expression of the peptides of interest, cells are lysed in lysis buffer (20 mM HEPES, pH 8.0, 100 mM NaCl, 5 mM $MgCl_2$, 1 mM DTT, 1 mM PMSF, 1 mg/ml antipain, leupeptin, aprotinin, chymostatin, and pepstatin A). Cells are sonicated in ice water for 30 seconds total time in the following manner: 10 second sonication; cool 1 minute; repeat twice more.

The antibacterial activity or antivirulence activity of the peptides is then assessed by exposing strains of *S. aureus* to the bacterial lysate and determining the level of growth inhibition of the bacterial cells. The first validation strain—Rosenbach 'Oxford' strain of *S. aureus* 3R7089 strain [ATCC# 9144; NCIB 6571; NCTC 6571; NRRL β-314] is assayed in the presence and absence of subinhibitory levels of the β-lactam antibiotic ampicillin. The second, more susceptible *S. aureus* validation strain has a mutation in the femAB locus Maidhoff et al., *J. Bacteriol.,* 173: 3507-3513.

The MIC 50 (Minimum inhibitory concentration) and MIC 90 of the peptides of interest are be determined using a standard broth dilution method. Essentially, this method involves growing the bacterial strain in liquid media until log phase is reached. The bacterial lysates are serially diluted in media in which the *S. aureus* strains are grown in a 96-well plate. Following growth of the bacteria a standard amount (approximately $2\times10^4$ to $2\times10^5$ CFU/ml) of the *S. aureus* is added to each dilution of the bacterial lysate, with one well remaining as a negative control. The plate is then incubated at approximately 37° C. for 18-36 hours, and the amount of growth of the *S. aureus* in each well determined by determining the absorbance at $A_{600}$ using an ELISA plate reader.

Since mutation of sortase A/B alone does not confer a growth inhibitory phenotype, those peptides directed against Sortase targets are assayed for increased bacteriolysis in the presence of Lysostaphin (Thumm and Gotz, *Molecular Microbiology,* 23: 1251-1265, 1997), to which sortase loss-of-function mutants are particular susceptible Mazmanian et al., *Science,* 285: 760-763, 1999). Accordingly, the broth dilution method is performed in the presence of 10 U/ml of lysostatin (Sigma Aldrich, Sydney, Australia), before the determining the degree of autolysis at by absorbance measurement at OD578 essentially as described by Thumm and Gotz supra.

Inhibitory peptides are then tested to determine their antimicrobial activity against multiple strains of bacteria. Any inhibitory peptides which are identified from these primary screens and the secondary screens described below, will be tested against a panel of clinical isolates. This strategy maximises the chances of obtaining an inhibitor in the primary screen which can then be tested against clinical isolates.

To isolate the peptides of interest, the fragments that encode those peptides are amplified using PCR and cloned into the pTYB1 vector (New England Biolabs, Beverly, Mass., USA). The expression and purification methods are essentially those described by the manufacturers of the 'Impact T7' system (New England Biolabs, Beverly, Mass., USA). Vectors are transformed into BL21 cells and expression induced using IPTG. Cells are then lysed and the crude extract from *E. coli* containing a peptide of interest-intein-chitin binding domain fusion protein is passed over a 1 ml chitin column at 4° C. The column is washed with >10 column volumes of 20 mM HEPES (pH 8.0) 500 mM NaCl, 0.1 mM EDTA, 0.1% Triton-X100. The column is then quickly washed with 3 column volumes of 30 mM DTT (freshly diluted in cleavage buffer [20 mM HEPES (pH 8.0), 500 mM NaCl, 0.1 mM EDTA] (to cleave the intein tag from the peptide of interest. The flow to the column is stopped, and the column is left at 4° C. overnight. The peptide is eluted using 3 column volumes of cleavage buffer without DTT.

The isolated peptides are then dialysed against water overnight to remove any residual DTT. Peptides are then diluted in trimethylamine oxidase to ensure that appropriate folding occurs.

Each of the isolated peptides is then assessed using a microtitre broth dilution assay (described supra) to determine their MIC50 and MIC90 against a panel of common gram-positive bacterium, including penicillin resistant isolates of *Streptococcus pneumoniae* and MRSA. Those peptides that bind Sortase A and/or Sortase B are assayed for bacteriolysis in the presence and absence of Lysostaphin. Peptides that are capable of significantly inhibiting the growth rate of these bacteria are useful for the development of antibacterial therapeutics.

EXAMPLE 23

Compatibility of *S. aureus* and *E. coli* Infected with T7 Growing on Solid Media in Close Proximity Initial tests are carried out to establish whether the growth of an *E. coli* lawn containing T7 bacteriophage plaques is generally inhibitory to the growth of a lawn of *S. aureus* on top of a semipermeable membrane laid down on top of the phage overlay. The results of this assay suggested that both the *E. coli*/T7 culture, and the *S. aureus* culture are able to grow without any apparent interference. Accordingly, this assay format is utilised in determining those peptides that demonstrate antibacterial properties.

---

The invention claimed is:

1. An isolated peptide consisting of an amino acid sequence set forth in SEQ ID NO: 134.

2. An isolated peptide consisting of an amino acid sequence set forth in SEQ ID NO: 133.

3. An isolated peptide, consisting of a fusion between an amino acid sequence set forth in SEQ ID NO: 134 and an amino acid sequence capable of enhancing, increasing or assisting penetration or uptake of the peptide by cells, said fusion.

4. The isolated peptide of claim 3, wherein the amino acid sequence capable of enhancing, increasing or assisting penetration or uptake of the peptide by cells is the tat sequence of HIV.

5. An isolated peptide of claim 2, consisting of a fusion between the amino acid sequence set forth in SEQ ID NO: 133 and an amino acid sequence capable of enhancing, increasing or assisting penetration or uptake of the peptide by cells, of said fusion.

6. The isolated peptide of claim 5, wherein the amino acid sequence capable of enhancing, increasing or assisting penetration or uptake of the peptide by cells is the tat sequence of HIV.

7. A pharmaceutical formulation comprising an isolated peptide, wherein a isolated peptide consists of the amino acid sequence set forth in SEQ ID NO: 134 in combination with a pharmaceutically acceptable vehicle or carrier.

8. A pharmaceutical formulation comprising an isolated peptide, wherein a isolated peptide consists of the amino acid sequence set forth in SEQ ID NO: 133 in combination with a pharmaceutically acceptable vehicle or carrier.

9. An pharmaceutical formulation according to claim 7, wherein the isolated peptide consists of a fusion between the amino acid sequence set forth in SEQ ID NO: 134 and an amino acid sequence capable of enhancing, increasing or assisting penetration or uptake of the peptide by cells, said fusion.

10. The pharmaceutical formulation according to claim 9, wherein the amino acid sequence capable of enhancing, increasing or assisting penetration or uptake of the peptide by cells is the tat sequence of HIV.

11. An pharmaceutical formulation according to claim 8, wherein the isolated peptide consists of a fusion between the amino acid sequence set forth in SEQ ID NO: 133 and an amino acid sequence capable of enhancing, increasing or assisting penetration or uptake of the peptide by cells, of said fusion.

12. The pharmaceutical formulation according to claim 11, wherein the amino acid sequence capable of enhancing, increasing or assisting penetration or uptake of the peptide by cells is the tat sequence of HIV.

13. The pharmaceutical formulation according to claim 7, wherein said formulation is an emulsion.

14. The pharmaceutical formulation according to claim 8, wherein said formulation is an emulsion.

15. The pharmaceutical formulation according to claim 9, wherein said formulation is an emulsion.

16. The pharmaceutical formulation according to claim 10, wherein said formulation is an emulsion.

17. The pharmaceutical formulation according to claim 11, wherein said formulation is an emulsion.

18. The pharmaceutical formulation according to claim 12, wherein said formulation is an emulsion.

* * * * *